United States Patent
Xu et al.

(10) Patent No.: US 11,007,197 B2
(45) Date of Patent: *May 18, 2021

(54) EGFR MODULATORS AND USES THEREOF

(71) Applicant: ACEA Therapeutics, Inc., San Diego, CA (US)

(72) Inventors: Xiao Xu, San Diego, CA (US); Xiaobo Wang, San Diego, CA (US); Long Mao, San Diego, CA (US); Li Zhao, San Diego, CA (US); Biao Xi, San Diego, CA (US)

(73) Assignee: ACEA THERAPEUTICS, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/587,110

(22) Filed: Sep. 30, 2019

(65) Prior Publication Data

US 2020/0129516 A1   Apr. 30, 2020

Related U.S. Application Data

(60) Continuation of application No. 15/708,024, filed on Sep. 18, 2017, now Pat. No. 10,449,196, which is a continuation of application No. 14/712,794, filed on May 14, 2015, now Pat. No. 9,763,949, which is a division of application No. 13/843,554, filed on Mar. 15, 2013, now Pat. No. 9,034,885.

(60) Provisional application No. 61/680,231, filed on Aug. 6, 2012.

(51) Int. Cl.
*A61K 31/519* (2006.01)
*C07D 487/04* (2006.01)
*A61K 45/06* (2006.01)

(52) U.S. Cl.
CPC ............ *A61K 31/519* (2013.01); *A61K 45/06* (2013.01); *C07D 487/04* (2013.01)

(58) Field of Classification Search
CPC ........ A61K 31/519; A61P 35/00; A61P 17/06; A61P 25/28
USPC .................................................... 514/265.1
See application file for complete search history.

(56) References Cited

U.S. PATENT DOCUMENTS

| | | | |
|---|---|---|---|
| 3,974,277 A | 8/1976 | Horn et al. | |
| 7,192,752 B2 | 3/2007 | Xu et al. | |
| 7,459,303 B2 | 12/2008 | Wang et al. | |
| 7,468,255 B2 | 12/2008 | Xu et al. | |
| 7,470,533 B2 | 12/2008 | Xu et al. | |
| 7,560,269 B2 | 7/2009 | Wang et al. | |
| 7,732,127 B2 | 6/2010 | Wang et al. | |
| 8,685,988 B2 | 4/2014 | Xu et al. | |
| 8,975,249 B2 | 3/2015 | Lee et al. | |
| 9,034,885 B2 | 5/2015 | Xu et al. | |
| 9,464,089 B2 | 10/2016 | Xu et al. | |
| 9,586,965 B2 | 3/2017 | Xu et al. | |
| 9,763,949 B2* | 9/2017 | Xu ......................... | A61K 45/06 |
| 9,920,074 B2 | 3/2018 | Xu et al. | |
| 9,925,188 B2 | 3/2018 | Cherifson | |
| 10,449,196 B2 | 10/2019 | Xu et al. | |
| 10,533,011 B2* | 1/2020 | Mao ..................... | C07D 487/04 |
| 10,562,918 B2 | 2/2020 | Xu et al. | |
| 10,596,174 B2 | 3/2020 | Xu et al. | |
| 10,799,504 B2 | 10/2020 | Xu et al. | |
| 2004/0116422 A1 | 6/2004 | Kitano et al. | |
| 2008/0318950 A1 | 12/2008 | Ahn et al. | |
| 2009/0076037 A1 | 3/2009 | Connolly et al. | |
| 2010/0016296 A1 | 1/2010 | Singh et al. | |
| 2010/0029610 A1 | 2/2010 | Singh et al. | |
| 2010/0239631 A1 | 9/2010 | Bourke et al. | |
| 2010/0249092 A1 | 9/2010 | Singh et al. | |
| 2011/0207736 A1 | 8/2011 | Gray et al. | |
| 2012/0094999 A1 | 4/2012 | Gray et al. | |
| 2013/0190320 A1 | 7/2013 | Xu | |
| 2014/0038940 A1 | 2/2014 | Xu et al. | |
| 2014/0038981 A1 | 2/2014 | Xu et al. | |
| 2015/0133457 A1 | 5/2015 | Xu et al. | |
| 2015/0210702 A1 | 7/2015 | Xu et al. | |
| 2017/0224689 A1 | 8/2017 | Xu et al. | |
| 2018/0008607 A1 | 1/2018 | Xu et al. | |
| 2018/0251475 A1 | 9/2018 | Xu et al. | |
| 2018/0312510 A1 | 11/2018 | Mao et al. | |

FOREIGN PATENT DOCUMENTS

| | | |
|---|---|---|
| AU | 2013300106 A1 | 2/2014 |
| AU | 2013300106 A1 | 2/2015 |
| AU | 2013300106 B2 | 11/2017 |
| CA | 2881275 C | 10/2020 |
| CN | 102083800 A | 6/2011 |
| CN | 102482277 A | 5/2012 |
| CN | 103748096 | 4/2014 |
| CN | 103748096 A | 4/2014 |
| CN | 104306348 | 1/2015 |
| CN | 104306348 A | 1/2015 |

(Continued)

OTHER PUBLICATIONS

Baselga et al., "Critical Update and Emerging Trends in Epidermal Growth Factor Receptor Targeting in Cancer," Journal of Clinical Oncology (2005) 23(11):2445-2459.

Gura et al., "Systems for identifying new drugs are often faulty," Science (1997) 278:1041-1042.

Johnson et al., "Relationships between drug activity in NCI preclinical in vitro and in vivo models and early clinical trials," British Journal of Cancer (2001) 84:1424-1431.

Mellinghoff, "Why Do Cancer Cells Become "Addicted" to Oncogenic Epidermal Growth Factor Receptor?" PLoS Medicine (2007) 4(10):e321:1620-1622.

(Continued)

*Primary Examiner* — Jeffrey H Murray
(74) *Attorney, Agent, or Firm* — Rimon, P.C.

(57) ABSTRACT

The present invention relates to certain pyrrolopyrimidine derivatives, pharmaceutical compositions containing them, and methods of using them, including methods for the treatment of tumors and related diseases related to the dysregulation of kinase (such as EGFR (including HER), Alk, PDGFR, but not limited to) pathways.

18 Claims, 14 Drawing Sheets

(56) References Cited

FOREIGN PATENT DOCUMENTS

| CN | 107266453 B | 2/2020 |
|---|---|---|
| EP | 2802568 A | 7/2013 |
| EP | 2880035 A1 | 6/2015 |
| EP | 3019496 A2 | 5/2016 |
| EP | 2880035 B1 | 12/2016 |
| EP | 3170825 B1 | 4/2019 |
| JP | 45-24146 B1 | 8/1970 |
| JP | 2011-526299 A | 10/2011 |
| JP | 2012-526113 A | 10/2012 |
| JP | 2013-515786 A | 5/2013 |
| JP | 2015503625 A | 2/2015 |
| JP | 6215938 B2 | 10/2017 |
| JP | 6353788 B2 | 6/2018 |
| JP | 6353788 B2 | 7/2018 |
| JP | 6564771 B2 | 8/2019 |
| RU | 2015107831 A | 9/2016 |
| RU | 2015107831 A1 | 9/2016 |
| RU | 2645672 C2 | 2/2018 |
| WO | WO-01/32632 | 5/2001 |
| WO | WO-02/083653 | 10/2002 |
| WO | WO-03/026664 | 4/2003 |
| WO | WO-2004/021979 | 3/2004 |
| WO | 2004/045624 A1 | 6/2004 |
| WO | 2004045624 A1 | 6/2004 |
| WO | WO-2004/045624 | 6/2004 |
| WO | WO-2004/045624 A1 | 6/2004 |
| WO | WO-2005/062795 | 7/2005 |
| WO | WO-2005/066156 | 7/2005 |
| WO | WO-2005/084401 | 9/2005 |
| WO | WO-2006/009755 | 1/2006 |
| WO | WO-2006/014325 | 2/2006 |
| WO | 2007/039404 A1 | 4/2007 |
| WO | WO-2007/039404 A1 | 4/2007 |
| WO | WO-2007/042298 | 4/2007 |
| WO | WO-2007/055514 | 5/2007 |
| WO | WO-2007/071393 | 6/2007 |
| WO | WO-2007/103233 | 9/2007 |
| WO | WO-2007/126841 | 11/2007 |
| WO | WO-2008/073687 | 6/2008 |
| WO | WO-2008/094737 | 8/2008 |
| WO | WO-2008/150118 | 12/2008 |
| WO | WO-2009/017838 | 2/2009 |
| WO | WO-2009/020990 | 2/2009 |
| WO | WO-2009/032694 | 3/2009 |
| WO | WO-2009/032703 | 3/2009 |
| WO | WO-2009/051822 | 4/2009 |
| WO | WO-2009/131687 | 10/2009 |
| WO | WO-2009/143389 | 11/2009 |
| WO | WO-2009/158571 | 12/2009 |
| WO | WO-2010/045451 | 4/2010 |
| WO | WO-2010/090764 | 8/2010 |
| WO | 2010129053 A2 | 11/2010 |
| WO | WO-2010/129053 | 11/2010 |
| WO | 2011079231 A | 6/2011 |
| WO | 2011079231 A1 | 6/2011 |
| WO | WO-2011/079231 | 6/2011 |
| WO | 2011090760 A1 | 7/2011 |
| WO | WO-2011/090760 | 7/2011 |
| WO | WO-2011/090760 A1 | 7/2011 |
| WO | WO-2011/140338 | 11/2011 |
| WO | WO-2011/162515 | 12/2011 |
| WO | WO-2012/061299 | 5/2012 |
| WO | WO-2012/061303 | 5/2012 |
| WO | WO-2012/064706 | 5/2012 |
| WO | 2012094999 A1 | 7/2012 |
| WO | WO-2012/120048 | 9/2012 |
| WO | WO-2012/135801 | 10/2012 |
| WO | 2012/151561 A1 | 11/2012 |
| WO | WO-2012/156437 | 11/2012 |
| WO | WO-2013/106792 | 7/2013 |
| WO | 2014/025486 A1 | 2/2014 |
| WO | 2014025486 A1 | 2/2014 |
| WO | 2015/006754 A2 | 1/2015 |
| WO | 2015/006754 A3 | 1/2015 |
| WO | WO-2015/006754 | 1/2015 |
| WO | WO-2015/006754 A2 | 1/2015 |
| WO | 2017/059702 A1 | 4/2017 |
| WO | 2017059702 A1 | 4/2017 |
| WO | 2018/184206 A1 | 10/2018 |
| WO | 2018184206 A1 | 10/2018 |

OTHER PUBLICATIONS

Modjtahedi et al., "Epidermal growth factor receptor inhibitors in cancer treatment: advances, challenges and opportunities," Anti-Cancer Drugs (2009) 220(10):851-855. (Abstract).
Communication pursuant to Article 94(3) EPC for EP 13 701 326.4, dated Aug. 10, 2015, 5 pages.
First Examination Report for NZ 629807, dated Aug. 26, 2015, 2 pages.
Response to Office Action for CN 201380013279.0, filed Sep. 14, 2015, 30 pages.
Office Action for U.S. Appl. No. 14/329,890, dated Sep. 23, 2015, 16 pages.
Response to Communication pursuant to Rules 161(1) and 162 EPC for EP 13 745 491.4, dated Sep. 25, 2015, 4 pages.
The Second Office Action (translation) for CN 201380013279.0, dated Dec. 3, 2015, 3 pages.
Request for Continued Examination for U.S. Appl. No. 13/740,182, filed Dec. 17, 2015, 22 pages.
Response to Office Action for U.S. Appl. No. 14/329,890, filed Dec. 21, 2015, 14 pages.
Invitation to Respond to Written Opinion for SG 11201500872S, dated Dec. 22, 2015, 9 pages.
First Office Action (translation) for CN 201380001359.4, dated Jan. 13, 2016, 7 pages.
Communication pursuant to Article 94(3) EPC for EP 13 745 491.4, dated Jan. 25, 2016, 3 pages.
Supplemental Amendment for U.S. Appl. No. 13/740,182, filed Feb. 9, 2016, 16 pages.
Response to Office Action for CN 201380013279.0, filed Feb. 16, 2016, 26 pages.
Response to Communication pursuant to Art. 94(3) EPC for EP 13 701 326.4, filed Feb. 22, 2016, 66 pages.
Final Office Action for U.S. Appl. No. 14/329,890, dated Mar. 3, 2016, 5 pages.
Request for Continued Examination for U.S. Appl. No. 14/329,890, filed May 3, 2016, 17 pages.
Response to Written Opinion for SG 11201500872S, filed May 12, 2016, 22 pages.
Response to the Communication pursuant to Art. 94(3) EPC for EP 13 745 491.4, filed May 16, 2016, 27 pages.
The Third Office Action (translation) for CN 201380013279.0, dated May 17, 2016, 3 pages.
Communication pursuant to Article 94(3) EPC for EP 13 701 326.4, dated May 24, 2016, 5 pages.
Notice of Allowance for U.S. Appl. No. 14/329,890, dated May 27, 2016, 7 pages.
Response to Office Action for CN 201380001359.4, filed May 30, 2016, 31 pages.
Communication under Rule 71(3) EPC for EP 13 745 491.4, dated Jun. 20, 2016, 7 pages.
Office Action for U.S. Appl. No. 14/420,341, dated Jun. 3, 2016, 7 pages.
Corrected Notice of Allowance for U.S. Appl. No. 14/329,890, dated Jun. 20, 2016, 4 pages.
Second Office Action for CN 201380001359.4, dated Jul. 11, 2016, 11 pages.
Invitation to Respond to Written Opinion for SG 11201500872S, dated Aug. 1, 2016, 7 pages.
Response to the Third Office Action for CN 201380013279.0, filed Aug. 1, 2016, 24 pages.
Office Action for U.S. Appl. No. 13/740,182, dated Sep. 1, 2016, 20 pages.
Response to Office Action for U.S. Appl. No. 14/420,341, filed Sep. 1, 2016, 12 pages.

(56) References Cited

OTHER PUBLICATIONS

Patent Examination Report No. 1 for AU 2013207712, dated Sep. 19, 2016, 4 pages.
Final Office Action for U.S. Appl. No. 14/420,341, dated Sep. 22, 2016, 8 pages.
Xu et al., "AC0010, an irreversible EGFR inhibitor selectively targeting mutated EGFR and overcoming T790M-induced resistance in animal models and lung cancer patients," Molecular Cancer Therapeutics, Published Online Aug. 29, 2016, DOI: 10.1158/1535-7163.MCT-16-0281, 32 pages.
Notice of Reasons for Rejection for JP 2015-526540, dated Oct. 17, 2016, 6 pages.
Notice of Allowance for U.S. Appl. No. 14/420,341, dated Oct. 18, 2016, 16 pages.
Notice of Grounds of Rejection for JP 2014-552357, dated Nov. 4, 2016, 8 pages.
Decision to grant a European patent pursuant to Article 97(1) EPC, dated Nov. 10, 2016, 2 pages.
Response to Examination Report for NZ 629807, filed Nov. 24, 2016, 2 pages.
Decision of Rejection for CN 201380013279.0, dated Dec. 2, 2016, 1 page.
Further Examination Report for NZ 629807, dated Dec. 13, 2016, 2 pages.
European Search Report for EP 16202341.0, dated Feb. 22, 2017, 7 pages.
Notification of Defects in IL 237023, dated Jan. 4, 2017, 2 pages.
Response to Notice of Reason for Rejection for JP 2015-526540, dated Jan. 17, 2017, 35 pages.
Final Rejection for U.S. Appl. No. 13/740,182, dated Mar. 23, 2017, 26 pages.
Response to Examination Report No. 1 for AU 2013207712, filed Mar. 23, 2017, 35 pages.
Examination Report No. 2 for AU 2013207712, dated Apr. 3, 2017, 6 pages.
Request for re-examination for CN 201380013279.0, dated Mar. 15, 2017, 256 pages.
Communication pursuant to Art 94(3) for EP 13 701 326.4, dated Feb. 1, 2017, 5 pages.
Response to Notice of grounds of rejection for JP 2014-552357, dated Feb. 3, 2017, 20 pages.
Third Office Action for CN 201380001359.4, dated Jan. 25, 2017, 15 pages.
Further Examination Report Acceptance for NZ 629807, dated Apr. 4, 2017, 1 page.
Response to Written Opinion for SG 11201500872s, dated Dec. 23, 2016, 25 pages.
Notice of Eligibility to Grant for SG 11201500872s, dated Feb. 1, 2017, 6 pages.
Extended European Search Report for EP 16202341.0, dated Feb. 22, 2017, 7 pages.
Amendment after Notice of Allowance for U.S. Appl. No. 14/329,890, dated Aug. 8, 2016, 3 pages.
Non-final Rejection for U.S. Appl. No. 15/271,124, dated Jan. 17, 2017, 6 pages.
Response to Examination Report for NZ 629807, dated Nov. 24, 2016, 163 pages.
Response to Further Examination Report for NZ 629807, dated Mar. 8, 2017, 168 pages.
Office Action for RU 2015107831, dated Apr. 5, 2017, 14 pages.
Response to Third Office Action for CN 201380001359.4, filed Apr. 10, 2017, 24 pages.
Response to Office Action for U.S. Appl. No. 15/271,124, filed Apr. 17, 2017, 15 pages.
Communication pursuant to Article 94(3) EPC for EP 14 748 351.5, dated Apr. 3, 2017, 3 pages.
Notice of Abandonment for Canadian patent application CA2,861,010, dated Jan. 11, 2019, 1 page.
Response to 4th Office Action for Chinese patent application CN201380013279.0, dated Mar. 15, 2017, 256 pages.
Response to 5th Office Action for Chinese patent application CN201380013279.0, dated Feb. 13, 2019, 10 pages.
Notification of Granting Patent Right for Chinese patent application CN201380013279.0, dated Mar. 5, 2019, 1 page with extra 2 pages of an English language equivalent or summary.
Notification of Going Through the Formalities of Registration for Chinese patent application CN201380013279.0, dated Mar. 5, 2019, 1 page with extra 1 page of an English language equivalent or summary.
Certificate of Invention Patent for Chinese patent application CN201380013279.0, dated Jun. 11, 2019, 2 pages with extra a page of an English language equivalent or summary.
Granted pamphlet for Chinese patent application CN201380013279.0, dated Jun. 11, 2019, 96 pages.
Opinion Examining Division for European patent application EP13701326.4, dated May 9, 2019, 5 pages.
Summons to attend oral proceedings pursuant to Rule 115(1) EPC for European patent application EP13701326.4, dated May 9, 2019, 2 pages.
Notice of Allowance for U.S. Appl. No. 15/708,024, dated Jun. 3, 2019, 15 pages.
Non-Final Office Action for U.S. Appl. No. 15/437,722, dated Feb. 25, 2019, 27 pages.
Notice of file corrected application paper for U.S. Appl. No. 14/420,341, dated Nov. 2, 2016, 3 pages.
Notification of Transmittal of the International Search Report and Written Opinion of the International Search Authority or the Declaration for international patent application PCT/US2013/050163, dated Sep. 4, 2013, 10 pages.
Notice of grant for patent for Australian patent application AU 2013300106, dated Mar. 15, 2018, 1 page.
Office Action for Canadian patent application CA2,881,275, dated Jun. 27, 2019, 5 pages.
Patent Certificate from Israel for International patent application PCT/US2013/050163 (International Publication No. WO/2014/025486), dated Dec. 21, 2018, 2 pages.
Response to Office Action for Japanese patent application JP2015-526540, dated Jan. 17, 2017, 35 pages.
Office Action for European patent application EP16202341.0, dated May 8, 2018, 5 pages.
Decision to Grant for European patent application EP16202341.0, dated Mar. 18, 2019, 2 pages.
Patent Certificate for European patent application EP3170825, dated Apr. 10, 2019, 1 page.
Response to First Examination Report for Chinese patent application CN20170229308.7, dated Jan. 7, 2019, 18 pages with extra 17 pages in English.
Second Office Action for Chinese patent application CN201710229308.7, dated Apr. 24, 2019, 4 pages with extra 4 pages of an English language equivalent or summary.
Second Office Action Form Chinese patent application CN201710229308.7, dated Apr. 24, 2019, 3 pages.
Amended Claims for Chinese patent application CN201710229308.7, dated Jul. 2, 2019, 4 pages with extra 3 pages of an English language equivalent or summary.
Certificate of Grant for Australian patent application AU2014287016, dated Feb. 14, 2019, 1 page.
Office Action for Canadian patent application CA2,917,364, dated Jun. 5, 2019, 8 pages.
Response to First Office Action for Chinese patent application CN201480049793.4, dated May 2, 2018, 50 pages.
Second Office Action for Chinese patent application CN201480049793.4, dated Aug. 30, 2018, 5 pages.
Decision of Rejection for Chinese patent application CN201480049793.4, dated Mar. 14, 2019, 6 pages with extra 10 pages of an English language equivalent or summary.
Pending claims for Chinese patent application CN201480049793.4, dated Jun. 11, 2019, 6 pages.
Request Reexamination for Chinese patent application CN201480049793.4, dated Jun. 11, 2019, 29 pages.
Notification of Acceptance of Request for Reexamination for Chinese patent application CN201480049793.4, dated Jun. 21, 2019, 2 pages.

(56) References Cited

OTHER PUBLICATIONS

Office Action for European patent application EP14748351.5, dated Feb. 8, 2019, 233 pages.
Claims for European patent application EP14748351.5, dated Jun. 5, 2019, 4 pages in German and another 4 pages in French.
Certificate of Invention Patent for Chinese patent application CN201380013279.0, patent No. ZL 2013 8 0013279.0, dated Jun. 11, 2019, 1 page with extra 1 page of an English language equivalent or summary.
Notification of Acceptance of Request for Reexamination for Chinese patent application CN201480049793.4, dated Jun. 21, 2019, 2 pages.
Notice of Grant for Japanese patent application JP2016-525833, dated Jul. 2, 2019, 4 pages.
Patent Certificated for Russian patent application RU2016104388, dated May 30, 2019, 1 page.
Notice of Acceptance for Chinese patent application CN2014800497934, dated Jun. 11, 2019, 1 page.
Noline Filing Notification for Japanese patent application JP2018-537705, dated Jun. 7, 2019, 1 page.
Claims and Amended Claims for Chinese patent application CN201710229308.7, dated Jul. 2, 2019, 4 pages with extra 3 pages of an English language equivalent or summary.
Request Reexamination for Chinese patent application CN201480049793.4, dated Jun. 11, 2019, 28 pages.
Response to third Office Action for Mexican patent application MX/a/2016/000261, dated Jun. 28, 2019, 2 pages and another 7 pages of Claims.
First page of Amended Specifications for South African patent application ZA201904490, dated Jul. 9, 2019, 1 page.
Amended Claims for Japanese patent application JP2018-537705, dated Jun. 7, 2019, 9 pages.
Filing Petition for Japanese patent application JP2018-537705, dated Jun. 7, 2019, 2 pages.
Request Examination for Japanese patent application JP2018-537705, dated Jun. 7, 2019, 1 pages.
Amendment for Japanese patent application JP2018-537705, dated Jun. 7, 2019, 13 pages.
Response to Notice of Omitted Item(s) for U.S. Appl. No. 15/882,924, dated May 24, 2018, 4 pages.
Response to Restriction Requirement for for U.S. Appl. No. 15/882,924, dated Feb. 5, 2019, 9 pages.
Chapter II Demand with Response to Written Opinion and Article 34 Amendments for international patent application PCT/CN2016/087857, dated Aug. 7, 2017, 4 pages.
Chapter I Request Form for international patent application PCT/CN2016/087857, dated Aug. 7, 2017, 4 pages.
Claim Amendments under PCT Article 34 (Appendix A) for international patent application PCT/CN2016/087857, dated Aug. 7, 2017, 17 pages.
Claim Amendments under PCT Article 34 (Appendix B) for international patent application PCT/CN2016/087857, dated Aug. 7, 2017, 17 pages.
Application for a patent and acknowledgement of receipt for South African patent application ZA201904490, dated Jul. 9, 2019, 8 page.
Amendment in Response to Non-Final Office Action for U.S. Appl. No. 15/435,722, dated Feb. 2, 2019, 5 pages.
Response to Restriction Requirement for U.S. Appl. No. 15/882,924, dated Aug. 16, 2019, 9 pages.
Decision to grannt a European patent pursuant to Article 97(1) EPC for European patent application EP14748351.5, dated Aug. 20, 2019, 2 pages.
Patent Certificate for Japanese patent application JP2016-525833, dated Aug. 2, 2019, 3 pages.
Notice of Allowance for Mexican patent application MX/a/2016/000261, dated Aug. 6, 2019, 2 pages.
Letters Patent for New Zealand patent application NZ 715687, dated Jul. 30, 2019, 1 page.

Office Action for U.S. Appl. No. 15/882,924, dated Feb. 19, 2019, 44 pages.
Baselga et al., "Critical Update and Emerging Trends in Epidermal Growth Factor Receptor Targeting in Cancer," Journal of Clinical Oncology, (2005) 23(11): 2445-2459 DOI: 10.1200/JCO.2005.11.890.
Bouaziz et al., "Regulatory B cells as inhibitors of immune responses and inflammation," Immunological Reviews 2008 vol. 224: 201-2 I 4.
Cortot et al., "Resistance to Irreversible EGF Receptor Tyrosine Kinase Inhibitors through a Multistep Mechanism Involving the IGF1R Pathway," Cancer Res; 73(2) Jan. 15, 2013, p. 834-844 DOI: 10.1158/0008-5472.CAN-12-066.
Honigberg et al., "The Bruton tyrosine kinase inhibitor PCI-32765 blocks B-cell activation and is efficacious in models of autoimmune disease and B-cell malignancy," PNAS, Jul. 20, 2010, vol. 107, No. 29, p. 13075-13080.
Mellinghoff Ingo, "Why Do Cancer Cells Become "Addicted" to Oncogenic Epidermal Growth Factor Receptor?," PloS Medicine, Oct. 2007, vol. 4, Issue 10, e321, p. 1620-1622.
Caira R. Mino, "Crystalline Polymorphism of Organic Compounds," Topics in Current Chemistry, vol. 198 @ Springer Verlag Berlin Heidelberg 1998, p. 163-208.
Modjtahedi et al., "Epidermal growth factor receptor inhibitors in cancer treatment: advances, challenges and ppportunities," Anti-Cancer Drugs, Nov. 2009, vol. 20, Issue 10, p. 851-855 doi: 10.1097/CAD.0b013e3283330590.
Petter et al., "A novel small-molecule drug pl,atfmm lo silence cancer targets-application to the pan -E,rbB kinases," 2009 AACR Annual! Meeting Apr. 18-22, 2009 Denver, CO, 2 pages.
RN1348622-25-2 Registry, Entered STN: Dec. 4, 2011, STN Tokyo, 1 page.
Bhagwat S. Shripad, "Kinase inhibitors for the treatment of inflammatory and autoimmune disorders," Purinergic Signalling (2009) 5: 107-115 DOI 10.1007/sl 1302-008-9117-z.
Xu et al., "AC0010, an irreversible EGFR inhibitor selectively targeting mutated EGFR and overcoming T790M-induced resistance in animal models and lung cancer patients," Mol Cancer Ther, 15(11) Nov. 2016, p. 2586-5898 DOI: 10.1158/1535-7163.MCT-16-0281.
Non-Final Office Action for U.S. Appl. No. 13/740,182, dated Sep. 13, 2019, 16 pages.
3rd Examination Report for Australian patent application 2013207712, dated Jun. 19, 2017, 11 pages.
Response to 3rd Examination Report for Australian patent application AU2013207712, dated Aug. 15, 2017, 28 pages.
Notice of Acceptance for Australian patent application AU2013207712, dated Aug. 22, 2017, 3 pages.
Notice of Grant for Australian patent application AU2013207712, dated Dec. 18, 2017, 144 pages.
Notice of Abandonment for Canadian patent application CA 2,861,010, dated Nov. 26, 2018, 1 page.
Response to Office Action for Chinese patent application CN201380013279, dated Mar. 15, 2017, 136 pages.
Official filing receipt for Chinese patent application CN201380013279, dated Feb. 13, 2019,1 pages.
Response to 5th Office Action for Chinese patent application CN201380013279, dated Feb. 13, 2019, 10 pages.
Notification of Granting Patent Right for for Chinese patent application CN201380013279, dated Mar. 5, 2019, 1 page with extra 2 pages of English language equivalent or summary.
Notification of Patent Registration for Chinese patent application CN201380013279, dated Mar. 5, 201, 1 page with extra 1 page of English language equivalent or summary.
Certificate of Invention Patent for Chinese patent application CN201380013279, dated Jun. 11, 2019, 2 pages with extra 1 page of English language equivalent or summary.
Granted Pamphlet for Chinese patent application CN201380013279, dated Jun. 11, 2019, 96 pages.
Opinion Examination Division for European patent application EP13701326A, dated May 9, 2019, 5 pages.

(56) References Cited

OTHER PUBLICATIONS

Summons to attend oral proceedings pursuant to Rule 115l(1) EPC for European patent application EP13701326.4, dated May 9, 2019, 2 pages.
Notice of Grounds of Rejection for Japanese patent application JP2014-552357, dated Feb. 6, 2018, 2 pages with extra 2 pages of English language equivalent or summary.
Amendment for Japanese patent application JP2014-552357, dated Apr. 23, 2019, 5 pages.
??? Written Opinion ??? for Japanese patent application JP2014-552357, dated Apr. 23, 2019, 2 pages.
Grant Notice for Japanese patent application JP2014-552357, dated May 15, 2019, 3 pages.
Notice of Allowability for U.S. Appl. No. 15/708,024, dated Sep. 5, 2019, 16 pages.
Issue Notification for U.S. Appl. No. 15/708,024, dated Oct. 2, 2019, 1 page.
Response to Office Action for Australian patent application AU2013300106, dated Oct. 26, 2017, 38 pages.
Clean claims for Canadian patent application CA2881275, dated Dec. 24, 2019, 17 pages.
Response to Office Action for Canadian patent application CA2881275, dated Dec. 24, 2019, 49 pages.
Post Hearing Written submission for Indian patent application IN914/DELNP/2015, dated Nov. 25, 2019, 48 pages.
Patent Certificate for Israel patent application IL237023, dated Dec. 12, 2018, 2 pages.
Response to Examination Report for New Zealand patent application NZ629807, dated Nov. 24, 2016, 163 pages.
Notice of Eligibility for Grant and Examination Report for Singapore patent application SG11201500872S, dated Feb. 1, 2017, 6 pages.
Office Action for Mexican patent application MX/a/2015/001715, dated Aug. 15, 2018, 3 pages.
Office Action for European patent application EP16 202 341.0, dated May 11, 2018, 5 pages.
Pending claims for European patent application EP16 202 341.0, dated May 18, 2018, 5 pages.
Response to Office Action for European patent application EP16 202 341.0, dated Sep. 10, 2018, 34 pages.
Decision to Grant for for European patent application EP16 202 341.0, dated Mar. 18, 2019, 2 pages.
Patent Certificate for for European patent application EP16 202 341.0, dated Apr. 10, 2019, 1 pages.
Search Report for Chinese patent application CN201710229308.7, dated Aug. 28, 2018, 2 pages with extra 2 pages of English language equivalent or summary.
Response to Office Action for Chinese patent application CN201710229308.7, dated Jan. 21, 2019, 17 pages.
2nd Office Action for Chinese patent application CN201710229308.7, dated Apr. 24, 2019, 4 pages with extra 7 pages of English language equivalent or summary.
Amended claims for Chinese patent application CN201710229308.7, dated Jul. 2, 2019, 3 pages.
Claims for Chinese patent application CN201710229308.7, dated Jul. 2, 2019, 4 pages.
Response to Office Action for Chinese patent application CN201710229308.7, dated Sep. 30, 2019, 4 pages.
Filing Certificate for Hong Kong patent application HK17112259.2, dated Apr. 15, 2019, 1 page.
Response to Restriction Requirement for U.S. Appl. No. 14/329,890, dated Aug. 3, 2015, 12 pages.
Notice of Acceptance for New Zealand patent application NZ715687, dated Apr. 3, 2019, 1 page.
Search Report for Russian patent application RU2016104388, dated Apr. 25, 2018, 3 pages with extra 4 pages of English language equivalent or summary.
Office Action for Russian patent application RU2016104388, dated Apr. 27, 2018, 13 pages with extra 10 pages of English language equivalent or summary.
Response to Office Action for Russian patent application RU2016104388, dated Jul. 27, 2018, 4 pages.
Office Action for Russian patent application RU2016104388, dated Aug. 16, 2018, 6 pages with extra 4 pages of English language equivalent or summary.
Patent Certificate for Russian patent application RU2016104388, dated May 30, 2019, 1 page.
1st page of Amended Specification for South African patent application ZA201904490, dated Jul. 9, 2019, 1 page.
Claims filed for South African patent application ZA201904490, dated Jul. 9, 2019, 4 page.
Filing particulars for South African patent application ZA201904490, dated Jul. 9, 2019, 8 page.
1st Preliminary Amendment for U.S. Appl. No. 15/766,736, dated Apr. 6, 2018, 10 pages.
Amendment in Response to Non-Final Office Action for U.S. Appl. No. 15/766,736, dated Jun. 11, 2019, 16 pages.
Notice of Allowance for U.S. Appl. No. 15/766,736, dated Jul. 16, 2019, 6 pages.
International Search Report for international patent application PCT/CN2016/087857, dated Apr. 13, 2017, 4 pages.
Written Opinion of the International Search Authority for international patent application PCT/CN2016/087857, dated Apr. 13, 2017, 6 pages.
Chapter I Demand with Response to International Search Report for international patent application PCT/CN2016/087857, dated Aug. 7, 2017, 4 pages.
Claims as Amended under Article (Appendix A) for international patent application PCT/CN2016/087857, dated Aug. 7, 2017, 17 pages.
Claims (Appendix B) for international patent application PCT/CN2016/087857, dated Aug. 7, 2017, 17 pages.
Communication pursuant to Rules 161(2) and 162 EPC for European patent application EP16853009.5, dated May 17, 2018, 3 pages.
Response to the Communication pursuant to Rules 161(2) and 162 EPC for European patent application EP16853009.5, dated Nov. 8, 2018, 23 pages.
Supplemental partial European Search Report for for European patent application EP16853009.5, dated Mar. 6, 2019, 3 pages.
Supplemental partial European Search Report for European patent application EP16853009.5, dated Apr. 26, 2019, 2019, 4 pages.
European Search Opinion for European patent application EP16853009.5, dated May 6, 2019, 10 pages.
Communication pursuant to Rules 70(2) and 70a(2) EPC for European patent application EP16853009.5, dated May 27, 2019, 1 page.
Voluntary Amendment for Australian patent application AU2016334141, dated May 16, 2018, 4 pages.
Accepted Claims for Australian patent application AU2016334141, dated Nov. 27, 2019, 8 pages.
Notice of Acceptance and Bibliographic Attachment for Australian patent application AU2016334141, dated Dec. 4, 2019, 3 pages.
Communication of European publication number and information on the application of Article 67(3) EPC for European patent application EP16853009.5, dated Jul. 18, 2018, 1 page.
Communication pursuant to Rule 164(1) EPC for European patent application EP16853009.5, dated Mar. 21, 2019, 17 page.
Extended European Search Report for European patent application EP16853009.5, dated May 8, 2019, 17 pages.
Claims marked-up for European patent application EP16853009.5, dated Dec. 2, 2019, 6 pages.
Claims for European patent application EP16853009.5, dated Dec. 2, 2019, 3 pages.
Response to the Communication pursuant to Rules 70(2) and 70a(2) EPC for European patent application EP16853009.5, dated Dec. 2, 2019, 5 pages.
Filing Request for Examination for Japanese patent application JP2018537705, dated Jun. 7, 2019, 1 page.
Filing Voluntary Amendment for Japanese patent application JP2018537705, dated Jun. 7, 2019, 13 pages.
Online Filing Notification for Japanese patent application JP2018537705, dated Jun. 7, 2019, 1 pages.

(56) References Cited

OTHER PUBLICATIONS

Amended Description for Mexican patent application MX/a/2018/004332, dated Dec. 19, 2018, 84 pages.
Amended Figures for Mexican patent application MX/a/2018/004332, dated Dec. 19, 2018, 58 pages.
Official receipt for Mexican patent application MX/a/2018/004332, dated Dec. 19, 2018, 2 pages.
Office Action for U.S. Appl. No. 15/882,924, dated Aug. 6, 2018, 10 pages.
Response to Restriction Requirement for U.S. Appl. No. 15/882,924, dated Feb. 5, 2019, 9 pages.
Non-Final Office Action for for U.S. Appl. No. 15/882,924, dated Feb. 19, 2019, 44 pages.
Response to Non-Final Office Action for U.S. Appl. No. 15/882,924, dated Aug. 18, 2019, 9 pages.
Notice of Allowance for U.S. Appl. No. 15/882,924, dated Sep. 19, 2019, 20 pages.
Response to Office Action for Australian patent application AU2014287016, dated Sep. 11, 2018, 48 pages.
Standard Patent Certificate for Australian patent application AU2014287016, dated Feb. 14, 2019, 1 pages.
Clean claims for Canadian patent application CA2917364, dated Nov. 29, 2019, 10 pages.
Response to Office Action for Canadian patent application CA2917364, dated Nov. 29, 2019, 45 pages.
Response to 1st Office Action for Chinese patent application CN201480049793.4, dated Apr. 18, 2018, 46 pages.
Decision of Rejection for Chinese patent application CN201480049793.4, dated Mar. 14, 2019, 6 pages with extra 10 pages of English language equivalent or summary.
Filing documents for for Chinese patent application CN201480049793.4, dated Jun. 11, 2019, 28 pages.
Filing receipt for for Chinese patent application CN201480049793.4, dated Jun. 11, 2019, 1 pages.
Communication pursuant to Article 94(3) EPC for European patent application EP14 748 351.5, dated May 28, 2019, 4 pages.
Response to communication pursuant to Article 94(3) EPC for European patent application EP14 748 351.5, dated Jun. 5, 2019, 4 pages in German and another.
Claims for European patent application EP14 748 351.5, dated Jay 28, 2019, 4 pages and another 4 pages in French.
Decision to grant a European patent pursuant to Article 97(1)EPC for European patent application EP14748351.5, dated Aug. 20, 2019, 2 pages.
Notification of Defects in Iseaeli Patent application IL1243420, dated May 15, 2018, 2 pages with extra 4 pages of English language equivalent or summary.
Office Action for Israeli patent application IL243420, dated Aug. 23, 2018, 16 pages.
Response to Office Action for Israeli patent application IL243420, dated Sep. 13, 2018, 2 pages.
Office Action for Israeli patent application IL243420, dated May 27, 2019, 3 pages with extra 2 pages of English language equivalent or summary.
Amended Specification for Israeli patent application IL243420, dated Oct. 28, 2019, 197 pages.
Response to Office Action for Israeli patent application IL243420, dated Oct. 28, 2019, 1 page.
Specification for Israeli patent application IL243420, dated Oct. 28, 2019, 197 pages.
Further Examination Report for Indian patent application IN201617004306, dated Apr. 30, 2019, 7 pages.
Notice of Grounds of Rejection for Japanese patent application JP2016-525833, dated Mar. 12, 2019, 4 pages with extra 6 pages of English language equivalent or summary.
Response to Office Action for Japanese patent application JP2016-525833, dated Jun. 7, 2019, 16 pages.
1st page of Letters Patent for Japanese patent application JP2016-525833, dated Aug. 2, 2019, 3 pages.
Examination Request for South Korean patent application KR1020167002970, dated Aug. 6, 2018, 2 pages.
Amendment for South Korean patent application KR1020167002970, dated Aug. 6, 2018, 33 pages.
Response to 2nd Office Action for Mexican patent application MX/a/2016/000261, dated Feb. 5, 2019, 14 pages.
3rd Office Action for Mexican patent application MX/a/2016/000261, dated Apr. 30, 2019, 6 pages with 4 pages of English language equivalent or summary.
Claims in Response to 3rd Office Action for Mexican patent application MX/a/2016/000261, dated Jun. 28, 2019, 7 pages.
Response to 3rd Office Action for Mexican patent application MX/a/2016/000261, dated Jun. 28, 2019, 2 pages.
1st Examination Report for New Zealand patent application NZ715687, dated Aug. 22, 2018, 6 pages.
Response to Examination Report for New Zealand patent application NZ715687, dated Feb. 18, 2019, 6 pages.
Further Examination Report for New Zealand patent application NZ715687, dated Mar. 18, 2019, 2 pages.
Response to 1st Examination Report for New Zealand patent application NZ715687, dated Mar. 29, 2019, 272 pages.
Bhagwat et al., "Kinase inhibitors for the treatment of inflammatory and autoimmune disorders," Purinergic Signalling (2009) 5:107-115 DOI 10.1007/s11302-008-9117-z.
Cortot et al., "Resistance to Irreversible EGF Receptor Tyrosine Kinase Inhibitors through a Multistep Mechanism Involving the IGF1R Pathway," Cancer Res; 73(2) Jan. 15, 2013, 834-43. doi: 10.1158/0008-5472.CAN-12-2066.
Communication under Rule 71(3) EPC for European patent application EP13 701 326.4, dated Jan. 21, 2020, 61 pages.
Notification of Reason for Refusal for South Korae patent application KR10-2015-7006007, dated Jan. 20, 2020, 5 pages with extra 6 pages of English language equivalent or summary.
Office Action for Canadian patent application CA2,861,010, dated Jan. 31, 2020, 3 pages.
Notice of Allowance for Canadian patent application CA2,881,275, dated Jun. 27, 2019, 1 pages.
Claims for Canadian patent application CA2,881,275, dated Dec. 24, 2019, 17 pages.
Notification of Reason for Refusal for Korean patent application KR10-2015-7006007, dated Jan. 20, 2020, 5 pages with extra 6 pages of English language equivalent or summery.
Amendment for Korean patent application KR10-2015-7006007, dated Jul. 14, 2020, 20 pages.
Argument in response for Korean patent application KR10-2015-7006007, dated Jul. 14, 2020, 29 pages.
Pending Claims for Korean patent application KR10-2015-7006007, dated Jan. 20, 2020, 5 pages in English.
Decision to Refuse a Patent for Korean patent application KR10-2015-7006007, dated Sep. 22, 2020, 5 pages with extra 5 pages of English language equivalent or summary.
Amendment for Korean patent application KR10-2015-7006007, dated Oct. 16, 2020, 8 pages.
Argument in response for Korean patent application KR10-2015-7006007, dated Oct. 16, 2020, 11 pages.
Pending Claims (marked-up) for Korean patent application KR10-2015-7006007, dated Oct. 16, 2020, 1 page.
Notice for Granting Patent for Korean patent application KR10-2015-7006007, dated Oct. 23, 2020, 5 pages.
The Original Certificate of Patent for Korean patent application KR10-2015-7006007, dated Nov. 16, 2020, 4 pages.
Hearing Notice for Indian patent application IN914DELNP2015, dated Oct. 16, 2019, 2 pages.
Hearing Notice for Indian patent application IN914DELNP2015, dated Jan. 10, 2020, 3 pages.
Hearing Notice for Indian patent application IN914DELNP2015, dated Feb. 11, 2020, 3 pages.
Post-Hearing Written Submissions for Indian patent application IN914DELNP2015, dated Dec. 9, 2020, 20 pages.
Letter Patent for Mexican patent application MX/a/2015/001715, dated Dec. 19, 2018, 256 pages.

(56) References Cited

OTHER PUBLICATIONS

International Search Report for international patent application PCT/US2013/050163 (WO2014025486), dated Feb. 13, 2014, 4 pages.
Written Opinion on the International Searching Authority for International Search Report for international patent application PCT/US2013/050163 (WO2014025486), dated Feb. 6, 2015, 4 pages.
International Preliminary Report on Patentability for international patent application PCT/US2013/050163 (WO2014025486), dated Feb. 10, 2015, 5 pages.
Notification of Reason for Refusal for South Koraen patent application KR10-2015-7006007, dated Jan. 20, 2020, 5 pages with extra 6 pages of English language equivalent or summary.
Wu et al., "Phase I/II Study of AC0010, Mutant-Selective EGFR Inhibitor, in Non-Small Cell Lung Cancer (NSCLC) Patents with EGFR T790M Mutation," Abstract, Journal of Thoracic Oncology, vol. 12, No. 15 Jan. 2017, p. S437, 2 pages.
Clinical Data Summary from Wu et al., "Phase I/II study of AC0010, mutant-selective EGFR inhibitor, in non-small cell lung cancer (NSCLC) patents with EGFR T790M mutation," J Thorac Oncol 2017; 12 Suppl 1:S437, 1 page.
Xu et al., "AC0010, an Irreversible EGFR Inhibitor Selectively Targeting Mutated EGFR and Overcoming T790M-Induced Resistance in Animal Models and Lung Cancer Patients," Mol Cancer Ther; 15(11), Nov. 2016, p. OF1-OF12 doi:10.1158/1535-7163. MCT-16-0281.
Abbot et al., "Synthesis of heteroaryl-fused pyrazoles as P38 kinase inhibitors," Heterocycles (2009) 78)11):2811-2826.
Andries et al., "TMC125, a novel next-generation nonnucleoside reverse transcriptase inhibitor active against nonnucleoside reverse transcriptase inhibitor-resistant human immunodeficiency virus type 1," Antimicrobial Agents and Chemotherapy (2004) 48(12):4680-4686.
Avizienyte et al.,"Comparison of the EGFR resistance mutation profiles generated by EGFR-targeted tyrosine kinase inhibitors and the impact of drug combinations," Biochem. J. (2008) 415:197-206.
Bagshawe, "Antibody-directed enzyme prodrug therapy: A review," Drug Dev. Res. (1995) 34(2):220-230.
Bean et al., "Acquired Resistance to Epidermal Growth Factor Receptor Kinase Inhibitors Associated with a Novel T854A Mutation in a Patient with EGFR-Mutant Lung Adenocarcinoma," Clin. Cancer Res. (2008) 14(22):7519-7525.
Berge et al., "Pharmaceutical Salts," J. Pharm. Sci. (1977) 66:1-19.
Bertolini et al., "A new rational hypothesis for the pharmacophore of the active metabolite of leflunomide, a potent immunosuppressive drug," J. Med. Chem. (1997) 40(13):2011-2016.
Blair et al., "Structure-guided development of affinity probes for tyrosine kinases using chemical agents," Nature Chemical Biology (2007) 3(4):229-238.
Bodor, "Novel approaches to the design of safer drugs: soft drugs and site-specific chemical delivery systems," Adv. Drug. Res. (1984) 13:255-331.
Carter et al., "Inhibition of drug-resistant mutants of ABL, KIT, and EGF receptor kinases," Proc. Natl. Acad. Sci. 2005, 102(31), 11011-11016.
Chamberlain et al., "Discovery of 4,6-bis-anilino-1H-pyrrolo[2,3-d]pyrimidines: Potent inhibitors of the IGF-1 R receptor tyrosine kinase," Bioorganic & Medicinal Chemistry Letters (2009) 19:469-473.
Chamberlain et al., "Optimization of a series of 4,6-bis-anilino-1H-pyrrolo[2,3-d]pyrimidine inhibitors of IGF-1R: Elimination of an acid-mediated decomposition pathway," Bioorganic & Medicinal Chemistry Letters (2009) 19:373-377.
Chamberlain et al., "Optimization of 4,6-bis-anilino-1H-pyrrolo[2,3-d]pyrimidine IGF-1R tyrosine kinase inhibitors towards JNK selectivity," Bioorganic & Medicinal Chemistry Letters (2009) 19:360-364.
CI-1033 (Canertinib, PD183805), Selleck Chemicals, retrieved from the Internet Aug. 15, 2013, 5 pages.

Frenkel et al., "Concentration and pH Dependent Aggregation of Hydrophobic Drug Molecules and Relevance to Oral Bioavailability," J. Med. Chem. (2005) 48:1974-1983.
Fry et al., "Specific, irreversible inactivation of the epidermal growth factor receptor and erbB2, by a new class of tyrosine kinase inhibitor," PNAS USA (1998) 95:12022-12027.
Ghosh et al., "2,4-bis(aryloxy)pyrimidines as antimicrobial agents," J. Med. Chem. (1968) 11(6):1237-1238.
International Search Report and Written Opinion for PCT/US2013/021338, dated Jun. 12, 2013, 25 pages.
International Search Report and Written Opinion for PCT Appln. No. PCT/US2013/050163, dated Sep. 4, 2013, 10 pages.
Kato et al., "Ketene and its derivatives. XVII. Reaction of diketene with imidates," Chemical and Pharmaceutical Bulletin (1967) 15(9):1334-1338.
Kumar et al., "Structure and Clinical Relevance of the Epidermal Growth Factor Receptor in Human Cancer," J. Clin. Oncol. 2008, 26(10), 1742-1751 (Apr. 2008).
Li et al., "BIBW2992, an irreversible EGFR/HER2 inhibitor highly effective in preclinical lung cancer models," Oncogene (2008) 27(34):4702-4711.
Ludovici et al., "Evolution of Anti-HIV Drug Candidates. Part 3: Diarylpyrimidine (DAPY) Analogues," Bioorganic & Medicinal Chemistry Letters (2001) 11:2235-2239.
Patani et al., "Bioisosterism: A Rational Approach in Drug Design," Chem. Rev. (1996) 96:3147-3176.
Petter et al., A novel small-molecule drug platform to silence cancer targets—Application to the pan-ErbB kinases, Poster from AACR 2009, Denver, CO-Abstr. 3746 (presented on Apr. 18-22, 2009).
Profft et al., "Uber in 2- und 6-Stellung substituierte 4-Methylpyrimidine," Archiv der Pharmazie (1962) 295(9):649-662.
Raymond et al., "Epidermal growth factor receptor tyrosine kinase as a target for anticancer therapy," Drugs (2000) 60(Suppl 1):15-23.
Rotili et al., "Diarylpyrimidine-Dihydrobenzyloxopyrimidine Hybrids: New, Wide-Spectrum Anti-HIV-1 Agents Active at (Sub)-Nanomolar Level," J. Med. Chem. (2011) 54(8):3091-3096.
Shan et al., "Prodrug strategies based on intramolecular cyclization reactions," J. Pharm. Sci. (1997) 86(7):765-767.
Slichenmeyer et al., "CI-1033, a pan-erbB tyrosine kinase inhibitor," Semin. Oncol. (2001) 28(5 Suppl. 16):80-85.
Smaill et al., "Tyrosine Kinase Inhibitors. 17. Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions," J. Med. Chem. (2000) 43:1380-1397.
U.S. Appl. No. 61/076,450, filed Jun. 27, 2008.
Zhou et al., "Discovery of selective irreversible inhibitors for EGFR-T790M," Bioorganic & Medicinal Chemistry Letters (2011) 21:638-643.
Zhou et al., "Novel mutant-selective EGFR kinase inhibitors against EGFR T790M," Nature (2009) 462(24/31):1070-1074.
Restriction Requirement for U.S. Appl. No. 13/917,514, dated Sep. 10, 2013, 8 pages.
Response to Restriction Requirement for U.S. Appl. No. 13/917,514, filed Oct. 9, 2013, 13 pages.
Notice of Allowance for U.S. Appl. No. 13/917,514, dated Nov. 14, 2013, 10 pages.
Restriction Requirement for U.S. Appl. No. 13/740,182, dated Apr. 11, 2014, 13 pages.
International Preliminary Report on Patentability for PCT/US2013/021338, dated Jul. 15, 2014, 15 pages.
Response to Office Action for U.S. Appl. No. 13/740,182, filed Aug. 15, 2014, 16 pages.
Han et al., "Novel Hybrids of (Phenylsulfonyl)furoxan and Anilinopyrimidine as Potent and Selective Epidermal Growth Factor Receptor Inhibitors for Intervention of Non-Small-Cell Lung Cancer," Journal of Medicinal Chemistry (2013) 56:4738-4748.
Invitation to Pay Additional Fees for PCT/US2014/046442, dated Oct. 7, 2014, 6 pages.
Office Action for U.S. Appl. No. 13/740,182, dated Dec. 12, 2014, 17 pages.

(56) References Cited

OTHER PUBLICATIONS

International Search Report and Written Opinion for PCT/US2014/046442, dated Jan. 5, 2015, 22 pages.
International Preliminary Report on Patentability for PCT/US2013/050163, dated Feb. 10, 2015, 5 pages.
Response to Communication pursuant to Rules 161(1) and 162 EPC for EP 13 701 326.4, filed Feb. 26, 2015, 11 pages.
Communication pursuant to Rules 161(1) and 162 EPC for EP 13745491.4, dated Mar. 17, 2015, 2 pages.
Mino R. Caira, "Crystalline Polymorphism of Organic Compounds," Topics in Current Chemistry, vol. 198 @ Springer Verlag Berlin Heidelberg 1998, p. 163-208.
IN, Office Action for Indian Patent application 201617004306, dated Apr. 30, 2019, 7 pages.
EP, Extended European Search Report for European patent application 168530095, dated May 8, 2019, 17 pages.
JP, RN 1348622-25-2 Registry,Database Registry [Online] Retrieved from STN, Dec. 4, 2011, Search Date: Jun. 27, 2018, (in Office Action of Mar. 12, 2019 for JP patent application 2016-525833), 1 page.
Filling receipt for Chinese patent application CN2014800497934, dated Jun. 11, 2019, 1 page.
Decision to Grant for European patent application EP14748351.5, dated Aug. 16, 2019, 2 pages.
Letters Patent for Japanese patent application JP2016-525833, dated Aug. 2, 2019, 3 pages.
Notice of Allowance for Mexican patent application MX/a/2016/000261, dated Jun. 8, 2019, 2 pages.
Certificate of Patent for Russian patent application RU2016104388, dated May 30, 2019, 1 page.
Amended Claims for Chinese patent application CN20171029308.7, dated Jul. 2, 2019, 3 pages (An English language equivalent or summary).
Claims for Chinese patent application CN20171029308.7, dated Jul. 2, 2019, 4 pages.
Response to Non-Final Office Action for U.S. Appl. No. 15/882,924, dated Aug. 16, 2019, 7 pages.
Terminal Disclaimer to Obviate a Double Patenting Rejection over a "Prior" Patent for U.S. Appl. No. 15/882,924, dated Aug. 16, 2019, 2 pages.
Claims for European patent application EP14748351, dated Jun. 5, 2019, 4 pages in French and another 4 pages in German.
Office Action for Israel patent application IL243420, dated May 27, 2019, 3 pages with extra 2 pages of an English anguage equivalent or summary.
Response to 3rd Office Action (Claims) for Mexican patent application MXa2016000261, dated Jun. 28, 2019, 7 pages.
Response to 3rd Office Action for Mexican patent application MXa2016000261, dated Jun. 28, 2019, 6 pages.
Amended Specification (1st page) for South African patent application ZA201904490, dated Jul. 9, 2019, 1 page.
Filing particulars for South African patent application ZA201904490, dated Jul. 9, 2019, 8 pages.
Response to Non-Final Office Action for U.S. Appl. No. 15/766,736, dated Jun. 11, 2019, 16 pages.
Chapter II Demand with Response to Written Opinion and Article 34 Amendments for international patent application PCT/CN2016/087857, dated Aug. 7, 2019, 4 pages.
Chapter II Demand request form for international patent application PCT/CN2016/087857, dated Aug. 7, 2019, 4 pages.
Claims Amendments under PCT Articles 34 (Appendix A) for international patent application PCT/CN2016/087857, dated Aug. 7, 2019, 17 pages.
Claims as Amended under PCT Articles 34 (Appendix B) for international patent application PCT/CN2016/087857, dated Aug. 7, 2019, 17 pages.
Communication pursuant to Rules 70(2) and 70a(2) EPC for European patent application EP16853009, dated May 27, 2019, 1 page.
Filing Request Examination for Japanese patent application JP2018537705, dated Jun. 7, 2019, 1 pages.

First Preliminary Amendment for U.S. Appl. No. 14/712,794, dated May 14, 2015, 6 pages.
Second Preliminary Amendment for U.S. Appl. No. 14/712,794, dated May 28, 2015, 17 pages.
Non-Final Rejection for U.S. Appl. No. 14/712,794, dated Mar. 8, 2016, 20 pages.
Declaration of Xiao Xu Pursuant to 37 C.F.R. 1.132 for U.S. Appl. No. 14/712,794, dated Jul. 8, 2016, 7 pages.
Amendment in Response to Non-Final Office Action under 37 C.F.R. 1.111 for U.S. Appl. No. 14/712,794, dated Jul. 8, 2016, 27 pages.
Final Rejection for U.S. Appl. No. 14/712,794, dated Jul. 22, 2016, 6 pages.
Request for Continued Examination for U.S. Appl. No. 14/712,794, dated Oct. 6, 2016, 4 pages.
Response Filed with Request for Continued Examination for U.S. Appl. No. 14/712,794, dated May 14, 2015, 6 pages.
Notice of Allowance for U.S. Appl. No. 14/712,794, dated Dec. 2, 2016, 7 pages.
Request for Continued Examination for U.S. Appl. No. 14/712,794, dated Apr. 13, 2017, 3 pages.
Notice of Allowance for U.S. Appl. No. 14/712,794, dated Apr. 24, 2017, 4 pages.
Applicant Initial Interview Summary for U.S. Appl. No. 14/712,794, dated Jun. 15, 2017, 2 pages.
Notice of Allowance for U.S. Appl. No. 14/712,794, dated Jun. 15, 2017, 6 pages.
Summary of Interview with Examiner for U.S. Appl. No. 14/712,794, dated Jul. 17, 2017, 2 pages.
Applicant Initial Interview Summary for U.S. Appl. No. 14/712,794, dated Jul. 21, 2017, 3 pages.
Summary of Interview with Examiner for U.S. Appl. No. 14/712,794, dated Aug. 16, 2017, 2 pages.
Non-Final Rejection for U.S. Appl. No. 15/435,722, dated Jul. 3, 2017, 48 pages.
Amendment in Response to Non-Fianl Office Action under 37 C.F.R. 1.111 for U.S. Appl. No. 15/435,722, dated Oct. 26, 2017, 33 pages.
Terminal Disclaimer for U.S. Appl. No. 15/435,722, dated Oct. 26, 2017, 2 pages.
Final Rejection for U.S. Appl. No. 15/435,722, dated Feb. 7, 2018, 15 pages.
Request for Continued Examination for U.S. Appl. No. 15/435,722, dated Jun. 7, 2018, 13 pages.
Terminal Disclaimer for U.S. Appl. No. 15/435,722, dated Jun. 7, 2018, 2 pages.
Notice of Allowance for U.S. Appl. No. 15/435,722, dated Jul. 18, 2018, 7 pages.
Request for Continued Examination for U.S. Appl. No. 15/435,722, dated Oct. 18, 2018, 3 pages.
Notice of Allowance for U.S. Appl. No. 15/435,722, dated Nov. 1, 2018, 7 pages.
Request for Continued Examination for U.S. Appl. No. 15/435,722, dated Feb. 1, 2019, 3 pages.
Non-Final Rejection for U.S. Appl. No. 15/435,722, dated Feb. 25, 2019, 5 pages.
Amendment in Response to Non-Final Office Action for U.S. Appl. No. 15/435,722, dated Aug. 23, 2019, 5 pages.
Terminal Disclaimer for U.S. Appl. No. 15/435,722, dated Aug. 23, 2019, 2 pages.
Notice of Allowance for U.S. Appl. No. 15/435,722, dated Oct. 29, 2019, 7 pages.
Notice of Non-Complaint Information Disclosure Statement for U.S. Appl. No. 15/435,722, dated Jan. 29, 2020, 1 page.
Notice of Non-Complaint Information Disclosure Statement for U.S. Appl. No. 15/435,722, dated Jan. 31, 2020, 1 page.
First Preliminary Amendment under 37 C.F.R. 1.115 for U.S. Appl. No. 14/420,341, dated Feb. 6, 2015, 19 pages.
Requirement for Restriction/Election for U.S. Appl. No. 14/420,341, dated Feb. 22, 2016, 8 pages.
Response to Restriction Requirement for U.S. Appl. No. 14/420,341, dated Apr. 22, 2016, 12 pages.

(56) References Cited

OTHER PUBLICATIONS

Non-Final Rejection for U.S. Appl. No. 14/420,341, dated Jun. 3, 2016, 7 pages.
Amendment in Response to Non-Final Office Action under 37 C.F.R. 1.111 for U.S. Appl. No. 14/420,341, dated Sep. 1, 2016, 12 pages.
Terminal Disclaimer for U.S. Appl. No. 14/420,341, dated Sep. 1, 2016, 3 pages.
Final Rejection for U.S. Appl. No. 14/420,341, dated Sep. 22, 2016, 8 pages.
Proposed Amendments to the Claims for U.S. Appl. No. 14/420,341, dated Oct. 5, 2016, 9 pages.
Applicant Initial Interview Summary for U.S. Appl. No. 14/420,341, dated Oct. 18, 2016, 2 pages.
Notice to File Corrected Application Papers for U.S. Appl. No. 14/420,341, dated Nov. 2, 2016, 3 pages.
Summary of Interview with Examiner for U.S. Appl. No. 14/420,341, dated Nov. 18, 2016, 2 pages.
Notice of Non-Complaint Information Disclosure Statement for U.S. Appl. No. 14/420,341, dated Jan. 27, 2017, 1 page.
U.S. Response to Notice for U.S. Appl. No. 13/740,182, dated Apr. 3, 2013, 4 pages.
U.S. Response to Non-Final Office Action for U.S. Appl. No. 13/740,182, dated Mar. 12, 2015, 21 pages.
U.S. Non-Final Rejection for U.S. Appl. No. 13/740,182, dated Oct. 18, 2017, 19 pages.
U.S. Response to Non-Final Office Action for U.S. Appl. No. 13/740,182, dated Jan. 18, 2018, 14 pages.
U.S. Final Office Action for U.S. Appl. No. 13/740,182, dated Jun. 1, 2018, 28 pages.
U.S. Response to Non-Final Office Action for U.S. Appl. No. 13/740,182, dated Nov. 30, 2018, 10 pages.
WO, Communication relating to the results of the partial international search for international patent application PCT/US2013/021338, dated Aug. 3, 2012, 9 pages.
WO, International search report and written opinion for international patent application PCT/US2013/021338, dated Jun. 12, 2013, 25 pages.
WO, Written opinion of the International searching authority for international patent application PCT/US2013/021338, dated Jul. 15, 2014, 15 pages.
CA, Notice of a requisition in accordance with subsection 30(2) of the patent rules for Canadian patent application 2,861,010, PCT/US2013/021338, dated May 25, 2018, 4 pages.
CN, 5th Office Action for Chinese patent application 201380013279.0, dated Dec. 5, 2018, 3 pages with extra 3 pages of English translation.
EP, Communication of European publication number and Information on the application of Article 67(3) EPC for European patent application 13701326.4, dated Oct. 22, 2014, 1 page.
EP, Communication pursuant to Article 94(3) EPC for European patent application 13701326.4, dated Oct. 27, 2017, 2 pages.
EP, Request to grant an extension of the term for European patent application 13701326.4, dated Nov. 20, 2018, 2 pages.
EP, Extension of time limit pursuant to Rule 132(2) EPC for European patent application 13701326.4, dated Nov. 26, 2018, 2 pages.
EP, Response to the Communication pursuant to Art. 94(3) EPC, dated Mar. 5, 2018, 7 pages.
CN, Response to 2nd Office Action for CN patent application 2014800497934, dated Nov. 2, 2018, 39 pages. (English).
CN, Response to 1st Examination Report for CN patent application 2017102293087, dated Jan. 7, 2019, 18 pages.
EP, Response to Office Action 94(3) EPC for European patent application 147483515, dated Sep. 28, 2018, 80 pages.
EP, Intent to Grant for European patent application 162023410, dated Oct. 25, 2018, 160 pages.
EP, Response to Office Action for European patent application 137013264, dated Jan. 21, 2019, 28 pages.
IN, Response to 1st Examination Report for Indian patent application IN914DELNP2014, dated Jan. 21, 2019, 7 pages.
MX, Response to 1st Office Action for Mexican patent application MXa2016000261, dated Oct. 25, 2018, 23 pages (English).
MX, 2nd Office Action for Mexican patent application MXa2016000261, dated Nov. 23, 2018, pages, including extra 6 pages of English translation.
MX, Response to Formality Office Action for Mexican patent application MXa2018004332, dated Dec. 19, 2018, 2 pages.
AU, Response to 2nd Examination Report for Australia patent application 2013207712, dated Jun. 1, 2017, 27 pages.
Response to Notification of Reexamination (translation) for CN 201380013279.0, dated Oct. 20, 2017, 12 pages.
Response to Notice of Grounds for Rejection for JP 2014-552357, dated Oct. 26, 2017, 14 pages.
Response to Examination Report for AU 2013300106, dated Oct. 26, 2017, 38 pages.
Examination Report for AU 2013300106, dated Oct. 27, 2017, 3 pages.
Response to Examination Report for AU 2013300106, dated Nov. 10, 2017, 34 pages.
Notice of Acceptance for AU 2013300106, dated Nov. 21, 2017, 3 pages.
Response to Official Action for RU 2015107831, filed Nov. 13, 2017, 28 pages.
Decision on grant of patent for invention for RU 2015107831, dated Nov. 24, 2017, 37 pages (Including English translation).
Notification of Defects in Patent Application IL No. 237023, dated Nov. 14, 2017, 2 pages (English translation).
Response to Communication pursuant to Article 94(3) EPC for EP 14 748 351.5, dated Nov. 14, 2017, 15 pages.
Communication pursuant to Article 94(3) EPC for EP 13 701 326.4, dated Oct. 27, 2017, 5 pages.
Examination Report No. 1 for AU 2014287016, dated Nov. 15, 2017, 6 pages.
International Search Report and Written Opinion for PCT/CN2016/087857, dated Sep. 29, 2016, 10 pages.
Non-final Rejection for U.S. Appl. No. 13/740,182, dated Oct. 18, 2017, 17 pages.
First Office Action for CN 2017121302212480, dated Dec. 18, 2017, 10 pages.
Communication pursuant to Article 94(3) EPC for EP 14 748 351.5, dated Dec. 20, 2017, 4 pages.
Notice of Grant for Patent for AU 20132077120, dated Dec. 18, 2017, 144 pages.
Voluntary amendment for CN 201380013279.0, dated Jan. 11, 2018, 14 pages.
Response to Non-Final Rejection for U.S. Appl. No. 13/740,182, dated Jan. 18, 2018, 14 pages.
Non-Final Office Action for U.S. Appl. No. 15/708,024, dated Feb. 9, 2018, 13 pages.
Final Rejection for U.S. Appl. No. 13/740,182, dated Jun. 1, 2018, 28 pages.
Office Action Response for PCT/US2013/021338, dated Apr. 23, 2018, part one 5 pages (in Japanese) and part two 2 pages (in English).
Response to the Communication pursuant for Article 94(3) EPC for European Patent Application 14 748 351.5, dated Apr. 27, 2018, 14 pages.
Bouaziz et al., "Regulatory B cells as inhibitors of immune responses and inflammation," Immunological Reviews, 2008, vol. 224:201-214.
Shripad S. Bhagwat, "Kinase inhibitors for the treatment of inflammatory and autoimmune disorders," Purinergic Signalling (2009) 5:107-115 DOI 10.1007/s11302-008-9117-z.
CN, Response to 5th Office Action for CN patent application 2013800132790, dated Feb. 13, 2019, 10 pages.
CN, Official filing receipt for CN patent application 2013800132790, dated Feb. 13, 2019, 1 page.
CN, Notification of Granting Patent Right for CN patent application 2013800132790, dated Mar. 5, 2019, 1 page with additional 2 pages of an English language equivalent or summary.

(56) References Cited

OTHER PUBLICATIONS

CN, Notification of Patent Registration for CN patent application 2013800132790, dated Mar. 5, 2019, 1 page with additional 1 page of an English language equivalent or summary.
U.S. Non-Final Office Action for U.S. Appl. No. 15/435,722, dated Feb. 25, 2019, 27 pages.
CA, Notice of Abandonment for CA patent application 2861010, dated Jan. 11, 2019, 1 page.
EP, Decision of Grant for European patent application EP16202341, dated Mar. 18, 2019, 2 pages.
IL, Patent Certificate for Israel patent application 237923, dated Dec. 21, 2018, 2 pages.
CN, Response to Office Action for CN patent application 2017102293087, dated Jan. 21, 2019, 17 pages.
HK, Filing Certificate for HK patent application 17112259, dated Apr. 15, 2019, 1 page.
U.S. Response to Restriction Requirement for U.S. Appl. No. 15/882,924, dated Feb. 5, 2019, 9 pages.
U.S. Non-Final Office Action for U.S. Appl. No. 15/882,924, dated Feb. 19, 2019, 44 pages.
AU, Standard Patent Certificate for Australia patent application 2014287016, dated Feb. 14, 2019, 1 page.
CN, Decision of Rejection for CN patent application 201480049793, dated Mar. 14, 2019, 6 pages with additional 10 pages of an English language equivalent or summary.
EP, Office Action for European patent application EP147483515, dated Feb. 8, 2019, 233 pages.
JP Notice of Grounds of Rejection for Japanese patent application JP 2016-525833, dated Mar. 12, 2019, 4 pages with additional 6 pages of an English language equivalent or summary.
MX, 2nd Office Action for Mexico patent application MX/a/2016/000261, dated Dec. 3, 2018, 6 pages.
MX, Response to 2nd Office Action for Mexico patent application MX/a/2016/000261, dated Feb. 5, 2019, 14 pages.
NZ, Response to Examination Report for New Zealand patent application 715687, dated Feb. 18, 2019, 6 pages.
NZ, Response to Office Action for New Zealand patent application 715687, dated Mar. 29, 2019, 272 pages.
NZ, Patent Notice of Acceptance for New Zealand patent application NZ715687, dated Apr. 3, 2019, 1 page.
NZ, Examination Report with Issues for New Zealand patent application NZ715687, dated Mar. 18, 2019, 2 pages.
U.S. First Preliminary Amendment for U.S. Appl. No. 15/766,736, dated Apr. 6, 2018, 10 pages.
U.S. Non-Final Office Action for U.S. Appl. No. 15/766,736, dated Dec. 12, 2018, 7 pages.
WO, Written Opinion for international patent application PCT/CN2016/087857, dated Sep. 18, 2016, 6 pages.
WO, International Search Report for international patent application PCT/CN2016/087857, dated Sep. 29, 2016, 4 pages.
WO, International Preliminary Report on Patentability for international patent application PCT/CN2016/087857, dated Jan. 23, 2018, 45 pages.
EP, Partial Search Repot for European patent application 168530095, dated Mar. 25, 2019, 17 pages.
EP, Communication pursuant to Rules 161(2) and 162 EPC for international patent application European phase application EP 168530095, dated May 17, 2018, 3 pages.
EP, Response to Office Action for international patent application European phase application EP 168530095, dated Nov. 8, 2018, 23 pages.
EP, Search Report for European patent application 168530095, dated Mar. 21, 2019, 15 pages.
MX, Formality Office Action for Mexico patent application MX/a/2018/004332, dated Aug. 15, 2018, 2 pages.
MX, Response to Formality Office Action for Mexico patent application MX/a/2018/004332, dated Dec. 19, 2018, 2 pages.
WO, Written Opinion for international patent application PCT/CN2017/079724, dated Jan. 2, 2018, 7 pages.
WO, International Search Report for international patent application PCT/CN2017/079724, dated Jan. 5, 2018, 6 pages.
WO, Notification Concerning Availability of the Publication of the International Application for international patent application PCT/CN2017/079724, dated Oct. 11, 2018, 1 page.
Response to Non-Final Office Action for U.S. Appl. No. 13/843,554, filed Dec. 19, 2014, 19 pages.
Notice of Allowance for U.S. Appl. No. 13/843,554, dated Jan. 13, 2015, 8 pages.
Restriction Requirement for U.S. Appl. No. 13/843,554, dated Jun. 30, 2014, 8 pages.
Response to Restriction Requirement for U.S. Appl. No. 13/843,554, filed Aug. 5, 2014, 3 pages.
Office Action for U.S. Appl. No. 13/843,554, dated Aug. 19, 2014, 7 pages.
Notice of Reasons for Rejection for JP 2015-526540, dated Apr. 25, 2017, 5 pages.
Response to Second Office Action for CN 201380001359.4, dated Nov. 25, 2016, 46 pages.
Response to Non-final Rejection for U.S. Appl. No. 13/740,182, dated Dec. 1, 2016, 17 pages.
Response to Communication pursuant to Art 94(3) for EP 13 701 326.4, dated Dec. 2, 2016, 25 pages.
Patent Examination Report No. 1 for AU 2013300106, dated Nov. 23, 2016, 3 pages.
Restriction Requirement for U.S. Appl. No. 14/420,341, dated Feb. 22, 2016, 8 pages.
Response to Restriction Requirement for U.S. Appl. No. 14/420,341, filed Apr. 22, 2016, 12 pages.
Response to the Second Office Action for CN 201380013279.0, filed Feb. 22, 2016, 26 pages.
Request for Continued Examination for U.S. Appl. No. 13/740,182, filed May 23, 2017, 21 pages.
Response to the communication pursuant to Article 94(3) EPC for EP 14 748 351.5, filed Jun. 13, 2017, 13 pages.
Examination Report No. 3 for AU 2013207712, dated Jun. 19, 2017, 11 pages.
Response to Official Action for RU 2015107831, filed Jun. 30, 2017, 6 pages.
Communication pursuant to Article 94(3) EPC for EP 14 748 351.5, dated Jul. 13, 2017, 6 pages.
Notice of Grounds for Rejection (translation) for JP 2014-552357, dated Aug. 1, 2017, 6 pages.
Office Action for JP 2017-005935, dated Aug. 3, 2017, 2 pages.
Official Action (translation) for RU 2015107831, dated Aug. 11, 2017, 3 pages.
Response to examination report for AU 2013207712, filed Aug. 15, 2017, 28 pages.
Notice of acceptance for AU 2013207712, dated Aug. 22, 2017, 3 pages.
Notice of Allowance for JP 2015-526540, dated Sep. 4, 2017, 3 pages.
Notification of Reexamination (translation) for CN 201380013279.0, dated Sep. 8, 2017, 1 page.
Response to Communication pursuant to Art 94(3) for EP 13 701 326.4, dated Jun. 29, 2017, 21 pages.
Notice of Allowance for U.S. Appl. No. 15/271,124, dated Jul. 10, 2017, 7 pages.
Request for Continued Examination for U.S. Appl. No. 15/271,124, dated Oct. 10, 2017, 3 pages.
Notice of Allowance for U.S. Appl. No. 15/271,124, dated Oct. 25, 2017, 7 pages.
Bhagwat, "Kinase inhibitors for the treatment of inflammatory and autoimmune disorders," Purinergic Signalling (2009) 5:107-115.
Bouaziz et al., "Regulatory B cells as inhibitors of immune responses and inflammation," Immunological Reviews (2008) 224:201-214.
Honigberg et al., "The bruton tyrosine kinase inhibitor PCI-32765 blocks B-cell activation and is efficacious in models of autoimmune disease and B-cell malignancy," PNAS (2010) 107(29):13075-13080.
Mellinghoff, "Why do cancer cells become "addicted" to oncogenic epidermal growth factor receptor," PLOS (2007) 4(10):e321.

(56) References Cited

OTHER PUBLICATIONS

Modjtahedi et al., "Epidermal growth factor receptor inhibitors in cancer treatment: advances, challenges and opportunities," Anticancer drugs (2009) 20(10):851-855 Abstract.
Response to Notification of Reexamination for CN 201380013279.0; dated Oct. 20, 2017, 12 pages.
International Search Report and Written Opinion for PCT/CN20161087857, dated Sep. 29, 2016, 10 pages.
Response to Non-Final Rejection for U.S. Appl. No. 15/435,722, dated Oct. 26, 2017, 33 pages.
First Office Action for CN 201480049793.4, dated Dec. 18, 2017, 19 pages.
Notice of Grant for Patent for AU 2013207712, dated Dec. 18, 2017, 144 pages.
NZ, First examination report for application 715687, dated Aug. 22, 2018, 6 pages.
RU, Search report for 2016104388, dated Apr. 25, 2018, 3 pages, including extra 4 pages of English translation.
RU Official action for application 2016104388/04(006925), dated Apr. 27, 2018, 13 pages, including extra 10 pages of English translation.
RU, Response to office action for application 2016104388, dated Jul. 27, 2018 4 pages.
RU Office action for application 2016104388/04(006925), dated Aug. 16, 2018, 6 pages including extra 4 pages of English translation.
Cortot, Alexis B.; et al., Resistance to Irreversible EGF Receptor Tyrosine Kinase Inhibitors through a Multistep Mechanism Involving the IGF1R Pathway. Cancer Research, 2013, 73(2), 834-843 (English).
Zhou et al. "Novel mutant-selective EGFR kinase inhibitors against EGFR T790M", Nature, vol. 462, No. 7276, Dec. 24, 2009, p. 1070-1074, XP005505337 4, ISSN: 0028-0836, DOI: 10.1 038/nature08622.
Han, et al. "Novel Hybrids of (Phenylsulfonyl) furoxan and Anilinopyrimidine as Potent and Selective Epidermal Growth Factor Receptor Inhibitors for Intervention of Non-Small-Cell Lung Cancer" Journal of Medicinal Chemistry, 2013, vol. 56, p. 4738-4748, dx.doi.org/jm400463q.
Zhou et al. "Discovery of selective irreversible inhibitors for EGFR-1790M" Bioorganic & Medicinal Chemostry Letters, (2011) p. 638-643.
MX, 2nd Office Action for Mexican patent application MXa2016000261, dated Nov. 23, 2018, pages, including extra 6 pages of English translation.
U.S. 1st Preliminary Amendment for U.S. Appl. No. 15/708,024, dated Sep. 24, 2017, 3 pages.
U.S. 2nd Preliminary Amendment for U.S. Appl. No. 15/708,024, dated Dec. 4, 2017, 7 pages.
U.S. Non-final Office Action for U.S. Appl. No. 15/708,024, dated Feb. 9, 2018, 13 pages.
U.S. Response to Non-final Office Action for U.S. Appl. No. 15/708,024, dated Aug. 9, 2018, 8 pages.
U.S. Notice of Allowance for U.S. Appl. No. 15/708,024, dated Oct. 3, 2018, 7 pages.
Office Action for U.S. Appl. No. 15/435,722, dated Jul. 3, 2017, 48 pages.
The First Office Action (translation) for CN 201380013279.0, dated Apr. 29, 2015, 3 pages.
Response to Written Opinion with Chapter II Demand and Article 34 Amendments for PCT/US2014/046442, filed May 11, 2015, 62 pages.
Restriction Requirement for U.S. Appl. No. 14/329,890, dated Jun. 3, 2015, 9 pages.
Final Office Action for U.S. Appl. No. 13/740,182, dated Jun. 30, 2015, 28 pages.
International Preliminary Report on Patentability for PCT/US14/46442, dated Jul. 28, 2015, 5 pages.
Response to Restriction Requirement for U.S. Appl. No. 14/329,890, filed Aug. 3, 2015, 12 pages.
Response to the First Office Action for CN 201380013279.0, filed Sep. 14, 2015, 30 pages.
Second Office Action for CN 201380013279.0, dated Dec. 3, 2015, 3 pages.
Response to Final Office Action for U.S. Appl. No. 13/740,182 dated Dec. 17, 2015, 22 pages.
Written Opinion and Search Report for SG 11201500872S dated Dec. 22, 2015, 9 pages.
Response to Communication pursuant to Article 94(3) EPC for EP 13701326.4, dated Feb. 22, 2016, 66 pages.
Office Action for U.S. Appl. No. 14/712,794 dated Mar. 8, 2016, 20 pages.
Response to Communication pursuant to Article 94(3) EPC for EP 13 745 491.4, filed May 16, 2016, 27 pages.
Response to Office Action for U.S. Appl. No. 14/712,794, filed Jul. 8, 2016, 34 pages.
Final Office Action for U.S. Appl. No. 14/712,794, dated Jul. 22, 2016, 6 pages.
Decision of Rejection for CN 201380013279.0, dated Dec. 2, 2016, 9 pages (1 page).
Non-final Rejection for U.S. Appl. No. 13/740,182, dated Sep. 1, 2016, 20 pages.
Notice of grounds of rejection for JP 2014-552357, dated Nov. 4, 2016, 13 pages.
Notice of Reason for Rejection for JP 2015-526540, dated Oct. 17, 2016, 10 pages.
Request for Continued Examination for U.S. Appl. No. 13/740,182, dated Dec. 17, 2015, 14 pages.
Request for Continued Examination for U.S. Appl. No. 14/712,794, filed Oct. 6, 2016, 27 pages.
Response to Second Office Action for CN 201380001359.4, dated Nov. 25, 2016.
Supplemental response for U.S. Appl. No. 13/740,182, dated Feb. 9, 2016, 16 pages.
Decision to Grant for EP 13745491.4, dated Nov. 10, 2016, 2 pages.
Response for Non-final Rejection for U.S. Appl. No. 15/271,124, dated Apr. 17, 2017, 15 pages.
Response to JPOA 2014552357, dated Oct. 26, 2017, 7 pages.
Response to Non-final Rejection for U.S. Appl. No. 15/271,124, dated Oct. 26, 2017, 41 pages.
Response to Non-Final Office Action under 37 C.F.R. 1.111 for U.S. Appl. No. 15/435,722, filed Oct. 26, 2017, 33 pages.
U.S. First Preliminary Amendment Under 37 C.F.R. 1.115 for U.S. Appl. No. 15/766,736 (PCT/CN2016/087857), dated Apr. 6, 2018, 10 pages.
U.S. Notice of the Office communication for U.S. Appl. No. 15/882,924, dated Aug. 6, 2018, 10 pages.
U.S. Office communication for U.S. Appl. No. 14/420,341, dated Nov. 2, 2016, 3 pages.
Australian, Examination report No. 1 for standard patent application 2014287016, dated Nov. 15, 2017, 6 pages.
Australian, Notice of grant for patent for 2013300106, dated Mar. 15, 2018, 1 pages.
Australian, Response to office action for application 2016334141, dated May 16, 2018, 4 pages.
Australian, Response to APO for application 2014287016, dated Sep. 11, 2018, 48 pages.
CA, Notice of requisition for PCT/US 2013021338, dated May 25, 2018, 4 pages.
CN, Response to 1st office action for 201480049793.4, dated May 2, 2018, 50 pages.
CN, 4th office action for application 201380013279.0, dated Jun. 1, 2018, 3 pages, including extra 4 pages English translation.
CN, Response to 4th office action for application 2013800132790, dated Jul. 23, 2018, 10 pages.
CN, Search report for application 201710229308.7, dated Aug. 28, 2018, 2 pages, including extra 2 pages English translation.
CN, 2nd office action for 201480049793.4, dated Aug. 30, 2018, 5 pages, including extra 3 pages English translation.
CN, 1st office action for application 201710229308.7, dated Sep. 5, 2018, 5 pages ( extra 6 pages for English translation).
EP, Communication pursuant to Article 94(3) ERC for application 14 748 351.5-1462, dated Dec. 20, 2017, 4 pages.

(56) References Cited

OTHER PUBLICATIONS

EP, Communication pursuant to Article 94(3) EPC for application 16202341.0-1116, dated May 8, 2018, 5 Pages.
EP, Communication pursuant to Rules 161(2) and 162 EPC for application 16853009.5-1109, dated May 23, 2018, 3 pages.
EP, Response to Notice of Omitted Item(s) for U.S. Appl. No. 15/882,924, dated May 24, 2018, 4 pages.
EP, Communication pursuant to Artide 94(3) EPC for application 14748351.5-1116, dated May 24, 2018, 4 pages.
EP, Communication pursuant to Article 94(3) EPC for application 13701326.4-1114, dated Jul. 13, 2018, 8 pages.
EP, Communication of European publication number and information on the application of Article 67(3) EPC for application 16853009.5-1109 / 3359159 PCT/CN2016087857, dated Jul. 18, 2018, 1 page.
EP, Response to the Communication pursuant to Art. 94(3) EPC for application 16 202 341.0, dated Sep. 10, 2018, 34 pages.
India, First examination report for application 914/DELNP/2015 (PCT/US2013050163), dated Jun. 26, 2018, 6 pages.
Israel, Response to Notification of defects in patent application 243420, dated May 15, 2018, 2 pages with 4 page s of English translation.
Israel, Response to office action for application 243420, dated Aug. 23, 2018, 16 pages.
Israel, Response to office action for application 243420, dated Sep. 13, 2018, 2 pages (translation).
JP, Notice of the reasons of rejection for application 2014-552357, dated Feb. 6, 2018, 2 pages, including extra 2 pages English translation.
JP, Written opinion for application 2014-552357, dated Apr. 23, 2018, 2 pages.
JP, Amendment for application 2014-552357, dated Apr. 23, 2018, 5 pages.
JP, Patent granted for application 2014-552357, dated May 15, 2018, 3 pages.
JP, Notice of grounds of rejection for application 2016-525833, dated Jul. 31, 2018, 6 pages, including extra 8 pages of English translation.
Korea, Written request for examination for 10-2016-7002970, dated Aug. 6 2018, 2 pages.
Korea, Amendment for 10-2016-7002970, dated Aug. 6, 2018, 33 pages.
Mexico, 1st requisition for application MXA2015001715, dated Aug. 15, 2018, 3 pages.
Mexico, Response to 1st requisition for application MX/a/2016/000261, dated Sep. 3, 2018, 7 pages.
Zhou et al. "Novel mutant-selective EGFR kinase inhibitors against EGFR T790M", Nature, val. 462, No. 7276, Dec. 24, 2009, p. 1070-1074, XP005505337 4, ISSN: 0028-0836, DOI: 10.1 038/nature08622.
U.S. Patent Issue Notification for U.S. Appl. No. 13/843,554, dated May 19, 2015, 1 page.
U.S. First Preliminary amendment for U.S. Appl. No. 14/712,794, dated May 14, 2015, 6 pages.
U.S. Second Preliminary amendment for U.S. Appl. No. 14/712,794, dated May 28, 2015, 17 pages.
U.S. Response to non-final office action for U.S. Appl. No. 14/712,794, dated Jul. 8, 2016, 27 pages.
U.S. Response to final office action for U.S. Appl. No. 14/712,794, dated Oct. 6, 2016, 24 pages.
U.S. Final Office action for U.S. Appl. No. 15/435,722, dated Feb. 7, 2018, 15 pages.
U.S. Response to Final office action for U.S. Appl. No. 15/435,722, dated Jun. 7, 2018, 10 pages.
U.S. Notice of allowance for U.S. Appl. No. 15/435,722, dated Nov. 1, 2018, 7 pages.
U.S. Response to Final Office action for U.S. Appl. No. 14/420,341, dated Oct. 5, 2016, 9 pages.
CN, Response to First Office action for CN patent application 201380001359.4, dated May 19, 2016, 44 pages (English).
CN, Response to Third Office action for CN patent application 201380001359.4, dated Apr. 6, 2017, 11 pages (English).
CN, Notice of patent issued for CN patent application 201380001359.4, patent No. ZL201380001359.4, dated Oct. 24, 2017, 4 pages.
CN, Allowed clain for CN patent application 201380001359.4, dated Aug. 7, 2018, 3 pages (English).
BR, Request for Examination for Brazil patent application 1120150027091, dated Apr. 14, 2016, 1 page.
CA, Request for Examination for Canadian patent application 2881275 (PCT/US2013/050163), dated Jul. 11, 2018, 1 page.
IN, Response to First Examination report or Indian patent application 914/DELNP/2015, dated Jul. 16, 2018, 22 pages.
IL, Response to Office action for Isreal patent application 237023, dated Apr. 27, 2017, 46 pages.
IL, Second Office action for Isreal patent application 237023, dated Nov. 14, 2017, 2 pages.
IL, Response to Second Office action for Isreal patent application 237023, dated Nov. 29, 2017, 2 pages.
IL, Official notification Prior to acceptance for Isreal patent application 237023, dated May 31, 2018, 2 pages.
JP, First Examination repoit for Japan patent application 2015-526540, dated Oct. 17, 2016, 6 pages (English).
JP, First Examination repoit ffor Japan patent application 2015-526540, dated Oct. 17, 2016, 6 pages.
JP, Response to First Office action (claims) for Japan patent application 2015-526540, dated Jan. 17, 2017, 17 pages (English).
JP, Response to First Office action (instruction) for Japan patent application 2015-526540, dated Jan. 17, 2017, 47 pages (English).
JP, Second Examination report for Japan patent application 2015-526540, dated Apr. 25, 2017, 5 pages (English).
JP, Response to Second Examination report for Japan patent application 2015-526540, dated Jun. 26, 2017, 42 pages (English).
JP, Notice of allowance for JP patent application 2015-526540, dated Aug. 31, 2017, 3 pages.
KR, Written Request for Examination for KR patent application 10-2015-7006007, dated Apr. 9, 2018, 2 pages.
NZ, First Examination report for New Zealand patent application 629807, dated Aug. 26, 2015, 2 pages.
NZ, Further Examination report for New Zealand patent application 629807, dated Dec. 13, 2016, 2 pages.
NZ, Notice of Acceptance of further examination report for New Zealand patent application 629807, dated Apr. 4, 2017, 1 page.
RU, Response to Office action for RU patent application 2015107831/04, dated Jun. 30, 2017, 6 pages.
RU, Response to Office action for RU patent application 2015107831/04, dated Jun. 30, 2017, 3 pages (English).
ZA, Accepted claims for South African patent application 2015/00762, dated Oct. 14, 2016, 14 page.
MX, Notice of allowance for MX patent application MX/a/2015/001715, dated Oct. 30, 2018, 1 page.
EP, Extended search report for European patent application 16202341.0, dated Feb. 22, 2017, 7 pages.
CN, First Examination report for CN patent application 2017102293087, dated Sep. 30, 2018, 6 pages (English).
CN, First Examination report for CN patent application 2017102293087, dated Sep. 30, 2018, 6 pages.
CN, Office Action for CN patent application 2013800013594.4, dated Jan. 25, 2017, 15 pages (English).
IL, Office Action for Israel patent application 237023, dated Jan. 4, 2017, 2 pages (English).
NZ, Response to Examination Report for New Zealand patent application 629807, dated Mar. 8, 2017, 71 pages.
SG, Office Action,Search Report and Written Opinion for Singapore patent application 11201500872S, dated Dec. 22, 2015, 9 pages.
WO, Notification, International Search Report and Written Opinion for international patent application PCT/US2013/050163, dated Sep. 4, 2013, 10 pages.
Office Action for U.S. Appl. No. 13/740,182, dated Apr. 11, 2014, 13 pages.
Interview Summary for U.S. Appl. No. 13/740,182, dated Jul. 2, 2014, 2 pages.
Response to the Restriction Requirement for U.S. Appl. No. 13/740,182, dated Aug. 15, 2014, 16 pages.

(56) References Cited

OTHER PUBLICATIONS

Non-Final Rejection for U.S. Appl. No. 13/740,182, dated Dec. 12, 2014, 17 pages.
Response to Office Action for U.S. Appl. No. 13/740,182, dated Mar. 12, 2015, 21 pages.
Final Rejection for U.S. Appl. No. 13/740,182, dated Jun. 30, 2015, 28 pages.
Request for Continued Examination, Amendment, Claims, and Arguments for U.S. Appl. No. 13/740,182, dated Dec. 17, 2015, 22 pages.
Supplemental Response or Supplemental Amendment, Specification, Claims, Arguments in Response to Office Action for U.S. Appl. No. 13/740,182, dated Feb. 9, 2016, 16 pages.
Response to Office Action for U.S. Appl. No. 13/740,182, dated Dec. 1, 2016, 17 pages.
Office Action for U.S. Appl. No. 13/740,182, dated Mar. 23, 2017, 26 pages.
Request for Continued Examination for U.S. Appl. No. 13/740,182, dated May 23, 2017, 3 pages.
Amendment with Request for Continued Examination for U.S. Appl. No. 13/740,182, dated May 23, 2017, 18 pages.
Terminal Disclaimer for U.S. Appl. No. 13/740,182, dated May 23, 2017, 2 pages.
Response to Office Action for U.S. Appl. No. 13/740,182, dated Jan. 18, 2018, 14 pages.
Final Rejection for U.S. Appl. No. 13/740,182, dated Jun. 1, 2018, 24 pages.
Request for Continued Examination Transmittal for U.S. Appl. No. 13/740,182, dated Nov. 30, 2018, 3 pages.
Amendment Accompanying Request for Continued Examination for U.S. Appl. No. 13/740,182, dated Nov. 30, 2018, 10 pages.
Non-Final Rejection for U.S. Appl. No. 13/740,182, dated Sep. 13, 2019, 16 pages.
Response to Office Action for U.S. Appl. No. 13/740,182, dated Mar. 12, 2020, 8 pages.
Notice of Allowance for U.S. Appl. No. 13/740,182, dated May 29, 2020, 10 pages.
Request for Corrected Filing Receipt for U.S. Appl. No. 13/740,182, dated Aug. 21, 2020, 38 pages.
Response to Request for Corrected Filing Receipt for U.S. Appl. No. 13/740,182, dated Aug. 26, 2020, 1 page.
Notice Regarding Power of Attorney for U.S. Appl. No. 13/740,182, dated Aug. 26, 2018, a page.
Amendment after Notice of Allowance for U.S. Appl. No. 13/740,182, dated Aug. 27, 2020, 2 pages.
Notice of Acceptance of Request under 37 CFR 1.48(a) for U.S. Appl. No. 13/740,182, dated Aug. 27, 2020, 5 pages.
Request for Restriction/Election for U.S. Appl. No. 13/843,554, dated Jun. 30, 2014, 8 pages.
Response to Request for Restriction/Election for U.S. Appl. No. 13/843,554, dated Aug. 5, 2014, 3 pages.
Non-Final Rejection for U.S. Appl. No. 13/843,554, dated Aug. 19, 2014, 8 pages.
Response to Non-Final Office Action under 37 C.F.R. 1.111 for U.S. Appl. No. 13/843,554, dated Dec. 19, 2014, 20 pages.
First Preliminary Amendment under 37 C.F.R. 1.115 for U.S. Appl. No. 13/917,514, dated Jul. 1, 2013, 5 pages.
Requirement for Restriction/Election for U.S. Appl. No. 13/917,514, dated Sep. 10, 2013, 8 pages.
Response to Restriction Requirement for U.S. Appl. No. 13/917,514, dated Oct. 9, 2013, 6 pages.
Second Preliminary Amendment for U.S. Appl. No. 15/708,024, dated Dec. 4, 2017, 7 pages.
Non-Final Rejection for U.S. Appl. No. 15/708,024, dated Feb. 9, 2018, 14 pages.
Amendment in Response to Non-Final Office Action under 37 C.F.R. 1.111 for U.S. Appl. No. 15/708,024, dated Aug. 9, 2018, 8 pages.
Terminal Disclaimer for U.S. Appl. No. 15/708,024, dated Jul. 1, 2013, 5 pages.
Notice of Allowance for U.S. Appl. No. 15/708,024, dated Oct. 3, 2018, 7 pages.
Request for Continued Examination for U.S. Appl. No. 15/708,024, dated Jan. 3, 2019, 3 pages.
Notice of Allowance for U.S. Appl. No. 15/708,024, dated Feb. 27, 2019, 13 pages.
Request for Continued Examination for U.S. Appl. No. 15/708,024, dated May 7, 2019, 3 pages.
Notice of Allowance for U.S. Appl. No. 15/708,024, dated Jun. 3, 2019, 10 pages.
Notice of Allowance for U.S. Appl. No. 15/708,024, dated Sep. 5, 2019, 5 pages.
Abbot et al., "Synthesis of heteroarly-fused pyrazoles as P38 kinase inhibitors," Heterocycles (2009) 78)11):2811-2826.
Andries et al., "TMC125, a novel next-generation nonnucleoside reverse transcriptase infiibitor active against nonnucleoside reverse transcriptase inhibitor-resistant human immunodeficiency virus type 1," Antimicrobial Agents and Chemotherapy (2004) 48(12):4680-4686.
Ghosh et al., "2,4-bis(aryloxy)pyrimidines as antimierobial agents," J. Med. Chem. (1968) 11(6):1237-1238.
Bean et al., "Acquired Resistance to Epidermal Growth Factor Receptor Kinase Inhibitors Associated with a Novel T854A Mutation in a Patient with EGFR-Mutant Lung denocarcinoma," Clin. Cancer Res. (2008) 14(22):7519-7525.
Chamberlain et al., "Discovery of 4,6-bis-anilino-1 H-pyrrolo[2,3-d]pyrimidines: Potent inhibitors of the IGF-1 R receptor tyrosine kinase," Bicorganic & Medicinal Chemistry Letters (2009) 19:469-473.
Chamberlain et al., "Optimization of 4,6-bis-anilino-1H-pyrrolo[2,3-d]pyrimidine IGF-1 R tyrosine kinase inhibitors. towards JNI< selectivity," Bioorganic & Medicinal Chemistry Letters (2009) 19:360-364.
U.S. Patent Issue Notification for U.S. Appl. No. 13/843,554, issued date May 19, 2015, 1 page.
JP, First Examination report for Japan patent application 2015-526540, dated Oct. 17, 2016, 6 pages (English).
JP, First Examination report ffor Japan patent application 2015-526540, dated Oct. 17, 2016, 6 pages.
U.S. Response to final Office Action for U.S. Appl. No. 13/740,182, dated Dec. 17, 2015, 19 pages.
U.S. First preliminary amendment for U.S. Appl. No. 15/271,124, dated Sep. 20, 2016, 12 pages.
U.S. Non Office Action U.S. Appl. No. 15/271,124, dated Feb. 14, 2018, 4 pages.
U.S. Non Final Office Action for U.S. Appl. No. 15/766,736, dated Dec. 12, 2018, 6 pages.
AU, Notice of acceptance for patent application for Australian patent application 2014287016, dated Oct. 8, 2018, 3 pages.
CN, Response to Office Action for CN patent application 2013800132790, dated Mar. 15, 2017, 128 pages.
CN, Response to Second Office Action for CN patent application 2013800132790, dated Feb. 22, 2016, 26 pages.
CN, First Office Action for CN patent application 201480049793.4, dated Dec. 18, 2017, 7 pages.
CN, First Office Action for CN patent application 201480049793.4, dated Dec. 18, 2017, 3 pages (English).
CN, Response to First Office Action for CN patent application 201480049793.4, dated May 2, 2018, 46 pages.
CN, Second Office Action for CN patent application 201480049793.4, dated Aug. 30, 2018, 3 pages (English).
CN, Response to Second Office Action for CN patent application 201480049793.4, dated Nov. 13, 2018, 5 pages.
EP, Office Action for European patent application 137013264, dated May 24, 2016, 5 pages.
EP, Office Action of Communication pursuant to Article 94(3) EPC for for European patent application 137013264, dated Oct. 27, 2017, 5 pages.
EP, Office Action of Communication pursuant to Rules 161(1) and 162 EPC for European patent application 147483515, dated Mar. 2, 2016, 2 pages.

(56) References Cited

OTHER PUBLICATIONS

EP, Office Action of Communication pursuant to Article 94(3) EPC for European patent application 147483515, dated Apr. 3, 2017, 3 pages.
EP, Response to Office Action for European patent application 147483515, dated Jun. 13, 2017, 13 pages.
EP, Office Action for European patent application 147483515, dated Jul. 13, 2017, 6 pages.
EP, Response to Office Action for European patent application 147483515, dated Nov. 14, 2017, 15 pages.
EP Response to Office Action of Communication pursuant to Article 94(3) EPC for European patent application 147483515, dated Apr. 27, 2018, 14 pages.
EP, Office Action for European patent application 168530095, dated May 17, 2018, 3 pages.
EP, Response to Office Action for European patent application 168530095, dated Nov. 8, 2018, 23 pages.
JP, Office Action for JP patent application 2014552357, dated Aug. 1, 2017, 6 pages.
JP, Office Action for JP patent application 2016525833, dated Aug. 9, 2018, 8 pages (English).
JP, Office Action for JP patent application 2016525833, dated Aug. 9, 2018, 6 pages.
JP, Response to Office Action for JP patent application 2016525833, dated Oct. 1, 2018, 27 pages (English).
JP, Response to Office Action for JP patent application 2016525833, dated Oct. 25, 2018, 12 pages.
MX, First Office Action for Mexico patent application MX/a/2016000261, dated Oct. 3, 2018, 6 pages (English).
MX, First Office Action for Mexico patent application MX/a/2016000261, dated Oct. 3, 2018, 7 pages.
MX, Response to First Office Action for Mexico patent application MX/a/2016000261, dated Nov. 13, 2018, 18 pages.
MX, Office Action for Mexico patent application 2018004332, dated Aug. 15, 2018, 2 pages.
RU, Office Action for Russia patent application 2016104388, dated Jun. 2, 2016, 2 pages (English).
RU, Office Action for Russia patent application 2016104388, dated Jun. 2, 2016, 2 pages.
RU, Response to Office Action for Russia patent application 2016104388, dated Sep. 28, 2016, 44 pages (English).
RU, Response to Office Action for Russia patent application 2016104388, dated Sep. 28, 2016, 33 pages.
RU, Response to Office Action for Russia patent application 2016104388, dated Dec. 10, 2018, 12 pages.
RU, Response to Office Action (Amended claims) for Russia patent application 2016104388, dated Dec. 10, 2018, 7 pages (English).
RU, Decision to Grant for Russia patent application 2016104388, dated Dec. 17, 2018, 12 pages.
RU, Decision to Grant for Russia patent application 2016104388, dated Dec. 17, 2018, 12 pages. (English).
SG, Notice of Eligibility for Grant for Singapore patent application 11201600062R, dated Jun. 11, 2018, 5 pages.
WO, International Search Report for international patent application WO2018184206, PCT/CN2017/079724, dated Jan. 5, 2018, 4 pages.
WO, Written Opinion for international patent application WO2018184206, PCT/CN2017/079724, dated Jan. 5, 2018, 7 pages.
WO, International Publication for international patent application WO2018184206, PCT/CN2017/079724, dated Oct. 11, 2018, 182 pages.
WO, Written Opinion for international patent application WO2017059702, dated Sep. 18, 2016, 6 pages.
WO, International Search Report for international patent application WO2017059702, dated Sep. 29, 2016, 4 pages.
WO, International Publication for international patent application WO2017059702, dated Apr. 13, 2017, 148 pages.
WO, International preliminary report on patentability for international patent application WO2017059702, dated Jan. 23, 2018, 45 pages.
First Examination Report for Indian patent application IN201617004306, dated Apr. 30, 2019, 7 pages.
Office Action for Japanese patent application JP2016-525833, dated Mar. 12, 2019, 4 pages with extra 6 pages of an English language equivalent or summary.
Amendment for Korean patent application KR10-2016-7002970, dated Aug. 8, 2018, 33 pages.
Written Request for Examination for Korean patent application KR10-2016-7002970, dated Aug. 8, 2018, 2 pages.
Response to Second Office Action for Mexican patent application MX/a/2016/000261, dated Feb. 5, 2019, 14 pages.
Third Office Action for Mexican patent application MX/a/2016/000261, dated Apr. 30, 2019, 6 pages with extra 4 pages of an English language equivalent or summary.
Response to Third Office Action (Claims) for Mexican patent application MX/a/2016/000261, dated Jun. 28, 2019, 7 pages.
Respnse to Third Office Action for Mexican patent application MX/a/2016/000261, dated Jun. 28, 2019, 2 pages.
Response to Examination Report for New Zealand patent application NZ715687, dated Mar. 29, 2019, 272 pages.
Notice of Acceptance for New Zealand patent application NZ715687, dated Apr. 3, 2019, 1 pages.
First Preliminary Amendment for U.S. Appl. No. 15/766,736, National State of PCT/CN2016/087857, dated Apr. 6, 2018, 10 pages.
Response to Non-Final Office Action for U.S. Appl. No. 15/766,736, National State of PCT/CN2016/087857, dated Jun. 11, 2019, 16 pages.
Notice of Allowance for U.S. Appl. No. 15/766,736, National State of PCT/CN2016/087857, dated Jul. 16, 2019, 6 pages.
CN, International Preliminary Report for International Patent Application PCT/CN2016/087857, dated Mar. 6, 2018, 15 pages.
CN, International Search Report for International Patent Application PCT/CN2016/087857, dated Apr. 13, 2017, 4 pages.
CN, Written Opinion of International Search Report of the International Searching Authority for International Patent Application PCT/CN2016/087857, dated Apr. 13, 2017, 6 pages.
CN, Chapter II Demand with Response to Written Opinion and Article 34 Amendments for International patent application PCT/CN2016/087857, dated Aug. 7, 2017, 4 pages.
CN, Chapter I request form for International patent application PCT/CN2016/087857, Aug. 7, 2017, 4 pages.
CN, Claim Amendments under PCT Article 34 (Appendix A) for International patent application PCT/CN2016/087857, Aug. 7, 2017, 17 pages.
CN, Claim Amendments under PCT Article 34 (Clean Version) (Appendix B) for International patent application PCT/CN2016/087857, Aug. 7, 2017, 17 pages.
Voluntary Amendments and Response to Office Action for Australian patent application AU2016334141, dated May 16, 2018, 4 pages.
Communication pursuant to Rules 70(2) and 70a(2) EPC for European patent application 16853009.5, dated May 27, 2019, 1 page.
CN, Written Opinion of the International Searching Authority for International patent application PCT/CN2017/079724, dated Jan. 2, 2018, 7 pages.
CN, International Search Report for International patent application PCT/CN2017/079724, dated Jan. 5, 2018, 6 pages.
Second Office Action for CN 201380013279.0, dated Dec. 3, 2015, 10 pages.
Response to Final Office Action for U.S. Appl. No. 13/740,182 dated Dec. 17, 2015, 19 pages.
Notice of Allowance for U.S. Appl. No. 14/712,794, dated Dec. 13, 2016, 7 pages.
Bean et al., "Acquired Resistance to Epidermal Growth Factor Receptor Kinase Inhibitors Associated with a Novel T854A Mutation in a Patient with EGFR-Mutant Luna Adenocarcinoma," Clin. Cancer Res. (2008) 14(22):7519-7525.
Smaill et al., "Tyrosine Kinase Inhibitors. 17. Irreversible Inhibitors of the Epidermal Growth Factor Receptor: 4-(Phenylamino)quinazoline- and 4-(Phenylamino)pyrido[3,2-d]pyrmidine-6-acrylamindes Bearing Additional Solubizing Functions," J. Med. Chem. (2000) 43:1380-1397.

(56) References Cited

OTHER PUBLICATIONS

Final Office Action for U.S. Appl. 14/329,890, dated Mar. 3, 2016, 5 pages.
Response to Office Action for U.S. Appl. No. 14/712,794, filed Jul. 8, 2016, 27 pages.

* cited by examiner

EGFR MODULATORS AND USES THEREOF

CROSS-REFERENCE TO RELATED APPLICATIONS

This application, is a continuation application of and claims priority to Non Provisional U.S. application Ser. No. 15/708,024 filed Sep. 18, 2017 and titled Novel EGFR Modulators and Uses Thereof, which is a continuation of Ser. No. 14/712,794, filed May 14, 2015, now U.S. Pat. No. 9,763,949, which is a divisional of Ser. No. 13/843,554, filed Mar. 15, 2013, now U.S. Pat. No. 9,034,885, which claims priority to U.S. Provisional Application 61/680,231, filed Aug. 6, 2012, the contents of each of which is incorporated by reference in its entirety. In certain aspects, this application relates to U.S. Provisional Application No. 61/586,718, filed Jan. 13, 2012, the disclosure of which is hereby incorporated by reference in its entirety.

TECHNICAL FIELD

The field of this invention is pharmaceutical compounds, compositions and methods, especially as they are related to compositions and methods for the treatment of proliferation disorders and related diseases related to the dysregulation of kinase (such as, but not limited to, EGFR (including HER), Alk, and PDGFR) pathways.

BACKGROUND ART

Protein kinases are a group of enzymes that regulate diverse, important biological processes including cell growth, proliferation, survival, invasion and differentiation, organ formation, tissue repair and regeneration, etc. Protein kinases exert their physiological functions through catalyzing the phosphorylation of protein and thereby modulating the cellular activities. Because protein kinases have profound effects on cells, their activities are highly regulated. Kinases are turned on or off by phosphorylation (sometimes by autophosphorylation), by binding of activator proteins or inhibitor proteins, or small molecules, or by controlling their location in the cell relative to their substrates. Dysfunctions in the activities of kinases, arising from genetic abnormalities or environmental factors, are known to be associated with many diseases. Several severe pathological states, including cancer and chronic inflammation, are associated with stimulation of intra-cellular signaling, and since kinases positively relay signaling events, their inhibition offers a powerful way to inhibit or control signal transduction cascades.

The epidermal growth factor receptor (EGFR; ErbB-1; HER1 in humans) is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). EGFR is the cell-surface receptor for members of the epidermal growth factor family (EGF-family) of extracellular protein ligands. Mutations affecting EGFR expression or activity could result in cancer. EGFR is reported deregulated in most solid tumor types i.e. lung cancer, breast cancer and brain tumor. It is estimated that mutations, amplifications or misregulations of EGFR or family members are implicated in about 30% of all epithelial cancers. Therapeutic approaches have been developed based on the inhibition of EGFR by either antibody drug or small molecular inhibitor drug, such as gefitinib and erlotinib. In the case of non-small cell lung cancer, gefitinib and erlotinib have shown benefit for about 10-40% of the patients. However, acquired resistant to gefitinib or erlotinib after a period of treatment become a major clinical problem. Research has confirmed that one main reason resistance developed is due to the presence of a new mutation of T790M, which is the gatekeeper of EGFR. Subsequently, inhibitors can overcome this T790M have been developed and showed advantage in the clinical trial, such as BIBW2992. However, these T790M targeted EGFR inhibitor still has relative inhibitory activity towards wild type EGFR which limit the clinical application. It is needed to further develop more efficient type of EGFR inhibitor which will target substantially the mutation and not substantially the wild type protein.

SUMMARY

The present invention is directed to certain pyrrolopyrimidine derivatives, pharmaceutical compositions, and methods of using these compounds and compositions to treat proliferation disorders.

The present disclosure provides a compound of Formula (VIII):

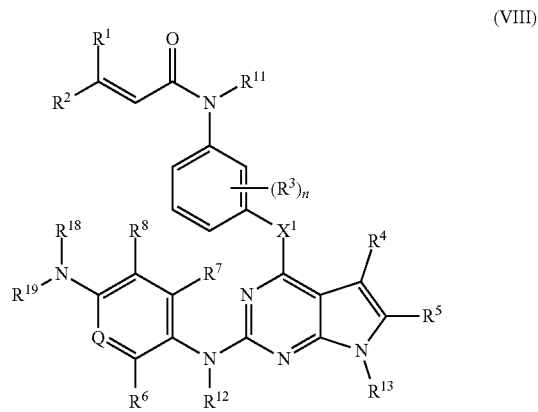

(VIII)

wherein
$X^1$ is O, NH, S, $CH_2$, or $CF_2$;
$R^1$ and $R^2$ are independently selected from hydrogen, halo, $C_{1-6}$ alkyl, and $C_{1-6}$ haloalkyl;
$R^3$ is selected from halo, hydroxyl, $C_{1-6}$ alkyl, $C_{1-6}$ alkoxy, cyano, and nitro;
n is a number from zero to 4;
$R^4$ is selected from hydrogen, $C_{1-6}$ alkyl, $C_{3-7}$ cycloalkyl, and $-NR^{22}R^{23}$
  wherein the alkyl or cycloalkyl is unsubstituted or substituted with hydroxyl or amino; and
  wherein each $R^{22}$ and $R^{23}$ are independently selected from hydrogen and $C_{1-6}$ alkyl or $R^{22}$ and $R^{23}$ may be joined to form a 3 to 10 membered ring;
$R^5$ is selected from hydrogen and $C_{1-6}$ alkyl;
$R^6$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;

$R^7$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;

$R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;

Q is $CR^9$ or N;

$R^9$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;

$R^{11}$ is selected from hydrogen and $C_{1-6}$ alkyl;

$R^2$ is selected from hydrogen and $C_{1-6}$ alkyl;

$R^{13}$ is selected from hydrogen, $C_{1-6}$ alkyl, $C_{1-6}$ acyl, $SO_2$—$C_{1-6}$alkyl, $C_{3-7}$ cycloalkyl, and $C_{6-20}$ aryl, wherein each alkyl or aryl is unsubstituted or substituted with hydroxyl, $C_{1-6}$ alkoxy, or halo; and —$NR^{18}R^{19}$ is

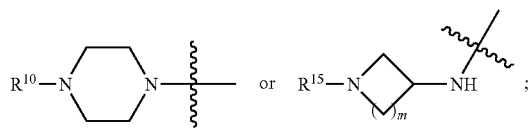

wherein $R^{10}$ is selected from hydrogen and $C_{1-6}$ alkyl;

$R^5$ is unsubstituted methyl, or is $C_{2-4}$alkyl unsubstituted or substituted with hydroxy, methoxy, or halo; and m is 1 or 2;

or $R^{19}$ and $R^9$ taken together form a 5- or 6-membered heteroaryl ring optionally substituted with $C_{1-6}$alkyl that is unsubstituted or substituted with amino, hydroxyl, or halo; and $R^{18}$ is hydrogen or $C_{1-6}$alkyl, or is absent to satisfy valency of the heteroaryl ring;

provided that neither of $R^6$ or $R^7$ is methoxy when —$NR^{18}R^{19}$ is

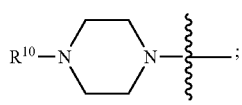

or a pharmaceutically acceptable salt thereof.

The present disclosure provides a compound of Formula (Ia) and (Ib):

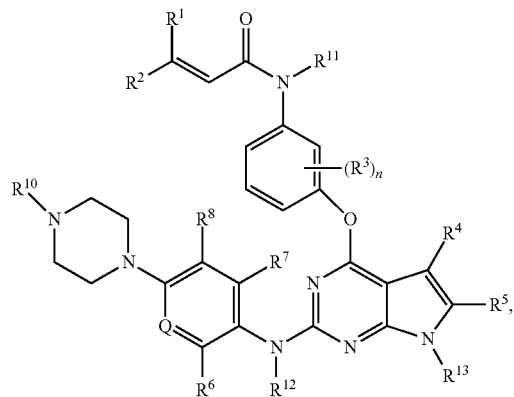

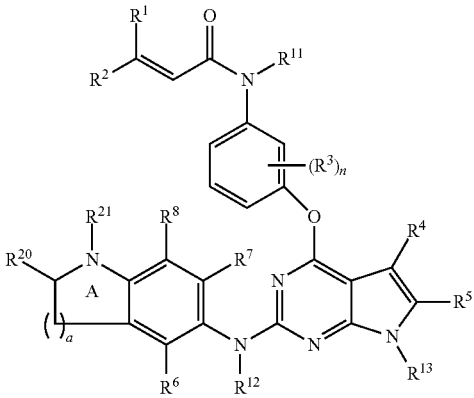

wherein $R^1$ and $R^2$ are independently selected from hydrogen, halo, $C_{1-6}$ alkyl, and $C_{1-6}$ haloalkyl;

$R^3$ is selected from halo, hydroxyl, $C_{1-6}$ alkyl, $C_{1-6}$ alkoxy, cyano, and nitro;

n is a number from zero to 4;

$R^4$ is selected from hydrogen, $C_{1-6}$ alkyl, $C_{3-7}$ cycloalkyl, and —$NR^{22}R^{23}$ wherein the alkyl or cycloalkyl is unsubstituted or substituted with hydroxyl or amino; and wherein each $R^{22}$ and $R^{23}$ are independently selected from hydrogen and $C_{1-6}$ alkyl or $R^{22}$ and $R^{23}$ may be joined to form a 3 to 10 membered ring;

$R^5$ is selected from hydrogen and $C_{1-6}$ alkyl;

$R^6$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;

$R^7$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;

$R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;

Q is $CR^9$ or N;

$R^9$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;

$R^{10}$ is selected from hydrogen and $C_{1-6}$ alkyl;

a is one or two;

Ring A is an aromatic ring;

$R^{20}$ and $R^{21}$ are independently selected from hydrogen and $C_{1-6}$ alkyl; wherein alkyl is unsubstituted or substituted with amino, hydroxyl, or halo; wherein $R^{21}$ may not present to satisfy valency;

$R^{11}$ is selected from hydrogen and $C_{1-6}$ alkyl;

$R^{12}$ is selected from hydrogen and $C_{1-6}$ alkyl; and $R^{13}$ is selected from hydrogen, $C_{1-6}$ alkyl, $C_{1-6}$ acyl, $SO_2$—$C_{1-6}$alkyl, $C_{3-7}$ cycloalkyl, and $C_{6-20}$ aryl, wherein each alkyl or aryl is unsubstituted or substituted with hydroxyl, $C_{1-6}$ alkoxy, or halo;

or a pharmaceutically acceptable salt thereof.

The present disclosure provides a compound of Formula (II):

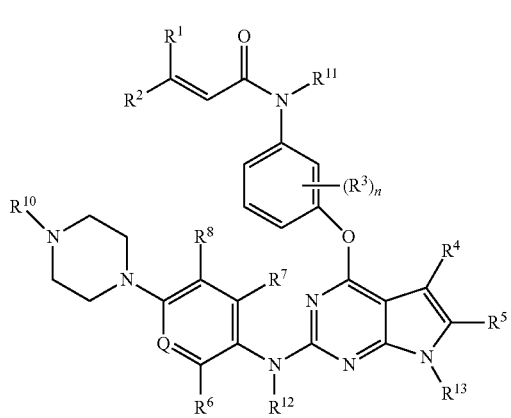
(II)

wherein

R¹ and R² are independently selected from hydrogen, halo, $C_{1-6}$ alkyl, and $C_{1-6}$ haloalkyl;

R³ is selected from halo, hydroxyl, $C_{1-6}$ alkyl, $C_{1-6}$ alkoxy, cyano, and nitro;

n is a number from zero to 4;

R⁴ is selected from hydrogen, $C_{1-6}$ alkyl, $C_{3-7}$ cycloalkyl, and —NR²²R²³;

wherein the alkyl or cycloalkyl is unsubstituted or substituted with hydroxyl or amino; and wherein each R²² and R²³ are independently selected from hydrogen and $C_{1-6}$ alkyl or R²² and R²³ may be joined to form a 3 to 10 membered ring;

R⁵ is selected from hydrogen and $C_{1-6}$ alkyl;

R⁶ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;

R⁷ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;

R⁸ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;

Q is CR⁹ or N;

R⁹ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;

R¹⁰ is selected from hydrogen and $C_{1-6}$ alkyl;

R¹¹ is selected from hydrogen and $C_{1-6}$ alkyl;

R¹² is selected from hydrogen and $C_{1-6}$ alkyl; and

R¹³ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo;

or a pharmaceutically acceptable salt thereof.

The present disclosure provides a compound of Formula (III):

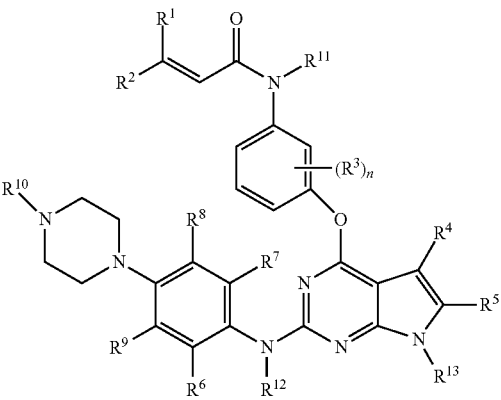
(III)

wherein

R¹ and R² are independently selected from hydrogen, halo, $C_{1-6}$ alkyl, and $C_{1-6}$ haloalkyl;

R³ is selected from halo, hydroxyl, $C_{1-6}$ alkyl, $C_{1-6}$ alkoxy, cyano, and nitro;

n is a number from zero to 4;

R⁴ is selected from hydrogen, $C_{1-6}$ alkyl, $C_{3-7}$ cycloalkyl, and —NR²²R²³ wherein the alkyl or cycloalkyl is unsubstituted or substituted with hydroxyl or amino; and wherein each R²² and R²³ are independently selected from hydrogen and $C_{1-6}$ alkyl or R²² and R²³ may be joined to form a 3 to 10 membered ring;

R⁵ is selected from hydrogen and $C_{1-6}$ alkyl;

R⁶ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;

R⁷ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;

R⁸ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;

R⁹ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;

R¹⁰ is selected from hydrogen and $C_{1-6}$ alkyl;

R¹¹ is selected from hydrogen and $C_{1-6}$ alkyl;

R¹² is selected from hydrogen and $C_{1-6}$ alkyl; and

R¹³ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo;

or a pharmaceutically acceptable salt thereof.

The present disclosure provides a compound of Formula (IV):

$$(IV)$$

wherein
R¹ and R² are independently selected from hydrogen, halo, $C_{1-6}$ alkyl, and $C_{1-6}$ haloalkyl;
R³ is selected from halo, hydroxyl, $C_{1-6}$ alkyl, $C_{1-6}$ alkoxy, cyano, and nitro;
n is a number from zero to 4;
R⁴ is selected from hydrogen, $C_{1-6}$ alkyl, $C_{3-7}$ cycloalkyl, and —NR²²R²³
  wherein the alkyl or cycloalkyl is unsubstituted or substituted with hydroxyl or amino; and
  wherein each R²² and R²³ are independently selected from hydrogen and $C_{1-6}$ alkyl or R²² and R²³ may be joined to form a 3 to 10 membered ring;
R⁵ is selected from hydrogen and $C_{1-6}$ alkyl;
R⁶ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;
R⁷ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;
R⁸ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;
R¹⁰ is selected from hydrogen and $C_{1-6}$ alkyl;
R¹¹ is selected from hydrogen and $C_{1-6}$ alkyl;
R¹² is selected from hydrogen and $C_{1-6}$ alkyl; and
R¹³ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo;
or a pharmaceutically acceptable salt thereof.

The present disclosure provides a compound of Formula (V):

$$(V)$$

wherein
R¹ and R² are independently selected from hydrogen, halo, $C_{1-6}$ alkyl, and $C_{1-6}$ haloalkyl;
R⁶ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;
R⁷ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;
R⁸ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;
Q is CR⁹ or N;
R⁹ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;
R¹⁰ is selected from hydrogen and $C_{1-6}$ alkyl;
R¹¹ is selected from hydrogen and $C_{1-6}$ alkyl;
R¹² is selected from hydrogen and $C_{1-6}$ alkyl; and
R¹³ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo;
or a pharmaceutically acceptable salt thereof.

The present disclosure provides a compound of Formula (VI):

$$(VI)$$

wherein
R¹ and R² are independently selected from hydrogen, halo, $C_{1-6}$ alkyl, and $C_{1-6}$ haloalkyl;
R⁸ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;
Q is CR⁹ or N;
R⁹ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;
R¹⁰ is selected from hydrogen and $C_{1-6}$ alkyl; and
R¹³ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo;
or a pharmaceutically acceptable salt thereof.

In certain embodiments, the present disclosure provides a compound of Formula (VII) as described below.

In certain embodiments, the compound of Formula (I)-(VIII) is a compound selected from those species described or exemplified in the detailed description below.

In a further aspect, the present disclosure provides a pharmaceutical composition comprising at least one compound of Formula (I)-(VIII) or a pharmaceutically acceptable salt thereof. Pharmaceutical compositions may further comprise a pharmaceutically acceptable carrier or excipient. The present disclosure also provides a compound of Formula (I)-(VIII) or a pharmaceutically acceptable salt thereof for use as a medicament.

In another aspect, the present disclosure provides a method of treating and/or preventing a proliferation disorder comprising administering to a subject in need of such treatment an effective amount of at least one compound of Formula (I)-(VIII) or a pharmaceutically acceptable salt thereof.

In another aspect, the present disclosure provides a compound of Formula (I)-(VIII) or a pharmaceutically acceptable salt thereof for use in therapy. In another aspect, the present disclosure provides a compound of Formula (I)-(VIII) or a pharmaceutically acceptable salt thereof for use in the treatment of a proliferation disorder. In another aspect, the present disclosure provides use of a compound of Formula (I)-(VIII) or a pharmaceutically acceptable salt thereof for the manufacture of a medicament for the treatment of a proliferation disorder.

In another aspect, the present disclosure provides a method of treating a condition associated with EGFR inhibitory activity targeting a mutated EGFR but not the wild type EGFR comprising administering to a subject in need of such treatment an effective amount of at least one compound of Formula (I)-(VIII) or a pharmaceutically acceptable salt thereof. In some embodiments, the mutated EGFR comprises a T790M mutation. The present disclosure provides use of a compound of Formula (I)-(VIII) in the preparation of a medicament for the treatment of such diseases and medical conditions, and the use of such compounds and salts for treatment of such diseases and medical conditions.

In another aspect, the present disclosure provides a method of inhibiting mutated EGFR in a cell comprising contacting the cell with an effective amount of at least one compound of Formula (I)-(VIII) or a salt thereof, and/or with at least one pharmaceutical composition of the embodiments, wherein the contacting is in vitro, ex vivo, or in vivo. In some embodiments, the mutated EGFR comprises a T790M mutation.

One of ordinary skill in the art will recognize that compounds of Formula (II)-(VI) are compounds of Formula (I), and that compounds of Formula (I)-(VII) are compounds of Formula (VIII).

Additional embodiments, features, and advantages of the invention will be apparent from the following detailed description and through practice of the invention.

For the sake of brevity, the disclosures of the publications cited in this specification, including patents, are herein incorporated by reference.

DETAILED DESCRIPTION

Figure 1:
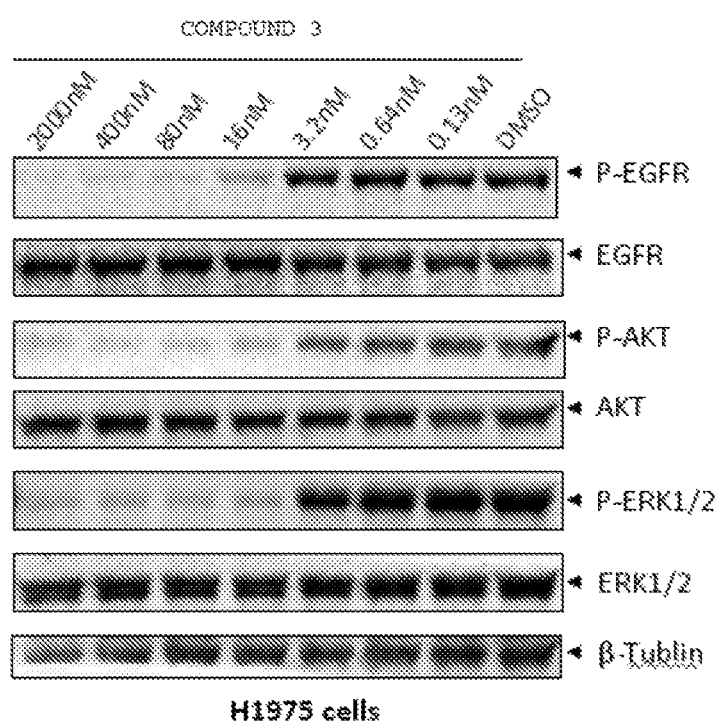
FIG. 1 shows SDS-PAGE of certain effectors of H1975 lung cancer cells treated with varying concentrations of Compound 3.

The present invention is directed to certain pyrrolopyrimidine derivatives, pharmaceutical compositions, and methods of using these compounds and compositions to treat proliferation disorders. The compounds as described herein exhibit anti-tumor, anticancer, anti-inflammation, anti-infectious, and anti-proliferation activity. In some embodiments, the compounds have been shown to possess anti-cancer activity in cell based assays as described herein using various cancer cell lines, which demonstrate very efficient EGFR inhibitory activity targeting substantially the mutation and not substantially the wild type protein. In some embodiments, the mutated EGFR comprises a T790M mutation. Accordingly, the compounds and compositions comprising the compounds of the embodiments are useful to treat conditions characterized by those mutated cancer cells. In certain instances, the compounds are useful to treat sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, and pancreatic cancer.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. This nomenclature has generally been derived using the commercially-available AutoNom software (MDL, San Leandro, Calif.).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Chemical Terms

The term "alkyl" refers to a straight- or branched-chain alkyl group having from 1 to 12 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkoxy" refers to an alkyl group as defined above, bonded to an oxygen atom. The alkoxy group is connected to the parent structure via the oxygen atom.

The term "amino" refers to an —NH$_2$ group, or a mono- or dialkylamino group.

The term "cycloalkyl" refers to a saturated or partially saturated, monocyclic, fused polycyclic, bridged polycyclic, or spiro polycyclic carbocycle having from 3 to 12 ring atoms per carbocycle. Illustrative examples of cycloalkyl groups include the following entities, in the form of properly bonded moieties:

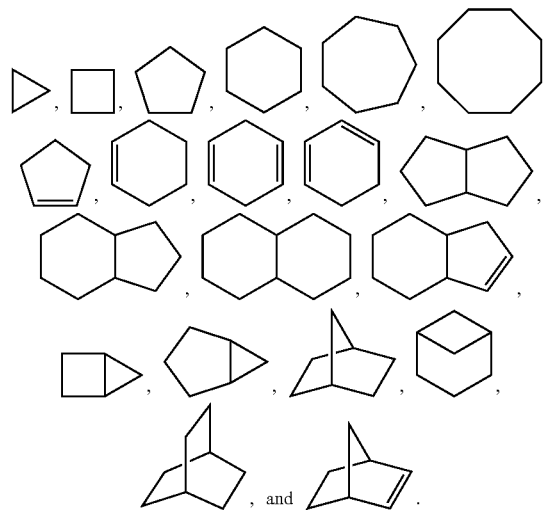

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

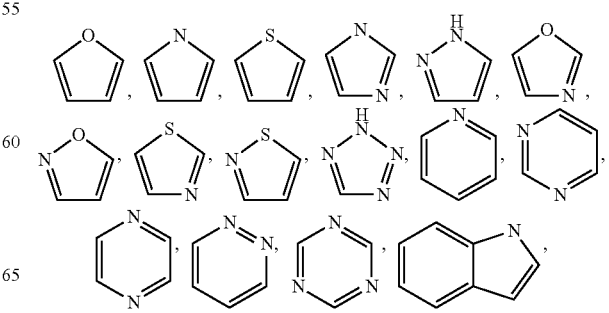

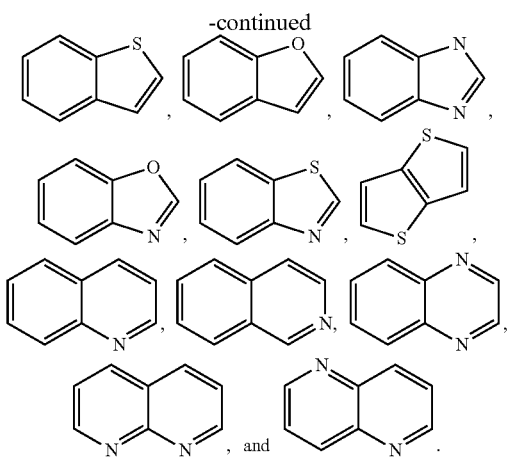

The term "halogen" represents chlorine, fluorine, bromine, or iodine. The term "halo" represents chloro, fluoro, bromo, or iodo. The term "haloalkyl" means an alkyl as defined above, substituted with one or more halogen atoms. The term "haloalkoxy" means an alkoxy as defined above, substituted with one or more halogen atoms.

The term "acyl" refers to a group R—C(O)— of from 1 to 10 carbon atoms of a straight, branched, or cyclic configuration or a combination thereof, attached to the parent structure through carbonyl functionality. Such group may be saturated or unsaturated, and aliphatic or aromatic.

The term "cyano" refers to the group —CN.
The term "nitro" refers to the group —$NO_2$.
The term "hydroxyl" refers to the group —OH.

Those skilled in the art will recognize that the species listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the embodiments include isotopes of hydrogen, carbon, nitrogen, oxygen, phosphorous, fluorine, chlorine, and iodine, such as $^2H$, $^3H$, C, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically-labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically-labeled compounds of the embodiments and prodrugs thereof can generally be prepared by carrying out the procedures disclosed in the schemes or in the examples and preparations described below by substituting a readily available isotopically-labeled reagent for a non-isotopically-labeled reagent.

The nomenclature "$C_{i-j}$" with j>i, when applied herein to a class of substituents, is meant to refer to embodiments for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The present disclosure provides pharmaceutically acceptable salts of the compounds represented by Formulae (I)-(VIII), preferably of those described above and of the specific compounds exemplified herein, and pharmaceutical compositions comprising such salts, and methods of using such salts.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

For a compound of Formulae (I)-(VIII) that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology. In certain embodiments, the pharmaceutically acceptable salt is the HCl salt, maleic acid salt, HBr salt, lactic acid salt, tartaric acid salt, or methanesulfonic acid salt.

The present disclosure provides pharmaceutically acceptable prodrugs of the compounds of Formulae (I)-(VIII), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formulae (I)-(VIII)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present disclosure provides pharmaceutically active metabolites of compounds of Formulae (I)-(VIII), and uses of such metabolites in the methods of the embodiments. A "pharmaceutically active metabolite" means a pharmacologically active product of metabolism in the body of a compound of Formulae (I)-(VIII) or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Representative Embodiments

Formula (VIII)

The present disclosure provides a compound of Formula (VIII). In some embodiments, $X^1$ is O or NH. In other embodiments, $X^1$ is $CH_2$ or $CF_2$. In still other embodiments, $X^1$ is O.

In some embodiments of Formula (VIII), $-NR^{18}R^{19}$ is

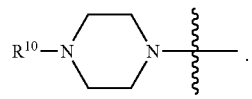

In other embodiments, $-NR^{18}R^{19}$ is

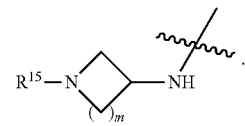

In some embodiments, $R^{15}$ is methyl, hydroxyethyl, methoxyethyl, or fluoroethyl. In other embodiments, $R^{15}$ is fluoroethyl. In some embodiments, m is 1. In other embodiments, m is 2.

In some embodiments, $R^9$ and $R^{19}$ taken together form an optionally substituted 5- or 6-membered heteroaryl ring. In some embodiments, $R^{19}$ and $R^9$ together form a 5- or 6-membered ring optionally substituted with $C_{1-6}$alkyl that is unsubstituted or substituted with amino. In some embodiments, the heteroaryl ring is substituted with dimethylaminomethyl or piperidinylmethyl. In other embodiments, $R^9$ and $R^{19}$ taken together form pyrrole or pyridine. In some embodiments, $R^{18}$ is dimethylaminoethyl.

In some embodiments, $R^6$ is methoxy. In other embodiments, $R^7$ is methoxy. In certain instances, $R^7$ is hydrogen or methoxy.

In some embodiments of Formula (VIII), each variable therein is defined as described below for any one of Formulas (I)-(VII) or embodiments thereof. In particular, certain embodiments of Formula (VIII) are as defined for each variable for Formula (I) below, and said definitions are incorporated herein by reference.

Formula (I)

The present disclosure provides a compound of Formula (Ia) and (Ib):

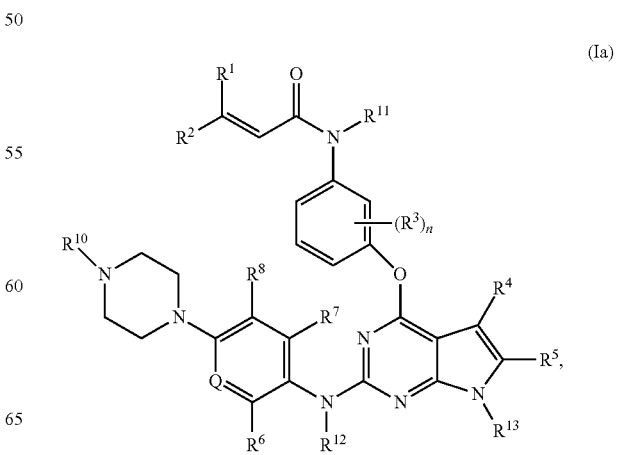

(Ia)

(Ib)

wherein
$R^1$ and $R^2$ are independently selected from hydrogen, halo, $C_{1-6}$ alkyl, and $C_{1-6}$ haloalkyl;
$R^3$ is selected from halo, hydroxyl, $C_{1-6}$ alkyl, $C_6$ alkoxy, cyano, and nitro;
n is a number from zero to 4;
$R^4$ is selected from hydrogen, $C_{1-6}$ alkyl, $C_{3-7}$ cycloalkyl, and —$NR^{22}R^{23}$;
wherein the alkyl or cycloalkyl is unsubstituted or substituted with hydroxyl or amino; and
wherein each $R^{22}$ and $R^{23}$ are independently selected from hydrogen and $C_{1-6}$ alkyl or $R^{22}$ and $R^{23}$ may be joined to form a 3 to 10 membered ring;
$R^5$ is selected from hydrogen and $C_{1-6}$ alkyl;
$R^6$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;
$R^7$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;
$R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;
Q is $CR^9$ or N;
$R^9$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;
$R^{10}$ is selected from hydrogen and $C_{1-6}$ alkyl;
a is one or two;
Ring A is an aromatic ring;
$R^{20}$ and $R^{21}$ are independently selected from hydrogen and $C_{1-6}$ alkyl; wherein alkyl is unsubstituted or substituted with amino, hydroxyl, or halo; wherein $R^{21}$ may not present to satisfy valency;
$R^{11}$ is selected from hydrogen and $C_{1-6}$ alkyl;
$R^{12}$ is selected from hydrogen and $C_{1-6}$ alkyl; and
$R^{13}$ is selected from hydrogen, $C_{1-6}$ alkyl, $C_{1-6}$ acyl, $SO_2$—$C_{1-6}$alkyl, $C_{3-7}$ cycloalkyl, and $C_{6-20}$ aryl,
wherein each alkyl or aryl is unsubstituted or substituted with hydroxyl, $C_{1-6}$ alkoxy, or halo;
or a pharmaceutically acceptable salt thereof.

Formula (I) is meant to refer to Formula (Ia) and Formula (Ib).

In Formula (I), $R^1$ and $R^2$ are independently selected from hydrogen, halo, $C_{1-6}$ alkyl, and $C_{1-6}$ haloalkyl. In certain instances, $R^1$ is hydrogen. In certain instances, $R^1$ is $C_{1-6}$ alkyl. In certain instances, $R^1$ is methyl or ethyl. In certain instances, $R^2$ is hydrogen. In certain instances, $R^2$ is $C_{1-6}$ alkyl. In certain instances, $R^2$ is methyl or ethyl. In certain instances, $R^1$ and $R^2$ are each hydrogen.

In Formula (I), n is a number from zero to 4. In certain instances, n is zero. In certain instances, n is one. In certain instances, n is 2. In certain instances, n is 3. In certain instances, n is 4.

In Formula (I), $R^3$ is selected from halo, hydroxyl, $C_{1-6}$ alkyl, $C_{1-6}$ alkoxy, cyano, and nitro. In certain instances, $R^3$ is halo. In certain instances, $R^3$ is hydroxyl. In certain instances, $R^3$ is $C_{1-6}$ alkyl. In certain instances, $R^3$ is $C_{1-6}$ alkoxy. In certain instances, $R^3$ is cyano. In certain instances, $R^3$ is nitro.

In Formula (I), $R^4$ is selected from hydrogen, $C_{1-6}$ alkyl, $C_{3-7}$ cycloalkyl, and —$NR^{22}R^{23}$; wherein the alkyl or cycloalkyl is unsubstituted or substituted with hydroxyl or amino; and wherein each $R^{22}$ and $R^{23}$ are independently selected from hydrogen and $C_{1-6}$ alkyl or $R^{22}$ and $R^{21}$ may be joined to form a 3 to 10 membered ring. In certain instances, $R^4$ is hydrogen. In certain instances, $R^4$ is $C_{1-6}$ alkyl. In certain instances, $R^4$ is $C_{3-7}$ cycloalkyl. In certain instances, $R^4$ is —$NR^{22}R^{23}$.

In certain instances, $R^4$ is unsubstituted $C_{1-6}$ alkyl. In certain instances, $R^4$ is $C_{1-6}$ alkyl that is substituted with hydroxyl. In certain instances, $R^4$ is $C_{1-3}$ alkyl that is substituted with hydroxyl. In certain instances, $R^4$ is $C_{1-6}$ alkyl that is substituted with amino. In certain instances, $R^4$ is $C_{1-6}$ alkyl that is substituted with —$NH_2$. In certain instances, $R^4$ is $C_{1-6}$ alkyl that is substituted with —$N(CH_3)_2$. In certain instances, $R^4$ is $C_{1-3}$ alkyl that is substituted with —$NH_2$. In certain instances, $R^4$ is $C_{1-3}$ alkyl that is substituted with —$N(CH_3)_2$.

In certain instances, $R^4$ is unsubstituted $C_{3-7}$ cycloalkyl. In certain instances, $R^4$ is unsubstituted $C_3$ cycloalkyl. In certain instances, $R^4$ is unsubstituted $C_4$ cycloalkyl. In certain instances, $R^4$ is unsubstituted $C_{5-6}$ cycloalkyl. In certain instances, $R^4$ is unsubstituted $C_7$ cycloalkyl.

In certain instances, $R^4$ is —$NR^{22}R^{23}$, wherein each $R^{22}$ and $R^{23}$ are independently selected from hydrogen and $C_{1-6}$ alkyl or $R^{22}$ and $R^{23}$ may be joined to form a 3 to 10 membered ring. In certain instances, $R^{22}$ and $R^{23}$ are hydrogen. In certain instances, $R^{22}$ and $R^{23}$ are $C_{1-6}$ alkyl. In certain instances, $R^{22}$ and $R^{23}$ are $C_{1-3}$ alkyl. In certain instances, $R^{22}$ and $R^{23}$ are methyl.

In certain instances, $R^{22}$ and $R^{23}$ may be joined to form a 3 to 10 membered ring, such that $R^4$ is where w is a number from 1 to 8. In certain instances, $R^{22}$ and $R^{23}$ may be joined to form a 3-membered ring. In certain instances, $R^{22}$ and $R^{23}$ may be joined to form a 4-membered ring. In certain instances, $R^{22}$ and $R^{23}$ may be joined to form a 5-membered ring. In certain instances, $R^{22}$ and $R^{23}$ may be joined to form a 6-membered ring. In certain instances, $R^{22}$ and $R^{23}$ may be joined to form a 7-membered ring.

In Formula (I), $R^5$ is selected from hydrogen and $C_{1-6}$ alkyl. In certain instances, $R^5$ is hydrogen. In certain instances, $R^5$ is $C_{1-6}$ alkyl. In certain instances, $R^5$ is methyl. In certain instances, $R^5$ is ethyl. In certain instances, $R^5$ is $C_{1-3}$ alkyl. In certain instances, $R^5$ is $C_{4-6}$ alkyl.

In Formula (I), $R^6$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro. In certain instances, $R^6$ is hydrogen. In certain instances, $R^6$ is halo. In certain instances, $R^6$ is fluoro. In certain instances, $R^6$ is chloro. In certain instances, $R^6$ is bromo. In certain instances, $R^6$ is $C_{1-6}$ alkyl. In certain instances, $R^6$ is $C_{1-6}$ haloalkyl. In certain instances, $R^6$ is $C_{2-6}$ alkoxy. In certain instances, $R^6$ is $C_{1-6}$ haloalkoxy. In certain instances, $R^6$ is hydroxyl. In certain instances, $R^6$ is cyano. In certain instances, $R^6$ is nitro.

In Formula (I), $R^7$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro. In certain instances, $R^7$ is hydrogen. In certain instances, $R^7$ is halo. In certain instances, $R^7$ is fluoro. In certain instances, $R^7$ is chloro. In certain instances, $R^7$ is bromo. In certain instances, $R^7$ is $C_{1-6}$ alkyl. In certain instances, $R^7$ is $C_{1-6}$ haloalkyl. In certain instances, $R^7$ is $C_{2-6}$ alkoxy. In certain instances, $R^7$ is $C_{1-6}$ haloalkoxy. In certain instances, $R^7$ is hydroxyl. In certain instances, $R^7$ is cyano. In certain instances, $R^7$ is nitro.

In Formula (I), $R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro. In certain instances, $R^8$ is hydrogen. In certain instances, $R^8$ is halo. In certain instances, $R^8$ is fluoro. In certain instances, $R^8$ is chloro. In certain instances, $R^8$ is bromo. In certain instances, $R^8$ is $C_{1-6}$ alkyl. In certain instances, $R^8$ is $C_{1-6}$ haloalkyl. In certain instances, $R^8$ is $C_{1-6}$ alkoxy. In certain instances, $R^8$ is $C_{1-6}$ haloalkoxy. In certain instances, $R^8$ is hydroxyl. In certain instances, $R^8$ is cyano. In certain instances, $R^8$ is nitro.

In Formula (I), Q is $CR^9$ or N. In certain instances, Q is $CR^9$. In certain instances, Q is N.

In Formula (I), $R^9$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro. In certain instances, $R^9$ is hydrogen. In certain instances, $R^9$ is halo. In certain instances, $R^9$ is fluoro. In certain instances, $R^9$ is chloro. In certain instances, $R^9$ is bromo. In certain instances, $R^9$ is $C_{1-6}$ alkyl. In certain instances, $R^9$ is $C_{1-6}$ haloalkyl. In certain instances, $R^9$ is $C_{1-6}$ alkoxy. In certain instances, $R^9$ is $C_{1-6}$ haloalkoxy. In certain instances, $R^9$ is hydroxyl. In certain instances, $R^9$ is nitro. In certain instances, $R^9$ is hydrogen or fluoro.

In Formula (I), $R^{10}$ is selected from hydrogen and $C_{1-6}$ alkyl. In certain instances, $R^{10}$ is hydrogen. In certain instances, $R^{10}$ is $C_{1-6}$ alkyl. In certain instances, $R^{10}$ is methyl. In certain instances, $R^{10}$ is ethyl. In certain instances, $R^{10}$ is $C_{1-3}$ alkyl. In certain instances, $R^{10}$ is $C_{4-6}$ alkyl.

In Formula (I), a is one or two and Ring A is an aromatic ring. In certain instances, a is one, as shown:

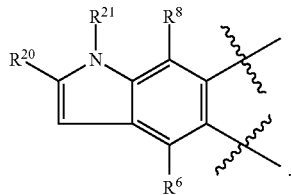

In certain instances, a is two, as shown:

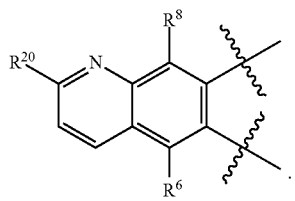

In Formula (I), $R^{20}$ and $R^{21}$ are independently selected from hydrogen and $C_{1-6}$ alkyl; wherein alkyl is unsubstituted or substituted with amino, hydroxyl, or halo; wherein $R^{21}$ may not present to satisfy valency. In certain instances, $R^{20}$ and $R^{21}$ are independently hydrogen. In certain instances, $R^{20}$ and $R^{21}$ are independently unsubstituted $C_{1-6}$ alkyl. In certain instances, $R^{20}$ and $R^{21}$ are independently $C_{1-6}$ alkyl, substituted with amino. In certain instances, $R^{20}$ and $R^{21}$ are independently $C_{1-6}$ alkyl, substituted with $-NR^{24}R^{25}$, wherein $R^{24}$ and $R^{25}$ are independently selected from hydrogen and $C_{1-6}$alkyl. In certain instances, $R^{20}$ and $R^{21}$ are independently $C_{1-6}$ alkyl, substituted with $-NR^{24}R^{25}$, wherein $R^{24}$ and $R^{25}$ are independently selected from hydrogen and $C_{1-3}$alkyl. In certain instances, $R^{20}$ and $R^{21}$ are independently $C_{1-6}$ alkyl, substituted with $-NR^{24}R^{25}$, wherein $R^{24}$ and $R^{25}$ are independently selected from hydrogen and methyl. In certain instances, $R^{20}$ and $R^{21}$ are independently $C_{1-3}$ alkyl, substituted with $-NR^{24}R^{25}$, wherein $R^{24}$ and $R^{25}$ are independently selected from hydrogen and methyl. In certain instances, $R^{20}$ and $R^{21}$ are independently $C_{1-6}$ alkyl, substituted with hydroxyl. In certain instances, $R^{20}$ and $R^{21}$ are $C_{1-6}$ alkyl, substituted with halo.

In Formula (I), $R^{11}$ is selected from hydrogen and $C_{1-6}$ alkyl. In certain instances, $R^{11}$ is hydrogen. In certain instances, $R^{11}$ is $C_{1-6}$ alkyl. In certain instances, $R^{11}$ is methyl. In certain instances, $R^{11}$ is ethyl. In certain instances, $R^{11}$ is $C_{1-3}$ alkyl. In certain instances, $R^{11}$ is $C_{4-6}$ alkyl.

In Formula (I), $R^{12}$ is selected from hydrogen and $C_{1-6}$ alkyl. In certain instances, $R^{12}$ is hydrogen. In certain instances, $R^{12}$ is $C_{1-6}$ alkyl. In certain instances, $R^{12}$ is methyl. In certain instances, $R^{12}$ is ethyl. In certain instances, $R^{12}$ is $C_{1-3}$ alkyl. In certain instances, $R^{12}$ is $C_{4-6}$ alkyl.

In Formula (I), $R^{13}$ is selected from hydrogen, $C_{1-6}$ alkyl, $C_{1-6}$ acyl, $SO_2-C_{1-6}$alkyl, $C_{3-7}$ cycloalkyl, and $C_{6-20}$ aryl, wherein each alkyl or aryl is unsubstituted or substituted with hydroxyl, $C_{1-6}$ alkoxy, or halo. In certain instances, $R^{13}$ is hydrogen. In certain instances, $R^{13}$ is $C_{1-6}$ alkyl. In certain instances, $R^{13}$ is $C_{1-6}$ acyl. In certain instances, $R^{13}$ is $SO_2-C_{1-6}$alkyl. In certain instances, $R^{13}$ is $C_{3-7}$ cycloalkyl. In certain instances, $R^{13}$ is $C_{6-20}$ aryl. In certain instances, $R^{13}$ is $C_{1-6}$alkyl substituted with hydroxyl or halo. In certain instances, $R^{13}$ is unsubstituted $C_{1-6}$ alkyl. In certain instances, $R^{13}$ is $C_{1-6}$ alkyl that is substituted with hydroxyl. In certain instances, $R^{13}$ is $-(CH_2)_mOH$, wherein m is a number from one to 3. In certain instances, $R^{13}$ is $-CH_2OH$. In certain instances, $R^{13}$ is $C_{1-6}$ alkyl that is substituted with $C_{1-6}$ alkoxy.

In certain instances, $R^{13}$ is $C_{1-6}$ alkyl that is substituted with halo. In certain instances, $R^{13}$ is $-(CH_2)_mX$, wherein m is a number from one to 3 and X is halo. In certain instances, $R^{13}$ is $C_{1-6}$ alkyl that is substituted with fluoro. In certain instances, $R^{13}$ is $-(CH_2)_mF$, wherein m is a number from one to 3. In certain instances, $R^{13}$ is $-(CH_2)_2F$.

In certain instances, $R^{13}$ is $C_{1-6}$ acyl. In certain instances, $R^{13}$ is $C_1$ acyl. In certain instances, $R^{13}$ is $C_2$ acyl. In certain instances, $R^{13}$ is $C_3$ acyl. In certain instances, $R^{13}$ is $C_{4-6}$ acyl.

In certain instances, $R^{13}$ is $SO_2-C_{1-6}$alkyl. In certain instances, $R^{13}$ is $SO_2-C_1$alkyl. n certain instances, $R^{13}$ is $SO_2-C_2$alkyl. In certain instances, $R^{13}$ is $SO_2-C_3$alkyl. In certain instances, $R^{13}$ is $SO_2-C_{4-6}$alkyl.

In certain instances, $R^{13}$ is $C_{3-7}$ cycloalkyl. In certain instances, $R^{13}$ is unsubstituted $C_3$ cycloalkyl. In certain instances, $R^{13}$ is unsubstituted $C_4$ cycloalkyl. In certain instances, $R^{13}$ is unsubstituted $C_{5-6}$ cycloalkyl. In certain instances, $R^{13}$ is unsubstituted $C_7$ cycloalkyl.

In certain instances, $R^{13}$ is unsubstituted $C_{6-20}$ aryl. In certain instances, $R^{13}$ is $C_{6-20}$ aryl that is substituted with hydroxyl. In certain instances, $R^{13}$ is $C_{6-20}$ aryl that is substituted with $C_{1-6}$ alkoxy. In certain instances, $R^{13}$ is $C_{6-20}$ aryl that is substituted with halo.

In certain instances, $R^6$, $R^7$, $R^8$, and $R^9$ are hydrogen. In certain instances, $R^6$, $R^7$, and $R^8$ are hydrogen and $R^9$ is halo. In certain instances, $R^6$, $R^7$, and $R^8$ are hydrogen and $R^9$ is fluoro.

In certain instances, $R^6$, $R^7$, $R^8$, and $R^9$ are hydrogen and $R^{10}$ is methyl. In certain instances, $R^6$, $R^7$, $R^8$ are hydrogen; $R^9$ is halo; and $R^{10}$ is methyl. In certain instances, $R^6$, $R^7$, $R^8$ are hydrogen; $R^9$ is fluoro; and $R^{10}$ is methyl.

In certain instances, $R^6$, $R^7$, $R^8$, and $R^9$ are hydrogen and $R^{13}$ is hydrogen. In certain instances, $R^6$, $R^7$, and $R^8$ are hydrogen; $R^9$ is halo; and $R^{13}$ is hydrogen. In certain instances, $R^6$, $R^7$, and $R^8$ are hydrogen; $R^9$ is fluoro; and $R^{13}$ is hydrogen.

In certain instances, $R^6$, $R^7$, $R^8$, and $R^9$ are hydrogen and $R^{13}$ is —$CH_2OH$. In certain instances, $R^6$, $R^7$, and $R^8$ are hydrogen; $R^9$ is halo; and $R^{13}$ is —$CH_2OH$. In certain instances, $R^6$, $R^7$, and $R^8$ are hydrogen; $R^9$ is fluoro; and $R^{13}$ is —$CH_2OH$.

In certain instances, $R^6$, $R^7$, $R^8$, and $R^9$ are hydrogen and $R^{13}$ is —$(CH_2)_mF$, wherein m is a number from one to 3. In certain instances, $R^6$, $R^7$, and $R^8$ are hydrogen; $R^9$ is halo; and $R^{13}$ is —$(CH_2)_mF$, wherein m is a number from one to 3. In certain instances, $R^6$, $R^7$, and $R^8$ are hydrogen; $R^9$ is fluoro; and $R^{13}$ is —$(CH_2)_mF$, wherein m is a number from one to 3.

Formula (II)

The present disclosure provides a compound of Formula (II):

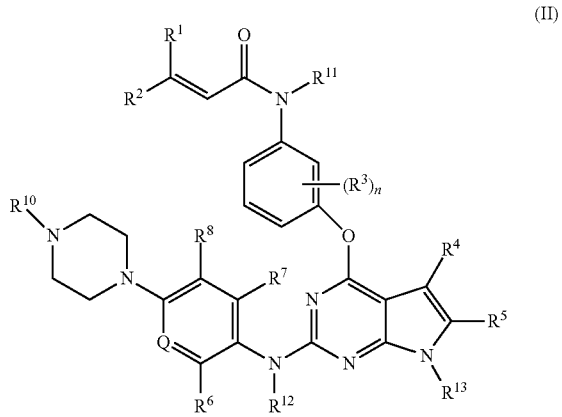

(II)

wherein
$R^1$ and $R^2$ are independently selected from hydrogen, halo, $C_{1-6}$ alkyl, and $C_{1-6}$ haloalkyl;
$R^3$ is selected from halo, hydroxyl, $C_{1-6}$ alkyl, $C_{1-6}$ alkoxy, cyano, and nitro;
n is a number from zero to 4;
$R^4$ is selected from hydrogen, $C_{1-6}$ alkyl, $C_{3-7}$ cycloalkyl, and —$NR^{22}R^{23}$
    wherein the alkyl or cycloalkyl is unsubstituted or substituted with hydroxyl or amino; and
    wherein each $R^{22}$ and $R^{23}$ are independently selected from hydrogen and $C_{1-6}$ alkyl or $R^{22}$ and $R^{21}$ may be joined to form a 3 to 10 membered ring;

$R^5$ is selected from hydrogen and $C_{1-6}$ alkyl;
$R^6$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;
$R^7$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;
$R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;
Q is $CR^9$ or N;
$R^9$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;
$R^{10}$ is selected from hydrogen and $C_{1-6}$ alkyl;
$R^{11}$ is selected from hydrogen and $C_{1-6}$ alkyl;
$R^{12}$ is selected from hydrogen and $C_{1-6}$ alkyl; and
$R^{13}$ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo;
or a pharmaceutically acceptable salt thereof.

In Formula (II), $R^1$ and $R^2$ are independently selected from hydrogen, halo, $C_{1-6}$ alkyl, and $C_{1-6}$ haloalkyl. In certain instances, $R^1$ is hydrogen. In certain instances, $R^1$ is $C_{1-6}$ alkyl. In certain instances, $R^1$ is methyl or ethyl. In certain instances, $R^2$ is hydrogen. In certain instances, $R^2$ is $C_{1-6}$ alkyl. In certain instances, $R^2$ is methyl or ethyl. In certain instances, $R^1$ and $R^2$ are hydrogen.

In Formula (II), n is a number from zero to 4. In certain instances, n is zero. In certain instances, n is one. In certain instances, n is 2. In certain instances, n is 3. In certain instances, n is 4.

In Formula (II), $R^3$ is selected from halo, hydroxyl, $C_{1-6}$ alkyl, $C_{1-6}$ alkoxy, cyano, and nitro. In certain instances, $R^3$ is halo. In certain instances, $R^3$ is hydroxyl. In certain instances, $R^3$ is $C_{1-6}$ alkyl. In certain instances, $R^3$ is $C_{1-6}$ alkoxy. In certain instances, $R^3$ is cyano. In certain instances, $R^3$ is nitro.

In Formula (II), $R^4$ is selected from hydrogen, $C_{1-6}$ alkyl, $C_{3-7}$ cycloalkyl, and —$NR^{22}R^{23}$; wherein the alkyl or cycloalkyl is unsubstituted or substituted with hydroxyl or amino; and wherein each $R^{22}$ and $R^{23}$ are independently selected from hydrogen and $C_{1-6}$ alkyl or $R^{22}$ and $R^{21}$ may be joined to form a 3 to 10 membered ring. In certain instances, $R^4$ is hydrogen. In certain instances, $R^4$ is $C_{1-6}$ alkyl. In certain instances, $R^4$ is $C_{3-7}$ cycloalkyl. In certain instances, $R^4$ is —$NR^{22}R^{23}$.

In certain instances, $R^4$ is unsubstituted $C_{1-6}$ alkyl. In certain instances, $R^4$ is $C_{1-6}$ alkyl that is substituted with hydroxyl. In certain instances, $R^4$ is $C_{1-3}$ alkyl that is substituted with hydroxyl. In certain instances, $R^4$ is $C_{1-6}$ alkyl that is substituted with amino. In certain instances, $R^4$ is $C_{1-6}$ alkyl that is substituted with —$NH_2$. In certain instances, $R^4$ is $C_{1-6}$ alkyl that is substituted with —$N(CH_3)_2$. In certain instances, $R^4$ is $C_{1-3}$ alkyl that is substituted with —$NH_2$. In certain instances, $R^4$ is $C_{1-3}$ alkyl that is substituted with —$N(CH_3)_2$.

In certain instances, $R^4$ is unsubstituted $C_{3-7}$ cycloalkyl. In certain instances, $R^4$ is unsubstituted $C_3$ cycloalkyl. In certain instances, $R^4$ is unsubstituted $C_4$ cycloalkyl. In certain instances, $R^4$ is unsubstituted $C_{5-6}$ cycloalkyl. In certain instances, $R^4$ is unsubstituted $C_7$ cycloalkyl.

In certain instances, $R^4$ is —$NR^{22}R^{23}$, wherein each $R^{22}$ and $R^{23}$ are independently selected from hydrogen and $C_{1-6}$ alkyl or $R^{22}$ and $R^{23}$ may be joined to form a 3 to 10 membered ring. In certain instances, $R^{22}$ and $R^{23}$ are hydrogen. In certain instances, $R^{22}$ and $R^{23}$ are $C_{1-6}$ alkyl. In certain instances, $R^{22}$ and $R^{23}$ are $C_{1-3}$ alkyl. In certain instances, $R^{22}$ and $R^{23}$ are methyl.

In certain instances, $R^{22}$ and $R^{23}$ may be joined to form a 3 to 10 membered ring, such that $R^4$ is

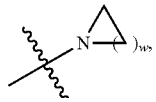

where w is a number from 1 to 8. In certain instances, $R^{22}$ and $R^{23}$ may be joined to form a 3-membered ring. In certain instances, $R^{22}$ and $R^{23}$ may be joined to form a 4-membered ring. In certain instances, $R^{22}$ and $R^{23}$ may be joined to form a 5-membered ring. In certain instances, $R^{22}$ and $R^{23}$ may be joined to form a 6-membered ring. In certain instances, $R^{22}$ and $R^{23}$ may be joined to form a 7-membered ring.

In Formula (II), $R^5$ is selected from hydrogen and $C_{1-6}$ alkyl. In certain instances, $R^5$ is hydrogen. In certain instances, $R^5$ is $C_{1-6}$ alkyl. In certain instances, $R^5$ is methyl. In certain instances, $R^5$ is ethyl. In certain instances, $R^5$ is $C_{1-3}$ alkyl. In certain instances, $R^5$ is $C_{4-6}$ alkyl.

In Formula (II), $R^6$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro. In certain instances, $R^6$ is hydrogen. In certain instances, $R^6$ is halo. In certain instances, $R^6$ is fluoro. In certain instances, $R^6$ is chloro. In certain instances, $R^6$ is bromo. In certain instances, $R^6$ is $C_{1-6}$ alkyl. In certain instances, $R^6$ is $C_{1-6}$ haloalkyl. In certain instances, $R^6$ is $C_{2-6}$ alkoxy. In certain instances, $R^6$ is $C_{1-6}$ haloalkoxy. In certain instances, $R^6$ is hydroxyl. In certain instances, $R^6$ is cyano. In certain instances, $R^6$ is nitro.

In Formula (II), $R^7$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro. In certain instances, $R^7$ is hydrogen. In certain instances, $R^7$ is halo. In certain instances, $R^7$ is fluoro. In certain instances, $R^7$ is chloro. In certain instances, $R^7$ is bromo. In certain instances, $R^7$ is $C_{1-6}$ alkyl. In certain instances, $R^7$ is $C_{1-6}$ haloalkyl. In certain instances, $R^7$ is $C_{2-6}$ alkoxy. In certain instances, $R^7$ is $C_{1-6}$ haloalkoxy. In certain instances, $R^7$ is hydroxyl. In certain instances, $R^7$ is cyano. In certain instances, $R^7$ is nitro.

In Formula (II), $R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro. In certain instances, $R^8$ is hydrogen. In certain instances, $R^8$ is halo. In certain instances, $R^8$ is fluoro. In certain instances, $R^8$ is chloro. In certain instances, $R^8$ is bromo. In certain instances, $R^8$ is $C_{1-6}$ alkyl. In certain instances, $R^8$ is $C_{1-6}$ haloalkyl. In certain instances, $R^8$ is $C_{1-6}$ alkoxy. In certain instances, $R^8$ is $C_{1-6}$ haloalkoxy. In certain instances, $R^8$ is hydroxyl. In certain instances, $R^8$ is cyano. In certain instances, $R^8$ is nitro.

In Formula (II), Q is $CR^9$ or N. In certain instances, Q is $CR^9$. In certain instances, Q is N.

In Formula (II), $R^9$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro. In certain instances, $R^9$ is hydrogen. In certain instances, $R^9$ is halo. In certain instances, $R^9$ is fluoro. In certain instances, $R^9$ is chloro. In certain instances, $R^9$ is bromo. In certain instances, $R^9$ is $C_{1-6}$ alkyl. In certain instances, $R^9$ is $C_{1-6}$ haloalkyl. In certain instances, $R^9$ is $C_{1-6}$ alkoxy. In certain instances, $R^9$ is $C_{1-6}$ haloalkoxy. In certain instances, $R^9$ is hydroxyl. In certain instances, $R^9$ is nitro.

In Formula (II), $R^{10}$ is selected from hydrogen and $C_{1-6}$ alkyl. In certain instances, $R^{10}$ is hydrogen. In certain instances, $R^{10}$ is $C_{1-6}$ alkyl. In certain instances, $R^{10}$ is methyl. In certain instances, $R^{10}$ is ethyl. In certain instances, $R^{10}$ is $C_{1-3}$ alkyl. In certain instances, $R^{10}$ is $C_{4-6}$ alkyl.

In Formula (II), $R^{11}$ is selected from hydrogen and $C_{1-6}$ alkyl. In certain instances, $R^{11}$ is hydrogen. In certain instances, $R^{11}$ is $C_{1-6}$ alkyl. In certain instances, $R^{11}$ is methyl. In certain instances, $R^{11}$ is ethyl. In certain instances, $R^{11}$ is $C_{1-3}$ alkyl. In certain instances, $R^{11}$ is $C_{4-6}$ alkyl.

In Formula (II), $R^{12}$ is selected from hydrogen and $C_{1-6}$ alkyl. In certain instances, $R^{12}$ is hydrogen. In certain instances, $R^{12}$ is $C_{1-6}$ alkyl. In certain instances, $R^{12}$ is methyl. In certain instances, $R^{12}$ is ethyl. In certain instances, $R^{12}$ is $C_{1-3}$ alkyl. In certain instances, $R^{12}$ is $C_{4-6}$ alkyl.

In Formula (II), $R^{13}$ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo. In certain instances, $R^{13}$ is hydrogen. In certain instances, $R^{13}$ is $C_{1-6}$ alkyl. In certain instances, $R^{13}$ is $C_{6-20}$ aryl.

In certain instances, $R^{13}$ is unsubstituted $C_{1-6}$ alkyl. In certain instances, $R^{13}$ is $C_{1-6}$ alkyl that is substituted with hydroxyl. In certain instances, $R^{13}$ is $-(CH_2)_m OH$, wherein m is a number from one to 3. In certain instances, $R^{13}$ is $-CH_2 OH$. In certain instances, $R^{13}$ is $C_{1-6}$ alkyl that is substituted with $C_{1-6}$ alkoxy.

In certain instances, $R^{13}$ is $C_{1-6}$ alkyl that is substituted with halo. In certain instances, $R^{13}$ is $-(CH_2)_m X$, wherein m is a number from one to 3 and X is halo. In certain instances, $R^{13}$ is $C_{1-6}$ alkyl that is substituted with fluoro. In certain instances, $R^{13}$ is $-(CH_2)_m F$, wherein m is a number from one to 3. In certain instances, $R^{13}$ is $-(CH_2)_2 F$.

In certain instances, $R^{13}$ is unsubstituted $C_{6-20}$ aryl. In certain instances, $R^{13}$ is $C_{6-20}$ aryl that is substituted with hydroxyl. In certain instances, $R^{13}$ is $C_{6-20}$ aryl that is substituted with $C_{1-6}$ alkoxy. In certain instances, $R^{13}$ is $C_{6-20}$ aryl that is substituted with halo.

In certain instances, $R^6$, $R^7$, $R^8$, and $R^9$ are hydrogen. In certain instances, $R^6$, $R^7$, and $R^8$ are hydrogen and $R^9$ is halo. In certain instances, $R^6$, $R^7$, and $R^8$ are hydrogen and $R^9$ is fluoro.

In certain instances, $R^6$, $R^7$, $R^8$, and $R^9$ are hydrogen and $R^{10}$ is methyl. In certain instances, $R^6$, $R^7$, $R^8$ are hydrogen; $R^9$ is halo; and $R^{10}$ is methyl. In certain instances, $R^6$, $R^7$, $R^8$ are hydrogen; $R^9$ is fluoro; and $R^{10}$ is methyl.

In certain instances, $R^6$, $R^7$, $R^8$, and $R^9$ are hydrogen and $R^{13}$ is hydrogen. In certain instances, $R^6$, $R^7$, and $R^8$ are hydrogen; $R^9$ is halo; and $R^{13}$ is hydrogen. In certain instances, $R^6$, $R^7$, and $R^8$ are hydrogen; $R^9$ is fluoro; and $R^{13}$ is hydrogen.

In certain instances, $R^6$, $R^7$, $R^8$, and $R^9$ are hydrogen and $R^{13}$ is $-CH_2 OH$. In certain instances, $R^6$, $R^7$, and $R^8$ are hydrogen; $R^9$ is halo; and $R^{13}$ is $-CH_2 OH$. In certain instances, $R^6$, $R^7$, and $R^8$ are hydrogen; $R^9$ is fluoro; and $R^{13}$ is $-CH_2 OH$.

In certain instances, $R^6$, $R^7$, $R^8$, and $R^9$ are hydrogen and $R^{13}$ is $-(CH_2)_m F$, wherein m is a number from one to 3. In certain instances, $R^6$, $R^7$, and $R^8$ are hydrogen; $R^9$ is halo; and $R^{13}$ is $-(CH_2)_m F$, wherein m is a number from one to 3. In certain instances, $R^6$, $R^7$, and $R^8$ are hydrogen; $R^9$ is fluoro; and $R^{13}$ is $-(CH_2)_m F$, wherein m is a number from one to 3.

Formula (III)

The present disclosure provides a compound of Formula (III):

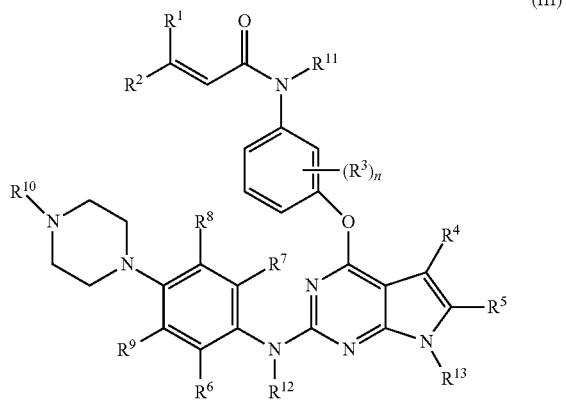

wherein
R$^1$ and R$^2$ are independently selected from hydrogen, halo, C$_{1-6}$ alkyl, and C$_{1-6}$ haloalkyl;
R$^3$ is selected from halo, hydroxyl, C$_{1-6}$ alkyl, C$_{1-6}$ alkoxy, cyano, and nitro;
n is a number from zero to 4;
R$^4$ is selected from hydrogen, C$_{1-6}$ alkyl, C$_{3-7}$ cycloalkyl, and —NR$^{22}$R$^{23}$;
  wherein the alkyl or cycloalkyl is unsubstituted or substituted with hydroxyl or amino; and
  wherein each R$^{22}$ and R$^{23}$ are independently selected from hydrogen and C$_{1-6}$ alkyl or R$^{22}$ and R$^{23}$ may be joined to form a 3 to 10 membered ring;
R$^5$ is selected from hydrogen and C$_{1-6}$ alkyl;
R$^6$ is selected from hydrogen, halo, C$_{1-6}$ alkyl, C$_{1-6}$ haloalkyl, C$_{2-6}$ alkoxy, C$_{1-6}$ haloalkoxy, hydroxyl, cyano, and nitro;
R$^7$ is selected from hydrogen, halo, C$_{1-6}$ alkyl, C$_{1-6}$ haloalkyl, C$_{2-6}$ alkoxy, C$_{1-6}$ haloalkoxy, hydroxyl, cyano, and nitro;
R$^8$ is selected from hydrogen, halo, C$_{1-6}$ alkyl, C$_{1-6}$ haloalkyl, C$_{1-6}$ alkoxy, C$_{1-6}$ haloalkoxy, hydroxyl, cyano, and nitro;
R$^9$ is selected from hydrogen, halo, C$_{1-6}$ alkyl, C$_{1-6}$ haloalkyl, C$_{1-6}$ alkoxy, C$_{1-6}$ haloalkoxy, hydroxyl, cyano, and nitro;
R$^{10}$ is selected from hydrogen and C$_{1-6}$ alkyl;
R$^{11}$ is selected from hydrogen and C$_{1-6}$ alkyl;
R$^{12}$ is selected from hydrogen and C$_{1-6}$ alkyl; and
R$^{13}$ is selected from hydrogen, C$_{1-6}$ alkyl, and C$_{6-20}$ aryl, wherein each alkyl or aryl is unsubstituted or substituted with hydroxyl, C$_{1-6}$ alkoxy, or halo;
or a pharmaceutically acceptable salt thereof.

In Formula (III), R$^1$ and R$^2$ are independently selected from hydrogen, halo, C$_{1-6}$ alkyl, and C$_{1-6}$ haloalkyl. In certain instances, R$^1$ is hydrogen. In certain instances, R$^1$ is C$_{1-6}$ alkyl. In certain instances, R$^1$ is methyl or ethyl. In certain instances, R$^2$ is hydrogen. In certain instances, R$^2$ is C$_{1-6}$ alkyl. In certain instances, R$^2$ is methyl or ethyl. In certain instances, R$^1$ and R$^2$ are hydrogen.

In Formula (III), n is a number from zero to 4. In certain instances, n is zero. In certain instances, n is one. In certain instances, n is 2. In certain instances, n is 3. In certain instances, n is 4.

In Formula (III), R$^3$ is selected from halo, hydroxyl, C$_{1-6}$ alkyl, C$_{1-6}$ alkoxy, cyano, and nitro. In certain instances, R$^3$ is halo. In certain instances, R$^3$ is hydroxyl. In certain instances, R$^3$ is C$_{1-6}$ alkyl. In certain instances, R$^3$ is C$_{1-6}$ alkoxy. In certain instances, R$^3$ is cyano. In certain instances, R$^3$ is nitro.

In Formula (III), R$^4$ is selected from hydrogen, C$_{1-6}$ alkyl, C$_{3-7}$ cycloalkyl, and —NR$^{22}$R$^{23}$; wherein the alkyl or cycloalkyl is unsubstituted or substituted with hydroxyl or amino; and wherein each R$^{22}$ and R$^{23}$ are independently selected from hydrogen and C$_{1-6}$ alkyl or R$^{22}$ and R$^{21}$ may be joined to form a 3 to 10 membered ring. In certain instances, R$^4$ is hydrogen. In certain instances, R$^4$ is C$_{1-6}$ alkyl. In certain instances, R$^4$ is C$_{3-7}$ cycloalkyl. In certain instances, R$^4$ is —NR$^{22}$R$^{23}$.

In certain instances, R$^4$ is unsubstituted C$_{1-6}$ alkyl. In certain instances, R$^4$ is C$_{1-6}$ alkyl that is substituted with hydroxyl. In certain instances, R$^4$ is C$_{1-3}$ alkyl that is substituted with hydroxyl. In certain instances, R$^4$ is C$_{1-6}$ alkyl that is substituted with amino. In certain instances, R$^4$ is C$_{1-6}$ alkyl that is substituted with —NH$_2$. In certain instances, R$^4$ is C$_{1-6}$ alkyl that is substituted with —N(CH$_3$)$_2$. In certain instances, R$^4$ is C$_{1-3}$ alkyl that is substituted with —NH$_2$. In certain instances, R$^4$ is C$_{1-3}$ alkyl that is substituted with —N(CH$_3$)$_2$.

In certain instances, R$^4$ is unsubstituted C$_{3-7}$ cycloalkyl. In certain instances, R$^4$ is unsubstituted C$_3$ cycloalkyl. In certain instances, R$^4$ is unsubstituted C$_4$ cycloalkyl. In certain instances, R$^4$ is unsubstituted C$_{5-6}$ cycloalkyl. In certain instances, R$^4$ is unsubstituted C$_7$ cycloalkyl.

In certain instances, R$^4$ is —NR$^{22}$R$^{23}$, wherein each R$^{22}$ and R$^{23}$ are independently selected from hydrogen and C$_{1-6}$ alkyl or R$^{22}$ and R$^{23}$ may be joined to form a 3 to 10 membered ring. In certain instances, R$^{22}$ and R$^{23}$ are hydrogen. In certain instances, R$^{22}$ and R$^{23}$ are C$_{1-6}$ alkyl. In certain instances, R$^{22}$ and R$^{23}$ are C$_{1-3}$ alkyl. In certain instances, R$^{22}$ and R$^{23}$ are methyl.

In certain instances, R$^{22}$ and R$^{23}$ may be joined to form a 3 to 10 membered ring, such that R$^4$ is

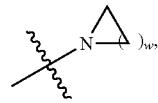

where w is a number from 1 to 8. In certain instances, R$^{22}$ and R$^{23}$ may be joined to form a 3-membered ring. In certain instances, R$^{22}$ and R$^{23}$ may be joined to form a 4-membered ring. In certain instances, R$^{22}$ and R$^{23}$ may be joined to form a 5-membered ring. In certain instances, R$^{22}$ and R$^{23}$ may be joined to form a 6-membered ring. In certain instances, R$^{22}$ and R$^{23}$ may be joined to form a 7-membered ring.

In Formula (III), R$^5$ is selected from hydrogen and C$_{1-6}$ alkyl. In certain instances, R$^5$ is hydrogen. In certain instances, R$^5$ is C$_{1-6}$ alkyl. In certain instances, R$^5$ is methyl. In certain instances, R$^5$ is ethyl. In certain instances, R$^5$ is C$_{1-3}$ alkyl. In certain instances, R$^5$ is C$_{4-6}$ alkyl.

In Formula (III), R$^6$ is selected from hydrogen, halo, C$_{1-6}$ alkyl, C$_{1-6}$ haloalkyl, C$_{2-6}$ alkoxy, C$_{1-6}$ haloalkoxy, hydroxyl, cyano, and nitro. In certain instances, R$^6$ is hydrogen. In certain instances, R$^6$ is halo. In certain instances, R$^6$ is fluoro. In certain instances, R$^6$ is chloro. In certain instances, R$^6$ is bromo. In certain instances, R$^6$ is C$_{1-6}$ alkyl. In certain instances, R$^6$ is C$_{1-6}$ haloalkyl. In certain instances, R$^6$ is C$_{2-6}$ alkoxy. In certain instances, R$^6$ is C$_{1-6}$ haloalkoxy. In certain instances, $R^6$ is hydroxyl. In certain instances, $R^6$ is cyano. In certain instances, $R^6$ is nitro.

In Formula (III), $R^7$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro. In certain instances, $R^7$ is hydrogen. In certain instances, $R^7$ is halo. In certain instances, $R^7$ is fluoro. In certain instances, $R^7$ is chloro. In certain instances, $R^7$ is bromo. In certain instances, $R^7$ is $C_{1-6}$ alkyl. In certain instances, $R^7$ is $C_{1-6}$ haloalkyl. In certain instances, $R^7$ is $C_{2-6}$ alkoxy. In certain instances, $R^7$ is $C_{1-6}$ haloalkoxy. In certain instances, $R^7$ is hydroxyl. In certain instances, $R^7$ is cyano. In certain instances, $R^7$ is nitro.

In Formula (III), $R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro. In certain instances, $R^8$ is hydrogen. In certain instances, $R^8$ is halo. In certain instances, $R^8$ is fluoro. In certain instances, $R^8$ is chloro. In certain instances, $R^8$ is bromo. In certain instances, $R^8$ is $C_{1-6}$ alkyl. In certain instances, $R^8$ is $C_{1-6}$ haloalkyl. In certain instances, $R^8$ is $C_{1-6}$ alkoxy. In certain instances, $R^8$ is $C_{1-6}$ haloalkoxy. In certain instances, $R^8$ is hydroxyl. In certain instances, $R^8$ is cyano. In certain instances, $R^8$ is nitro.

In Formula (III), $R^9$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro. In certain instances, $R^9$ is hydrogen. In certain instances, $R^9$ is halo. In certain instances, $R^9$ is fluoro. In certain instances, $R^9$ is chloro. In certain instances, $R^9$ is bromo. In certain instances, $R^9$ is $C_{1-6}$ alkyl. In certain instances, $R^9$ is $C_{1-6}$ haloalkyl. In certain instances, $R^9$ is $C_{1-6}$ alkoxy. In certain instances, $R^9$ is $C_{1-6}$ haloalkoxy. In certain instances, $R^9$ is hydroxyl. In certain instances, $R^9$ is cyano. In certain instances, $R^9$ is nitro.

In Formula (III), $R^{10}$ is selected from hydrogen and $C_{1-6}$ alkyl. In certain instances, $R^{10}$ is hydrogen. In certain instances, $R^{10}$ is $C_{1-6}$ alkyl. In certain instances, $R^{10}$ is methyl. In certain instances, $R^{10}$ is ethyl. In certain instances, $R^{10}$ is $C_{1-3}$ alkyl. In certain instances, $R^{10}$ is $C_{4-6}$ alkyl.

In Formula (III), $R^{11}$ is selected from hydrogen and $C_{1-6}$ alkyl. In certain instances, $R^{11}$ is hydrogen. In certain instances, $R^{11}$ is $C_{1-6}$ alkyl. In certain instances, $R^{11}$ is methyl. In certain instances, $R^{11}$ is ethyl. In certain instances, $R^{11}$ is $C_{1-3}$ alkyl. In certain instances, $R^{11}$ is $C_{4-6}$ alkyl.

In Formula (III), $R^1$ is selected from hydrogen and $C_{1-6}$ alkyl. In certain instances, $R^{12}$ is hydrogen. In certain instances, $R^{12}$ is $C_{1-6}$ alkyl. In certain instances, $R^{12}$ is methyl. In certain instances, $R^{12}$ is ethyl. In certain instances, $R^{12}$ is $C_{1-3}$ alkyl. In certain instances, $R^{12}$ is $C_{4-6}$ alkyl.

In Formula (III), $R^{13}$ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo. In certain instances, $R^{13}$ is hydrogen. In certain instances, $R^{13}$ is $C_{1-6}$ alkyl. In certain instances, $R^{13}$ is $C_{6-20}$ aryl.

In certain instances, $R^{13}$ is unsubstituted $C_{1-6}$ alkyl. In certain instances, $R^{13}$ is $C_{1-6}$ alkyl that is substituted with hydroxyl. In certain instances, $R^{13}$ is —$(CH_2)_m$OH, wherein m is a number from one to 3. In certain instances, $R^{13}$ is —$CH_2$OH. In certain instances, $R^{13}$ is $C_{1-6}$ alkyl that is substituted with $C_{1-6}$ alkoxy.

In certain instances, $R^{13}$ is $C_{1-6}$ alkyl that is substituted with halo. In certain instances, $R^{13}$ is —$(CH_2)_m$X, wherein m is a number from one to 3 and X is halo. In certain instances, $R^{13}$ is $C_{1-6}$ alkyl that is substituted with fluoro. In certain instances, $R^{13}$ is —$(CH_2)_m$F, wherein m is a number from one to 3. In certain instances, $R^{13}$ is —$(CH_2)_2$F.

In certain instances, $R^{13}$ is unsubstituted $C_{6-20}$ aryl. In certain instances, $R^{13}$ is $C_{6-20}$ aryl that is substituted with hydroxyl. In certain instances, $R^{13}$ is $C_{6-20}$ aryl that is substituted with $C_{1-6}$ alkoxy. In certain instances, $R^{13}$ is $C_{6-20}$ aryl that is substituted with halo.

In certain instances, $R^6$, $R^7$, $R^8$, and $R^9$ are hydrogen. In certain instances, $R^6$, $R^7$, and $R^8$ are hydrogen and $R^9$ is halo. In certain instances, $R^6$, $R^7$, and $R^8$ are hydrogen and $R^9$ is fluoro.

In certain instances, $R^6$, $R^7$, $R^8$, and $R^9$ are hydrogen and $R^{10}$ is methyl. In certain instances, $R^6$, $R^7$, $R^8$ are hydrogen; $R^9$ is halo; and $R^{10}$ is methyl. In certain instances, $R^6$, $R^7$, $R^8$ are hydrogen; $R^9$ is fluoro; and $R^{10}$ is methyl.

In certain instances, $R^6$, $R^7$, $R^8$, and $R^9$ are hydrogen and $R^{13}$ is hydrogen. In certain instances, $R^6$, $R^7$, and $R^8$ are hydrogen; $R^9$ is halo; and $R^{13}$ is hydrogen. In certain instances, $R^6$, $R^7$, and $R^8$ are hydrogen; $R^9$ is fluoro; and $R^{13}$ is hydrogen.

In certain instances, $R^6$, $R^7$, $R^8$, and $R^9$ are hydrogen and $R^{13}$ is —$CH_2OH$. In certain instances, $R^6$, $R^7$, and $R^9$ are hydrogen; $R^9$ is halo; and $R^{13}$ is —$CH_2OH$. In certain instances, $R^6$, $R^7$, and $R^8$ are hydrogen; $R^9$ is fluoro; and $R^{13}$ is —$CH_2OH$.

In certain instances, $R^6$, $R^7$, $R^8$, and $R^9$ are hydrogen and $R^{13}$ is —$(CH_2)_m$F, wherein m is a number from one to 3. In certain instances, $R^6$, $R^7$, and $R^8$ are hydrogen; $R^9$ is halo; and $R^{13}$ is —$(CH_2)_m$F, wherein m is a number from one to 3. In certain instances, $R^6$, $R^7$, and $R^8$ are hydrogen; $R^9$ is fluoro; and $R^{13}$ is —$(CH_2)_m$F, wherein m is a number from one to 3.

Formula (IV)

The present disclosure provides a compound of Formula (IV):

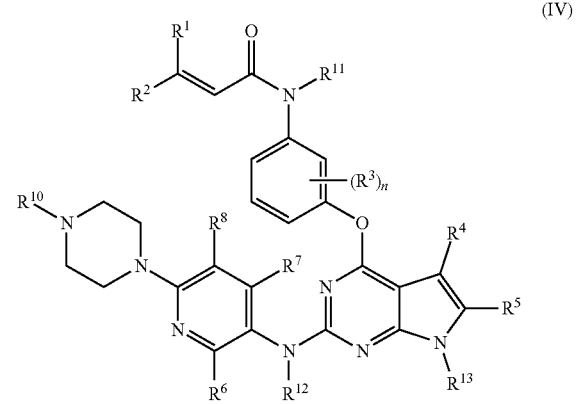

wherein
$R^1$ and $R^2$ are independently selected from hydrogen, halo, $C_{1-6}$ alkyl, and $C_{1-6}$ haloalkyl;
$R^3$ is selected from halo, hydroxyl, $C_{1-6}$ alkyl, $C_{1-6}$ alkoxy, cyano, and nitro;
n is a number from zero to 4;
$R^4$ is selected from hydrogen, $C_{1-6}$ alkyl, $C_{3-7}$ cycloalkyl, and —$NR^{22}R^{23}$;
  wherein the alkyl or cycloalkyl is unsubstituted or substituted with hydroxyl or amino; and
  wherein each $R^{22}$ and $R^{23}$ are independently selected from hydrogen and $C_{1-6}$ alkyl or $R^{22}$ and $R^{23}$ may be joined to form a 3 to 10 membered ring;
$R^5$ is selected from hydrogen and $C_{1-6}$ alkyl;

$R^6$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;

$R^7$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;

$R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;

$R^{10}$ is selected from hydrogen and $C_{1-6}$ alkyl;

$R^{11}$ is selected from hydrogen and $C_{1-6}$ alkyl;

$R^{12}$ is selected from hydrogen and $C_{1-6}$ alkyl; and $R^{13}$ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo;

or a pharmaceutically acceptable salt thereof.

In Formula (IV), $R^1$ and $R^2$ are independently selected from hydrogen, halo, $C_{1-6}$ alkyl, and $C_{1-6}$ haloalkyl. In certain instances, $R^1$ is hydrogen. In certain instances, $R^1$ is $C_{1-6}$ alkyl. In certain instances, $R^1$ is methyl or ethyl. In certain instances, $R^2$ is hydrogen. In certain instances, $R^2$ is $C_{1-6}$ alkyl. In certain instances, $R^2$ is methyl or ethyl. In certain instances, $R^1$ and $R^2$ are hydrogen.

In Formula (IV), n is a number from zero to 4. In certain instances, n is zero. In certain instances, n is one. In certain instances, n is 2. In certain instances, n is 3. In certain instances, n is 4.

In Formula (IV), $R^3$ is selected from halo, hydroxyl, $C_{1-6}$ alkyl, $C_{1-6}$ alkoxy, cyano, and nitro. In certain instances, $R^3$ is halo. In certain instances, $R^3$ is hydroxyl. In certain instances, $R^3$ is $C_{1-6}$ alkyl. In certain instances, $R^3$ is $C_{1-6}$ alkoxy. In certain instances, $R^3$ is cyano. In certain instances, $R^3$ is nitro.

In Formula (IV), $R^4$ is selected from hydrogen, $C_{1-6}$ alkyl, $C_{3-7}$ cycloalkyl, and $-NR^{22}R^{23}$; wherein the alkyl or cycloalkyl is unsubstituted or substituted with hydroxyl or amino; and wherein each $R^{22}$ and $R^{23}$ are independently selected from hydrogen and $C_{1-6}$ alkyl or $R^{22}$ and $R^{21}$ may be joined to form a 3 to 10 membered ring. In certain instances, $R^4$ is hydrogen. In certain instances, $R^4$ is $C_{1-6}$ alkyl. In certain instances, $R^4$ is $C_{3-7}$ cycloalkyl. In certain instances, $R^4$ is $-NR^{22}R^{23}$ In certain instances, $R^4$ is unsubstituted $C_{1-6}$ alkyl. In certain instances, $R^4$ is $C_{1-6}$ alkyl that is substituted with hydroxyl. In certain instances, $R^4$ is $C_{1-3}$ alkyl that is substituted with hydroxyl. In certain instances, $R^4$ is $C_{1-6}$ alkyl that is substituted with amino. In certain instances, $R^4$ is $C_{1-6}$ alkyl that is substituted with $-NH_2$. In certain instances, $R^4$ is $C_{1-6}$ alkyl that is substituted with $-N(CH_3)_2$. In certain instances, $R^4$ is $C_{1-3}$ alkyl that is substituted with $-NH_2$. In certain instances, $R^4$ is $C_{1-3}$ alkyl that is substituted with $-N(CH_3)_2$.

In certain instances, $R^4$ is unsubstituted $C_{3-7}$ cycloalkyl. In certain instances, $R^4$ is unsubstituted $C_3$ cycloalkyl. In certain instances, $R^4$ is unsubstituted $C_4$ cycloalkyl. In certain instances, $R^4$ is unsubstituted $C_{5-6}$ cycloalkyl. In certain instances, $R^4$ is unsubstituted $C_7$ cycloalkyl.

In certain instances, $R^4$ is $-NR^{22}R^{23}$, wherein each $R^{22}$ and $R^{23}$ are independently selected from hydrogen and $C_{1-6}$ alkyl or $R^{22}$ and $R^{23}$ may be joined to form a 3 to 10 membered ring. In certain instances, $R^{22}$ and $R^{23}$ are hydrogen. In certain instances, $R^{22}$ and $R^{23}$ are $C_{1-6}$ alkyl. In certain instances, $R^{22}$ and $R^{23}$ are $C_{1-3}$ alkyl. In certain instances, $R^{22}$ and $R^{23}$ are methyl.

In certain instances, $R^{22}$ and $R^{23}$ may be joined to form a 3 to 10 membered ring, such that $R^4$ is

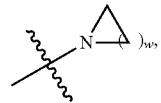

where w is a number from 1 to 8. In certain instances, $R^{22}$ and $R^{23}$ may be joined to form a 3-membered ring. In certain instances, $R^{22}$ and $R^{23}$ may be joined to form a 4-membered ring. In certain instances, $R^{22}$ and $R^{23}$ may be joined to form a 5-membered ring. In certain instances, $R^{22}$ and $R^{23}$ may be joined to form a 6-membered ring. In certain instances, $R^{22}$ and $R^{23}$ may be joined to form a 7-membered ring.

In Formula (IV), $R^5$ is selected from hydrogen and $C_{1-6}$ alkyl. In certain instances, $R^5$ is hydrogen. In certain instances, $R^5$ is $C_{1-6}$ alkyl. In certain instances, $R^5$ is methyl. In certain instances, $R^5$ is ethyl. In certain instances, $R^5$ is $C_{1-3}$ alkyl. In certain instances, $R^5$ is $C_{4-6}$ alkyl.

In Formula (IV), $R^6$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro. In certain instances, $R^6$ is hydrogen. In certain instances, $R^6$ is halo. In certain instances, $R^6$ is fluoro. In certain instances, $R^6$ is chloro. In certain instances, $R^6$ is bromo. In certain instances, $R^6$ is $C_{1-6}$ alkyl. In certain instances, $R^6$ is $C_{1-6}$ haloalkyl. In certain instances, $R^6$ is $C_{2-6}$ alkoxy. In certain instances, $R^6$ is $C_{1-6}$ haloalkoxy. In certain instances, $R^6$ is hydroxyl. In certain instances, $R^6$ is cyano. In certain instances, $R^6$ is nitro.

In Formula (IV), $R^7$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro. In certain instances, $R^7$ is hydrogen. In certain instances, $R^7$ is halo. In certain instances, $R^7$ is fluoro. In certain instances, $R^7$ is chloro. In certain instances, $R^7$ is bromo. In certain instances, $R^7$ is $C_{1-6}$ alkyl. In certain instances, $R^7$ is $C_{1-6}$ haloalkyl. In certain instances, $R^7$ is $C_{2-6}$ alkoxy. In certain instances, $R^7$ is $C_{1-6}$ haloalkoxy. In certain instances, $R^7$ is hydroxyl. In certain instances, $R^7$ is cyano. In certain instances, $R^7$ is nitro.

In Formula (IV), $R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro. In certain instances, $R^8$ is hydrogen. In certain instances, $R^8$ is halo. In certain instances, $R^8$ is fluoro. In certain instances, $R^8$ is chloro. In certain instances, $R^8$ is bromo. In certain instances, $R^8$ is $C_{1-6}$ alkyl. In certain instances, $R^8$ is $C_{1-6}$ haloalkyl. In certain instances, $R^8$ is $C_{1-6}$ alkoxy. In certain instances, $R^8$ is $C_{1-6}$ haloalkoxy. In certain instances, $R^8$ is hydroxyl. In certain instances, $R^8$ is cyano. In certain instances, $R^8$ is nitro.

In Formula (IV), $R^{10}$ is selected from hydrogen and $C_{1-6}$ alkyl. In certain instances, $R^{10}$ is hydrogen. In certain instances, $R^{10}$ is $C_{1-6}$ alkyl. In certain instances, $R^{10}$ is methyl. In certain instances, $R^{10}$ is ethyl. In certain instances, $R^{10}$ is $C_{1-3}$ alkyl. In certain instances, $R^{10}$ is $C_{4-6}$ alkyl.

In Formula (IV), $R^{11}$ is selected from hydrogen and $C_{1-6}$ alkyl. In certain instances, $R^{12}$ is hydrogen. In certain instances, $R^{11}$ is $C_{1-6}$ alkyl. In certain instances, $R^{11}$ is methyl. In certain instances, $R^{11}$ is ethyl. In certain instances, $R^{11}$ is $C_{1-3}$ alkyl. In certain instances, $R^{11}$ is $C_{4-6}$ alkyl.

In Formula (IV), $R^{12}$ is selected from hydrogen and $C_{1-6}$ alkyl. In certain instances, $R^{12}$ is hydrogen. In certain instances, $R^{12}$ is $C_{1-6}$ alkyl. In certain instances, $R^{12}$ is methyl. In certain instances, $R^{12}$ is ethyl. In certain instances, $R^{12}$ is $C_{1-3}$ alkyl. In certain instances, $R^{12}$ is $C_{4-6}$ alkyl.

In Formula (IV), $R^{13}$ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo. In certain instances, $R^{13}$ is hydrogen. In certain instances, $R^{13}$ is $C_{1-6}$ alkyl. In certain instances, $R^{13}$ is $C_{6-20}$ aryl.

In certain instances, $R^{13}$ is unsubstituted $C_{1-6}$ alkyl. In certain instances, $R^{13}$ is $C_{1-6}$ alkyl that is substituted with hydroxyl. In certain instances, $R^{13}$ is —$(CH_2)_m$OH, wherein m is a number from one to 3. In certain instances, $R^{13}$ is —$CH_2$OH. In certain instances, $R^{13}$ is $C_{1-6}$ alkyl that is substituted with $C_{1-6}$ alkoxy.

In certain instances, $R^{13}$ is $C_{1-6}$ alkyl that is substituted with halo. In certain instances, $R^{13}$ is —$(CH_2)_m$X, wherein m is a number from one to 3 and X is halo. In certain instances, $R^{13}$ is $C_{1-6}$ alkyl that is substituted with fluoro. In certain instances, $R^{13}$ is —$(CH_2)_m$F, wherein m is a number from one to 3. In certain instances, $R^{13}$ is —$(CH_2)_2$F.

In certain instances, $R^{13}$ is unsubstituted $C_{6-20}$ aryl. In certain instances, $R^{13}$ is $C_{6-20}$ aryl that is substituted with hydroxyl. In certain instances, $R^{13}$ is $C_{6-20}$ aryl that is substituted with $C_{1-6}$ alkoxy. In certain instances, $R^{13}$ is $C_{6-20}$ aryl that is substituted with halo.

In certain instances, $R^6$, $R^7$, and $R^8$ are hydrogen. In certain instances, $R^6$, $R^7$, and R are hydrogen and $R^{10}$ is methyl. In certain instances, $R^6$, $R^7$, and $R^8$ are hydrogen and $R^{13}$ is hydrogen. In certain instances, $R^6$, $R^7$, and $R^8$ are hydrogen and $R^{13}$ is —$CH_2$OH. In certain instances, $R^6$, $R^7$, and $R^8$ are hydrogen and $R^{13}$ is hydrogen. In certain instances, $R^6$, $R^7$, and $R^8$ are hydrogen and $R^{13}$ is —$(CH_2)_m$F, wherein m is a number from one to 3.

Formula (V)

The present disclosure provides a compound of Formula (V):

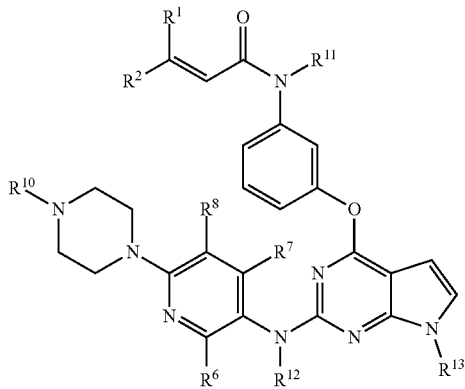

(V)

wherein $R^1$ and $R^2$ are independently selected from hydrogen, halo, $C_{1-6}$ alkyl, and $C_{1-6}$ haloalkyl;

$R^6$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;

$R^7$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;

$R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;

Q is $CR^9$ or N;

$R^9$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;

$R^{10}$ is selected from hydrogen and $C_{1-6}$ alkyl;

$R^{11}$ is selected from hydrogen and $C_{1-6}$ alkyl;

$R^{12}$ is selected from hydrogen and $C_{1-6}$ alkyl;

$R^{13}$ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo;

or a pharmaceutically acceptable salt thereof.

In Formula (V), $R^1$ and $R^2$ are independently selected from hydrogen, halo, $C_{1-6}$ alkyl, and $C_{1-6}$ haloalkyl. In certain instances, $R^1$ is hydrogen. In certain instances, $R^1$ is $C_{1-6}$ alkyl. In certain instances, $R^1$ is methyl or ethyl. In certain instances, $R^2$ is hydrogen. In certain instances, $R^2$ is $C_{1-6}$ alkyl. In certain instances, $R^2$ is methyl or ethyl. In certain instances, $R^1$ and $R^2$ are hydrogen.

In Formula (V), $R^6$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro. In certain instances, $R^6$ is hydrogen. In certain instances, $R^6$ is halo. In certain instances, $R^6$ is fluoro. In certain instances, $R^6$ is chloro. In certain instances, $R^6$ is bromo. In certain instances, $R^6$ is $C_{1-6}$ alkyl. In certain instances, $R^6$ is $C_{1-6}$ haloalkyl. In certain instances, $R^6$ is $C_{2-6}$ alkoxy. In certain instances, $R^6$ is $C_{1-6}$ haloalkoxy. In certain instances, $R^6$ is hydroxyl. In certain instances, $R^6$ is cyano. In certain instances, $R^6$ is nitro.

In Formula (V), $R^7$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro. In certain instances, $R^7$ is hydrogen. In certain instances, $R^7$ is halo. In certain instances, $R^7$ is fluoro. In certain instances, $R^7$ is chloro. In certain instances, $R^7$ is bromo. In certain instances, $R^7$ is $C_{1-6}$ alkyl. In certain instances, $R^7$ is $C_{1-6}$ haloalkyl. In certain instances, $R^7$ is $C_{2-6}$ alkoxy. In certain instances, $R^7$ is $C_{1-6}$ haloalkoxy. In certain instances, $R^7$ is hydroxyl. In certain instances, $R^7$ is cyano. In certain instances, $R^7$ is nitro.

In Formula (V), $R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro. In certain instances, $R^8$ is hydrogen. In certain instances, $R^8$ is halo. In certain instances, $R^8$ is fluoro. In certain instances, $R^8$ is chloro. In certain instances, $R^8$ is bromo. In certain instances, $R^8$ is $C_{1-6}$ alkyl. In certain instances, $R^8$ is $C_{1-6}$ haloalkyl. In certain instances, $R^8$ is $C_{1-6}$ alkoxy. In certain instances, $R^8$ is $C_{1-6}$ haloalkoxy. In certain instances, $R^8$ is hydroxyl. In certain instances, $R^8$ is cyano. In certain instances, $R^8$ is nitro.

In Formula (V), Q is $CR^9$ or N. In certain instances, Q is $CR^9$. In certain instances, Q is N.

In Formula (V), $R^9$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro. In certain instances, $R^9$ is hydrogen. In certain instances, $R^9$ is halo. In certain instances, $R^9$ is fluoro. In certain instances, $R^9$ is chloro. In certain instances, $R^9$ is bromo. In certain instances, $R^9$ is $C_{1-6}$ alkyl. In certain instances, $R^9$ is $C_{1-6}$ haloalkyl. In certain instances, $R^9$ is $C_{1-6}$ alkoxy. In certain instances, $R^9$ is $C_{1-6}$ haloalkoxy. In certain instances, $R^9$ is hydroxyl. In certain instances, $R^9$ is cyano. In certain instances, $R^9$ is nitro.

In Formula (V), $R^{10}$ is selected from hydrogen and $C_{1-6}$ alkyl. In certain instances, $R^{10}$ is hydrogen. In certain instances, $R^{10}$ is $C_{1-6}$ alkyl. In certain instances, $R^{10}$ is methyl. In certain instances, $R^{10}$ is ethyl. In certain instances, $R^{10}$ is $C_{1-3}$ alkyl. In certain instances, $R^{10}$ is $C_{4-6}$ alkyl.

In Formula (V), $R^{11}$ is selected from hydrogen and $C_{1-6}$ alkyl. In certain instances, $R^{11}$ is hydrogen. In certain instances, $R^{11}$ is $C_{1-6}$ alkyl. In certain instances, $R^{11}$ is methyl. In certain instances, $R^{11}$ is ethyl. In certain instances, $R^{11}$ is $C_{1-3}$ alkyl. In certain instances, $R^{11}$ is $C_{4-6}$ alkyl.

In Formula (V), $R^{12}$ is selected from hydrogen and $C_{1-6}$ alkyl. In certain instances, $R^{12}$ is hydrogen. In certain instances, $R^{12}$ is $C_{1-6}$ alkyl. In certain instances, $R^{12}$ is methyl. In certain instances, $R^{12}$ is ethyl. In certain instances, $R^{12}$ is $C_{1-3}$ alkyl. In certain instances, $R^{12}$ is $C_{4-6}$ alkyl.

In Formula (V), $R^{13}$ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo. In certain instances, $R^{13}$ is hydrogen. In certain instances, $R^{13}$ is $C_{1-6}$ alkyl. In certain instances, $R^{13}$ is $C_{6-20}$ aryl.

In certain instances, $R^{13}$ is unsubstituted $C_{1-6}$ alkyl. In certain instances, $R^{13}$ is $C_{1-6}$ alkyl that is substituted with hydroxyl. In certain instances, $R^{13}$ is —$(CH_2)_m OH$, wherein m is a number from one to 3. In certain instances, $R^{13}$ is —$CH_2OH$. In certain instances, $R^{13}$ is $C_{1-6}$ alkyl that is substituted with $C_{1-6}$ alkoxy.

In certain instances, $R^{13}$ is $C_{1-6}$ alkyl that is substituted with halo. In certain instances, $R^{13}$ is —$(CH_2)_m X$, wherein m is a number from one to 3 and X is halo. In certain instances, $R^{13}$ is $C_{1-6}$ alkyl that is substituted with fluoro. In certain instances, $R^{13}$ is —$(CH_2)_m F$, wherein m is a number from one to 3. In certain instances, $R^{13}$ is —$(CH_2)_2 F$.

In certain instances, $R^{13}$ is unsubstituted $C_{6-20}$ aryl. In certain instances, $R^{13}$ is $C_{6-20}$ aryl that is substituted with hydroxyl. In certain instances, $R^{13}$ is $C_{6-20}$ aryl that is substituted with $C_{1-6}$ alkoxy. In certain instances, $R^{13}$ is $C_{6-20}$ aryl that is substituted with halo.

In certain instances, $R^6$, $R^7$, $R^8$, and $R^9$ are hydrogen. In certain instances, $R^6$, $R^7$, and $R^8$ are hydrogen and $R^9$ is halo. In certain instances, $R^6$, $R^7$, and $R^8$ are hydrogen and $R^9$ is fluoro.

In certain instances, $R^6$, $R^7$, $R^8$, and $R^9$ are hydrogen and $R^{10}$ is methyl. In certain instances, $R^6$, $R^7$, $R^8$ are hydrogen; $R^9$ is halo; and $R^{10}$ is methyl. In certain instances, $R^6$, $R^7$, $R^8$ are hydrogen; $R^9$ is fluoro; and $R^{10}$ is methyl.

In certain instances, $R^6$, $R^7$, $R^8$, and $R^9$ are hydrogen and $R^{13}$ is hydrogen. In certain instances, $R^6$, $R^7$, and $R^8$ are hydrogen; $R^9$ is halo; and $R^{13}$ is hydrogen. In certain instances, $R^6$, $R^7$, and $R^8$ are hydrogen; $R^9$ is fluoro; and $R^{13}$ is hydrogen.

In certain instances, $R^6$, $R^7$, $R^8$, and $R^9$ are hydrogen and $R^{13}$ is —$CH_2OH$. In certain instances, $R^6$, $R^7$, and $R^9$ are hydrogen; $R^9$ is halo; and $R^{13}$ is —$CH_2OH$. In certain instances, $R^6$, $R^7$, and $R^8$ are hydrogen; $R^9$ is fluoro; and $R^{13}$ is —$CH_2OH$.

In certain instances, $R^6$, $R^7$, $R^8$, and $R^9$ are hydrogen and $R^{13}$ is —$(CH_2)_m F$, wherein m is a number from one to 3. In certain instances, $R^6$, $R^7$, and $R^8$ are hydrogen; $R^9$ is halo; and $R^{13}$ is —$(CH_2)_m F$, wherein m is a number from one to 3. In certain instances, $R^6$, $R^7$, and $R^8$ are hydrogen; $R^9$ is fluoro; and $R^{13}$ is —$(CH_2)_m F$, wherein m is a number from one to 3.

Formula (VI)

The present disclosure provides a compound of Formula (VI):

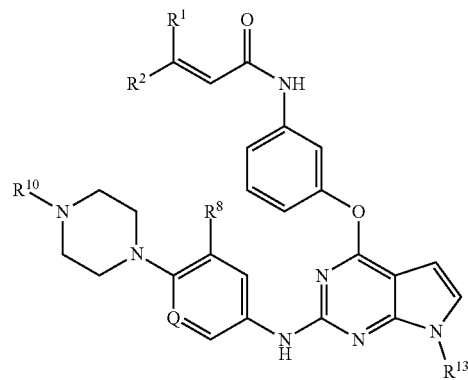

(VI)

wherein
$R^1$ and $R^2$ are independently selected from hydrogen, halo, $C_{1-6}$ alkyl, and $C_{1-6}$ haloalkyl;
$R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;
Q is $CR^9$ or N;
$R^9$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;
$R^{10}$ is selected from hydrogen and $C_{1-6}$ alkyl; and
$R^{13}$ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo;
or a pharmaceutically acceptable salt thereof.

In Formula (VI), $R^1$ and $R^2$ are independently selected from hydrogen, halo, $C_{1-6}$ alkyl, and $C_{1-6}$ haloalkyl. In certain instances, $R^1$ is hydrogen. In certain instances, $R^1$ is $C_{1-6}$ alkyl. In certain instances, $R^1$ is methyl or ethyl. In certain instances, $R^2$ is hydrogen. In certain instances, $R^2$ is $C_{1-6}$ alkyl. In certain instances, $R^2$ is methyl or ethyl. In certain instances, $R^1$ and $R^2$ are hydrogen.

In Formula (VI), $R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro. In certain instances, $R^8$ is hydrogen. In certain instances, $R^8$ is halo. In certain instances, $R^8$ is fluoro. In certain instances, $R^8$ is chloro. In certain instances, $R^8$ is bromo. In certain instances, $R^8$ is $C_{1-6}$ alkyl. In certain instances, $R^8$ is $C_{1-6}$ haloalkyl. In certain instances, $R^8$ is $C_{1-6}$ alkoxy. In certain instances, $R^8$ is $C_{1-6}$ haloalkoxy. In certain instances, $R^8$ is hydroxyl. In certain instances, $R^8$ is cyano. In certain instances, $R^8$ is nitro.

In Formula (VI), Q is $CR^9$ or N. In certain instances, Q is $CR^9$. In certain instances, Q is N.

In Formula (VI), $R^9$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro. In certain instances, $R^9$ is hydrogen. In certain instances, $R^9$ is halo. In certain instances, $R^9$ is fluoro. In certain instances, $R^9$ is chloro. In certain instances, $R^9$ is bromo. In certain instances, $R^9$ is $C_{1-6}$ alkyl. In certain instances, $R^9$ is $C_{1-6}$ haloalkyl. In certain instances, $R^9$ is $C_{1-6}$ alkoxy. In certain instances, $R^9$ is $C_{1-6}$ haloalkoxy. In certain instances, $R^9$ is hydroxyl. In certain instances, $R^9$ is cyano. In certain instances, $R^9$ is nitro.

In Formula (VI), $R^{10}$ is selected from hydrogen and $C_{1-6}$ alkyl. In certain instances, $R^{10}$ is hydrogen. In certain instances, $R^{10}$ is $C_{1-6}$ alkyl. In certain instances, $R^{10}$ is methyl. In certain instances, $R^{10}$ is ethyl. In certain instances, $R^{10}$ is $C_{1-3}$ alkyl. In certain instances, $R^{10}$ is $C_{4-6}$ alkyl.

In Formula (VI), $R^{13}$ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo. In certain instances, $R^{13}$ is hydrogen. In certain instances, $R^{13}$ is $C_{1-6}$ alkyl. In certain instances, $R^{13}$ is $C_{6-20}$ aryl.

In certain instances, $R^{13}$ is unsubstituted $C_{1-6}$ alkyl. In certain instances, $R^{13}$ is $C_{1-6}$ alkyl that is substituted with hydroxyl. In certain instances, $R^{13}$ is —$(CH_2)_m$OH, wherein m is a number from one to 3. In certain instances, $R^{13}$ is —$CH_2$OH. In certain instances, $R^{13}$ is $C_{1-6}$ alkyl that is substituted with $C_{1-6}$ alkoxy.

In certain instances, $R^{13}$ is $C_{1-6}$ alkyl that is substituted with halo. In certain instances, $R^{13}$ is —$(CH_2)_m$X, wherein m is a number from one to 3 and X is halo. In certain instances, $R^{13}$ is $C_{1-6}$ alkyl that is substituted with fluoro. In certain instances, $R^{13}$ is —$(CH_2)_m$F, wherein m is a number from one to 3. In certain instances, $R^{13}$ is —$(CH_2)_2$F.

In certain instances, $R^{13}$ is unsubstituted $C_{6-20}$ aryl. In certain instances, $R^{13}$ is $C_{6-20}$ aryl that is substituted with hydroxyl. In certain instances, $R^{13}$ is $C_{6-20}$ aryl that is substituted with $C_{1-6}$ alkoxy. In certain instances, $R^{13}$ is $C_{6-20}$ aryl that is substituted with halo.

In certain instances, $R^8$ and $R^9$ are hydrogen. In certain instances, $R^8$ is hydrogen and $R^9$ is halo. In certain instances, $R^8$ is hydrogen and $R^9$ is fluoro.

In certain instances, $R^8$ and $R^9$ are hydrogen and $R^{10}$ is methyl. In certain instances, $R^8$ is hydrogen; $R^9$ is halo; and $R^1$ is methyl. In certain instances, $R^8$ is hydrogen; $R^9$ is fluoro; and $R^{10}$ is methyl.

In certain instances, $R^8$ and $R^9$ are hydrogen and $R^{13}$ is hydrogen. In certain instances, $R^9$ is hydrogen; $R^9$ is halo; and $R^{13}$ is hydrogen. In certain instances, $R^9$ is hydrogen; $R^9$ is fluoro; and $R^{13}$ is hydrogen.

In certain instances, $R^8$ and $R^9$ are hydrogen and $R^{13}$ is —$CH_2$OH. In certain instances, $R^8$ is hydrogen; $R^9$ is halo; and $R^{13}$ is —$CH_2$OH. In certain instances, $R^8$ is hydrogen; $R^9$ is fluoro; and $R^{13}$ is —$CH_2$OH.

In certain instances, $R^8$ and $R^9$ are hydrogen and $R^{13}$ is —$(CH_2)_m$F, wherein m is a number from one to 3. In certain instances, $R^9$ is hydrogen; $R^9$ is halo; and $R^{13}$ is —$(CH_2)_m$F, wherein m is a number from one to 3. In certain instances, $R^9$ is hydrogen; $R^9$ is fluoro; and $R^{13}$ is —$(CH_2)_m$F, wherein m is a number from one to 3.

Formula (VII)

The present disclosure provides a compound of Formula (VII):

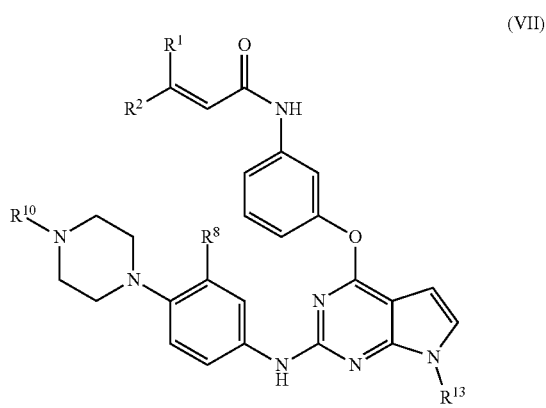

(VII)

wherein $R^1$ and $R^2$ are independently selected from hydrogen, halo, $C_{1-6}$ alkyl, and $C_{1-6}$ haloalkyl;

$R^8$ is selected from halo, $C_{1-6}$ alkyl, $C_{1-6}$ haloalkyl, $C_{1-6}$ alkoxy, $C_{1-6}$ haloalkoxy, hydroxyl, cyano, and nitro;

$R^{10}$ is $C_{1-6}$ alkyl; and $R^{13}$ is hydrogen or $C_{1-6}$ alkyl;

or a pharmaceutically acceptable salt thereof.

In some embodiments of Formula (VII), $R^1$ and $R^2$ are each hydrogen. In other embodiments, $R^8$ is halo, methyl, methoxy, or cyano. In still other embodiments, $R^8$ is halo. In still other embodiments, $R^8$ is fluoro. In some embodiments, $R^{10}$ is methyl, ethyl, or isopropyl. In other embodiments, $R^{10}$ is methyl. In some embodiments, $R^{13}$ is hydrogen, methyl, ethyl, or isopropyl. In other embodiments, $R^{13}$ is hydrogen.

In some embodiments of compounds of Formulae (I)-(VI), $R^6$ and $R^7$ may also be methoxy, provided that neither $R^6$ nor $R^7$ is methoxy when $R^{10}$ is methyl.

In certain embodiments, the present disclosure provides a compound selected from:

| Compound | Structure | Chemical Name |
|---|---|---|
| 1 | ![structure] | N-(3-((2-((4-(4-methylpiperazin-1-yl)phenyl)amino)-7H-pyrrolo[2,3-d]pyrimidin-4-yl)oxy)phenyl)acrylamide |

-continued

| Compound | Structure | Chemical Name |
|---|---|---|
| 2 | 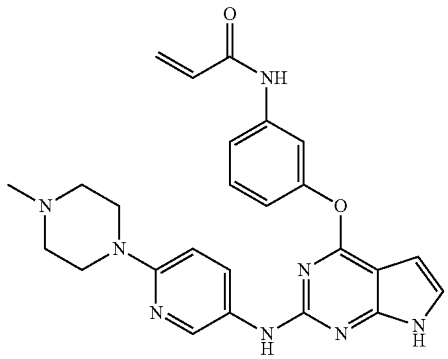 [SMILES: C=CC(=O)Nc1cccc(Oc2nc(Nc3ccc(N4CCN(C)CC4)nc3)nc3[nH]ccc23)c1] | N-(3-((2-((6-(4-methylpiperazin-1-yl)pyridin-3-yl)amino)-7H-pyrrolo[2,3-d]pyrimidin-4-yl)oxy)phenyl)acrylamide |
| 3 | 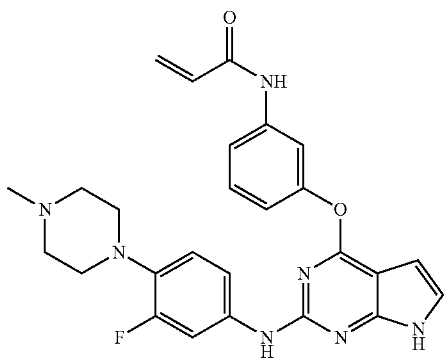 [SMILES: C=CC(=O)Nc1cccc(Oc2nc(Nc3ccc(N4CCN(C)CC4)c(F)c3)nc3[nH]ccc23)c1] | N-(3-((2-((3-fluoro-4-(4-methylpiperazin-1-yl)phenyl)amino)-7H-pyrrolo[2,3-d]pyrimidin-4-yl)oxy)phenyl)acrylamide |
| 4 | 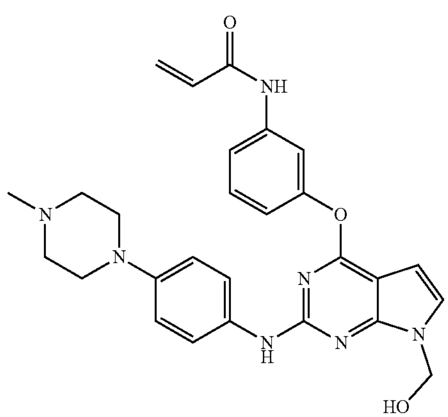 [SMILES: C=CC(=O)Nc1cccc(Oc2nc(Nc3ccc(N4CCN(C)CC4)cc3)nc3c2ccn3CO)c1] | N-(3-((7-(hydroxymethyl)-2-((4-(4-methylpiperazin-1-yl)phenyl)amino)-7H-pyrrolo[2,3-d]pyrimidin-4-yl)oxy)phenyl)acrylamide |
| 5 | 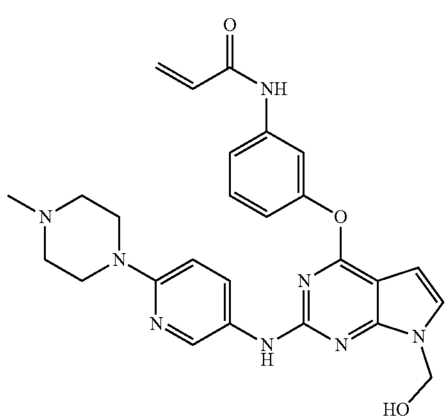 [SMILES: C=CC(=O)Nc1cccc(Oc2nc(Nc3ccc(N4CCN(C)CC4)nc3)nc3c2ccn3CO)c1] | N-(3-((7-(hydroxymethyl)-2-((6-(4-methylpiperazin-1-yl)pyridin-3-yl)amino)-7H-pyrrolo[2,3-d]pyrimidin-4-yl)oxy)phenyl)acrylamide |

-continued

| Compound | Structure | Chemical Name |
|---|---|---|
| 6 | 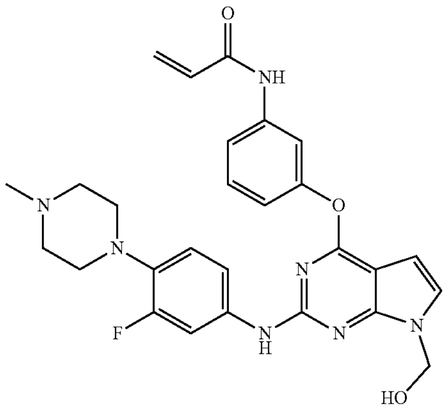 [SMILES: C=CC(=O)Nc1cccc(Oc2nc(Nc3ccc(N4CCN(C)CC4)c(F)c3)nc3c2ccn3CO)c1] | N-(3-((2-((3-fluoro-4-(4-methylpiperazin-1-yl)phenyl)amino)-7-(hydroxymethyl)-7H-pyrrolo[2,3-d]pyrimidin-4-yl)oxy)phenyl)acrylamide; and |
| 7 | | N-(3-((7-(2-fluoroethyl)-2-((4-(4-methylpiperazin-1-yl)phenyl)amino)-7H-pyrrolo[2,3-d]pyrimidin-4-yl)oxy)phenyl)acrylamide | and pharmaceutically acceptable salts thereof.

In certain embodiments, the present disclosure provides a compound selected from:

| Compound | Structure | Chemical Name |
|---|---|---|
| 8 | 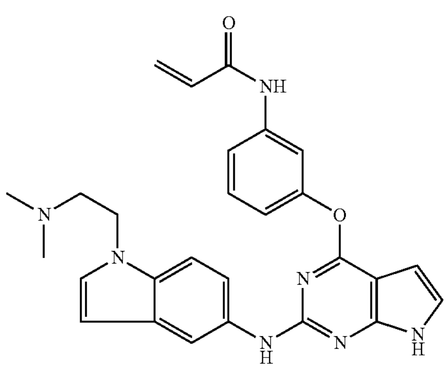 [SMILES: C=CC(=O)Nc1cccc(Oc2nc(Nc3ccc4c(ccn4CCN(C)C)c3)nc3[nH]ccc23)c1] | N-(3-((2-((1-(2-(dimethylamino)ethyl)-1H-indol-5-yl)amino)-7H-pyrrolo[2,3-d]pyrimidin-4-yl)oxy)phenyl)acrylamide |

-continued

| Compound | Structure | Chemical Name |
|---|---|---|
| 9 | 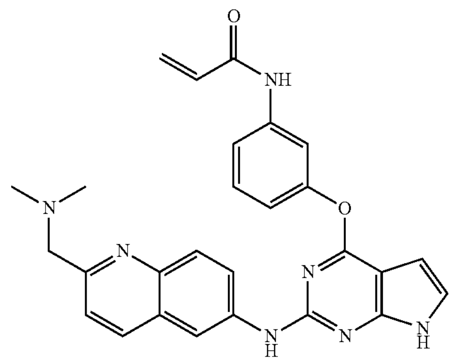 [SMILES: C=CC(=O)Nc1cccc(Oc2nc(Nc3ccc4nc(CN(C)C)ccc4c3)nc3[nH]ccc23)c1] | N-(3-((2-((2-((dimethylamino)methyl)quinolin-6-yl)amino)-7H-pyrrolo[2,3-d]pyrimidin-4-yl)oxy)phenyl)acrylamide |
| 10 | 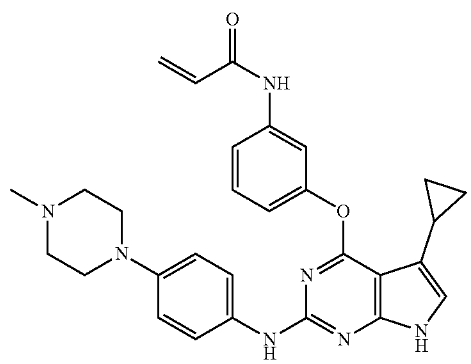 [SMILES: C=CC(=O)Nc1cccc(Oc2nc(Nc3ccc(N4CCN(C)CC4)cc3)nc3[nH]cc(C4CC4)c23)c1] | N-(3-((5-cyclopropyl-2-((4-(4-methylpiperazin-1-yl)phenyl)amino)-7H-pyrrolo[2,3-d]pyrimidin-4-yl)oxy)phenyl)acrylamide |
| 11 | 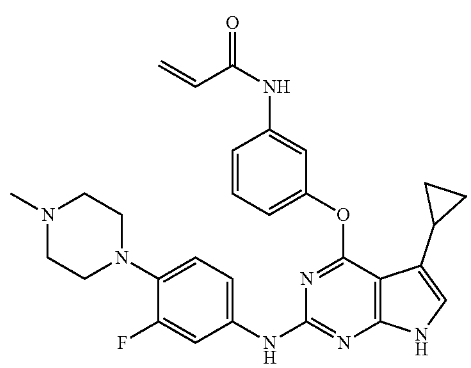 [SMILES: C=CC(=O)Nc1cccc(Oc2nc(Nc3ccc(N4CCN(C)CC4)c(F)c3)nc3[nH]cc(C4CC4)c23)c1] | N-(3-((5-cyclopropyl-2-((3-fluoro-4-(4-methylpiperazin-1-yl)phenyl)amino)-7H-pyrrolo[2,3-d]pyrimidin-4-yl)oxy)phenyl)acrylamide |
| 12 | 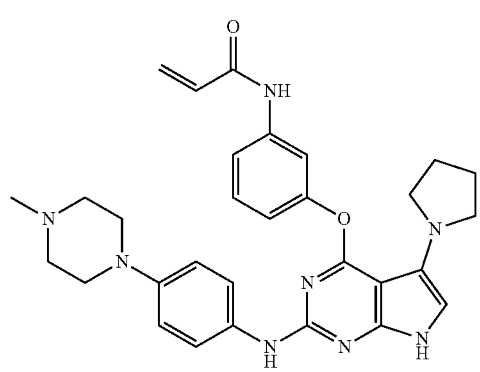 [SMILES: C=CC(=O)Nc1cccc(Oc2nc(Nc3ccc(N4CCN(C)CC4)cc3)nc3[nH]cc(N4CCCC4)c23)c1] | N-(3-((2-((4-(4-methylpiperazin-1-yl)phenyl)amino)-5-(pyrrolidin-1-yl)-7H-pyrrolo[2,3-d]pyrimidin-4-yl)oxy)phenyl)acrylamide |

-continued

| Compound | Structure | Chemical Name |
|---|---|---|
| 13 | 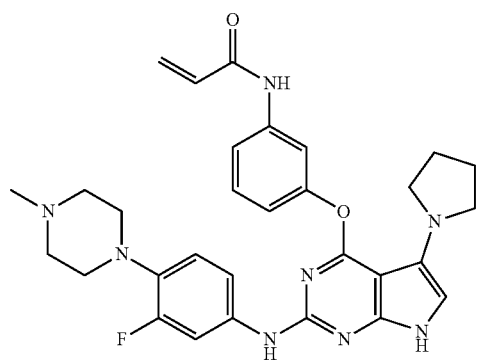 [SMILES: C=CC(=O)Nc1cccc(Oc2nc(Nc3ccc(N4CCN(C)CC4)c(F)c3)nc3[nH]cc(N4CCCC4)c23)c1] | N-(3-((2-((3-fluoro-4-(4-methylpiperazin-1-yl)phenyl)amino)-5-(pyrrolidin-1-yl)-7H-pyrrolo[2,3-d]pyrimidin-4-yl)oxy) phenyl)acrylamide |
| 14 | 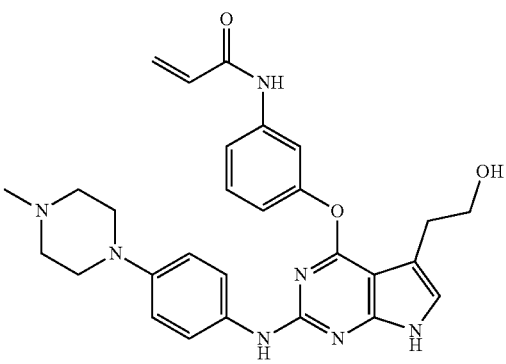 [SMILES: C=CC(=O)Nc1cccc(Oc2nc(Nc3ccc(N4CCN(C)CC4)cc3)nc3[nH]cc(CCO)c23)c1] | N-(3-((5-(2-hydroxyethyl)-2-((4-(4-methylpiperazin-1-yl)phenyl)amino)-7H-pyrrolo[2,3-d]pyrimidin-4-yl)oxy) phenyl)acrylamide |
| 15 | 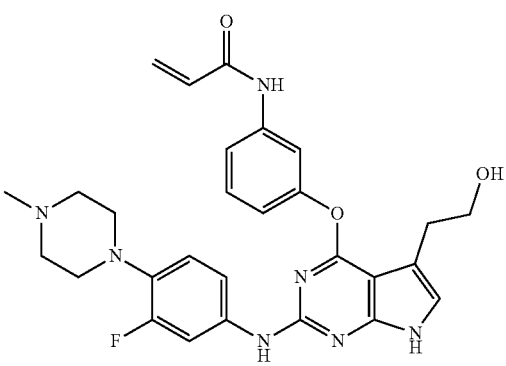 [SMILES: C=CC(=O)Nc1cccc(Oc2nc(Nc3ccc(N4CCN(C)CC4)c(F)c3)nc3[nH]cc(CCO)c23)c1] | N-(3-((2-((3-fluoro-4-(4-methylpiperazin-1-yl)phenyl)amino)-5-(2-hydroxyethyl)-7H-pyrrolo[2,3-d]pyrimidin-4-yl)oxy) phenyl)acrylamide |
| 16 | 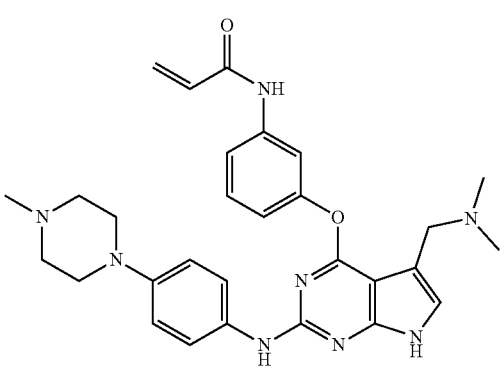 | N-(3-((5-((dimethylamino)methyl)-2-((4-(4-methylpiperazin-1-yl)phenyl)amino)-7H-pyrrolo[2,3-d]pyrimidin-4-yl)oxy) phenyl)acrylamide |

| Compound | Structure | Chemical Name |
| --- | --- | --- |
| 17 | 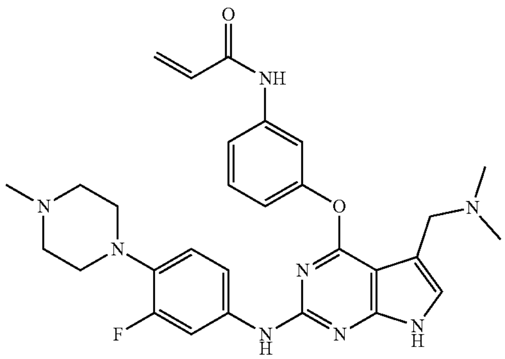 | N-(3-((5-((dimethylamino)methyl)-2-((3-fluoro-4-(4-methylpiperazin-1-yl)phenyl)amino)-7H-pyrrolo[2,3-d]pyrimidin-4-yl)oxy)phenyl)acrylamide |
| 18 | 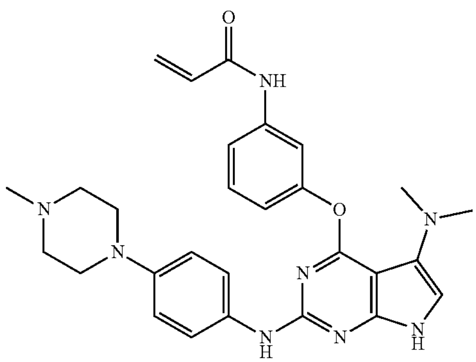 | N-(3-((5-(dimethylamino)-2-((4-(4-methylpiperazin-1-yl)phenyl)amino)-7H-pyrrolo[2,3-d]pyrimidin-4-yl)oxy)phenyl)acrylamide |
| 19 | 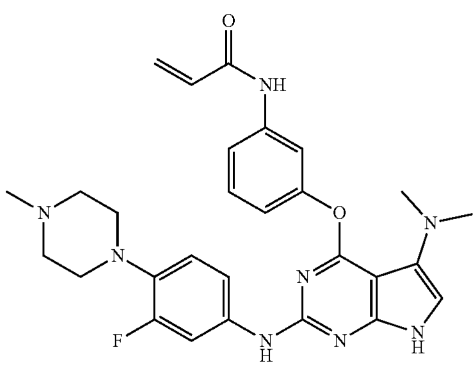 | N-(3-((5-(dimethylamino)-2-((3-fluoro-4-(4-methylpiperazin-1-yl)phenyl)amino)-7H-pyrrolo[2,3-d]pyrimidin-4-yl)oxy)phenyl)acrylamide |
| 20 | 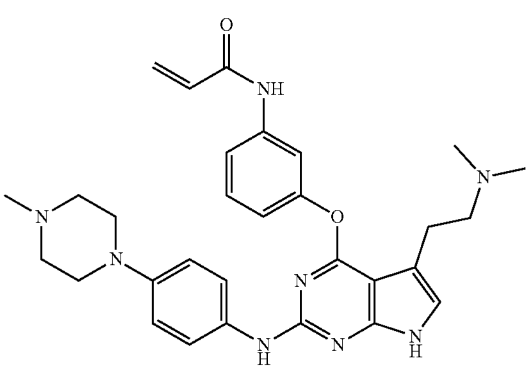 | N-(3-((5-(2-(dimethylamino)ethyl)-2-((4-(4-methylpiperazin-1-yl)phenyl)amino)-7H-pyrrolo[2,3-d]pyrimidin-4-yl)oxy)phenyl)acrylamide |

| Compound | Structure | Chemical Name |
|---|---|---|
| 21 | 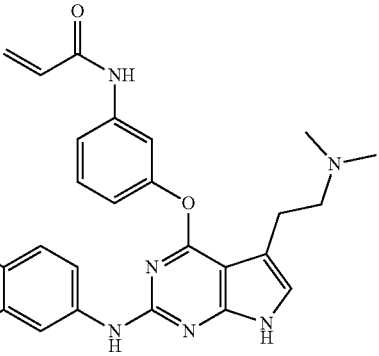 | N-(3-((5-(2-(dimethylamino)ethyl)-2-((3-fluoro-4-(4-methylpiperazin-1-yl)phenyl)amino)-7H-pyrrolo[2,3-d]pyrimidin-4-yl)oxy)phenyl)acrylamide |
| 22 | 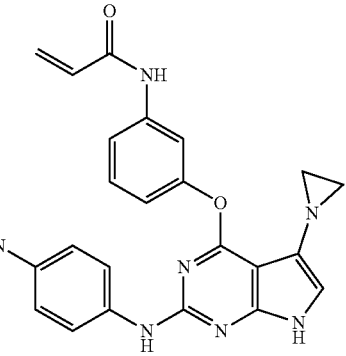 | N-(3-((5-(aziridin-1-yl)-2-((4-(4-methylpiperazin-1-yl)phenyl)amino)-7H-pyrrolo[2,3-d]pyrimidin-4-yl)oxy)phenyl)acrylamide |
| 23 | 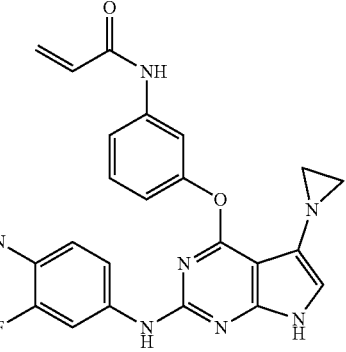 | N-(3-((5-(aziridin-1-yl)-2-((3-fluoro-4-(4-methylpiperazin-1-yl)phenyl)amino)-7H-pyrrolo[2,3-d]pyrimidin-4-yl)oxy)phenyl)acrylamide |
| 24 | 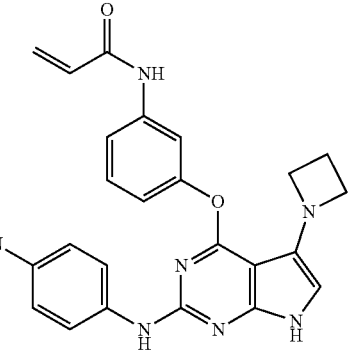 | N-(3-((5-(azetidin-1-yl)-2-((4-(4-methylpiperazin-1-yl)phenyl)amino)-7H-pyrrolo[2,3-d]pyrimidin-4-yl)oxy)phenyl)acrylamide |

-continued

| Compound | Structure | Chemical Name |
|---|---|---|
| 25 | 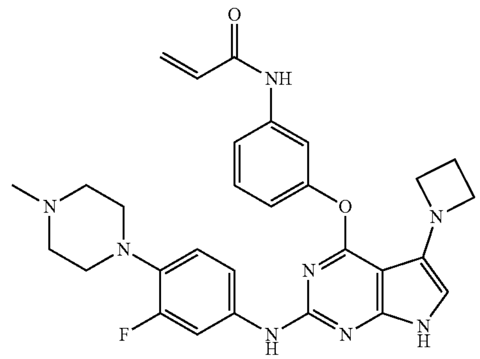 [SMILES: C=CC(=O)Nc1cccc(Oc2nc(Nc3ccc(N4CCN(C)CC4)c(F)c3)nc3[nH]cc(N4CCC4)c23)c1] | N-(3-((5-(azetidin-1-yl)-2-((3-fluoro-4-(4-methylpiperazin-1-yl)phenyl)amino)-7H-pyrrolo[2,3-d]pyrimidin-4-yl)oxy)phenyl)acrylamide |
| 26 | 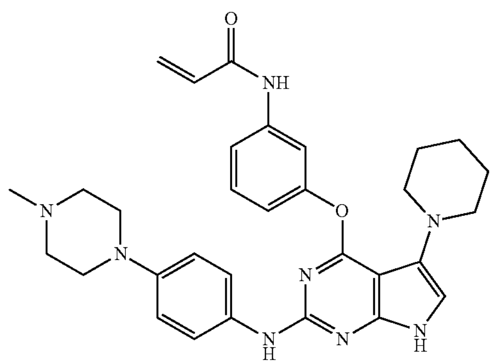 [SMILES: C=CC(=O)Nc1cccc(Oc2nc(Nc3ccc(N4CCN(C)CC4)cc3)nc3[nH]cc(N4CCCCC4)c23)c1] | N-(3-((2-((4-(4-methylpiperazin-1-yl)phenyl)amino)-5-(piperidin-1-yl)-7H-pyrrolo[2,3-d]pyrimidin-4-yl)oxy)phenyl)acrylamide |
| 27 | 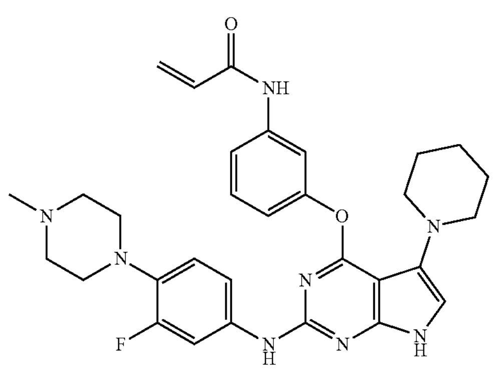 [SMILES: C=CC(=O)Nc1cccc(Oc2nc(Nc3ccc(N4CCN(C)CC4)c(F)c3)nc3[nH]cc(N4CCCCC4)c23)c1] | N-(3-((2-((3-fluoro-4-(4-methylpiperazin-1-yl)phenyl)amino)-5-(piperidin-1-yl)-7H-pyrrolo[2,3-d]pyrimidin-4-yl)oxy)phenyl)acrylamide |
| 28 | 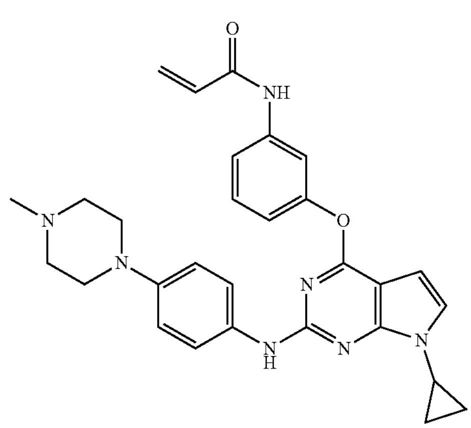 [SMILES: C=CC(=O)Nc1cccc(Oc2nc(Nc3ccc(N4CCN(C)CC4)cc3)nc3c2ccn3C2CC2)c1] | N-(3-((7-cyclopropyl-2-((4-(4-methylpiperazin-1-yl)phenyl)amino)-7H-pyrrolo[2,3-d]pyrimidin-4-yl)oxy)phenyl)acrylamide |

-continued
| Compound | Structure | Chemical Name |
|---|---|---|
| 29 | 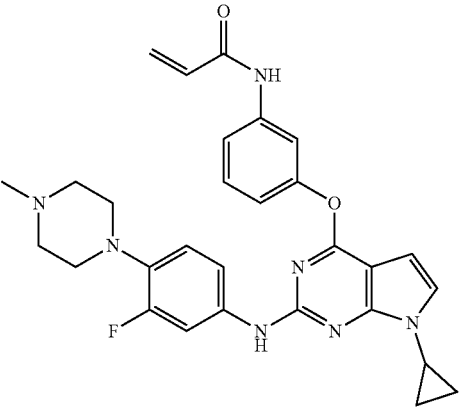 [SMILES: C=CC(=O)Nc1cccc(Oc2nc(Nc3ccc(N4CCN(C)CC4)c(F)c3)nc3c2ccn3C2CC2)c1] | N-(3-((7-cyclopropyl-2-((3-fluoro-4-(4-methylpiperazin-1-yl)phenyl)amino)-7H-pyrrolo[2,3-d]pyrimidin-4-yl)oxy)phenyl)acrylamide |
| 30 | 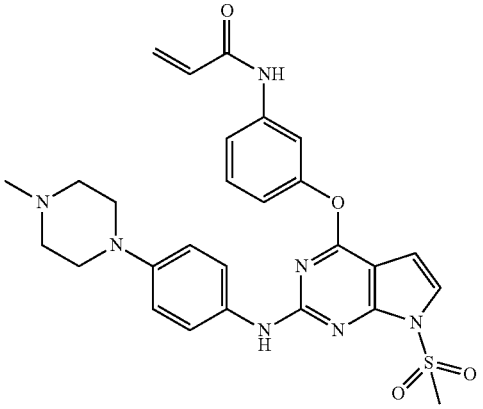 [SMILES: C=CC(=O)Nc1cccc(Oc2nc(Nc3ccc(N4CCN(C)CC4)cc3)nc3c2ccn3S(C)(=O)=O)c1] | N-(3-((2-((4-(4-methylpiperazin-1-yl)phenyl)amino)-7-(methylsulfonyl)-7H-pyrrolo[2,3-d]pyrimidin-4-yl)oxy)phenyl)acrylamide |
| 31 | 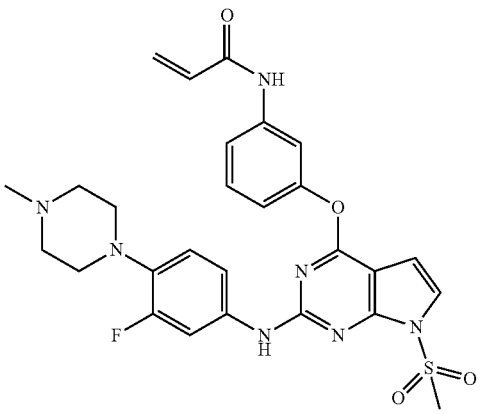 [SMILES: C=CC(=O)Nc1cccc(Oc2nc(Nc3ccc(N4CCN(C)CC4)c(F)c3)nc3c2ccn3S(C)(=O)=O)c1] | N-(3-((2-((3-fluoro-4-(4-methylpiperazin-1-yl)phenyl)amino)-7-(methylsulfonyl)-7H-pyrrolo[2,3-d]pyrimidin-4-yl)oxy)phenyl)acrylamide |

-continued

| Compound | Structure | Chemical Name |
|---|---|---|
| 32 | 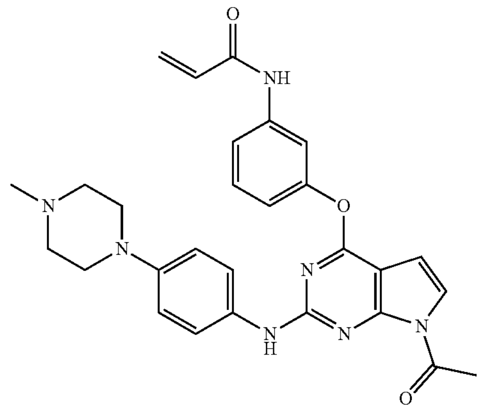 [SMILES: C=CC(=O)Nc1cccc(Oc2nc(Nc3ccc(N4CCN(C)CC4)cc3)nc3c2ccn3C(C)=O)c1] | N-(3-((7-acetyl-2-((4-(4-methylpiperazin-1-yl)phenyl)amino)-7H-pyrrolo[2,3-d]pyrimidin-4-yl)oxy)phenyl)acrylamide |
| 33 | 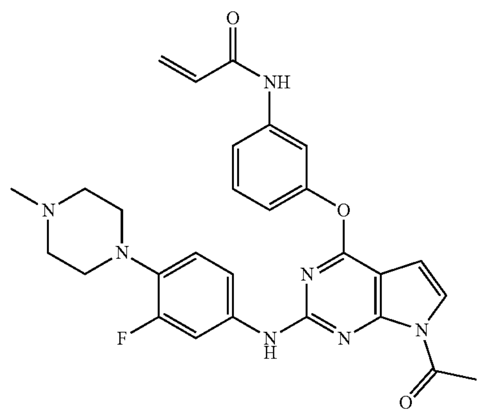 [SMILES: C=CC(=O)Nc1cccc(Oc2nc(Nc3ccc(N4CCN(C)CC4)c(F)c3)nc3c2ccn3C(C)=O)c1] | N-(3-((7-acetyl-2-((3-fluoro-4-(4-methylpiperazin-1-yl)phenyl)amino)-7H-pyrrolo[2,3-d]pyrimidin-4-yl)oxy)phenyl)acrylamide |
| 34 | 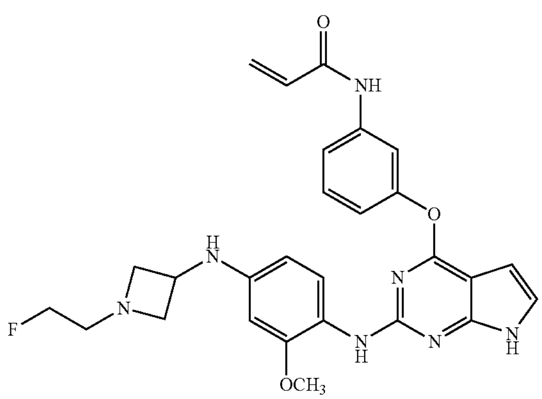 [SMILES: C=CC(=O)Nc1cccc(Oc2nc(Nc3ccc(NC4CN(CCF)C4)cc3OC)nc3[nH]ccc23)c1] | N-(3-(2-(4-(1-(2-fluoroethyl)azetidin-3-ylamino)-2-methoxyphenylamino)-7H-pyrrolo[2,3-d]pyrimidin-4-yloxy)phenyl)acrylamide |
| 35 | 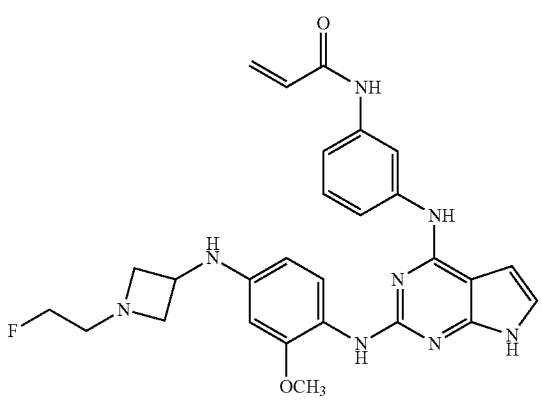 | N-(3-(2-(4-(1-(2-fluoroethyl)azetidin-3-ylamino)-2-methoxyphenylamino)-7H-pyrrolo[2,3-d]pyrimidin-4-ylamino)phenyl)acrylamide; and |

| Compound | Structure | Chemical Name |
|---|---|---|
| 36 | 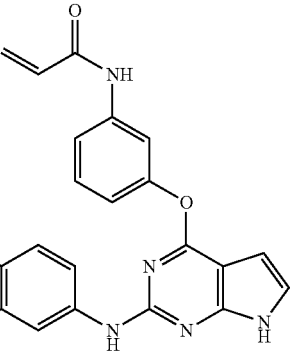 | N-(3-((2-((2-(piperidin-1-ylmethyl)quinolin-6-yl)amino)-7H-pyrrolo[2,3-d]pyrimidin-4-yl)oxy)phenyl)acrylamide | and pharmaceutically acceptable salts thereof.

In certain embodiments, the present disclosure provides Compound 3, N-(3-((2-((3-fluoro-4-(4-methylpiperazin-1-yl)phenyl)amino)-7H-pyrrolo[2,3-d]pyrimidin-4-yl)oxy)phenyl)acrylamide,

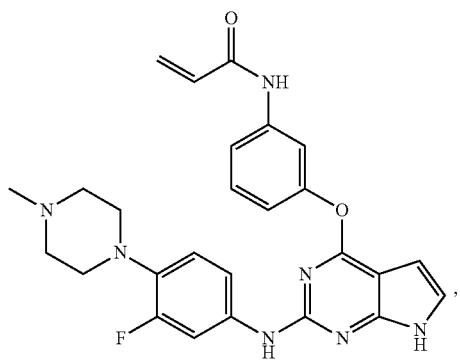 [SMILES: C=CC(=O)Nc1cccc(Oc2nc(Nc3ccc(N4CCN(C)CC4)c(F)c3)nc3[nH]ccc23)c1]

and pharmaceutically acceptable salts thereof. In certain embodiments, the present disclosure provides the maleate salt of Compound 3, N-(3-((2-((3-fluoro-4-(4-methylpiperazin-1-yl)phenyl)amino)-7H-pyrrolo[2,3-d]pyrimidin-4-yl)oxy)phenyl)acrylamide. In certain embodiments, the present disclosure provides the hydrochloride salt of Compound 3, N-(3-((2-((3-fluoro-4-(4-methylpiperazin-1-yl)phenyl)amino)-7H-pyrrolo[2,3-d]pyrimidin-4-yl)oxy)phenyl)acrylamide.

The disclosed pharmaceutical compositions can be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. Preferably, the compositions are formulated for intravenous or oral administration.

For oral administration, the compounds of the embodiments may be provided in a solid form, such as a tablet or capsule, or as a solution, emulsion, or suspension. To prepare the oral compositions, the compounds of the embodiments may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s)

mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, the compounds of the embodiments may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the pharmaceutical compositions may be administered using, for example, a spray formulation also containing a suitable carrier.

For topical applications, the compounds of the embodiments are preferably formulated as creams or ointments or a similar vehicle suitable for topical administration. For topical administration, the compounds of the embodiments may be mixed with a pharmaceutical carrier at a concentration of about 0.1% to about 10% of drug to vehicle. Another mode of administering the compounds of the embodiments may utilize a patch formulation to effect transdermal delivery.

In certain embodiments, the present disclosure provides pharmaceutical composition comprising a compound of formulae (I)-(VIII) and methylcellulose. In certain embodiments, methylcellulose is in a suspension of about 0.1, 0.2, 0.3, 0.4, or 0.5 to about 1%. In certain embodiments, methylcellulose is in a suspension of about 0.1 to about 0.5, 0.6, 0.7, 0.8, 0.9, or 1%. In certain embodiments, methylcellulose is in a suspension of about 0.1 to about 1%. In certain embodiments, methylcellulose is in a suspension of about 0.1, 0.2, 0.3, 0.4, 0.5, 0.6, 0.7, 0.8, 0.8, or 1%. In certain embodiments, methylcellulose is in a suspension of about 0.5%.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

One of ordinary skill in the art may modify the formulations within the teachings of the specification to provide numerous formulations for a particular route of administration. In particular, the compounds may be modified to render them more soluble in water or other vehicle. It is also well within the ordinary skill of the art to modify the route of administration and dosage regimen of a particular compound in order to manage the pharmacokinetics of the present compounds for maximum beneficial effect in a patient.

The term "subject" refers to a mammalian patient in need of such treatment, such as a human.

The compounds can be administered to a subject in need of treatment for a proliferation disorder. An example of a proliferation disorder is cancer. In certain instances, the compounds are useful to treat sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, and pancreatic cancer.

In one aspect, the compounds and pharmaceutical compositions of the embodiments can be administered to a subject in need of treatment of a condition associated with EGFR inhibitory activity targeting substantially a mutated EGFR but not substantially the wild type EGFR. In some embodiments, the mutated EGFR comprises a T790M mutation. The present disclosure provides use of a compound of Formulae (I)-(VIII) in the preparation of a medicament for the treatment of such conditions, and the use of such compounds and salts for treatment of such conditions.

In another aspect, the present disclosure provides a method of inhibiting mutated EGFR in a cell comprising contacting the cell with an effective amount of at least one compound of Formulae (I)-(VIII) or a salt thereof, and/or with at least one pharmaceutical composition of the embodiments, wherein the contacting is in vitro, ex vivo, or in vivo. In some embodiments, the mutated EGFR comprises a T790M mutation.

In the inhibitory methods of the embodiments, an "effective amount" means an amount sufficient to inhibit mutated EGFR but not the wild type EGFR. In some embodiments, the mutated EGFR comprises a T790M mutation. Measuring the degree of inhibition may be performed by routine analytical methods such as those described below. Such modulation is useful in a variety of settings, including in vitro assays. Other settings include ex vivo and in vivo.

In treatment methods according to the embodiments, an "effective amount" means an amount or dose sufficient to generally bring about the desired therapeutic benefit in subjects needing such treatment. Effective amounts or doses of the compounds of the embodiments may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about 1 ag to 2 mg of active agent per kilogram of subject's body weight per day, preferably about 0.05 to 100 mg/kg/day, or about 1 to 35 mg/kg/day, or about 0.1 to 10 mg/kg/day. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The methods of the embodiments comprise administering an effective amount of at least one compound of Formula (I)-(VIII) or the embodiments thereof; optionally the compound may be administered in combination with one or more additional therapeutic agents, particularly therapeutic agents known to be useful for treating a proliferative disorder or cancer afflicting the subject.

The additional active ingredients may be administered in a separate pharmaceutical composition from a compound of the embodiments or may be included with a compound of the embodiments in a single pharmaceutical composition. The additional active ingredients may be administered simultaneously with, prior to, or after administration of a compound of the embodiments.

Chemical Synthesis

Exemplary chemical entities useful in methods of the embodiments will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I). One of ordinary skill in the art will also recognize that the methods described in these exemplary schemes are also applicable to the preparation of compounds of Formula (VIII), as well as compounds of Formulae (II)-(VII).

A representative synthesis for subject compounds is shown in Scheme 1.

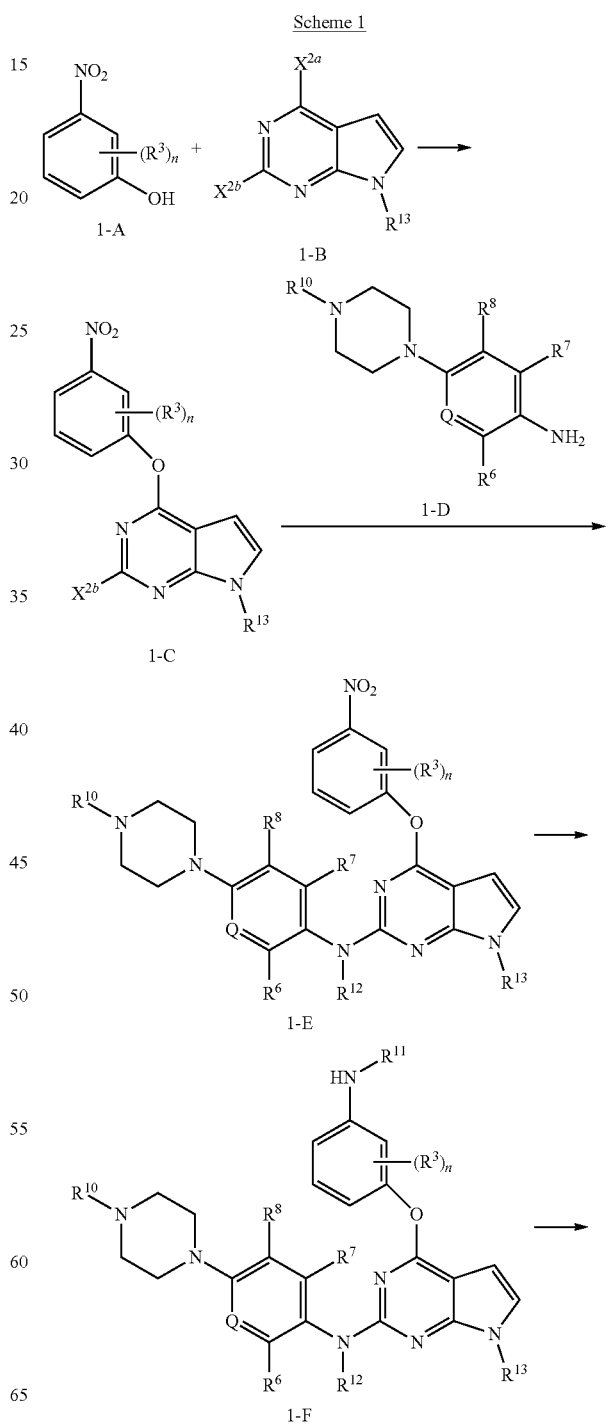

-continued

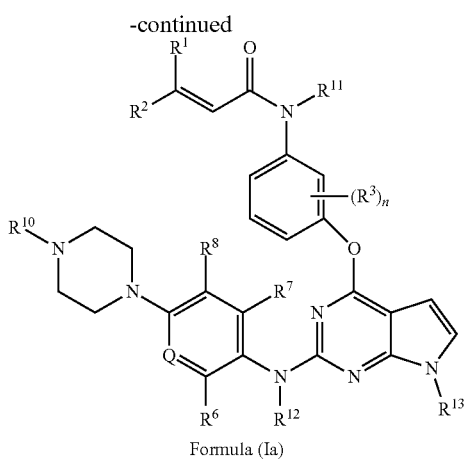

Formula (Ia)

In Scheme 1, the variables are as defined herein. As discussed below, $X^{2a}$ and $X^{2b}$ comprise a leaving group. Starting materials may be obtained from commercial sources or via well-established synthetic procedures.

Referring to Scheme 1, reaction of Compound 1-A with Compound 1-B through a nucleophilic reaction forms Compound 1-C. In Compound 1-A, the hydroxyl group is a nucleophile that can provide the ether linkage in Compound 1-C. The nucleophile can react in a nucleophilic substitution in which the nucleophile displaces a leaving group on the other reactant. In alternative embodiments, aniline or thiophenol analogs of 1-A are used to access compounds in which $X^1$ is NH or S. In Compound 1-B, $X^{2a}$ comprises a leaving group. Examples of leaving groups include, but are not limited to, halo, triflate, fluorosulfonate, tosylate, or mesylate.

With continued reference to Scheme 1, reaction of Compound 1-C with Compound 1-D under conditions of Buchwald-Hartwig cross-coupling reaction provides Compound 1-E. In Compound 1-D, the amino group is a nucleophile that can provide the amino linkage in Compound 1-E. The nucleophile can react in a nucleophilic aromatic substitution in which the nucleophile displaces a leaving group on the other reactant. In Compound 1-C, $X^{2b}$ comprises a leaving group. Examples of leaving groups include, but are not limited to, halo, triflate, fluorosulfonate, tosylate, or mesylate.

With continued reference to Scheme 1, the nitro group in Compound 1-E is reduced to give an amino group in Compound 1-F. The reduction of nitro group can be carried out using an acid catalyst and a metal, or using a metallic catalyst under hydrogen gas. In the acid catalyst reaction, iron, zinc, lithium, sodium, or tin (typically, tin chloride) can be used as the metal, and inorganic acids such as hydrochloric acid, sulfuric acid, nitric acid, or phosphoric acid; organic carboxylic acids such as acetic acid or trifluoroacetic acid; amine acid salts such as ammonium chloride, can be used as the acid catalyst. Also, in the reduction using a metallic catalyst under hydrogen gas, palladium, nickel, platinum, ruthenium, or rhodium, can be used as the metallic catalyst.

With continued reference to Scheme 1, amidation of Compound 1-F gives a compound of Formula (I). In the amidation reaction, Compound 1-F reacts with an acryloyl derivative comprising a leaving group. Examples of leaving groups include, but are not limited to, halo, triflate, fluorosulfonate, tosylate, or mesylate. An amidation reaction can be carried out in a solvent, such as dimethylformamide or dichloromethane, in the presence of a base, such as triethylamine or diisopropylethylamine. The amidation reaction can be conducted using a coupling agent, such as for example, dicyclohexylcarbodiimide (DCC), 1-ethyl-3-(3-dimethylaminopropyl) carbodiimide (EDC), or N-[dimethylamino-1H-1,2,3-triazole[4,5-b]-pyridin-1-ylmethylene]-N-methyl-methaneaminium (HATU) together with 1-hydroxy-1H-benzotriazole (HOBT).

In certain embodiments, a representative synthesis for subject compounds is shown in Scheme 2.

Scheme 2

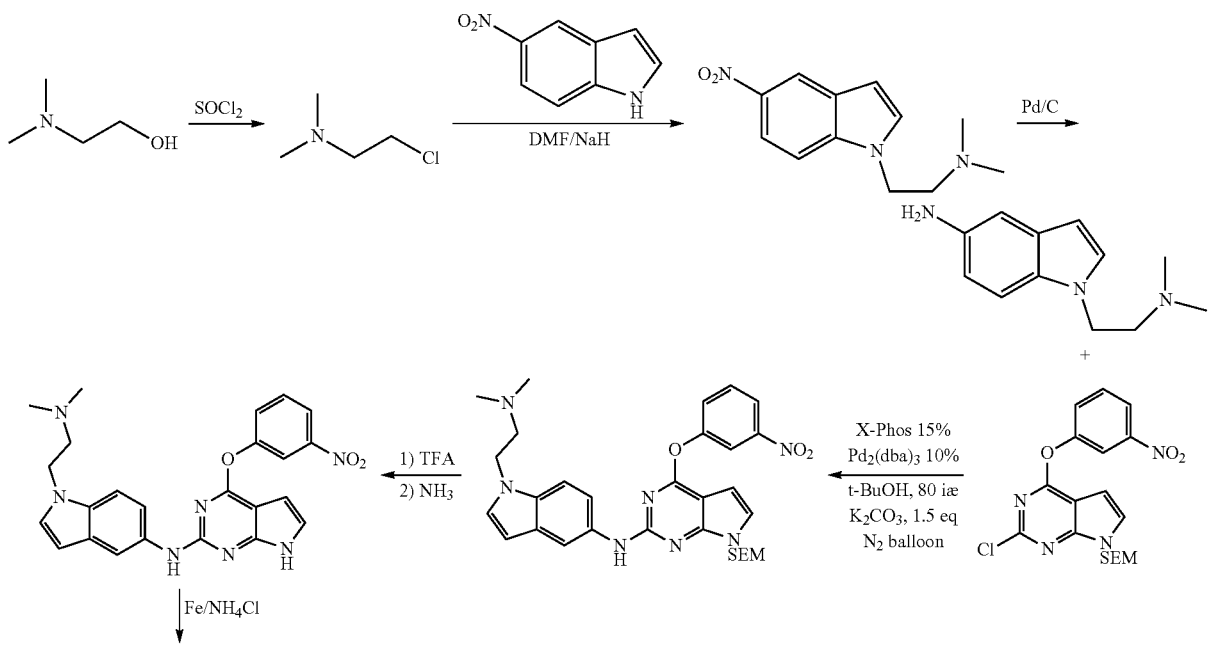

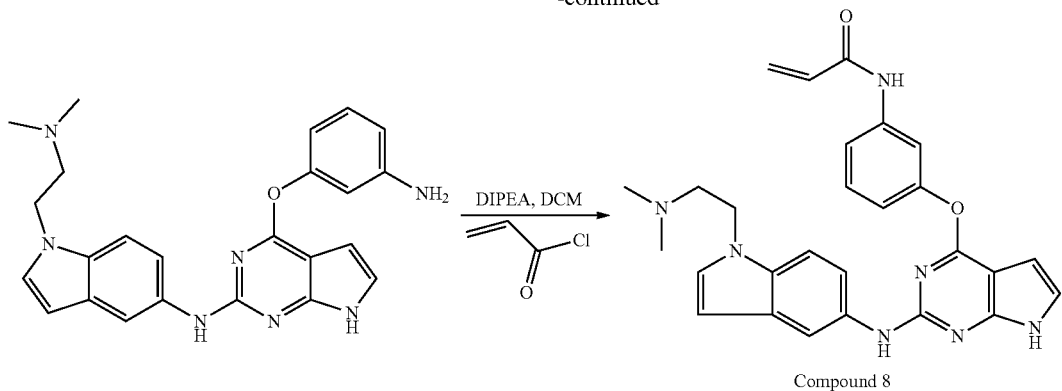
Compound 8
In certain embodiments, a representative synthesis for subject compounds is shown in Scheme 3.
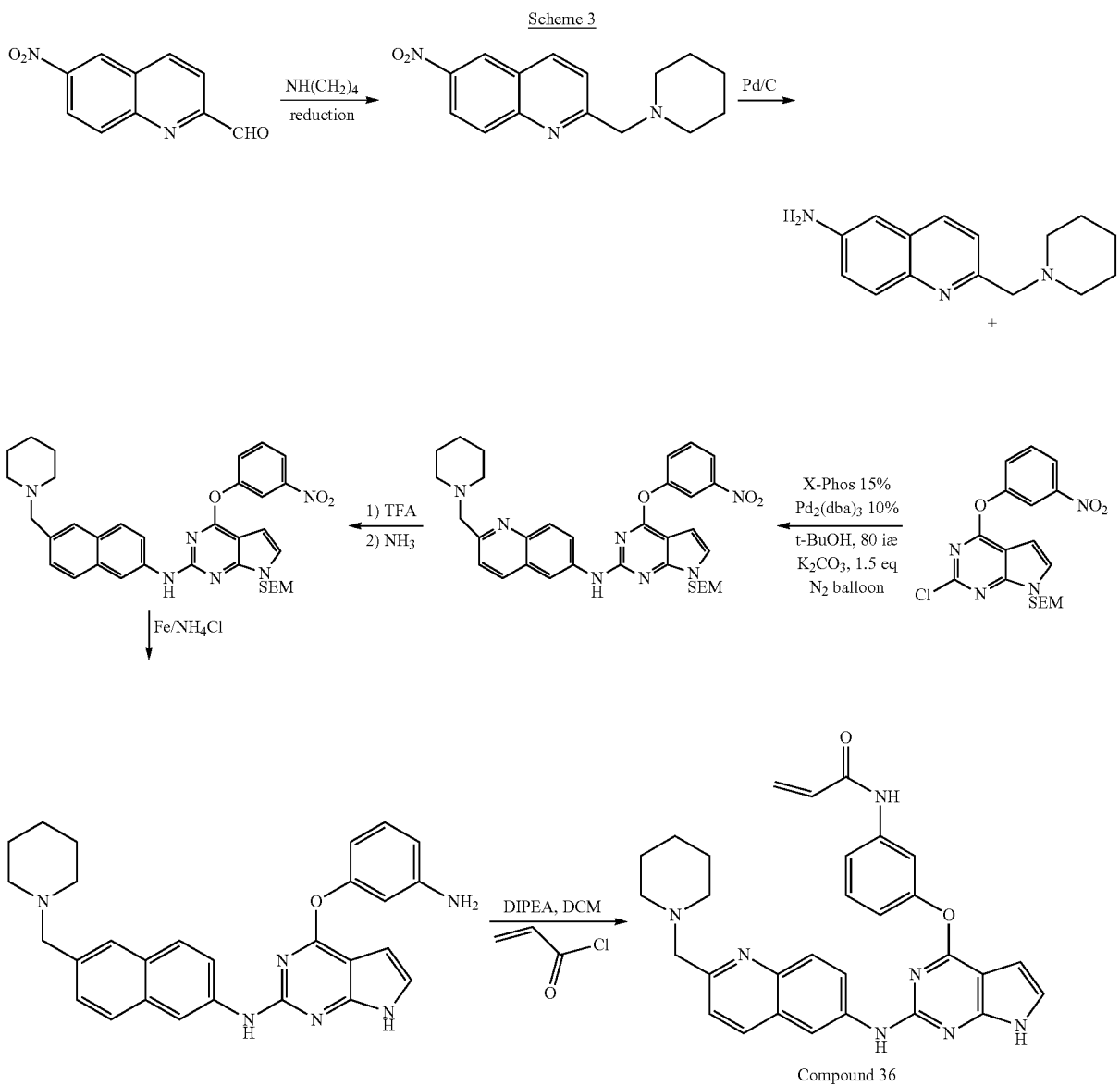
Compound 36

In certain embodiments, a representative synthesis for subject compounds is shown in Scheme 4.
Scheme 4
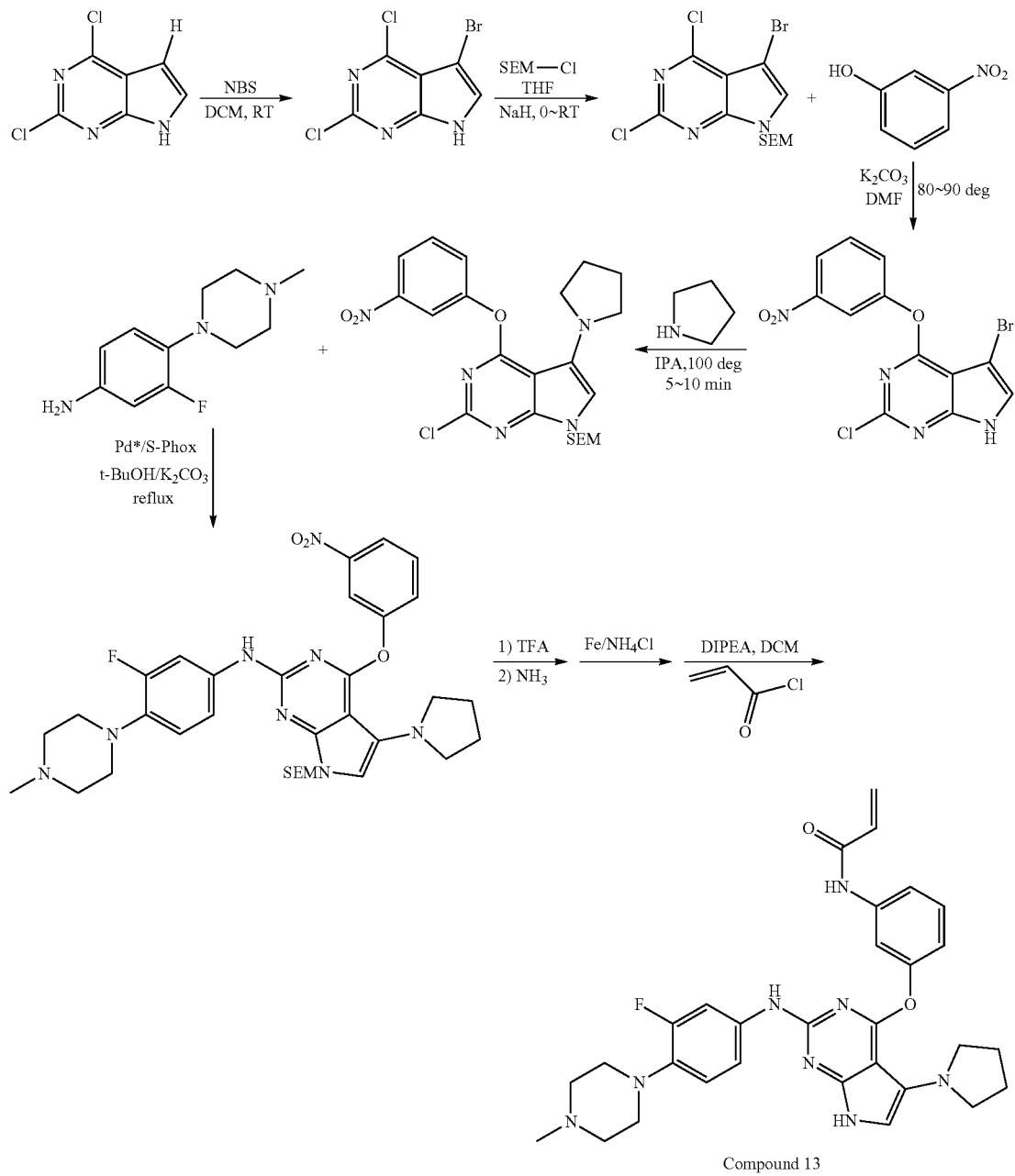
In certain embodiments, a representative synthesis for subject compounds is shown in Scheme 5.
Scheme 5
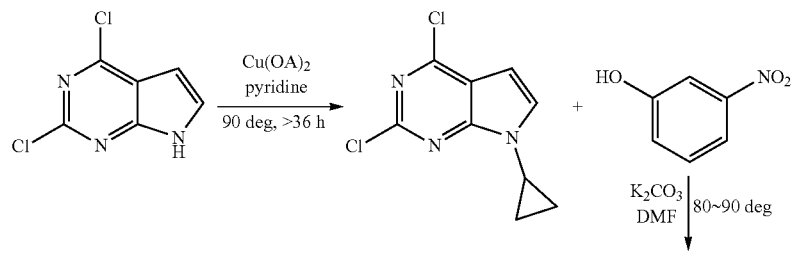

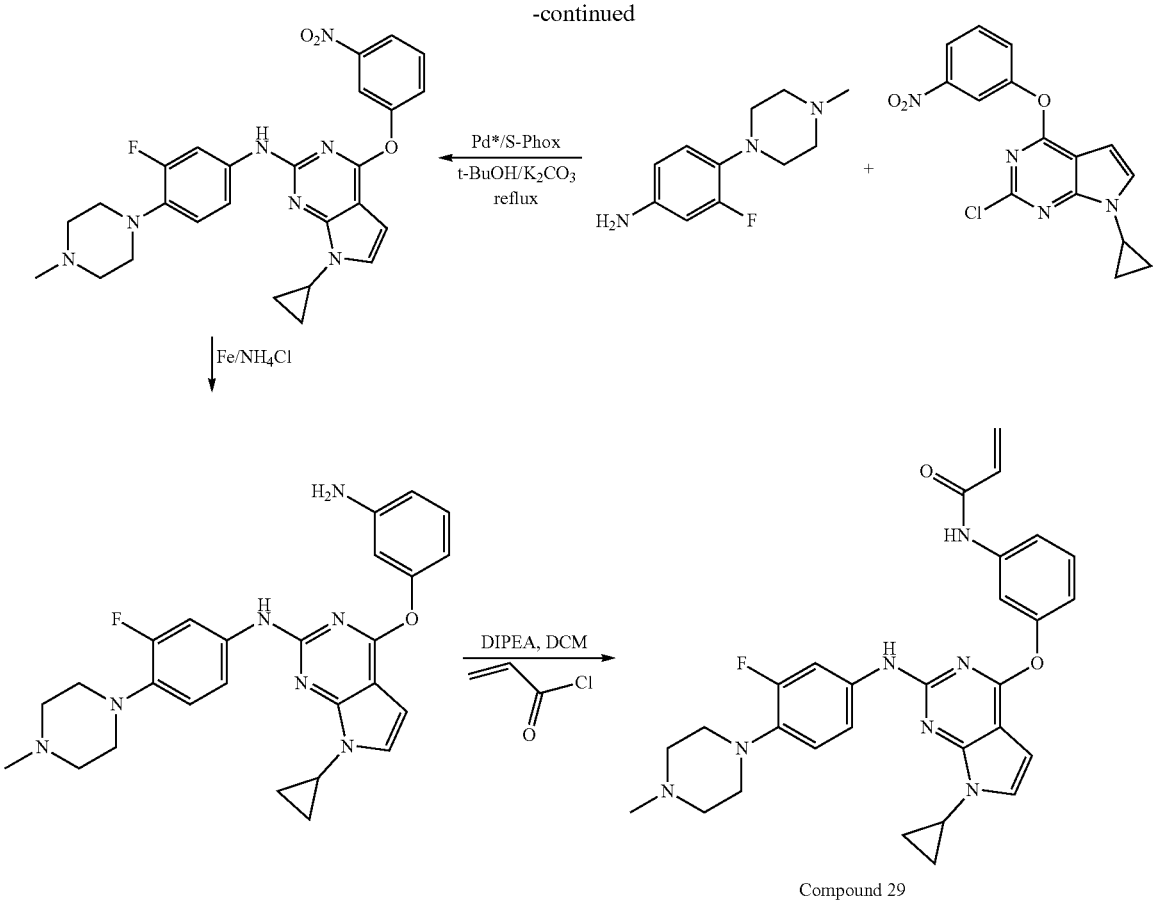
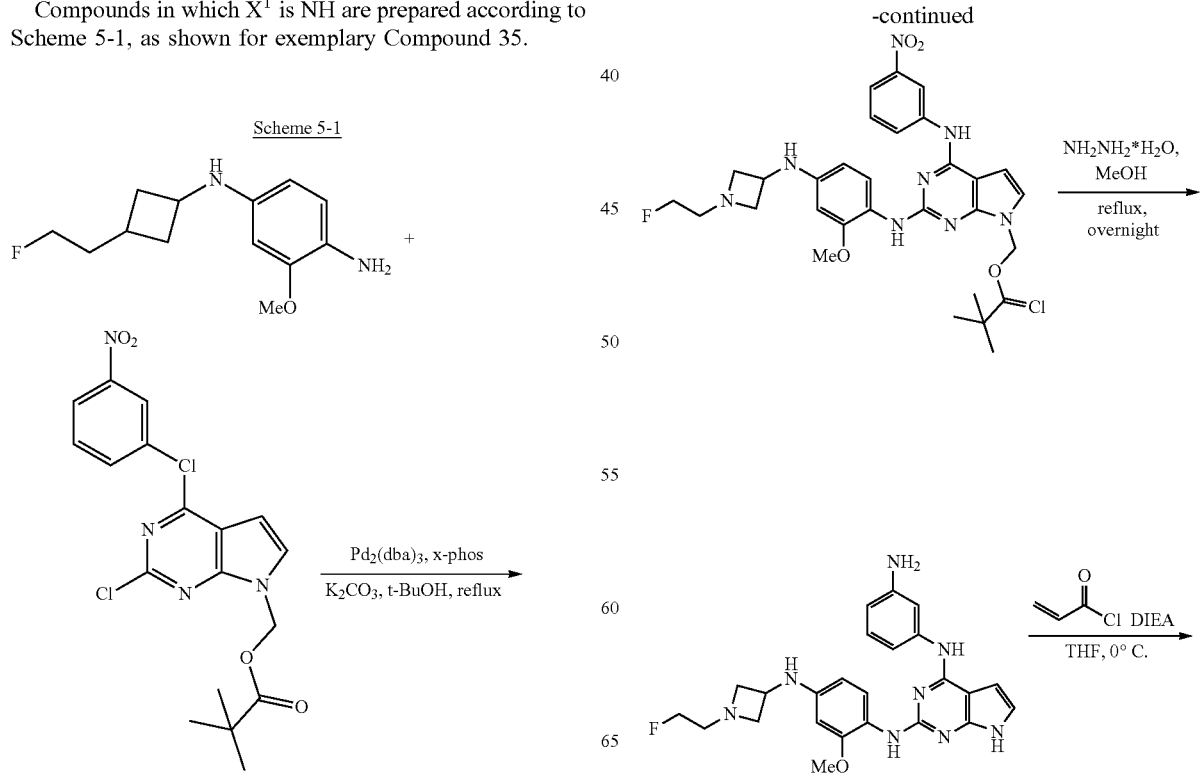
Compounds in which $X^1$ is NH are prepared according to Scheme 5-1, as shown for exemplary Compound 35.
Scheme 5-1

-continued

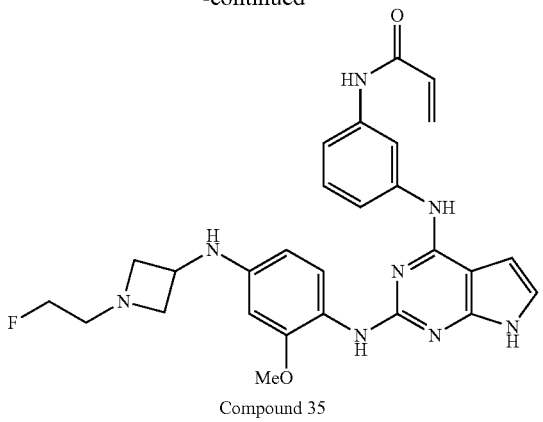

Compound 35

Accordingly and as described in more detail herein, the present disclosure provides a process of preparing a compound of the present disclosure, the process involves:
reacting a compound of formula with

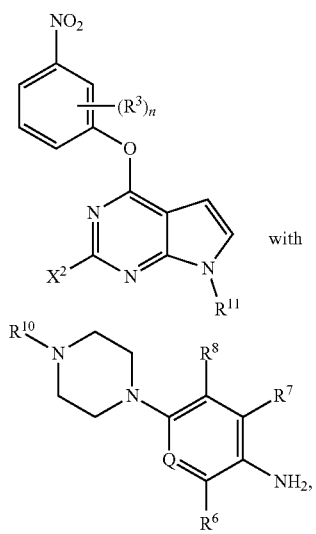

thereby producing a compound of formula

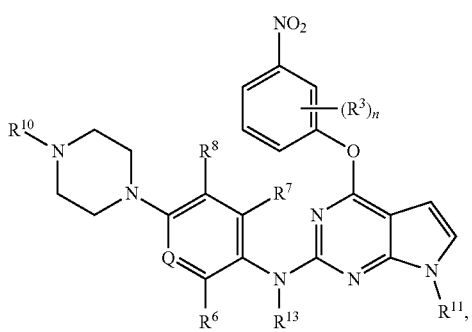

wherein $R^3$, $R^6$, $R^7$, $R^8$, $R^{10}$, $R^{11}$, $R^{12}$, $R^{13}$, Q, and n are defined herein and $X^2$ is a leaving group.

Accordingly and as described in more detail herein, the present disclosure provides a process of preparing a compound of the present disclosure, the process involves:

reacting a compound of formula

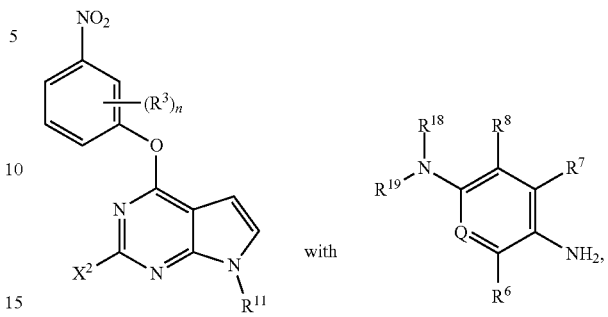

with thereby producing a compound of formula,

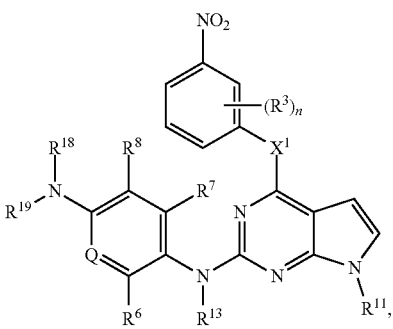

wherein $X^1$, $R^3$, $R^6$, $R^7$, $R^8$, $R^{10}$, $R^{11}$, $R^{12}$, $R^{13}$, $R^{18}$, $R^{19}$, Q, and n are defined herein and $X^2$ is a leaving group.

Accordingly and as described in more detail herein, the present disclosure provides a process of preparing a compound of the present disclosure, the process involves:

reducing the nitro group of the compound of formula

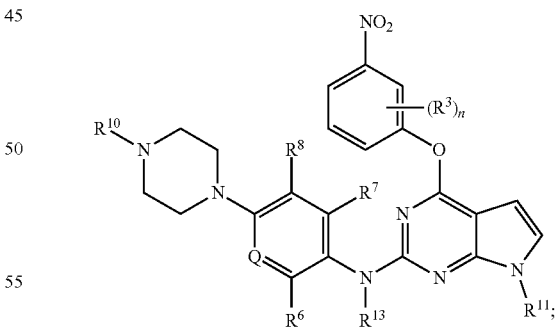

and performing an amidation reaction with an acryloyl derivative comprising a leaving group;

thereby producing a compound of Formula (I).

Accordingly and as described in more detail herein, the present disclosure provides a process of preparing a compound of the present disclosure, the process involves:

reducing the nitro group of the compound of formula

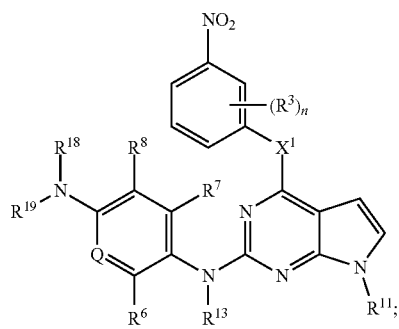

and performing an amidation reaction with an acryloyl derivative comprising a leaving group; thereby producing a compound of Formula (VIII).

In certain instances, the above processes further involving the step of forming a salt of a compound of the present disclosure. Embodiments are directed to the other processes described herein; and to the product prepared by any of the processes described herein.

EXAMPLES

The following examples are offered to illustrate but not to limit the invention.

Example 1: Synthesis of Compounds 1 and 4

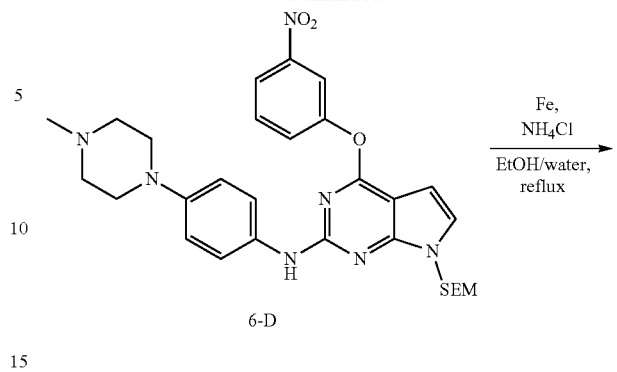

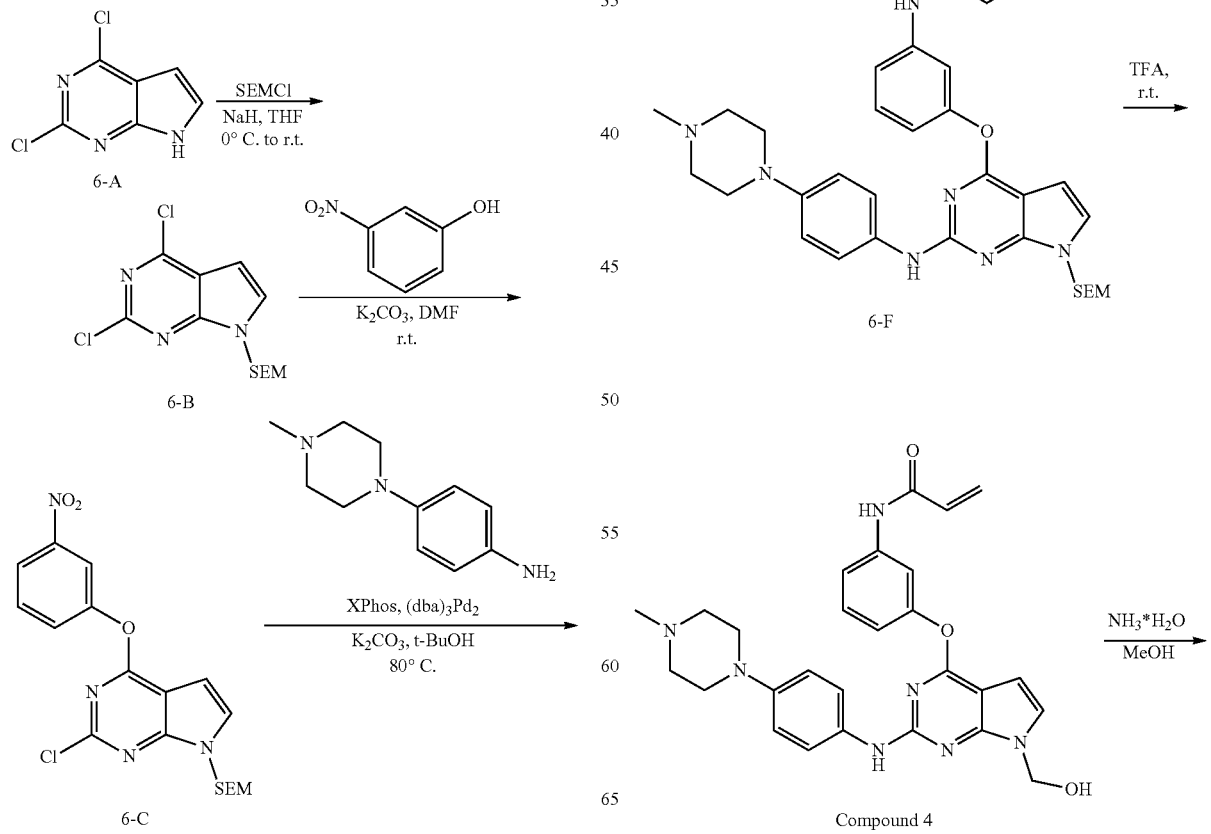

-continued

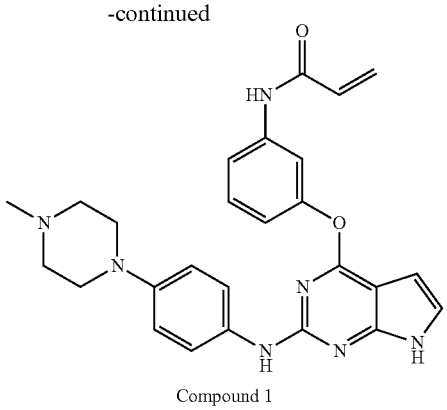

Compound 1

A synthesis of N-(3-((7-(hydroxymethyl)-2-((4-(4-methylpiperazin-1-yl)phenyl)amino)-7H-pyrrolo[2,3-d]pyrimidin-4-yl)oxy)phenyl)acrylamide (Compound 4) and N-(3-((2-((4-(4-methylpiperazin-1-yl)phenyl)amino)-7H-pyrrolo[2,3-d]pyrimidin-4-yl)oxy)phenyl)acrylamide (Compound 1) and their intermediates is shown in Scheme 6 and described below.

Synthesis of 2,4-dichloro-7-((2-(trimethylsilyl)ethoxy)methyl)-7H-pyrrolo[2,3-d]pyrimidine (Compound 6-B)

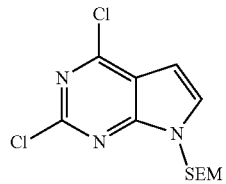 [SMILES: C[Si](C)(C)CCOCn1ccc2c(Cl)nc(Cl)nc21]

Sodium hydride (60%, 46.7 mg, 3.06 mmol) was added to a mixture of Compound 2-A (575 mg, 3.06 mmol) and 2-(trimethylsilyl)ethoxymethyl chloride (561 mg, 3.37 mmol) in tetrahydrofuran (5 mL) at 0° C. with stirring. The reaction mixture was allowed to warm to room temperature and stirred for 3 hours before quenching with water (5 mL). The mixture was extracted with ethyl acetate (10 mL×3). The organic layers were combined, washed with brine, dried over $Na_2SO_4$ and filtered. The filtrate was concentrated, and the crude material was purified by column chromatography (PE/EA=20/1) to give Compound 6-B (520 mg, yield 53.4%, M+H$^+$=319.27) as a pale yellow solid.

Synthesis of 2-chloro-4-(3-nitrophenoxy)-7-((2-(trimethylsilyl)ethoxy)methyl)-7H-pyrrolo[2,3-d]pyrimidine (Compound 6-C)

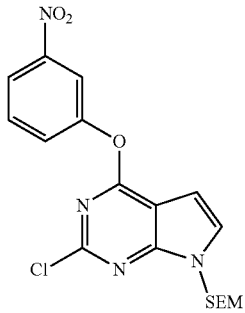 [SMILES: C[Si](C)(C)CCOCn1ccc2c(Oc3cccc([N+](=O)[O-])c3)nc(Cl)nc21]

To a mixture of Compound 6-B (200 mg, 0.628 mmol) and 3-nitrophenol (96.2 g, 0.691 mmol) in dimethylformamide (2 mL) was added $K_2CO_3$ (173.7 mg, 1.26 mmol). The reaction mixture was stirred at room temperature for 4 hours. The reaction mixture was then filtered. The filtrate was diluted with water, then extracted with ethyl acetate. The organic layer was washed with water, brine, and dried over $Na_2SO_4$. After filtration and removal of the volatiles in vacuo, the crude product was purified by flash column chromatography (PE/EA=20/1) affording Compound 6-C (200 mg, yield 75.6%, M+H$^+$=421.92) as a white solid.

Synthesis of 2-chloro-6-(difluoro(3-nitrophenyl)methyl)-9-(tetrahydro-2H-pyran-2-yl)-9H-purine (Compound 6-D)

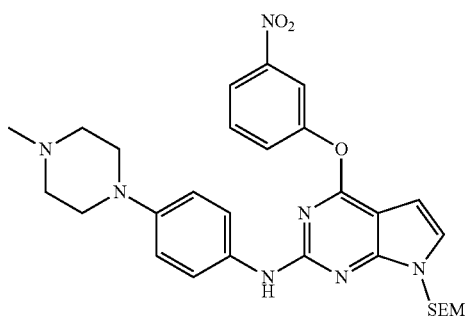 [SMILES: CN1CCN(c2ccc(Nc3nc(Oc4cccc([N+](=O)[O-])c4)c4ccn(COCC[Si](C)(C)C)c4n3)cc2)CC1]

A mixture of Compound 6-C (150 mg, 0.356 mmol), 4-(4-methylpiperazino) aniline (70 mg, 0.356 mmol), tris(dibenzylideneacetone)dipalladium (36 mg, 0.0356 mmol), dicyclohexyl (2',4',6'-triisopropylbiphenyl-2-yl) phosphine (100 mg, 0.214 mmol) and potassium carbonate (197 mg, 1.424 mmol) in tert-butanol (8 mL) was stirred under argon at 80° C. overnight. After cooling to room temperature, the reaction mixture was filtered through a pad of Celite. The pad of Celite was washed with methanol and the filtrate was concentrated under reduced pressure. The residue was purified by flash column chromatography (DCM/MeOH=20/1) to give Compound 6-D (180 mg, M+H$^+$=576.23) as yellow solid.

Synthesis of 4-(3-aminophenoxy)-N-(4-(4-methylpiperazin-1-yl)phenyl)-7-((2-(trimethylsilyl)ethoxy)methyl)-7H-pyrrolo[2,3-d]pyrimidin-2-amine (Compound 6-E)

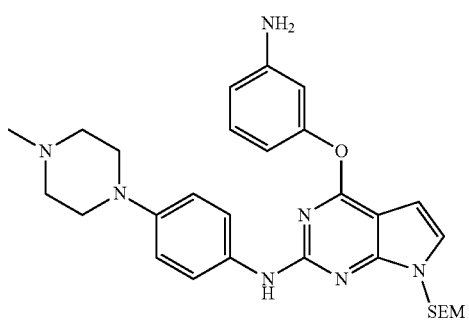 [SMILES: CN1CCN(c2ccc(Nc3nc(Oc4cccc(N)c4)c4ccn(COCC[Si](C)(C)C)c4n3)cc2)CC1]

Compound 6-D (180 mg, 0.312 mmol) was dissolved in ethanol (6 mL) and water (2 mL) was added. Iron powder (90 mg, 1.61 mmol) and ammonium chloride (230 mg, 4.3 mmol) were then added, and the resulting mixture was heated at reflux for 3 hours. The reaction mixture was cooled to room temperature and filtered through a pad of Celite. The ethanol was removed in vacuo, and the resulting residue was basified with sodium bicarbonate and extracted with ethyl acetate. The organic layer was separated and dried using anhydrous sodium sulfate, concentrated, and purified by flash chromatography with 20:1 dichloromethane-methanol to afford Compound 6-E (170 mg, M+H⁺=546) as a white solid.

Synthesis of N-(3-(2-(4-(4-methylpiperazin-1-yl)phenylamino)-7-((2-(trimethylsilyl)ethoxy)methyl)-7H-pyrrolo[2,3-d]pyrimidin-4-yloxy)phenyl)acrylamide (Compound 6-F)

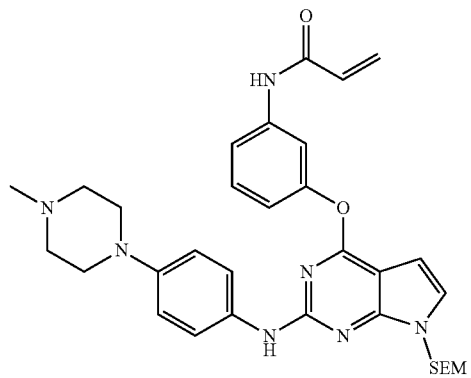 [SMILES: C=CC(=O)Nc1cccc(Oc2nc(Nc3ccc(N4CCN(C)CC4)cc3)nc3c2ccn3COCC[Si](C)(C)C)c1]

Acryloyl chloride (33.8 mg, 0.374 mmol) was added dropwise to a solution of Compound 6-E (170 mg, 0.312 mmol) and diisopropyethylamine (55 mg, 0.426 mmol) in methylene chloride (3 mL) at 0° C. The reaction mixture was stirred for 1 hour. Water was added to quench the reaction. The organic layer was washed with water, brine, and dried over Na₂SO₄. After filtration, removal of volatiles was performed in vacuo. The crude product was purified by flash chromatography (DCM/MeOH=20/1) afford Compound 6-F (125 mg, yield 66.9%, M+H⁺=600.8) as a white solid.

Synthesis of N-(3-(7-(hydroxymethyl)-2-(4-(4-methylpiperazin-1-yl)phenylamino)-7H-pyrrolo[2,3-d]pyrimidin-4-yloxy)phenyl)acrylamide (Compound 4)

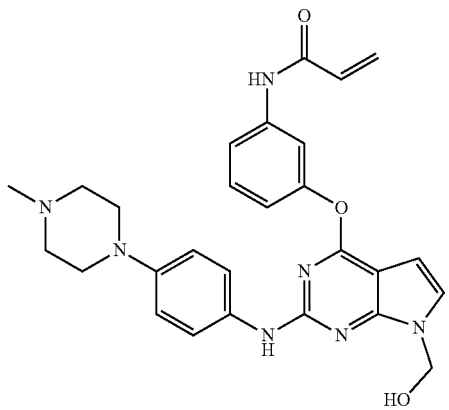 [SMILES: C=CC(=O)Nc1cccc(Oc2nc(Nc3ccc(N4CCN(C)CC4)cc3)nc3c2ccn3CO)c1]

Compound 6-F (125 mg, 0.208 mmol) in methylene chloride (3 mL) and trifluoroacetic acid (1 mL) was stirred at room temperature for 3 hours. Monitoring by thin layer chromatography indicated that all starting material had been consumed. Saturated aqueous NaHCO₃ was then added to the reaction mixture at 0° C. The reaction mixture was extracted with methylene chloride. The organic layer was washed with water, brine, dried over Na₂SO₄ and filtered. The filtrate was concentrated and the crude material was purified by column chromatography (DCM/MeOH=20/1) to give Compound 4 (70 mg, yield 71.5%, M+H⁺=500.5) as a white solid.

Synthesis of N-(3-(2-(4-(4-methylpiperazin-1-yl)phenylamino)-7H-pyrrolo[2,3-d]pyrimidin-4-yloxy)phenyl)acrylamide (Compound 1)

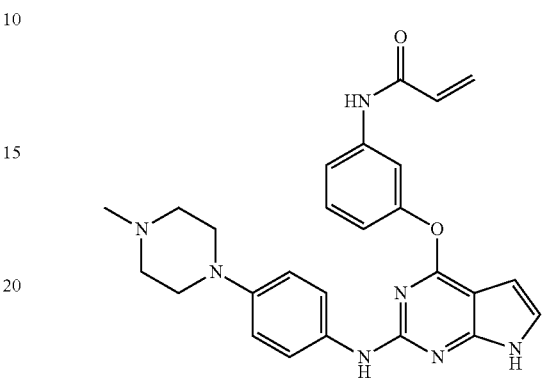

A solution of Compound 4 (100 mg, 0.2 mmol) in methanol (2 mL) was saturated with ammonia. The reaction mixture was stirred overnight at room temperature. Monitoring by LC-MS indicated that all starting material had been consumed. The solvent was concentrated and the crude material was purified by column chromatography (DCM/MeOH=20/1) to give Compound 1 (60 mg, yield 63.8%, M+H⁺=470.5) as a pale yellow solid.

Example 2: Synthesis of Compounds 2 and 5

Scheme 7

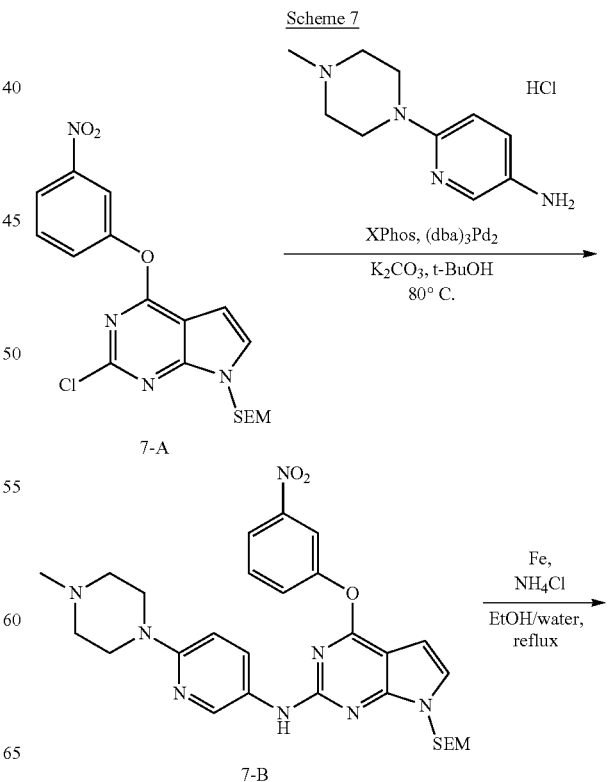

77

-continued

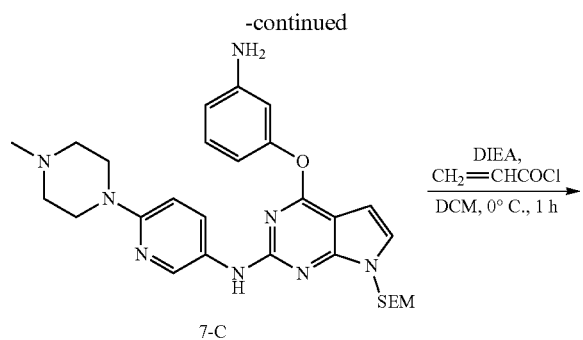

7-C

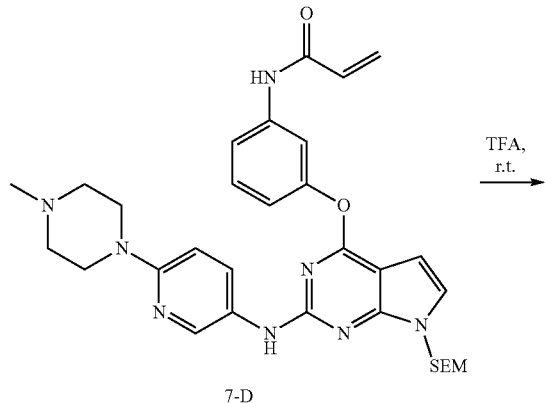

7-D

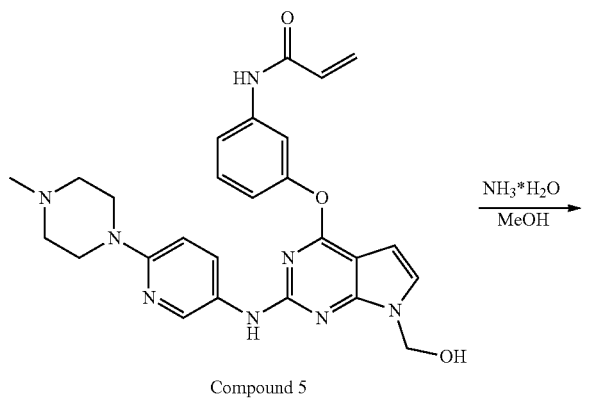

Compound 5

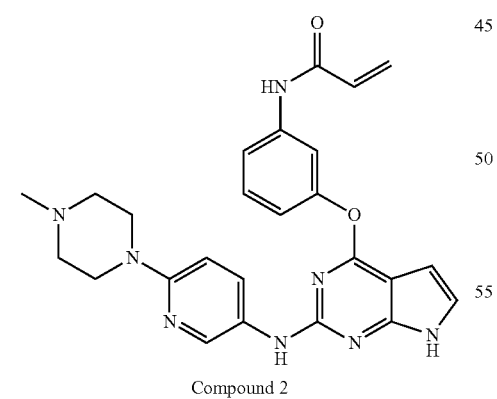

Compound 2

A synthesis of N-(3-(7-(hydroxymethyl)-2-(6-(4-methylpiperazin-1-yl)pyridin-3-ylamino)-7H-pyrrolo[2,3-d]pyrimidin-4-yloxy)phenyl)acrylamide (Compound 5) and N-(3-(2-(6-(4-methylpiperazin-1-yl)pyridin-3-ylamino)-7H-pyrrolo[2,3-d]pyrimidin-4-yloxy)phenyl)acrylamide (Compound 2) and their intermediates is shown in Scheme 7 and described below.

78

Synthesis of N-(6-(4-methylpiperazin-1-yl)pyridin-3-yl)-4-(3-nitrophenoxy)-7-((2-(trimethylsilyl)ethoxy)methyl)-7H-pyrrolo[2,3-d]pyrimidin-2-amine (Compound 7-B)

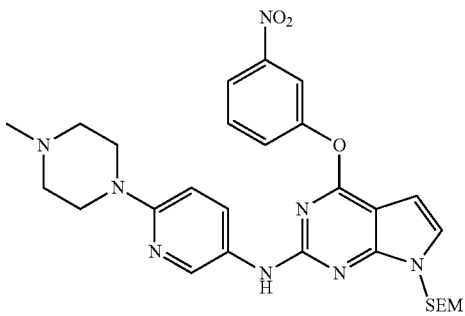 [SMILES: CN1CCN(c2ccc(Nc3nc(Oc4cccc([N+](=O)[O-])c4)c4ccn(COCC[Si](C)(C)C)c4n3)cn2)CC1]

Compound 7-B (yield 62% from 3, M+H$^+$=577.3) was prepared according to the procedure of Compound 6-D using 3-amino-6-(4-Methyl-1-piperazinyl)pyridine hydrochloride instead of 4-(4-Methylpiperazino) aniline.

Synthesis of 4-(3-aminophenoxy)-N-(6-(4-methylpiperazin-1-yl)pyridin-3-yl)-7-((2-(trimethylsilyl)ethoxy)methyl)-7H-pyrrolo[2,3-d]pyrimidin-2-amine (Compound

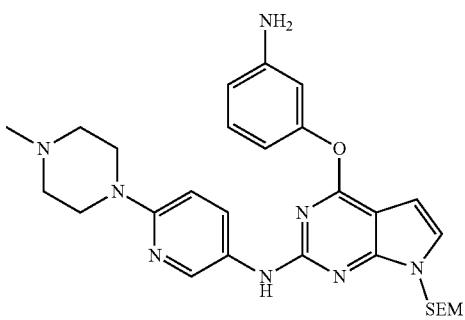 [SMILES: CN1CCN(c2ccc(Nc3nc(Oc4cccc(N)c4)c4ccn(COCC[Si](C)(C)C)c4n3)cn2)CC1]

Compound 7-C (yield 80% from Compound 7-B, M+H$^+$=547.3) was prepared according to the procedure of Compound 6-E.

Synthesis of N-(3-(2-(6-(4-methylpiperazin-1-yl)pyridin-3-ylamino)-7-((2-(trimethylsilyl)ethoxy)methyl)-7H-pyrrolo[2,3-d]pyrimidin-4-yloxy)phenyl)acrylamide (Compound 7-D)

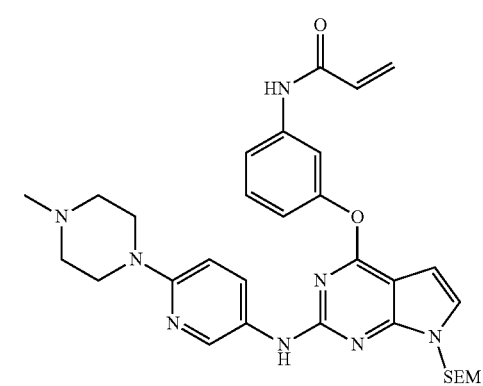 [SMILES: C=CC(=O)Nc1cccc(Oc2nc(Nc3ccc(N4CCN(C)CC4)nc3)nc3c2ccn3COCC[Si](C)(C)C)c1]

Compound 7-D (yield 67% from Compound 7-C, M+ H+=601.3) was prepared according to the procedure of Compound 6-F.

Synthesis of N-(3-(7-(hydroxymethyl)-2-(6-(4-methylpiperazin-1-yl)pyridin-3-ylamino)-7H-pyrrolo[2,3-d]pyrimidin-4-yloxy)phenyl)acrylamide (Compound 5)

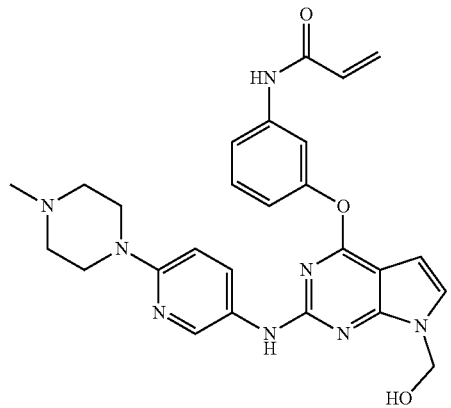 [SMILES: C=CC(=O)Nc1cccc(Oc2nc(Nc3ccc(N4CCN(C)CC4)nc3)nc3c2ccn3CO)c1]

Compound 7-E (yield 70% from Compound 5, M+ H+=501.6) was prepared according to the procedure of Compound 4.

Synthesis of N-(3-(2-(6-(4-methylpiperazin-1-yl)pyridin-3-ylamino)-7H-pyrrolo[2,3-d]pyrimidin-4-yloxy)phenyl)acrylamide (Compound 2)

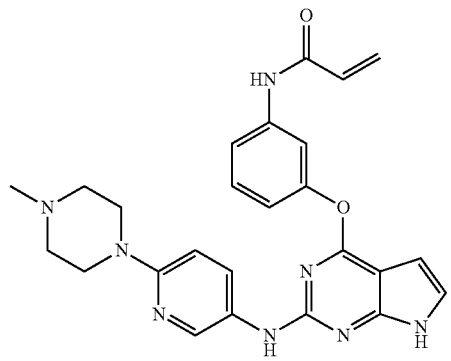 [SMILES: C=CC(=O)Nc1cccc(Oc2nc(Nc3ccc(N4CCN(C)CC4)nc3)nc3[nH]ccc23)c1]

Compound 2 (yield 62% from Compound 5, M+ H+=471.5) was prepared according to the procedure of Compound 1.

Example 3: Synthesis of Compounds 3 and 6

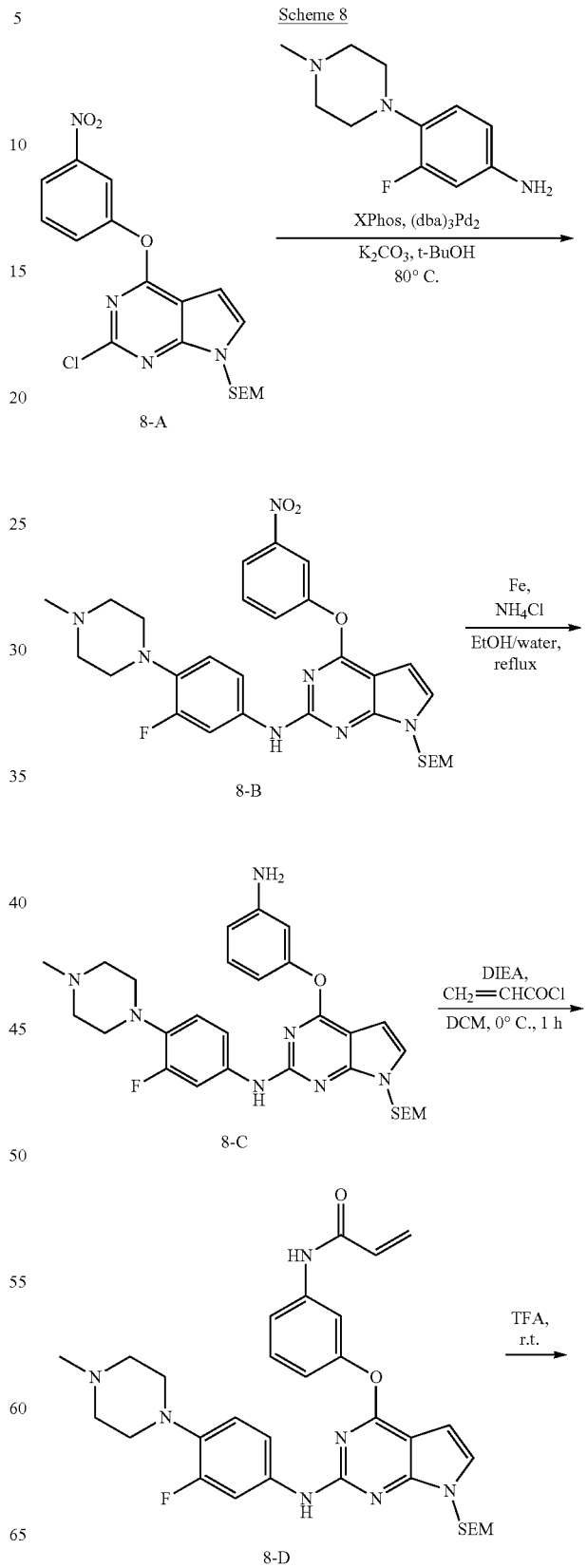

Scheme 8

81

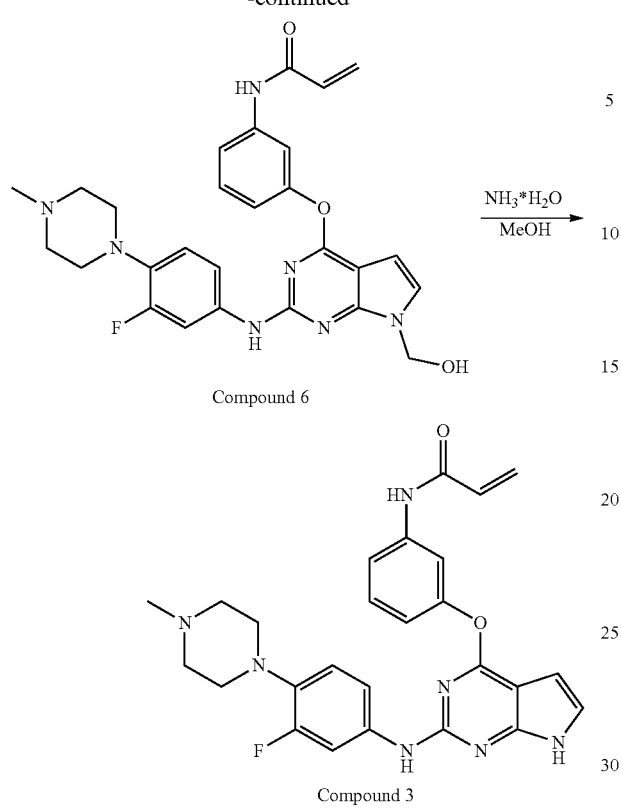

Compound 6

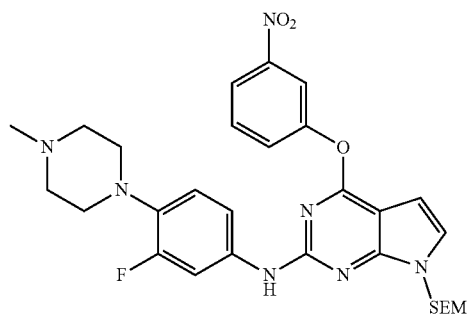 [SMILES: CN1CCN(c2ccc(Nc3nc(Oc4cccc([N+](=O)[O-])c4)c4ccn(COCC[Si](C)(C)C)c4n3)cc2F)CC1]

Compound 3

A synthesis of N-(3-(2-(3-fluoro-4-(4-methylpiperazin-1-yl)phenylamino)-7-(hydroxymethyl)-7H-pyrrolo[2,3-d]pyrimidin-4-yloxy)phenyl)acrylamide (Compound 6) and N-(3-(2-(3-fluoro-4-(4-methylpiperazin-1-yl)phenylamino)-7H-pyrrolo[2,3-d]pyrimidin-4-yloxy)phenyl)acrylamide (Compound 3) and their intermediates is shown in Scheme 8 and described below.

Synthesis of N-(3-fluoro-4-(4-methylpiperazin-1-yl)phenyl)-4-(3-nitrophenoxy)-7-((2-(trimethylsilyl)ethoxy)methyl)-7H-pyrrolo[2,3-d]pyrimidin-2-amine (Compound 8-B)

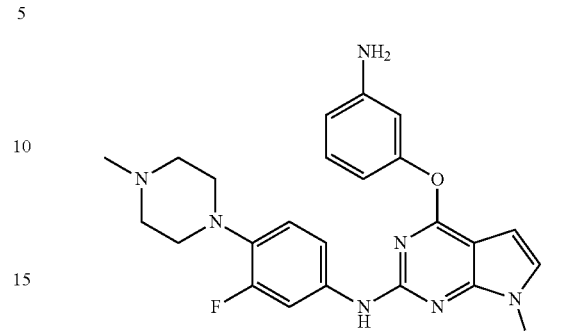

Compound 8-B (yield % from Compound 8-A, M+ H$^+$=594.3) was prepared according to the procedure of Compound 6-D using 3-fluoro-4-(4-methylpiperazin-1-yl) aniline instead of 4-(4-methylpiperazino) aniline.

82

Synthesis of 4-(3-aminophenoxy)-N-(3-fluoro-4-(4-methylpiperazin-1-yl)phenyl)-7-((2-(trimethylsilyl) ethoxy)methyl)-7H-pyrrolo[2,3-d]pyrimidin-2-amine (Compound 8-C)

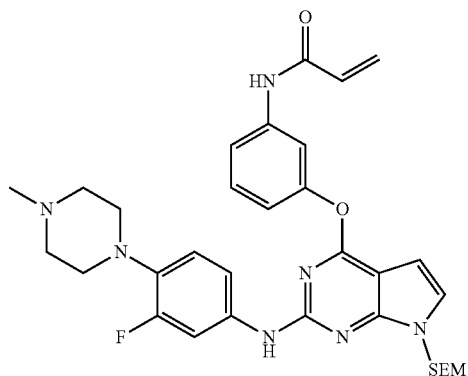 [SMILES: C=CC(=O)Nc1cccc(Oc2nc(Nc3ccc(N4CCN(C)CC4)c(F)c3)nc3c2ccn3COCC[Si](C)(C)C)c1]

Compound 8-C (yield 85% from Compound 8-B, M+ H$^+$=564.3) was prepared according to the procedure of Compound 6-E.

Synthesis of N-(3-(2-(3-fluoro-4-(4-methylpiperazin-1-yl)phenylamino)-7-((2-(trimethylsilyl)ethoxy)methyl)-7H-pyrrolo[2,3-d]pyrimidin-4-yloxy)phenyl)acrylamide (Compound 8-D)

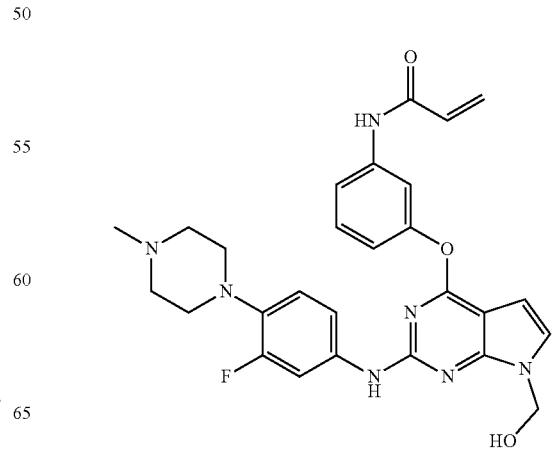

Compound 8-D (yield 75% from Compound 8-C, M+ H$^+$=618.3) was prepared according to the procedure of Compound 6-F.

Synthesis of N-(3-(2-(3-fluoro-4-(4-methylpiperazin-1-yl)phenylamino)-7-(hydroxymethyl)-7H-pyrrolo[2,3-d]pyrimidin-4-yloxy)phenyl)acrylamide (Compound 6)

Compound 6 (yield 78% from Compound 8-D, M+ H+=518.6) was prepared according to the procedure of Compound 4.

Synthesis of N-(3-(2-(3-fluoro-4-(4-methylpiperazin-1-yl)phenylamino)-7H-pyrrolo[2,3-d]pyrimidin-4-yloxy)phenyl)acrylamide (Compound 3)

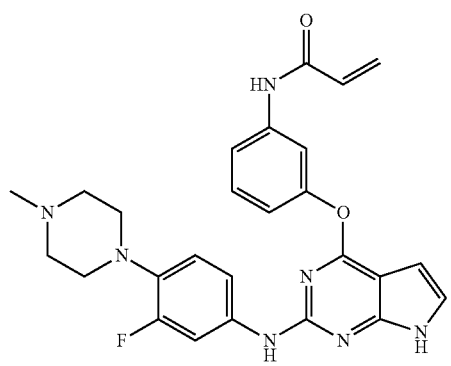 [SMILES: C=CC(=O)Nc1cccc(Oc2nc(Nc3ccc(N4CCN(C)CC4)c(F)c3)nc3[nH]ccc23)c1]

Compound 3 (yield 83% from Compound 6, M+ H+=488.5) was prepared according to the procedure of Compound 1.

Example 4: N-(3-(7-(2-fluoroethyl)-2-(4-(4-methylpiperazin-1-yl)phenylamino)-7H-pyrrolo[2,3-d]pyrimidin-4-yloxy)phenyl)acrylamide (Compound 7)

Scheme 9

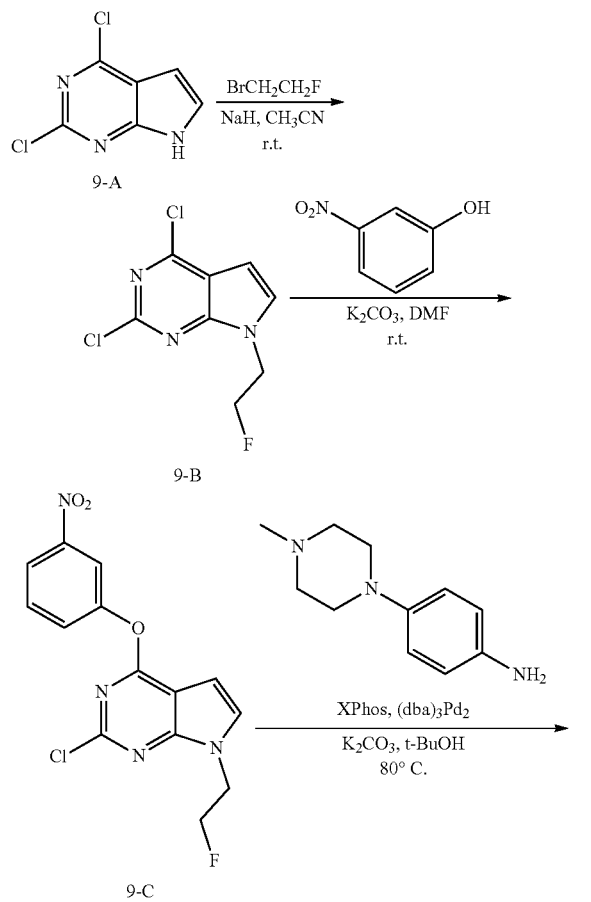

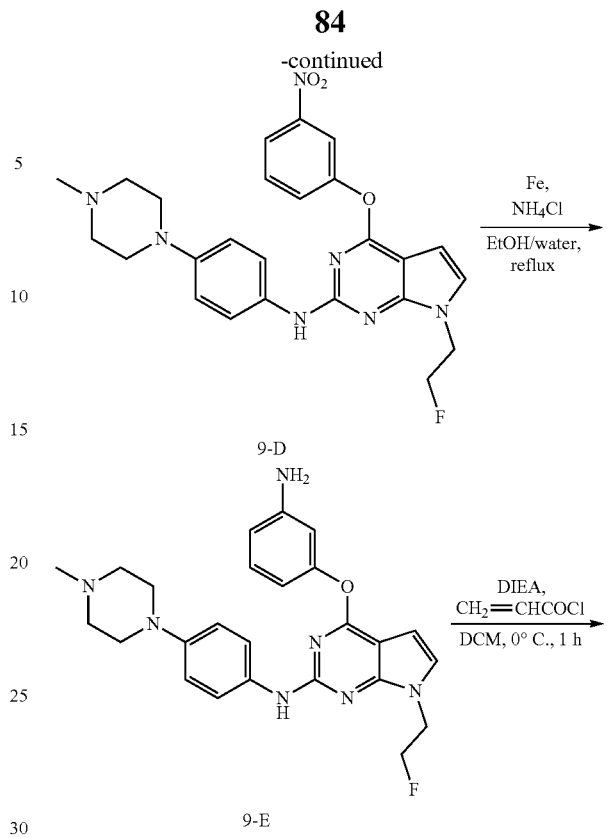

Compound 7

A synthesis of N-(3-(7-(2-fluoroethyl)-2-(4-(4-methylpiperazin-1-yl)phenylamino)-7H-pyrrolo[2,3-d]pyrimidin-4-yloxy)phenyl)acrylamide (Compound 7) and its intermediates is shown in Scheme 9 and described below.

Synthesis of 2, 4-dichloro-7-(2-fluoroethyl)-7H-pyrrolo[2,3-d]pyrimidine (Compound 9-B)

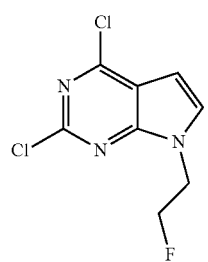 [SMILES: FCCn1ccc2c(Cl)nc(Cl)nc21]

Sodium hydride (60%, 424 mg, 10.6 mmol) was added to a mixture of Compound 9-A (1 g, 5.3 mmol) and BrCH$_2$CH$_2$F (1.519 g, 11.9 mmol) in acetonitrile (10 mL) at room temperature. The reaction mixture was stirred for 4 hours before quenching with water and then extracted with ethyl acetate. The organic layer was washed with brine, dried over Na$_2$SO$_4$ and filtered. The filtrate was concentrated and the crude material was purified by column chromatography (PE/EA=20/1) to give Compound 9-B (1.1 g, yield 90%, M+H$^+$=234.0) as a pale yellow solid.

Synthesis of 2-chloro-7-(2-fluoroethyl)-4-(3-nitrophenoxy)-7H-pyrrolo[2,3-d]pyrimidine (Compound 9-C)

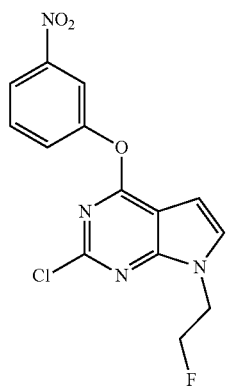 [SMILES: O=[N+]([O-])c1cccc(Oc2nc(Cl)nc3c2ccn3CCF)c1]

Compound 9-C (yield 82% from Compound 9-B, M+H$^+$=337.0) was prepared according to the procedure of Compound 6-C.

Synthesis of 7-(2-fluoroethyl)-N-(4-(4-methylpiperazin-1-yl)phenyl)-4-(3-nitrophenoxy)-7H-pyrrolo[2,3-d]pyrimidin-2-amine (Compound 9-D)

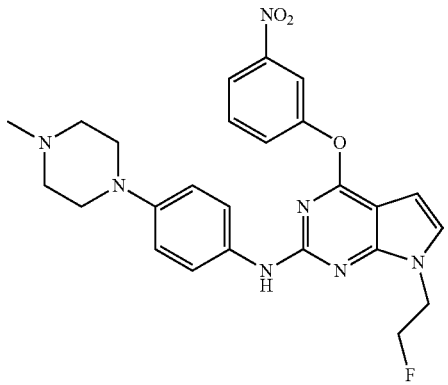 [SMILES: CN1CCN(c2ccc(Nc3nc(Oc4cccc([N+](=O)[O-])c4)c4ccn(CCF)c4n3)cc2)CC1]

Compound 9-D (yield 73% from Compound 9-C, M+H$^+$=492.2) was prepared according to the procedure of Compound 6-D.

Synthesis of 4-(3-aminophenoxy)-7-(2-fluoroethyl)-N-(4-(4-methylpiperazin-1-yl)phenyl)-7H-pyrrolo[2,3-d]pyrimidin-2-amine (Compound 9-E)

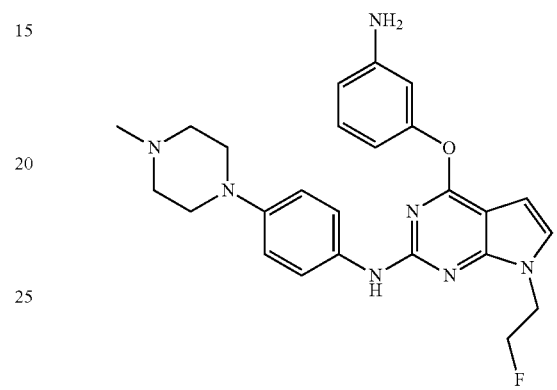

Compound 9-E (yield 81% from Compound 9-D, M+H$^+$=462.2) was prepared according to the procedure of Compound 6-E.

Synthesis of N-(3-(7-(2-fluoroethyl)-2-(4-(4-methylpiperazin-1-yl)phenylamino)-7H-pyrrolo[2,3-d]pyrimidin-4-yloxy)phenyl)acrylamide (Compound 7)

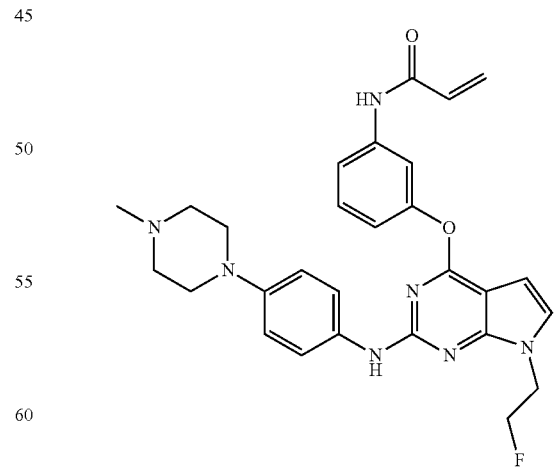

Compound 7 (yield 77% from Compound 9-E, M+H$^+$=516.6) was prepared according to the procedure of Compound 6-F.

Example 5: Synthesis of N-(3-(2-(4-(1-(2-fluoro-ethyl)azetidin-3-ylamino)-2-methoxyphenylamino)-7H-pyrrolo[2,3-d]pyrimidin-4-yloxy)phenyl)acrylamide (Compound 34)

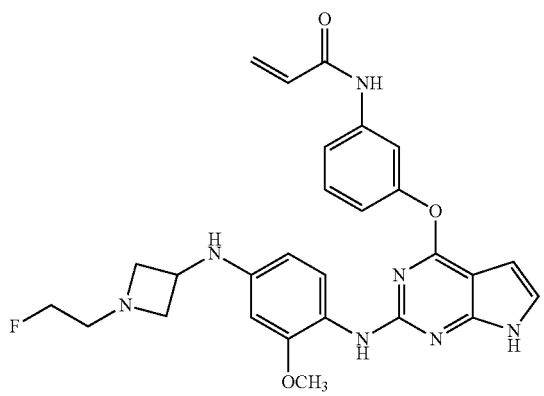 [SMILES: C=CC(=O)Nc1cccc(Oc2nc(Nc3ccc(NC4CN(CCF)C4)cc3OC)nc3[nH]ccc23)c1]

Synthesis of tert-butyl 3-(3-methoxy-4-nitrophenylamino)azetidine-1-carboxylate

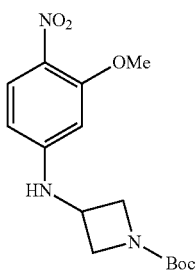 [SMILES: COc1cc(NC2CN(C(=O)OC(C)(C)C)C2)ccc1[N+](=O)[O-]]

Into a 100 mL 3-Neck round-bottomed flask equipped with reflux condenser were charged 4-fluoro-2-methoxy-1-nitrobenzene (4.086 g) and tert-butyl 3-aminoazetidine-1-carboxylate (4.4 g), triethylamine (9.6 mL), and dimethyl sulfoxide (20 mL). The reaction mixture was heated at 95° C. for 8 hours. The reaction mixture was poured into water (200 mL) and extracted with ethyl acetate (50 mL×3). The organic layer was washed with brine (50 mL×2), dried over sodium sulfate, and concentrated completely under reduced pressure at 40° C. to give the title compound (9 g) which was used without further purification.

Synthesis of N-(3-methoxy-4-nitrophenyl)azetidin-3-amine

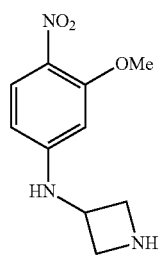 [SMILES: COc1cc(NC2CNC2)ccc1[N+](=O)[O-]]

To tert-butyl 3-(3-methoxy-4-nitrophenylamino)azetidine-1-carboxylate (9 g) was added TFA (18 mL) at room temperature. The reaction mixture was stirred for 15 min at room temperature and then was concentrated under reduced pressure at 40° C. to give the title compound as TFA salt (7.24 g).

Synthesis of 1-(2-fluoroethyl)-N-(3-methoxy-4-nitrophenyl)azetidin-3-amine

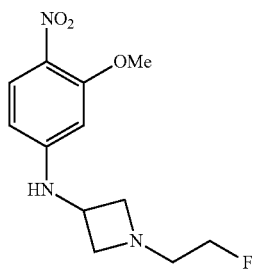 [SMILES: COc1cc(NC2CN(CCF)C2)ccc1[N+](=O)[O-]]

To N-(3-methoxy-4-nitrophenyl)azetidin-3-amine (3 g) were added Cs$_2$CO$_3$ (12 g) and 1,2-bromofluoroethane (1.5 g) in DMF (30 mL). The reaction mixture was heated at 50° C. for 8 h. The reaction mixture was poured in water and extracted in ethyl acetate (100 mL×3). The organic layer was washed with brine (100 mL×2), dried over sodium sulfate, and concentrated under reduced pressure. The crude material was purified by column chromatography (DCM/MeOH=50/1 as elution) to give the title compound (1.35 g, yield 51% over 3 steps) as a yellow solid.

Synthesis of N1-(1-(2-fluoroethyl)azetidin-3-yl)-3-methoxybenzene-1,4-diamine

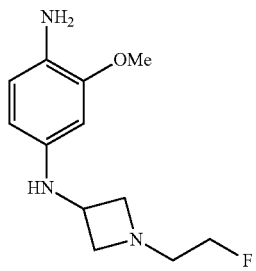 [SMILES: COc1cc(NC2CN(CCF)C2)ccc1N]

A solution of 1-(2-fluoroethyl)-N-(3-methoxy-4-nitrophenyl)azetidin-3-amine (2.6 g) and Pd/C (1 g) in 1,4-dioxane (50 mL) was hydrogenated for 4 hours at room temperature. The reaction mixture was filtered through diatomaceous earth, washing with MeOH. The filtrate was concentrated and purified by column chromatography (DCM/MeOH=50/1 as elution) to provide the title compound (1.57 g, yield 68%, M+$^H$=240.2).

Synthesis of (2-(4-(1-(2-fluoroethyl)azetidin-3-ylamino)-2-methoxyphenylamino)-4-(3-nitrophenoxy)-7H-pyrrolo[2,3-d]pyrimidin-7-yl)methyl pivalate

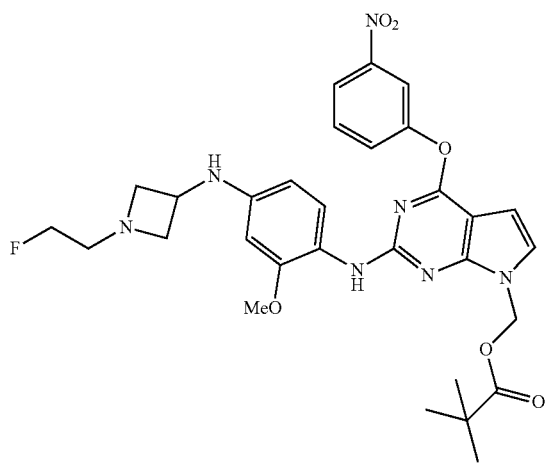 [SMILES: COc1cc(NC2CN(CCF)C2)ccc1Nc1nc(Oc2cccc([N+](=O)[O-])c2)c2ccn(COC(=O)C(C)(C)C)c2n1]

A mixture of N1-(1-(2-fluoroethyl)azetidin-3-yl)-3-methoxybenzene-1,4-diamine (870 mg, 3.64 mmol) and (2-chloro-4-(3-nitrophenoxy)-7H-pyrrolo[2,3-d]pyrimidin-7-yl)methyl pivalate (1.55 g, 3.83 mmol), potassium carbonate (1.35 g, 9.77 mmol), tris(dibenzylideneacetone)dipalladium (173 mg, 0.19 mmol) and dicyclohexyl (2',4',6'-triisopropylbiphenyl-2-yl)phosphine (222 mg, 0.47 mmol), a magnetite, and t-BuOH (35 mL) was heated to reflux and stirred under nitrogen for 2 h. The mixture was cooled to 40-50° C. and was filtered through diatomaceous earth, washing with ethyl acetate (50 mL). The filtrate was concentrated under reduced pressure. The crude material was purified by column chromatography (DCM/MeOH=50/1 as elution) to give the title compound (1.7 g, yield 74%, M+H$^+$=608.3) as a light yellow solid.

Synthesis of N1-(4-(3-aminophenoxy)-7H-pyrrolo[2,3-d]pyrimidin-2-yl)-N4-(1-(2-fluoroethyl)azetidin-3-yl)-2-methoxybenzene-1,4-diamine

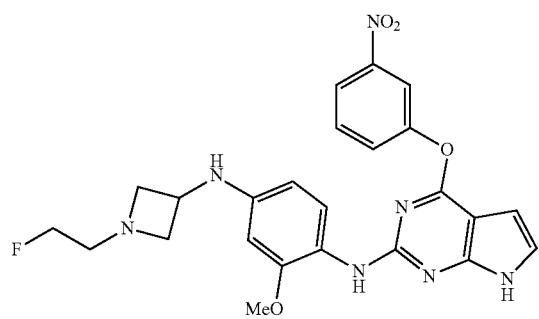 [SMILES: COc1cc(NC2CN(CCF)C2)ccc1Nc1nc(Oc2cccc([N+](=O)[O-])c2)c2cc[nH]c2n1]

A mixture of (2-(4-(1-(2-fluoroethyl)azetidin-3-ylamino)-2-methoxyphenylamino)-4-(3-nitrophenoxy)-7H-pyrrolo[2,3-d]pyrimidin-7-yl)methyl pivalate (530 mg, 0.87 mmol), NH$_2$NH$_2$.H$_2$O (98%, 2.5 mL), Pd/C (110 mg), a magnetite, and MeOH (10 mL) was stirred at reflux temperature overnight. The mixture was cooled to room temperature, and was filtered through diatomaceous earth, washing with MeOH (20 mL). The filtrate was concentrated under reduced pressure. NaHCO$_{3(aq)}$ was added, and the mixture was extracted with ethyl acetate (30 mL×3). The combined organic layers were concentrated under reduced pressure. The crude material was purified by column chromatography (DCM/MeOH=40/1 as elution) to give the title compound (125 mg, yield 31%, M+H$^+$=464.2) as a white solid.

Synthesis of N-(3-(2-(4-(1-(2-fluoroethyl)azetidin-3-ylamino)-2-methoxyphenylamino)-7H-pyrrolo[2,3-d]pyrimidin-4-yloxy)phenyl)acrylamide (Compound 34)

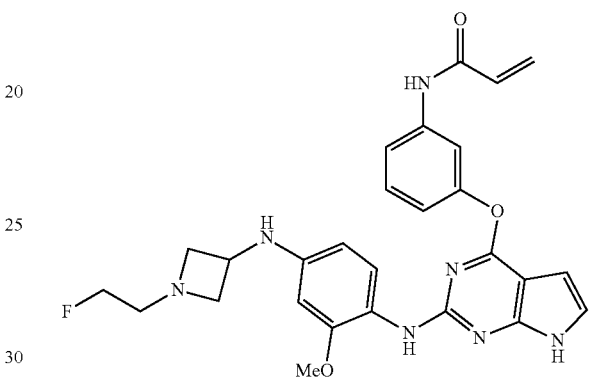

A 50 mL-round-bottom flask with a magnetite was charged with N1-(4-(3-aminophenoxy)-7H-pyrrolo[2,3-d]pyrimidin-2-yl)-N4-(1-(2-fluoroethyl)azetidin-3-yl)-2-methoxybenzene-1,4-diamine (125 mg, 0.27 mmol), diisopropylethylamine (43 mg, 0.33 mmol) and DCM (20 mL). The mixture was cooled with an ice bath until the temperature was below 0° C., and a solution of acryloyl chloride (33 mg, 0.33 mmol) in THF (2 mL) was added dropwise over 5 minutes. The title compound is isolated and purified by preparative HPLC or preparative LC/MS, or by other standard purification techniques.

Additional exemplary compounds not shown in these synthetic examples are prepared from appropriate starting materials using methods analogous to those described in the preceding schemes and examples.

Biological Example A

In Vitro Cell-Based Screening Using Real-Time Cell Electronic Sensing (RT-CES) System Some Assays and Examples Demonstrating the Anti-Cancer Effects of the compounds of the embodiments are described as below.

The pyrrolopyrimidine compounds in the embodiments are developed for the anticancer activities for cancer cells with certain molecular targets, i.e., EGFR (epidermal growth factor receptor). The anticancer efficacy of the pyrrolopyrimidine compounds may be preliminarily screened in vitro using a panel of EGFR cancer cell lines by real time electronic cell sensing (RT-CES) system from ACEA Biosciences, Inc. (or xCELLigence system from Roche Applied Sciences/ACEA Biosciences Inc.), which provides dynamic cell response information after exposing to an anticancer agent.

The details of this cell electronic sensing technology, called real-time cell electronic sensing (RT-CES®) and associated devices, systems and methods of use are described in U.S. Pat. Nos. 7,732,127; 7,192,752; 7,459,303; 7,468,255; 7,470,533; 7,560,269; U.S. provisional application No. 60/397,749, filed on Jul. 20, 2002; U.S. provisional application No. 60/435,400, filed on Dec. 20, 2002; U.S. Provisional application 60/469,572, filed on May 9, 2003, PCT application number PCT/US03/22557, filed on Jul. 18, 2003; PCT application number PCT/US03/22537, filed on Jul. 18, 2003; PCT application number PCT/US04/37696, filed on Nov. 12, 2004; PCT application number PCT/US05/04481, filed on Feb. 9, 2005; U.S. patent application Ser. No. 10/705,447, filed on Nov. 10, 2003; U.S. patent application Ser. No. 10/705,615, filed on Nov. 10, 2003; U.S. patent application Ser. No. 10/987,732, filed on Nov. 12, 2004; U.S. patent application Ser. No. 11/055,639, filed on Feb. 9, 2005, each of which is incorporated by reference. Additional details of RT-CES technology is further disclosed in U.S. provisional application No. 60/519,567, filed on Nov. 12, 2003, and U.S. provisional application No. 60/542,927, filed on Feb. 9, 2004, U.S. provisional application No. 60/548,713, filed on Feb. 27, 2004, U.S. provisional application No. 60/598,608, filed on Aug. 4, 2004; U.S. provisional application No. 60/598,609, filed on Aug. 4, 2004; U.S. provisional application No. 60/613,749, filed on Sep. 27, 2004; U.S. provisional application No. 60/613,872, filed on Sep. 27, 2004; U.S. provisional application No. 60/614,601, filed on Sep. 29, 2004; U.S. provisional application No. 60/630,071, filed on Nov. 22, 2004; U.S. provisional application No. 60/630,131, filed on Nov. 22, 2004, each of which is incorporated herein by reference.

For measurement of cell-substrate or cell-electrode impedance using RT-CES technology, microelectrodes having appropriate geometries are fabricated onto the bottom surfaces of microtiter plate or similar device, facing into the wells. Cells are introduced into the wells of the devices, and make contact to and attach to the electrode surfaces. The presence, absence or change of properties of cells affects the electronic and ionic passage on the electrode sensor surfaces. Measuring the impedance between or among electrodes provides information about biological status of cells present on the sensors. When there are changes to the biological status of the cells analogue, electronic readout signals are measured automatically and in real time, and are converted to digital signals for processing and analysis.

In a RT-CES system, a cell index is automatically derived and provided based on measured electrode impedance values. The cell index obtained for a given well reflects: 1) how many cells are attached to the electrode surfaces in this well; and 2) how well cells are attached to the electrode surfaces in this well. Thus, the more the cells of same type in similar physiological conditions attach the electrode surfaces, the larger the cell index. And, the better the cells attach to the electrode surfaces (e.g., the cells spread-out more to have larger contact areas, or the cells attach tighter to electrode surfaces), the larger the cell index. We have found that the cMet-addictive cell lines would produce a transient impedance response profile when treated with positive-control EGFR (epidermal growth factor receptor) inhibitors.

Through the use of the RT-CES system, the pyrrolopyrimidine compounds described in the examples above have been shown to produce a similar cell response impedance profile on RT-CES system to that generated by positive control inhibitors. In addition, these compounds have been shown to inhibit EGFR (epidermal growth factor receptor)-induced cell migration in several cell lines. In addition, these compounds have shown no or negligible effects when they were used to treat non-cMet addictive cancer cell lines.

The RT-CES system (or xCELLigence RTCA system) comprises three components, an electronic sensor analyzer, a device station and 16× or 96× microtiter plate devices (i.e. E-Plate 16 or E-Plate 96). Microelectrode sensor array was fabricated on glass slides with lithographical microfabrication methods and the electrode-containing slides are assembled to plastic trays to form electrode-containing wells. Each 16× (or 96×) microtiter plate device used in RT-CES system comprises up to 16 (or 96) such electrode-containing wells. The device station receives the 16× or 96× microtiter plate devices and is capable of electronically switching any one of the wells to the sensor analyzer for impedance measurement. In operation, the devices with cells cultured in the wells are placed into a device station (xCELLigence RTCA SP station or RT-CES SP station) that is located inside an incubator. Electrical cables connect the device station to the sensor analyzer (xCELLigence RTCA analyzer or RT-CES analyzer). Under the RT-CES or xCELLigence RTCA software control, the sensor analyzer can automatically select wells to be measured and continuously conduct impedance measurements. The impedance data from the analyzer is transferred to a computer, analyzed and processed by the integrated software.

Impedance measured between electrodes in an individual well depends on electrode geometry, ionic concentration in the well and whether there are cells attached to the electrodes. In the absence of the cells, electrode impedance is mainly determined by the ion environment both at the electrode/solution interface and in the bulk solution. In the presence of the cells, cells attached to the electrode sensor surfaces will alter the local ionic environment at the electrode/solution interface, leading to an increase in the impedance. The more cells there are on the electrodes, the larger the increase in cell-electrode impedance. Furthermore, the impedance change also depends on cell morphology and the extent to which cells attach to the electrodes.

To quantify cell status based on the measured cell-electrode impedance, a parameter termed Cell Index is derived, according to $$CI = \max_{i=1,\ldots,N}\left(\frac{R_{cell}(f_i)}{R_b(f_i)} - 1\right)$$

where $R_b(f)$ and $R_{cell}(f)$ are the frequency dependent electrode resistances (a component of impedance) without cells or with cell present, respectively. N is the number of the frequency points at which the impedance is measured. Thus, Cell Index is a quantitative measure of the status of the cells in an electrode-containing well. Under the same physiological conditions, more cells attached on to the electrodes leads to larger $R_{cell}(f)$ value, leading to a larger value for Cell Index. Furthermore, for the same number of cells present in the well, a change in the cell status such as morphology will lead to a change in the Cell Index. For example, an increase in cell adhesion or cell spreading leads to larger cell-electrode contact area which will lead to an increase in $R_{cell}(f)$ and thus a larger value for Cell Index. The Cell Index may also be calculated using a formula different from the one described here. Other methods for calculating the Cell Index based on impedance measurement can be found in U.S. Pat. Nos. 7,732,127; 7,192,752; 7,459,303; 7,468,255; 7,470,533; 7,560,269; PCT application number PCT/US04/37696, fined on Nov. 12, 2004, PCT application number PCT/US05/

04481, filed on Feb. 9, 2005, U.S. patent application Ser. No. 10/987,732, filed on Nov. 12, 2004, and U.S. patent application Ser. No. 11/055,639, filed on Feb. 9, 2005.

Biological Example B-1

Bioactivity of Pyrrolopyrimidine Compounds on EGFR Mutated Cell Lines

Material and Methods

Cell Culture and Reagents

All cell lines were obtained from the American Type Culture Collection and were maintained at 37° C. with 5% $CO_2$, in media supplemented with 10% fetal bovine serum and 1% L-glutamine-penicillin-streptomycin. H1975 and HCC827 cells were cultured with RPMI 1640 media. A431 cells were maintained in Dulbecco's Modification of Eagle's Medium. EGF (R&D), EGF inhibitors were resuspended and stored according to the manufacturers' instructions.

Cell Proliferation and Growth Inhibition Assay

Cell proliferation was assessed by WST assay (Roche, Indianapolis, Ind.) per the manufacturer's instructions. The H1975, HCC827 and A431 cells were seeded at 3,000, 3,000 and 4,000 cells per well onto 96-well plates, and after a 24-hour incubation, the cells were treated with test compounds for 72 hours. Cell viability was assayed by incubating the cells with WST-1 reagent for 2 hours, and then with the measurement of the absorbance at a wavelength of 450 nm. The data was calculated using GraphPad Prism version 4.0. The $IC_{50}$ values were fitted using a non-linear regression model with a sigmoidal dose response.

Western Blotting

H1975 and A431 cells were seeded onto 6-well plates at a concentration of $1 \times 10^6$ cells per well. After 24 hours of growth in serum-containing media, cells were incubated in serum-free media for 1 hour, and then treated with test compound for 2 hour. A431 cells were stimulated with 30 ng/mL EGF during the last 20 minutes of compound treatment. Western blots were done on the whole-cell extracts using phospho-specific EGFR (pY1068), total EGFR, phospho-Akt (Ser-473), total Akt, phospho-ERK1/2 (pT202/pY204) and total ERK1/2 antibodies (Cell Signaling Technology).

Tumor sections were snap-frozen in liquid nitrogen for protein isolation, and EGFR signal transduction was evaluated by Western blot with primary antibodies included the following: phospho-specific EGFR (pY1068), total EGFR, phospho-Akt (Ser-473), total Akt, phospho-ERK1/2 (pT202/pY204) and total ERK1/2.

ELISA Assay

H1975 and A431 cells were seeded onto each well of a 96-well plate at a density of $4 \times 10^4$ cells per well. After 24 hours of growth in serum-containing media, cells were treated with test compound in serum-free medium for 2 hours. A431 cells were stimulated with 30 ng/mL EGF during the last 15 minutes of compound treatment. Cells were washed with ice cold PBS before extraction with 100 μl per well cell lysis buffer. Phosphorylation of EGFR was measured using a sandwich ELISA assay with the pair of phospho-specific EGFR (pY1068) and total EGFR antibodies.

Results

Compound 3 Inhibits Proliferation of EGFR-Mutant Cells

The following compounds were tested.

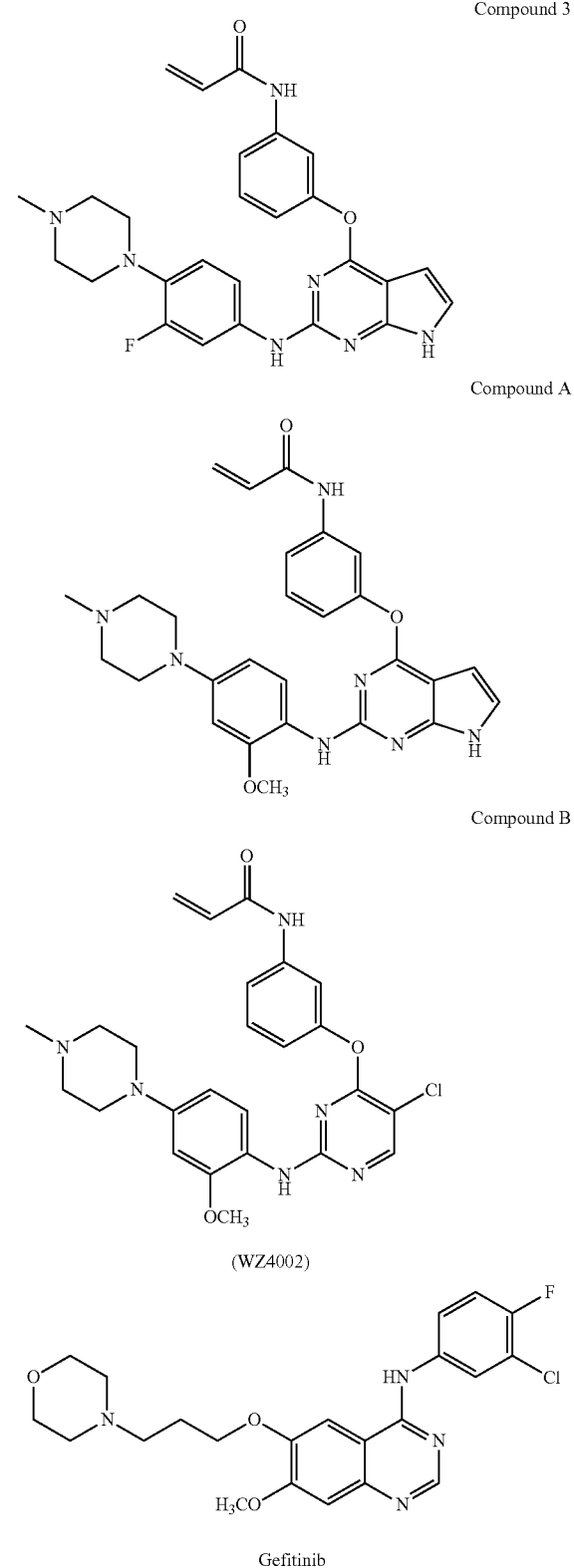

Compound 3

Compound A

Compound B (WZ4002)

Gefitinib

Sensitivity of cancer cell lines that express EGFR WT, Exon 19 Del, L858R/T790M and delE746-A750 to Compound 3, Compound B and gefitinib. Cell proliferation assays were performed with increasing concentrations of compounds for 72 hours using WST. $IC_{50}$ values were determined by GraphPad software. Compound 3 inhibits proliferation of the T790M-positive H1975 cells more potently than gefitinib.

TABLE 1

| Compound | H1975 cell (T790M/L858R) | A431 cell (WT) | HCC827 cell (delE746-A750) |
| --- | --- | --- | --- |
| Compound 3 | 0.61 µM | 10.8 µM | 0.019 µM |
| Compound B | 1.1 µM | 4.5 µM | 0.013 µM |
| Gefitinib | >10 µM | ND | 0.024 µM |

Compound 3 Inhibits EGFR Phosphorylation in H1975 Cells

Inhibition of EGFR phosphorylation and proliferation in H1975 cells treated with Compound 3. H1975 and A431 cells were incubated with various concentrations of Compound 3 or Compound B for 2 hours, and the whole cell extracts were directly harvested and tested for pEGFR by ELISA. $IC_{50}$ values were determined by GraphPad software.

TABLE 2

| Compound | H1975 cell (T790M/L858R) | A431 cell (WT) |
| --- | --- | --- |
| Compound 3 | 0.031 µM | 12.7 µM |
| Compound B | 0.063 µM | 8.9 µM |

Compound 3 Inhibits the EGFR Signaling Pathway in H1975 Cells

Exponentially growing H1975 lung cancer cells were treated with Compound 3 at indicated concentrations for 2 hours in serum-free medium. As shown in FIG. 1, whole cell extracts were resolved by SDS-PAGE before blotting onto nitrocellular membranes. Inhibition of phosphorylation of EGFR leads to inhibition of its downstream effectors p-Akt and p-ERK. All antibodies were obtained from Cell Signaling.

Compound 3 Inhibits the EGFR Signaling Pathway in H1975 Tumors

Figure 2:
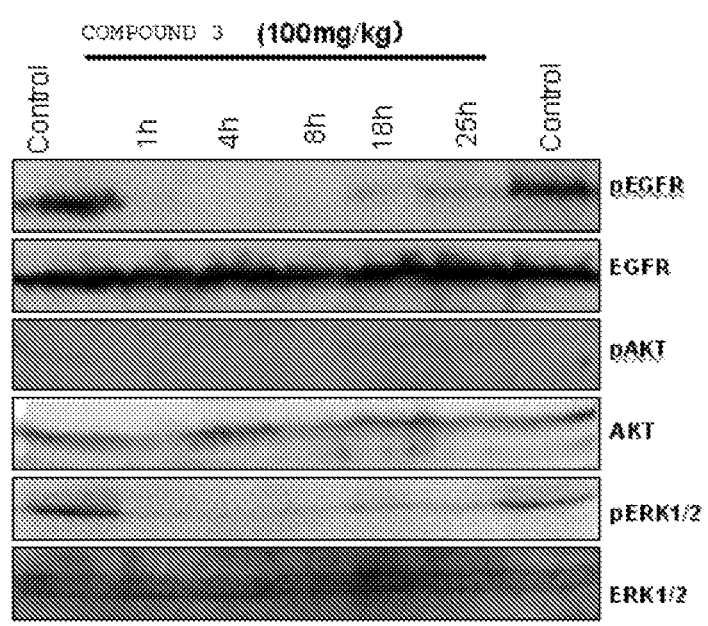
FIG. 2 shows immunoblots of certain effectors in tumors treated with Compound 3 at various time intervals.

Compound 3 was administered PO at 100 mg/kg, and tumors were harvested at 1, 4, 8, 18 and 25 hours after the single dose. As shown in FIG. 2, immunoblots were probed for pEGFR, total EGFR, pAkt, total Akt, p-ERK and total ERK. Compound 3 inhibited the phosphorylation of EGFR in a time-dependent manner, and the inhibition at EGFR leads to the inhibition of its downstream effectors p-Akt and p-ERK.

Comparison Between Compound 3 and Compound A
1. WST Result

TABLE 3

| Compound | H1975 cell (T790M/L858R) | A431 cell (WT) | HCC827 cell (delE746-A750) |
| --- | --- | --- | --- |
| Compound 3 | 0.73 µM | 0.62 µM | 0.011 µM |
| Compounds A | 1.63 µM | 4.17 µM | 0.023 µM |

2. ELISA Result

TABLE 4

| Compound | H1975 cell (T790M/L858R) | A431 cell (WT) | H1975 cell (T790M/L858R) EGF stimulate |
| --- | --- | --- | --- |
| Compound 3 | 0.0032 µM | 0.4737 µM | 0.025 µM |
| Compound A | 0.0088 µM | 1.0270 µM | 0.091 µM |

Biological Example B-2

Cell Culture and Reagents

All cell lines were obtained from the American Type Culture Collection and were maintained at 37° C. with 5% CO2, in media supplemented with 10% fetal bovine serum and 1% L-glutamine-penicillin-streptomycin. H1975 and HCC827 cells were cultured with RPMI 1640 media. A431 cells were maintained in Dulbecco's Modification of Eagle's Medium. GTL-16 cells, T47D cells and BxPC3 cells were cultured with RPMI 1640 media. NIH-3T3 cells, H460 cells and HepG2 cells were cultured with Dulbecco's Modification of Eagle's Medium. A549 cells were cultured with F-12K Nutrient Mixture media. H295R were cultured with DMEM: F12 Media. WST-1 reagent was obtained from Roche. EGF (R&D), EGF inhibitors were resuspended and stored according to the manufacturers' instructions.

Cell Proliferation and Growth Inhibition Assay

Cell proliferation was assessed by WST assay (Roche, Indianapolis, Ind.) per the manufacturer's instructions. The H1975, HCC-827 and A431 cells were seeded at 3,000, 3,000 and 4,000 cells per well onto 96-well plates, and after a 24 h incubation, the cells were treated with test compounds for 72 hrs. NIH-3T3 cells, A549 cells, H295R cells, GTL-16 cells, H460 cells, HepG2 cells, Hela cells, T47D cells and BxPC3 cells were seeded at 2,000, 2,000, 5,000, 5,000, 2,500, 5,000, 2,000, 5,000 and 5,000 cells per well onto 96-well plates. Cell viability was assayed by incubating the cells with WST-1 reagent for 3 hrs. Absorbance was measured at OD450-620 using the Beckman DTX880. The data was calculated using GraphPad Prism version 4.0. The IC50 were fitted using a non-linear regression model with a sigmoidal dose response.

ELISA Assays

The H1975, HCC-827 and A431 cells were seeded onto a 96-well plate at a density of 40,000, 40,000 and 60,000 cells per well respectively. After 24 h of growth in serum-containing media, cells were treated with test compound in serum-free medium for 2 h. A431 cells were stimulated with 50 ng/mL EGF during the last 15 min of compound treatment. Cells were washed with ice cold PBS before extraction with 100 µl per well cell lysis buffer. Phosphorylation of EGFR was measured using a sandwich ELISA assay with the pair of phospho-specific EGFR (pY1068) and total EGFR antibodies. The data was calculated using GraphPad Prism version 4.0. The IC50 were fitted using a non-linear regression model with a sigmoidal dose response.

Western Blotting

H1975, HCC-827 and A431 cells were seeded onto 6-well plates at a concentration of $1\times10^6$ cells per well. After 24 h of growth in serum-containing media, cells were incubated in serum-free media for 1 h, and then treated with test compound for 2 h. A431 cells were stimulated with 30 ng/mL EGF during the last 20 min of compound treatment. Western blots were performed on the whole-cell extracts using phospho-specific EGFR (pY1068), total EGFR, phospho-Akt (Ser-473), total Akt, phospho-ERK1/2 (pT202/pY204) and total ERK1/2 antibodies (Cell Signaling Technology). The density of blotting band was acquired using ImageJ software, and the IC50 of EGFR Tyr1068 phosphorylation was fitted using a non-linear regression model by GraphPad Prism version 4.0.

Compound 3 was orally administered at indicated dose (12.5, 50, 200 mg/kg), and Gefitinib (GF) was orally administrated at 100 mg/kg. The tumor tissues were harvested at 1, 4, 8, and 24 h at Day 1 and after the single dose, or harvested at Day 8 and after 8 consecutive doses for dose (12.5, 50 mg/kg). Tumor sections were snap-frozen in liquid nitrogen for protein isolation, and EGFR signal transduction was evaluated by Western blot with primary antibodies included the following: phospho-specific EGFR (pY1068), total EGFR.

Cell-Based Pulse Chase Assay for Irreversibility Assessment of Compound

The H1975 was seeded at 3000 cell per well in RTCA system (xCELLigence SP instrument, ACEA Biosciences). After one day culture, cell were treated with compound of compound 3, WZ4002 at concentration of 10 μM for 22 hrs then removed compared with drugs kept overtime. About 60 hours after recovery, cell subject to WST viability measuring.

Results

Compound 3 Inhibited the Proliferation of EGFR Mutation Harboring Cancer Cells.

Compound 3 achieved the inhibition of the proliferation of H1975 (T790M/L858R) cells with the IC50 at 91±60 nM, and with IC50 at 19±8 nM for HCC827(Del E746-A750) cells, whereas the sensitivity to A431(WT) cells is much lower (IC50=2113±1660 nM). In contrast, gefitinib, the first generation EGFR inhibitor, exhibited sensitivity to A431 cells, but had no activity on inhibiting the proliferation of T790M mutation harboring cells (IC50>20 uM).

| Compound | H1975 cell (T790M/L858R) | A431 cell (WT) | HCC827 cell (delE746-A750) |
|---|---|---|---|
| Compound 3 | 91 ± 60 nM | 2113 ± 1660 nM | 19 ± 8 nM |
| WZ4002 | 1905 ± 732 nM | 4393 ± 617 nM | 35 ± 12 nM |
| Gefitinib | >20000 nM | 523 ± 115 nM | 9 ± 1 nM |

Compound 3 Significantly Reduced the EGFR Tyr1068 Phosphorylation in EGFR Mutant Cells.

H1975 and A431 cells were incubated with various concentrations of compound 3 or WZ4002 for 2 h, and the whole cell extracts were directly harvested and tested for pEGFR by ELISA. IC50 values were determined by GraphPad software.

The cell-based ELISA assays verified that compound 3 significantly reduced the EGFR Tyr1068 phosphorylation in the EGFR mutant cell lines, while Gefitinib showed inhibition of the phosphorylation to a much less extent.

| Compound | H1975 cell (T790M/L858R) | A431 cell (WT) |
|---|---|---|
| compound 3 | 4 ± 2 nM | 650 ± 63 nM |
| WZ4002 | 32 ± 12 nM | 970 ± 340 nM |

As shown in the table below, Compound 3 significantly reduced the EGFR Tyr1068 phosphorylation and downstream signaling in the EGFR mutant cells, and is less effective in cell line expressing wild-type EGFR.

| EGFR genotype | Cell line | IC50 (nM) by WB (Tyr1068 phospho) | | |
|---|---|---|---|---|
| | | compound 3 | Gefitinib | WZ4002 |
| T790M/L858R | H1975 | 4.4 | 860 | 21 |
| DelE746-A750 | HCC-827 | 9.8 | 5.4 | 58 |
| Wild Type | A431 | 288 | 1.6 | 53 |
| Selectivity (A431/H1975) | | 65X | 0.002X | 2.5X |

Figure 9A:
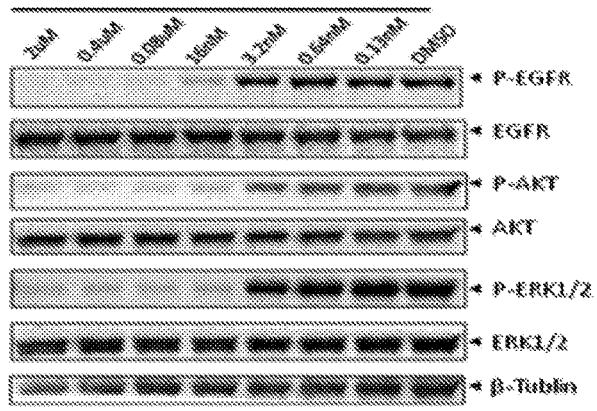
FIGS. 9A-9F show SDS-PAGE (9A, 9C, 9E) and inhibition graphs (9B, 9D, 9F) of EGFR-Tyr1068 phosphorylation and downstream signaling in H1975 lung cancer cells treated with varying concentrations of Compound 3 (9A, 9B), Gefitinib (9C, 9D), and WZ4002 (9E, 9F).
Figure 9B:
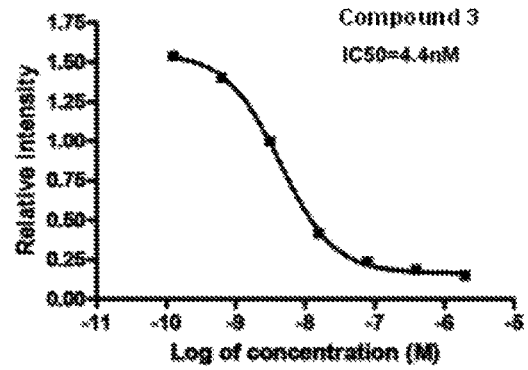
Figure 9C:
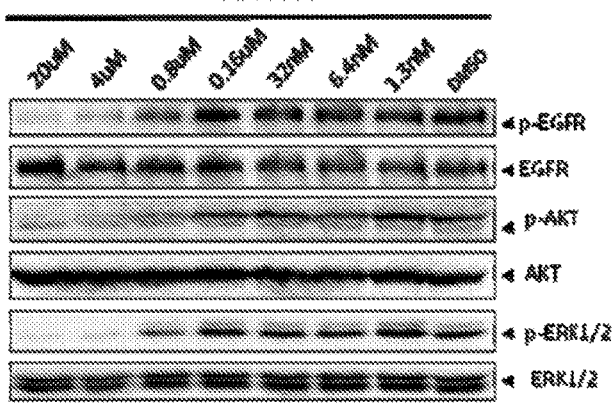
Figure 9D:
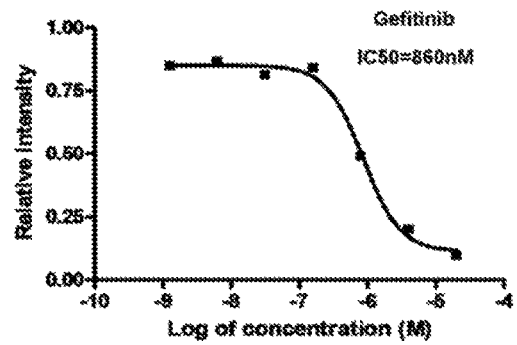
Figure 9E:
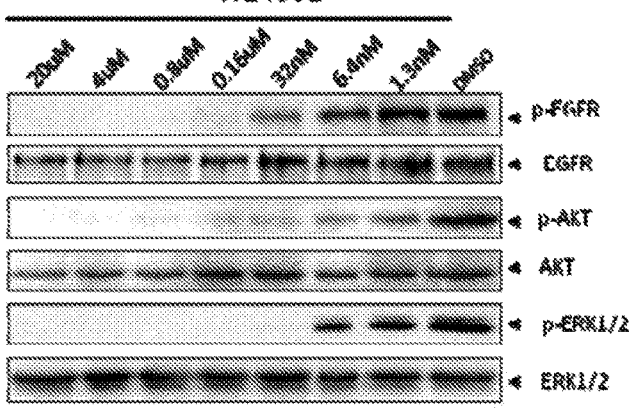
Figure 9F:
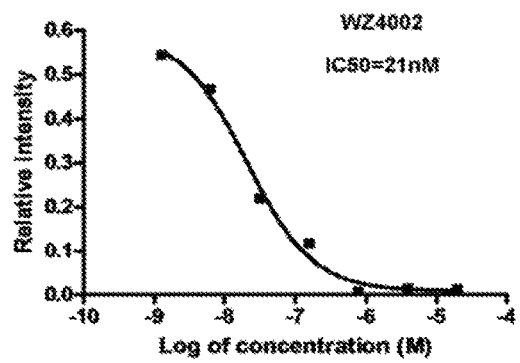

As shown in FIGS. 9A and 9B, Compound 3 inhibited EGFR-Tyr1068 phosphorylation and downstream signaling in H1975 EGFR mutant cells. Comparative data for Gefitinib and WZ4002 are shown in FIGS. 9C-9F.

Figure 10A:
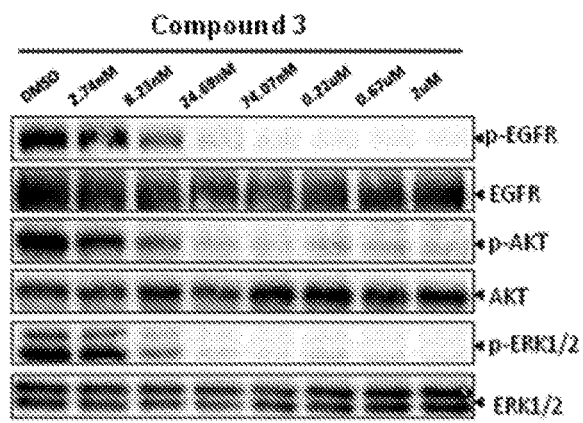
FIGS. 10A-10F show SDS-PAGE (10A, 10C, 10E) and inhibition graphs (10B, 10D, 10F) of EGFR-Tyr1068 phosphorylation and downstream signaling in HCC-827 EGFR mutant cells treated with varying concentrations of Compound 3 (10A, 10B), Gefitinib (10C, 10D), and WZ4002 (10E, 10F).
Figure 10B:
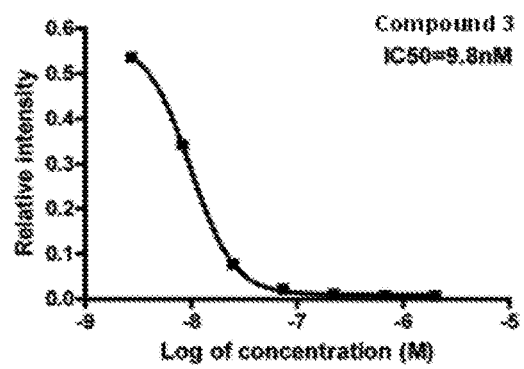
Figure 10C:
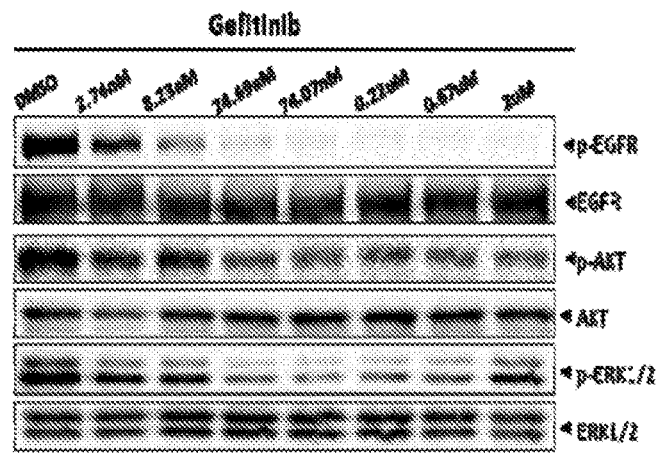
Figure 10D:
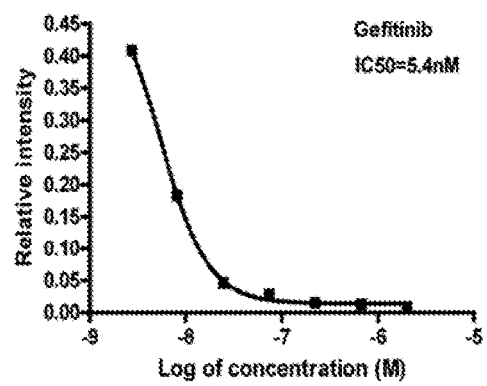
Figure 10E:
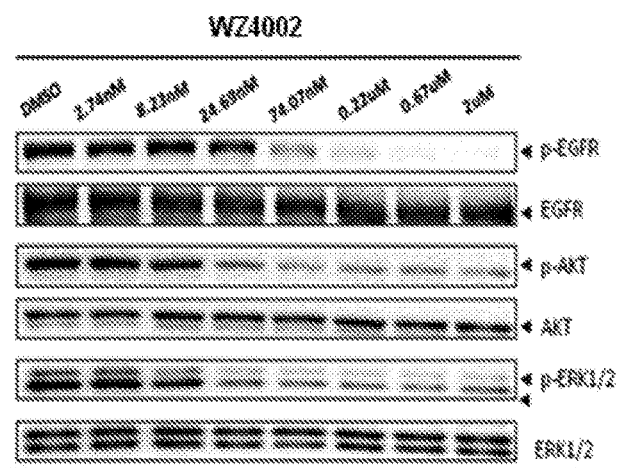
Figure 10F:
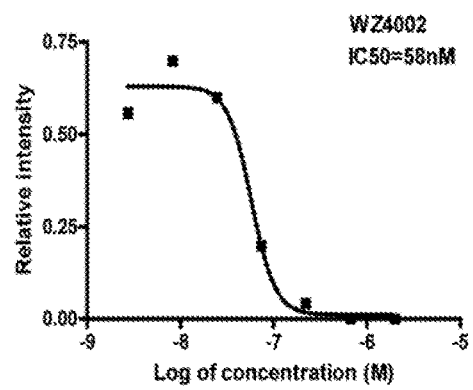

As shown in FIGS. 10A and 10B, Compound 3 inhibited EGFR-Tyr1068 phosphorylation and downstream signaling in HCC-827 EGFR mutant cells. Comparative data for Gefitinib and WZ4002 are shown in FIGS. 10C-10F.

Figure 11A:
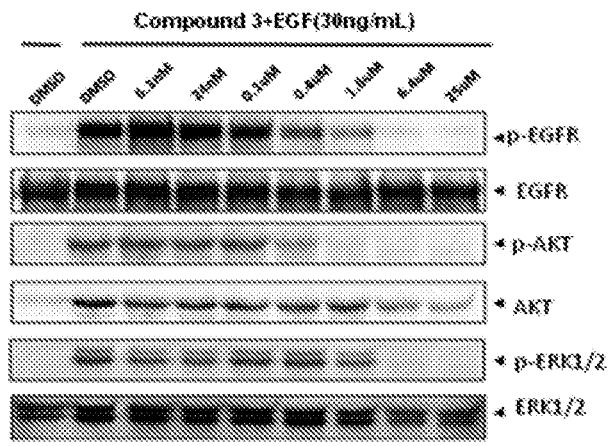
FIGS. 11A-11F show SDS-PAGE (11A, 11C, 11E) and inhibition graphs (11B, 11D, 11F) of EGFR-Tyr1068 phosphorylation and downstream signaling in A431 cells expressing WT EGFR that were treated with varying concentrations of Compound 3 (11A, 11B), Gefitinib (11C, 11D), and WZ4002 (11E, 11F).
Figure 11B:
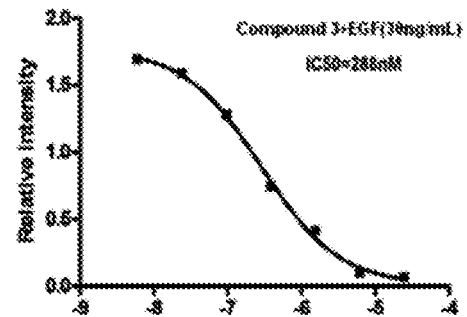
Figure 11C:
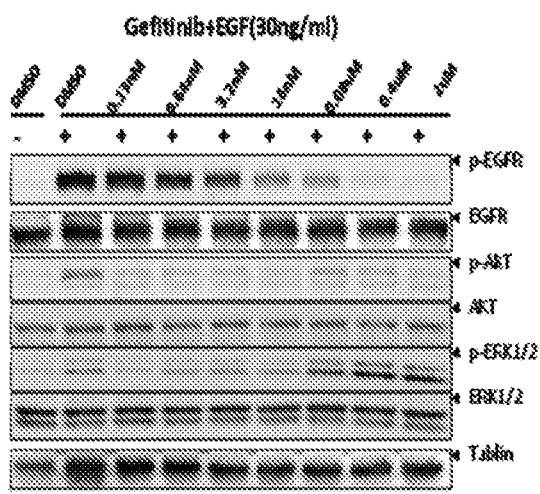
Figure 11D:
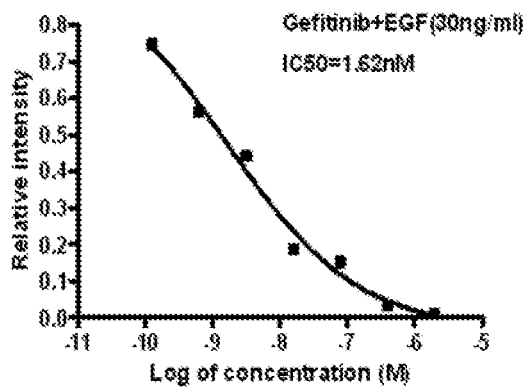
Figure 11E:
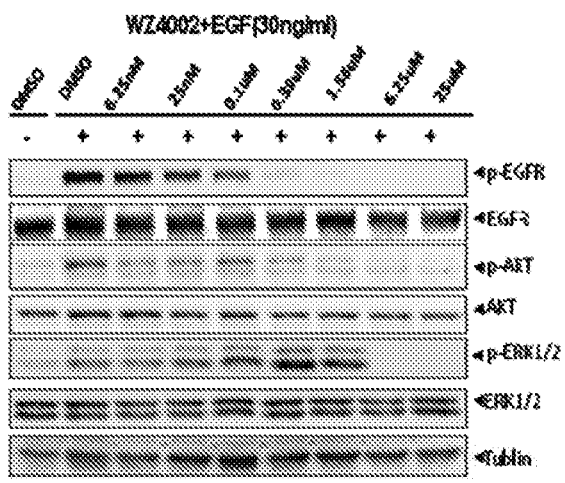
Figure 11F:
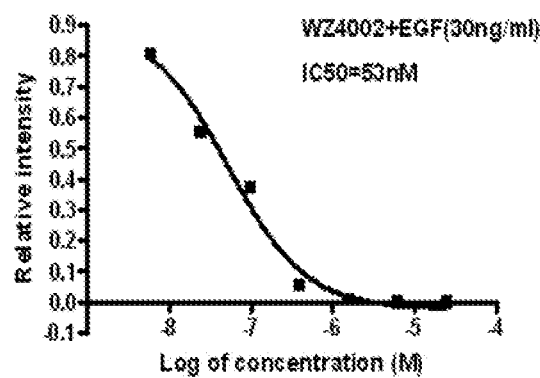

As shown in FIGS. 11A and 11B, Compound 3 was less effective on inhibiting EGFR-Tyr1068 phosphorylation and downstream signaling in A431 cells expressing WT EGFR. Comparative data for Gefitinib and WZ4002 are shown in FIGS. 11C-11F.

Compound 3 Inhibited the Phosphorylation of the EGFR in H1975 Tumors.

Compound 3 significantly inhibited the phosphorylation of the EGFR in H1975 tumor tissues, at all three dosages of 12.5, 50 and 200 mg/kg. The inhibition of EGFR phosphorylation by Compound 3 was dose- and time-dependent. In contrast, the inhibition of the phosphorylation of the EGFR was not detected for gefitinib with the dosage at 100 mg/kg.

Figure 12:
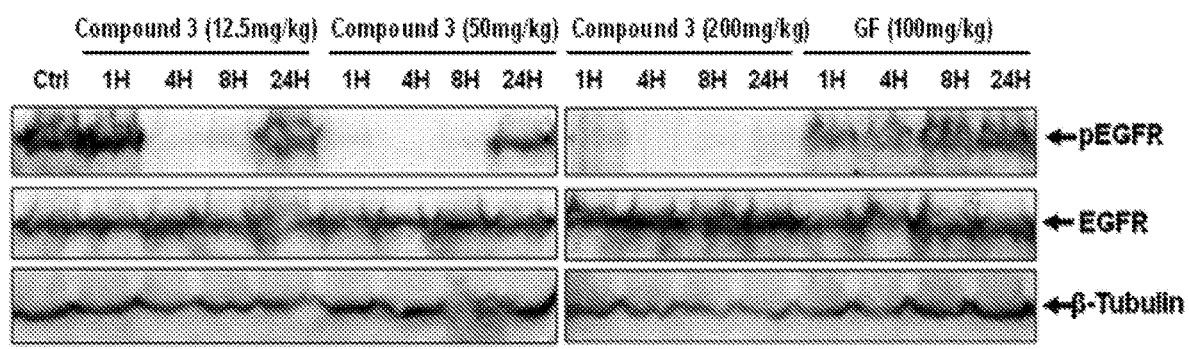
FIG. 12 shows the inhibition of phosphorylation of EGFR in H1975 tumor tissues when treated with a single dose of Compound 3 at 12.5, 50, and 200 mg/kg.

As shown in FIG. 12, Compound 3 inhibits the phosphorylation of the EGFR in H1975 tumor tissues at single-dose of compound 3.

Figure 13:
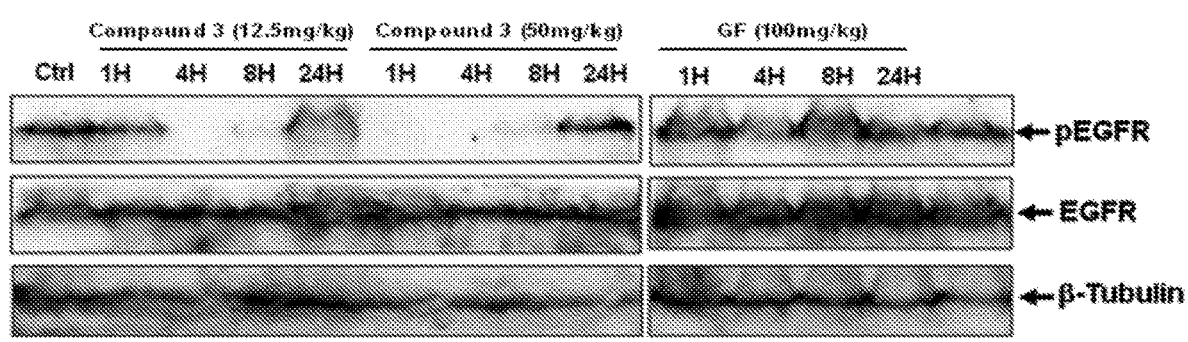
FIG. 13 shows the inhibition of phosphorylation of EGFR in H1975 tumor tissues when treated with eight doses of Compound 3 at 12.5 and 50 mg/kg, as compared to Gefitinib at 100 mg/kg.

As shown in FIG. 13, Compound 3 inhibits the phosphorylation of the EGFR in H1975 tumor tissues after 8 consecutive doses of compound 3.

Figure 14:
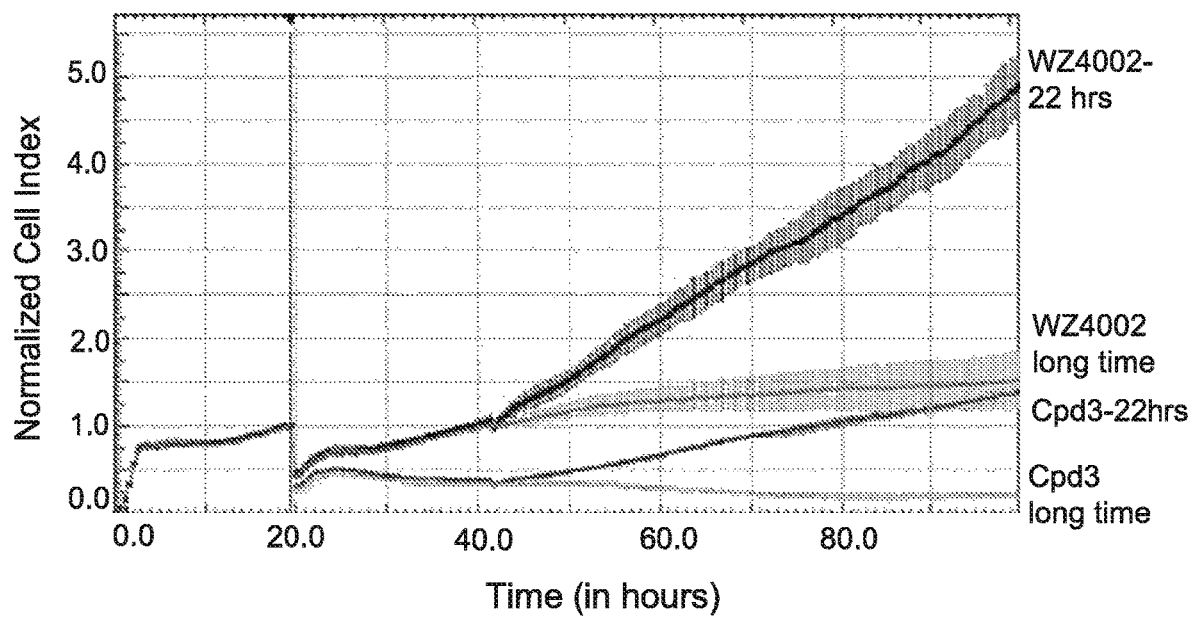
FIG. 14 shows the results of a cell-based pulse-chase assay that demonstrate that Compound 3 is an irreversible inhibitor of proliferation of H1975 cells with the EGFR T790M mutation.

As shown in FIG. 14, Compound 3 irreversibly inhibited the proliferation of H1975 cells harboring EGFR T790M mutation. The reversibility of compound 3 was assessed by a cell-based pulse chase assay. As shown in FIG. 14, upon compound 3 withdrawal following a 22-hr treatment, the inhibition of the proliferation of H1975 sustained (7.8±1.3%) up to 60 hrs. In contrast, the recovery from WZ4002 treatment was at 27±10%. The results of this study demonstrated that compound 3 is an irreversible inhibitor of EGFR, and exhibited strong binding property than WZ4002.

Viability in Comparison with Vehicle Control (%)

| | compound 3 for 22 hr treatment | WZ4002 for 22 hr treatment |
|---|---|---|
| Viability of H1975 cells (%) | 7.8 ± 1.3 | 27 ± 10 |

1. WST Result

| Compound | H1975 cell (T790M/L858R) | A431 cell (WT) | HCC827 cell (delE746-A750) |
|---|---|---|---|
| compound 3 | 0.19 uM | 2.03 uM | 0.011 uM |
| compound A | 1.16 uM | 9.14 uM | 0.023 uM |

2. ELISA Result

| Compound | H1975 cell (T790M/L858R) | A431 cell (WT) EGF stimulate | H1975 cell (T790M/L858R) |
|---|---|---|---|
| compound 3 | 0.0032 uM | 0.4737 uM | 0.025 uM |
| compound A | 0.0088 uM | 1.0270 uM | 0.091 uM |

Biological Example C

Evaluation of Efficacy of Compound 3 in the Treatment of H1975, HCC827, and A431 Xenograft Mouse Models This example evaluates the efficacy of Compound 3 in the treatment of NCI-H1975 (L858R/T790M) human non-small cell lung adenocarcinoma, HCC827 (L858R) human lung adenocarcinoma and A431 (WT) human skin epidermoid carcinoma xenograft tumor models in nude mice. Gefitinib, a first generation of reversible EGFR tyrosine kinase inhibitor, was used as a positive control on those three mouse xenograft tumor models.

Experimental Design and Dosing Schedule

Experimental Design and dosing schedule are shown below.

TABLE 5

NCI-H1975 Model

| Group | n | Treatment | Dose (mg/kg) | Dosing volume (μl/g) | Dosing route | Solvent | Days for dosing | Schedule |
|---|---|---|---|---|---|---|---|---|
| 1 | 8 | Vehicle | — | 16.7 | PO | PEG system | 14 | QD |
| 2 | 8 | Compound 3 | 25 | 10 | PO | PEG system | 14 | QD |
| 3 | 8 | Compound 3 | 50 | 10 | PO | PEG system | 14 | QD |
| 4 | 8 | Compound 3 | 100 | 16.7 | PO | PEG system | 14 | QD |
| 5 | 8 | Gefitinib | 100 | 10 | PO | 1% tween 80 | 14 | QD |

TABLE 6

HCC827 Model

| Group | n | Treatment | Dose (mg/kg) | Dosing volume (μl/g) | Dosing route | Solvent | Days for dosing | Schedule |
|---|---|---|---|---|---|---|---|---|
| 1 | 8 | Vehicle | — | 10 | PO | — | 35 | QD |
| 2 | 8 | Compound 3 | 50 | 10 | PO | PEG system | 35 | QD |
| 3 | 8 | Compound 3 | 50 | 10 | PO | 0.5% MC | 35 | QD |
| 4 | 8 | Gefitinib | 100 | 10 | PO | 1% tween 80 | 7 | QD |

TABLE 7

A431 Model

| Group | n | Treatment | Dose (mg/kg) | Dosing volume (μl/g) | Dosing route | Solvent | Days for dosing | Schedule |
|---|---|---|---|---|---|---|---|---|
| 1 | 8 | Vehicle | — | 16.7 | PO | PEG system | 14 | QD |
| 2 | 8 | Compound 3 | 100 | 16.7 | PO | PEG system | 14 | QD |
| 3 | 8 | Gefitinib | 100 | 10 | PO | 1% tween 80 | 14 | QD |

Note:
n: animal number;
Dosing volume: adjust dosing volume based on body weight;
PEG system: PEG200: alcohol: 5% dextrose = 4:1:5;
Treatment schedule was adjusted if body weight loss >15%.

Animal Housing

Animals

Details on the animals are shown below.
Species: Mouse
Strain: Nu/Nu nude
Age: 7-8 weeks
Sex: Female
Body weight: 20-25 g
Animal supplier: Vital River Laboratories, Beijing, China Housing Conditions The mice were kept in Individual Ventilation Cages at constant temperature and humidity with 4 animals in each cage at ACEA Bioscience Hangzhou Inc.
Temperature: about 20-26° C.
Humidity about 40-70%.
IVC Cages: Made of polycarbonate. The size is 300 mm×180 mm×150 mm. The bedding material is corn cob, which is changed twice per week.
Diet: Animals had free access to irradiation sterilized dry granule food during the entire study period.
Water: Animals had free access to sterile drinking water.
Cage identification: The identification labels for each cage contained the following information: number of animals, sex, strain, date received, treatment, study number, group number and the starting date of the treatment.
Animal identification: Animals were marked by ear cutting.

Experimental Methods and Procedures

Cell Culture

The NCI-H1975, HCC827 and A431 tumor cells were maintained in vitro as a monolayer culture in medium supplemented with 10% fetal bovine serum, 100 U/ml penicillin and 100 μg/ml streptomycin at 37° C. in an atmosphere of 5% $CO_2$ in air as ATCC recommended. The tumor cells were routinely subcultured twice weekly by trypsin-EDTA treatment. The cells growing in an exponential growth phase were harvested and counted for tumor inoculation.

Tumor Inoculation

Each mouse was inoculated subcutaneously at the right flank with H1975 cells ($5×10^6$), HCC827 ($5×10^6$) and A431 ($5×10^6$) respectively in 0.2 ml of medium for tumor development. The treatments were started when the tumor size reached approximately 200-250 $mm^3$. The testing articles were administrated to the mice according to the predetermined regimen as shown in the experimental design table.

Observations

All the procedures related to animal handling, care and the treatment in this study were performed according to the guidelines approved by the Institutional Animal Care and Use Committee (IACUC) following the guidance of the Association for Assessment and Accreditation of Laboratory Animal Care (AAALAC). At the time of routine monitoring, the animals were checked for any effects of tumor growth and treatments on normal behavior such as mobility, food and water consumption (by observation), body weight gain/loss (body weights were measured twice weekly), eye/hair matting and any other abnormal effect. Death and observed clinical signs were recorded on the basis of the numbers of animals within each subset. Animals that were observed to be in a continuing deteriorating condition were euthanized prior to death or before reaching a comatose state.

Tumor Measurements and the Endpoints

The major endpoint was to see if the tumor growth can be delayed or mice can be cured. Tumor size was measured twice weekly in two dimensions using a caliper, and the volume was expressed in $mm^3$ using the formula: V=0.5 a×b² where a and b are the long and short diameters of the tumor, respectively. The tumor size was then used for calculations of both T–C and T/C values. T–C was calculated with T as the median time (in days) required for the treatment group tumors to reach a predetermined size (e.g., 1,000 mm³), and C as the median time (in days) for the control group tumors to reach the same size. The T/C value (in percent) was an indication of antitumor effectiveness; T and C were the mean volume of the treated and control groups, respectively, on a given day. Tumor weight was measured at the study termination. The T/C value (in percent) was calculated where T and C were the mean tumor weights of the treated and control groups, respectively.

Statistical Analysis

Summary statistics, including mean and the standard error of the mean (SEM), are provided for the tumor volume of each group at each time point.

Statistical analysis of difference in tumor volume and tumor weight among the groups was conducted on the data obtained at the best therapeutic time point after the final dose (the 15$^{th}$ day after tumor inoculation).

A one-way ANOVA was performed to compare tumor volume and tumor weight among groups, and when a significant F-statistics (a ratio of treatment variance to the error variance) was obtained, comparisons between groups were carried out with LSD and Games-Howell test. All data were analyzed using SPSS 16.0. $p<0.05$ was considered to be statistically significant.

Results 5.1. Body Weights

Figure 3:
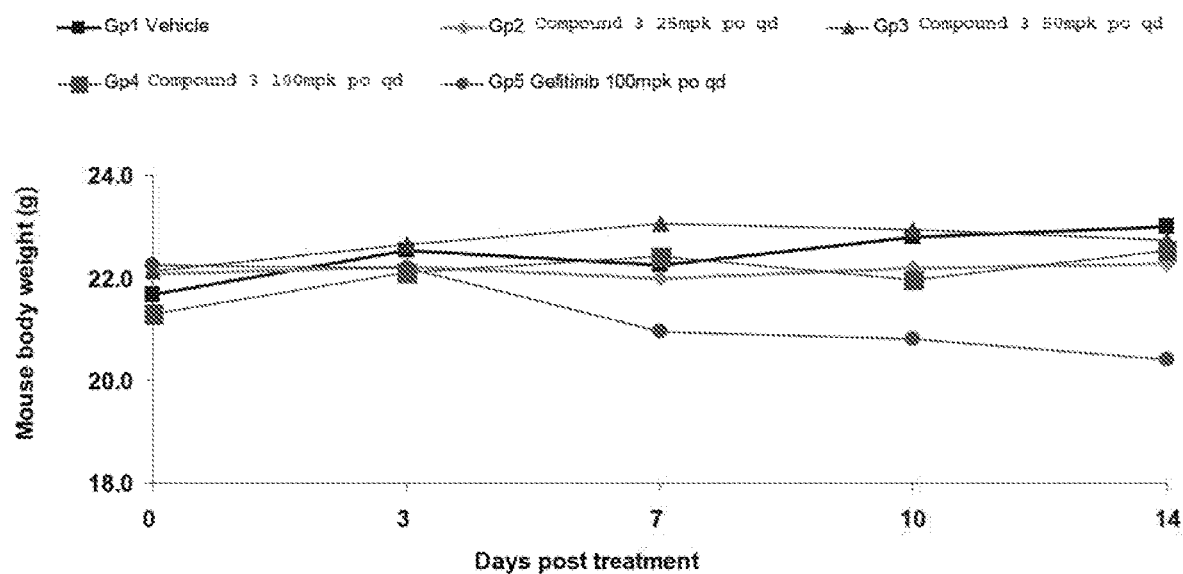
FIG. 3 shows a chart of mouse body weight changes in the different groups in NCI-H1975 model.
Figure 4:
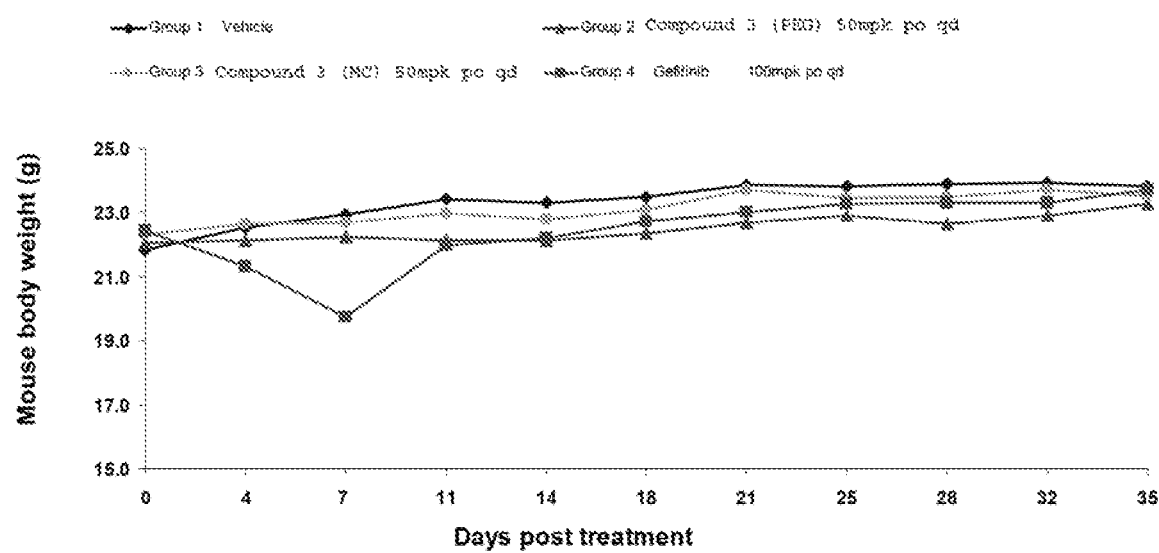
FIG. 4 shows a chart of mouse body weight changes in the different groups in HCC827 model.
Figure 5:
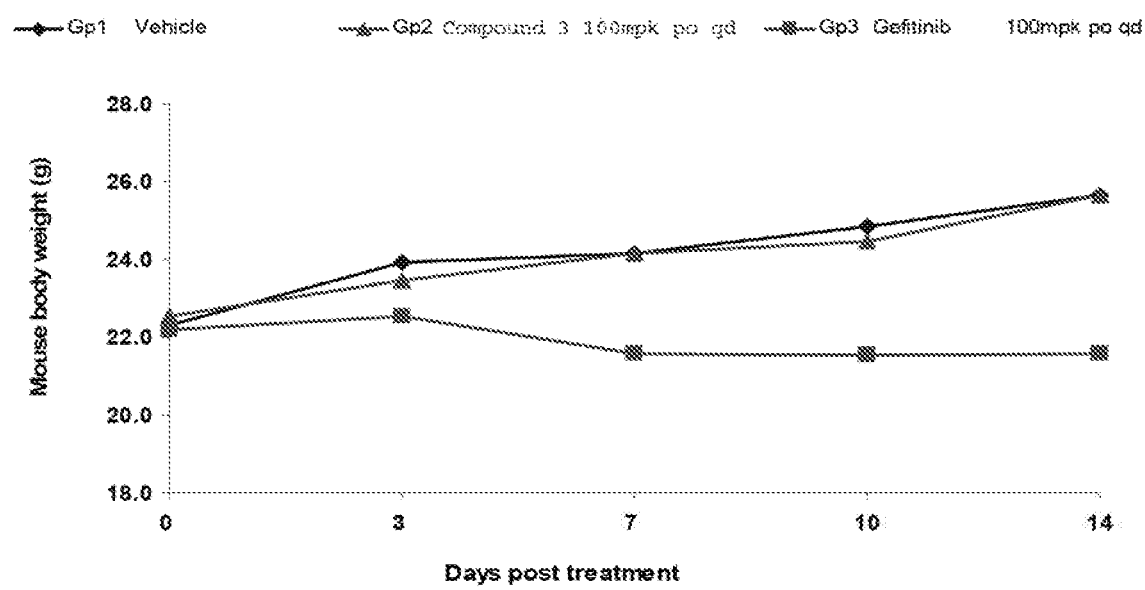
FIG. 5 shows a chart of mouse body weight changes in the different groups in A431 model.

The results of the body weight changes in the tumor-bearing mice for NCI-H1975, HCC827 and A431 models are shown in FIG. 3, FIG. 4, and FIG. 5, respectively.

The mouse body weights in different groups of the tumor-bearing mice at the end of treatment on NCI-H1975, HCC827 and A431 are shown in Table 8, Table 9 and Table 10 respectively.

TABLE 8

The Mouse Body Weights in the Different Groups on NCI-H1975 Model

| Treatment | Mouse Weight (g) $^a$ at day 23(14) | p |
|---|---|---|
| Vehicle | 22.99 ± 0.26 | — |
| Compound 3 25 mg/kg po qd | 22.28 ± 0.55 | 0.364 |

TABLE 8-continued

The Mouse Body Weights in the Different Groups on NCI-H1975 Model

| Treatment | Mouse Weight (g) $^a$ at day 23(14) | p |
|---|---|---|
| Compound 3 50 mg/kg po qd | 22.73 ± 0.33 | 0.737 |
| Compound 3 100 mg/kg po qd | 22.53 ± 0.66 | 0.555 |
| Gefitinib 100 mg/kg po qd | 20.43 ± 0.71 | 0.002 |

TABLE 9

The Mouse Body Weights in the Different Groups on HCC827 Model

| Treatment | Mouse Weight (g) $^a$ at day 25(14) | p |
|---|---|---|
| Vehicle | 23.83 ± 0.71 | — |
| Compound 3 (PEG) 50 mg/kg po qd | 23.26 ± 0.47 | 0.523 |
| Compound 3 (MC) 50 mg/kg po qd | 23.54 ± 0.67 | 0.743 |
| Gefitinib 100 mg/kg po qd | 23.70 ± 0.43 | 0.887 |

TABLE 10

The Mouse Body Weights in the Different Groups on A431 Model

| Treatment | Mouse Weight (g) $^a$ at day 25(14) | p |
|---|---|---|
| Vehicle | 25.64 ± 0.53 | — |
| Compound 3 100 mg/kg po qd | 25.66 ± 0.72 | 0.979 |
| Gefitinib 100 mg/kg po qd | 21.56 ± 0.51 | 0.000 |

Note:
$^a$ Mean ± SEM

Tumor Volumes

The tumor sizes of the different groups at different time points on NCI-H1975, HCC827 and A431 are shown in Table 11, Table 12, and Table 13, respectively.

TABLE 11

Tumor Sizes in the Different Treatment Groups on NCI-H1975 model

| | Tumor volume (mm³)$^a$ | | | | |
|---|---|---|---|---|---|
| Days | Vehicle, PO, QD — | Compound 3, PO, QD 25 mpk | Compound 3, PO, QD 50 mpk | Compound 3, PO, QD 100 mpk | Gefitinib, PO, QD 100 mpk |
| 9 | 215.01 ± 20.88 | 219.91 ± 22.33 | 215.95 ± 21.58 | 220.64 ± 22.95 | 215.95 ± 22.36 |
| 12 | 387.98 ± 45.76 | 284.09 ± 32.64 | 255.85 ± 34.44 | 181.40 ± 21.15 | 379.15 ± 46.00 |
| 16 | 828.95 ± 58.76 | 393.95 ± 42.09 | 268.23 ± 47.77 | 180.18 ± 26.25 | 737.84 ± 80.06 |
| 19 | 1425.22 ± 101.9 | 514.88 ± 55.57 | 346.01 ± 62.50 | 207.28 ± 42.54 | 1195.5 ± 67.91 |
| 23 | 2169.9 ± 170.8 | 670.36 ± 54.19 | 373.01 ± 63.35 | 232.25 ± 37.11 | 1702.5 ± 101.8 |

TABLE 12

Tumor Sizes in the Different Treatment Groups on HCC827 model

| | Tumor volume (mm³)$^a$ | | | |
|---|---|---|---|---|
| Days | Vehicle, PO, QD Vehicle | Compound 3, PO, QD 50 mpk (PEG) | Compound 3, PO, QD 50 mpk (0.5% MC) | Gefitinib, PO, QD 100 mpk |
| 14 | 215.94 ± 25.70 | 211.90 ± 23.00 | 211.14 ± 25.11 | 212.28 ± 26.35 |
| 18 | 291.15 ± 24.42 | 188.72 ± 28.03 | 216.63 ± 27.69 | 59.55 ± 25.20 |
| 21 | 353.24 ± 25.64 | 136.96 ± 16.40 | 245.14 ± 33.44 | 4.61 ± 3.16 |
| 25 | 453.43 ± 24.72 | 95.73 ± 15.38 | 216.42 ± 28.06 | 1.25 ± 1.25 |
| 28 | 519.39 ± 22.26 | 111.96 ± 22.05 | 231.08 ± 30.81 | 1.25 ± 1.25 |
| 32 | 638.78 ± 32.70 | 82.28 ± 24.08 | 277.59 ± 42.02 | 1.25 ± 1.25 |
| 35 | 762.43 ± 47.22 | 67.63 ± 24.22 | 293.64 ± 43.98 | 1.88 ± 1.32 |
| 39 | 1092.53 ± 99.28 | 69.44 ± 30.35 | 328.53 ± 43.51 | 1.88 ± 1.32 |
| 42 | 1324.76 ± 141.54 | 79.71 ± 28.86 | 302.31 ± 35.83 | 10.95 ± 6.13 |
| 46 | 1736.94 ± 217.03 | 84.26 ± 35.62 | 284.44 ± 27.00 | 23.71 ± 11.84 |
| 49 | 1920.11 ± 256.36 | 77.59 ± 42.07 | 299.28 ± 31.79 | 41.00 ± 20.52 |

TABLE 13

Tumor Sizes in the Different Treatment Groups on A431 model

| | Tumor volume (mm³)$^a$ | | |
|---|---|---|---|
| Days | Vehicle, PO, QD — | Compound 3, PO, QD 100 mpk | Gefitinib, PO, QD 100 mpk |
| 11 | 241.34 ± 28.69 | 240.95 ± 26.46 | 239.83 ± 23.30 |
| 14 | 472.09 ± 71.50 | 399.68 ± 42.62 | 203.74 ± 22.97 |
| 18 | 860.82 ± 120.62 | 867.62 ± 70.54 | 139.70 ± 26.94 |
| 21 | 1211.0 ± 157.77 | 1166.1 ± 94.08 | 139.70 ± 22.07 |
| 25 | 1666.6 ± 233.36 | 1627.7 ± 146.0 | 154.79 ± 32.62 |

Note:
$^a$Mean ± SEM

Tumor Growth Inhibition

The tumor growth inhibition on NCI-H1975, HCC827 and A431 models is summarized in Table 14, Table 15, and Table 16, respectively.

TABLE 14

Effect of Compounds in the Treatment of H1975 Xenografts Tumor Model

| Treatment | Tumor Size (mm³)$^a$ at day 23(14) | T/C (%) | T-C (days) at 300 mm³ | p |
|---|---|---|---|---|
| Vehicle | 2170 ± 171 | — | — | — |
| Compound 3 25 mg/kg po qd | 670 ± 54 | 28.5% | 2.11 | 0.000 |
| Compound 3 50 mg/kg po qd | 373 ± 63 | 16.0% | 6.76 | 0.000 |
| Compound 3 100 mg/kg po qd | 232 ± 37 | 9.9% | >14 | 0.000 |
| Gefitinib 100 mg/kg po qd | 1702 ± 102 | 77.4% | 0.08 | 0.345 |

TABLE 15

Effect of Compounds in the Treatment of HCC827 Xenografts Tumor Model

| Treatment | Tumor Size (mm³)$^a$ at day 49(35) | T/C (%) | TRR$^b$ at day 49(35) | T-C (days) at 300 mm³ | p |
|---|---|---|---|---|---|
| Vehicle | 1920 ± 256 | — | — | — | — |
| Compound 3 (PEG) 50 mg/kg po qd | 78 ± 42 | 2.8% | 71.4% | >35 | 0.001 |
| Compound 3 (MC) 50 mg/kg po qd | 299 ± 32 | 14.3% | −45.0% | 17.3 | 0.002 |
| Gefitinib 100 mg/kg po qd | 41 ± 21 | 2.4% | 75.7% | >35 | 0.001 |

TABLE 16

Effect of Compounds in the Treatment of A431 Xenografts Tumor Model

| Treatment | Tumor Size (mm³)$^a$ at day 25(14) | T/C (%) | T-C (days) at 300 mm³ | p |
|---|---|---|---|---|
| Vehicle | 1667 ± 233 | — | — | — |
| Compound 3 100 mg/kg po qd | 1628 ± 146 | 98.3% | 0.35 | 0.999 |
| Gefitinib 100 mg/kg po qd | 154 ± 33 | 8.7% | >14 | 0.001 |

Note:
$^a$Mean ± SEM
b. Tumor regression rate (%) = (1-tumor volume of after treatment/tumor volume of pretreatment) * 100%

Tumor Growth Curve

Figure 6:
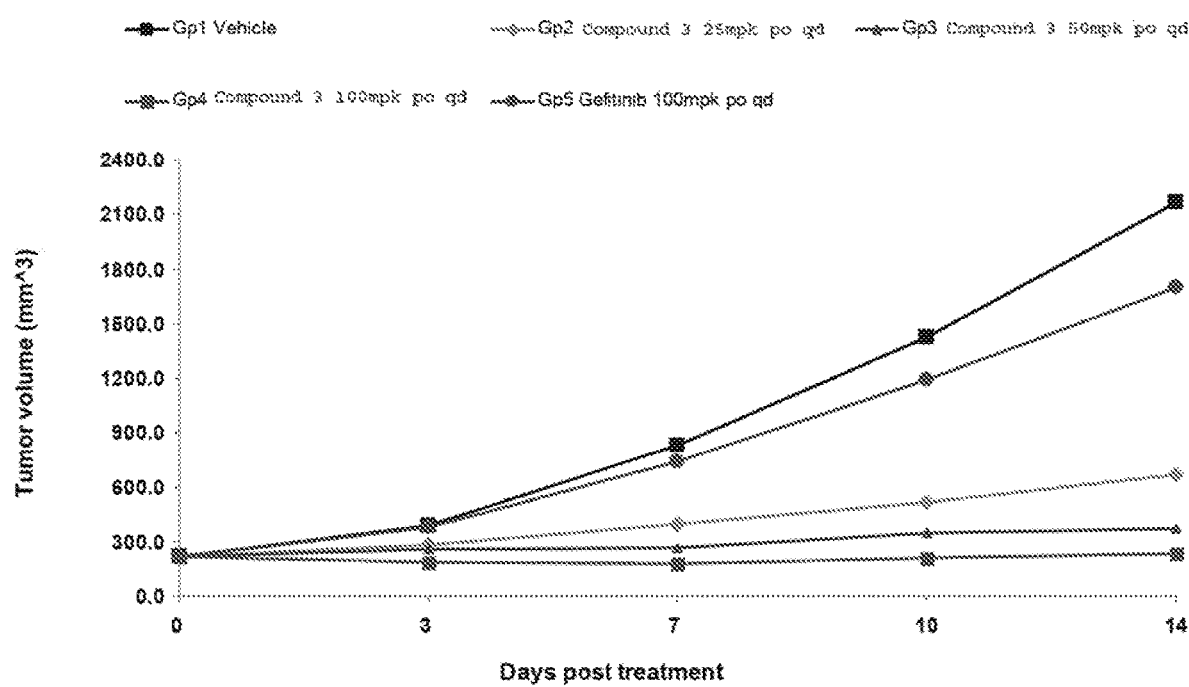
FIG. 6 shows a chart of the tumor volume of mice in the different groups in NCI-H1975 model.
Figure 7:
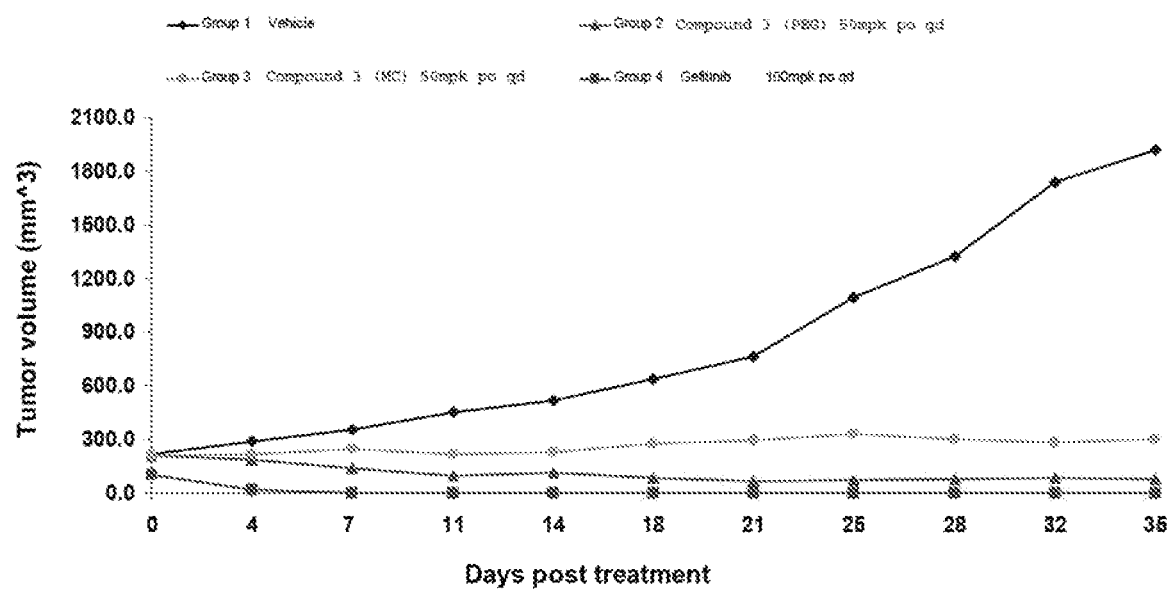
FIG. 7 shows a chart of the tumor volume of mice in the different groups in HCC827 model.
Figure 8:
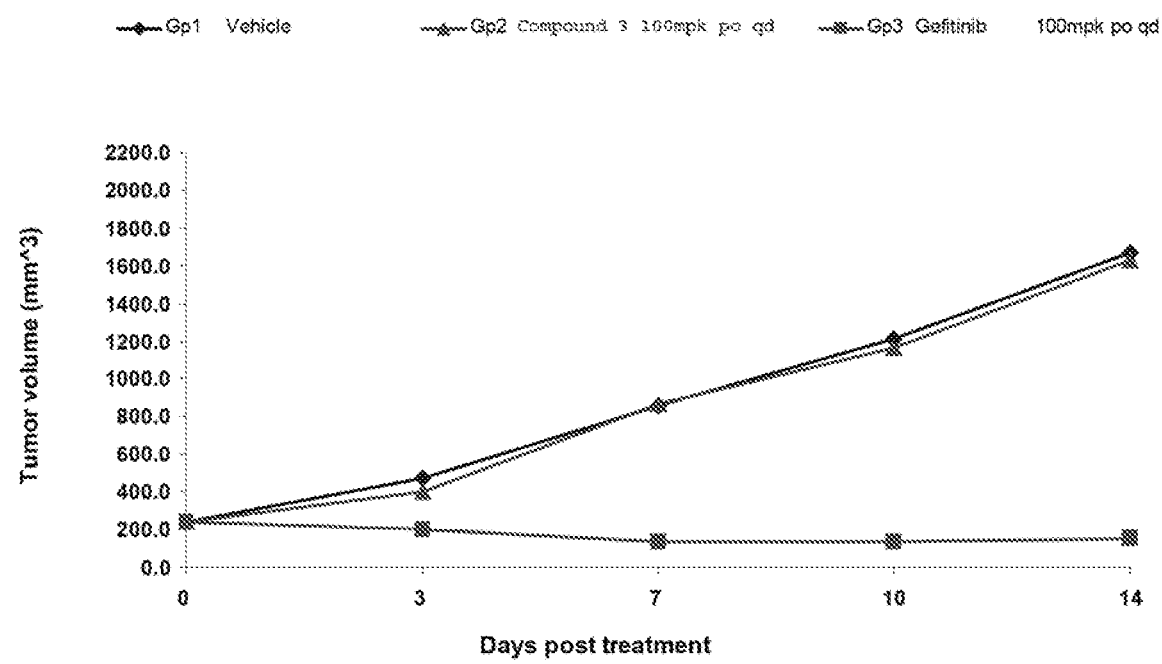
FIG. 8 shows a chart of the tumor volume of mice in the different groups in A431 model.

The tumor growth curve in different groups of the tumor-bearing mice on NCI-H1975, HCC827 and A431 models are shown in FIG. 6, FIG. 7, and FIG. 8, respectively.

Tumor Weights

The mouse tumor weights in different groups on NCI-H1975, HCC827 and A431 models are shown in Table 17, Table 18, and Table 19, respectively.

TABLE 17

The Antitumor Activity of Compounds in the Treatment of NCI-H1975 Model

| Treatment | Tumor Weight (g) at day 23(14) | IR$^a$ at day 23(14) | p |
|---|---|---|---|
| Vehicle | 1.99 ± 0.16 | — | — |
| Compound 3 25 mg/kg po qd | 0.70 ± 0.04 | 65.0% | 0.001 |
| Compound 3 50 mg/kg po qd | 0.34 ± 0.08 | 82.8% | 0.000 |
| Gefitinib 100 mg/kg po qd | 1.69 ± 0.11 | 15.1% | 0.717 |

TABLE 18

The Antitumor Activity of Compounds in the Treatment of HCC827 Model

| Treatment | Tumor Weight (g) at day 49(35) | IR$^a$ at day 49(35) | p |
|---|---|---|---|
| Vehicle | 1.94 ± 0.32 | — | — |
| Compound 3 (PEG) 50 mg/kg po qd | 0.06 ± 0.02 | 96.7% | .004 |
| Compound 3 (MC) 50 mg/kg po qd | 0.26 ± 0.04 | 86.5% | .008 |

TABLE 18-continued

The Antitumor Activity of Compounds in the Treatment of HCC827 Model

| Treatment | Tumor Weight (g) at day 49(35) | IR[a] at day 49(35) | p |
|---|---|---|---|
| Gefitinib 100 mg/kg po qd | 0.03 ± 0.02 | 98.3% | .004 |

TABLE 19

The Antitumor Activity of Compounds in the Treatment of A431 Model

| Treatment | Tumor Weight (g) at day 23(14) | IR[a] at day 23(14) | p |
|---|---|---|---|
| Vehicle | 1.67 ± 0.29 | — | — |
| Compound 3 100 mg/kg po qd | 1.60 ± 0.22 | 4.0% | 0.817 |
| Gefitinib 100 mg/kg po qd | 0.13 ± 0.03 | 92.5% | 0.000 |

[a]IR (Inhibition Rate) = (TW$_{Control}$ − TW$_{Treatment}$)/TW$_{Control}$ × 100%

Biological Example D

Synthesis of the Maleate Salt and Hydrochloride Salt of Compound 3 and Pharmacokinetic Study The synthesis of the maleate and hydrochloride salts from the free base of Compound 3 is shown below:

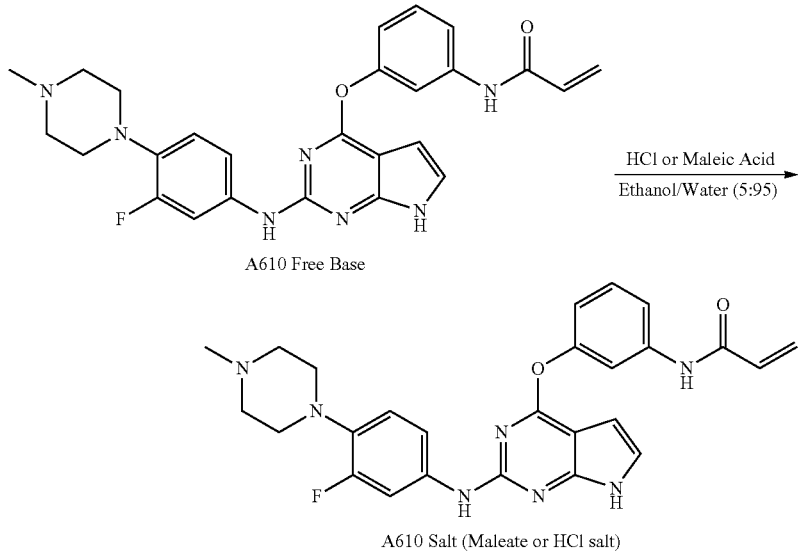

A610 Free Base

HCl or Maleic Acid
Ethanol/Water (5:95)

A610 Salt (Maleate or HCl salt)

To the free base of Compound 3 (2 g) in ethanol/water (5:95, 22 mL) at 40° C., maleic acid (1.2 eq.) or HCl (2.2 eq.) was added dropwise. After the solid was dissolved, the solution was cooled to room temperature, and stood for overnight. The resulting crystals (light yellow or off white) were collected, washed with cold water and dried overnight (over 85% yield).

Pharmacokinetic Studies on Rats with Compound 3 in Free Base, Maleate Salt and HCl Salt Forms:

A pharmacokinetic comparison study was performed on rats using Compound 3 in free base, maleate salt, and HCl salt forms. The detailed study conditions along with the experimental results are shown the table below:

TABLE 20

| Compound | Formulation | Sex | Animal Source | Dose (mg/kg) | Route | F % | AUClast (ng/mL*h) | t½ (h) | Cmax(po) or $C_0$ (iv) (ng/ml) |
|---|---|---|---|---|---|---|---|---|---|
| Compound 3 Free base | PEG200:D5W (50:50, v/v) | Female | Zhe Jiang AMS | 4.7 | i.v. | n/a | 2195 ± 140.2 | 1.6 ± 0.04 | 4102.1 ± 675.8 |

TABLE 20-continued

| Compound | Formulation | Sex | Animal Source | Dose (mg/kg) | Route | F % | AUClast (ng/mL*h) | t½ (h) | Cmax(po) or C₀ (iv) (ng/ml) |
|---|---|---|---|---|---|---|---|---|---|
| Compound 3 Free base | 0.5% MC | Female | Zhe Jiang AMS | 30.56 | p.o. | 10.7 ± 2.6 | 1526.8 ± 364.6 | 2.4 ± 0.6 | 242.0 ± 37.6 |
| Compound 3 HCl salt | 0.5% MC | Female | Zhe Jiang AMS | 40.88 | p.o. | 30.6 ± 8.2 | 5853.8 ± 1565.4 | 2.4 ± 1.0 | 1259.3 ± 359.0 |
| Compound 3 Maleate salt | 0.5% MC | Female | Zhe Jiang AMS | 42.00 | p.o. | 32.7 ± 9.8 | 6412.2 ± 1917.8 | 2.3 ± 0.4 | 1540.0 ± 528.5 |
| Compound 3 Free base | PEG200:D5W (50:50, v/v) | Female | Zhe Jiang AMS | 37.6 | p.o. | 23.0 ± 10.8 | 4041.0 ± 1892.3 | 2.8 ± 0.3 | 1263.3 ± 270.2 |

The results show that in the same formulation of 0.5% methylcellulose (MC), the salt forms (both maleate salt and HCl salt) had about a 3-fold better bioavailability compared to the free base form.

The invention claimed is:

1. A method of treating a condition selected from sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, pancreatic cancer, psoriasis and dry eye, comprising administering to a subject in need of such treatment an effective amount of a compound of Formula (IV):

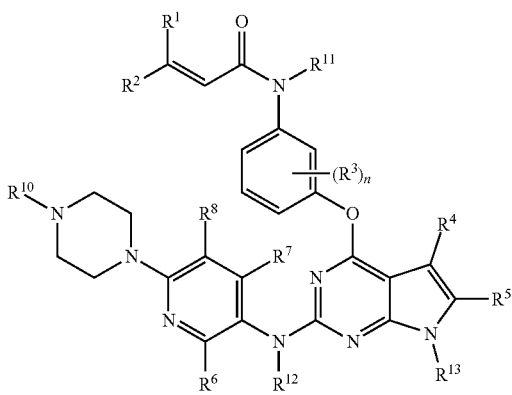

(IV)

wherein
$R^1$ and $R^2$ are independently selected from hydrogen, halo, $C_{1-6}$ alkyl, and $C_{1-6}$ haloalkyl;
$R^3$ is selected from halo, hydroxyl, $C_{1-6}$ alkyl, $C_{1-6}$ alkoxy, cyano, and nitro;
n is a number from zero to 4;
$R^4$ is selected from hydrogen, $C_{1-6}$ alkyl, $C_{3-7}$ cycloalkyl, and $NR^{22}R^{23}$;
  wherein the alkyl or cycloalkyl is unsubstituted or substituted with hydroxyl or amino; and
  wherein each $R^{22}$ and $R^{23}$ are independently selected from hydrogen and $C_{1-6}$ alkyl or $R^{22}$ and $R^{23}$ may be joined to form a 3 to 10 membered ring;
$R^5$ is selected from hydrogen and $C_{1-6}$ alkyl;
$R^6$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;
$R^7$ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;
$R^8$ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;
$R^{10}$ is selected from hydrogen and $C_{1-6}$ alkyl;
$R^{11}$ is selected from hydrogen and $C_{1-6}$ alkyl;
$R^{12}$ is selected from hydrogen and $C_{1-6}$ alkyl; and
$R^{13}$ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo;
or a pharmaceutically acceptable salt thereof.

2. The method of claim 1, wherein $R^1$ and $R^2$ are each hydrogen.

3. The method of claim 1, wherein $R^8$ is hydrogen or halo.

4. The method of claim 1, wherein $R^6$ and $R^7$ are each hydrogen.

5. The method of claim 1, wherein $R^{11}$ and $R^{12}$ are each hydrogen.

6. The method of claim 1, wherein $R^{10}$ is methyl, ethyl, or isopropyl.

7. The method of claim 1, wherein $R^{11}$ is hydrogen.

8. The method of claim 1, wherein the condition is selected from the group consisting of sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, and pancreatic cancer.

9. The method of claim 8, further comprising administering an effective amount of a second therapeutic agent for treating a proliferation disorder to the subject.

10. A method of treating a condition selected from sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, pancreatic cancer, psoriasis and dry eye, comprising administering to a subject in need of such treatment an effective amount of a compound of Formula (V):

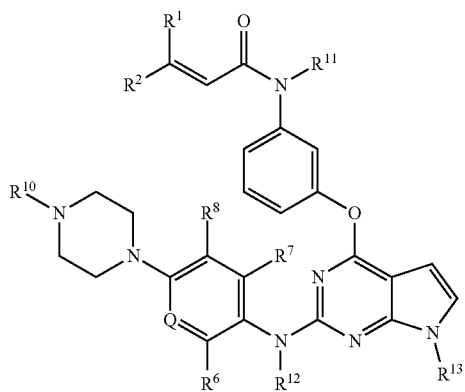

(V)

wherein
R¹ and R² are independently selected from hydrogen, halo, $C_{1-6}$ alkyl, and $C_{1-6}$ haloalkyl;
R⁶ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;
R⁷ is selected from hydrogen, halo, $C_{1-6}$ alkyl, $C_{1-6}$ haloalkyl, $C_{2-6}$ alkoxy, $C_{1-6}$ haloalkoxy, hydroxyl, cyano, and nitro;
R⁸ is selected from hydrogen, halo, $C_{1-6}$ alkyl, $C_{1-6}$ haloalkyl, $C_{1-6}$ alkoxy, $C_{1-6}$ haloalkoxy, hydroxyl, cyano, and nitro;
Q is $CR^9$ or N;
R⁹ is halo;
R¹⁰ is selected from hydrogen and $C_{1-6}$ alkyl;
R¹¹ is selected from hydrogen and $C_{1-6}$ alkyl;
R¹² is selected from hydrogen and $C_{1-6}$ alkyl; and
R¹³ is selected from hydrogen, $C_{1-6}$ alkyl, and $C_{6-20}$ aryl, wherein each alkyl or aryl is unsubstituted or substituted with hydroxyl, $C_{1-6}$ alkoxy, or halo;
or a pharmaceutically acceptable salt thereof.

11. The method of claim 10, wherein R¹ and R² are each hydrogen.

12. The method of claim 10, wherein R⁹ is F.

13. The method of claim 10, wherein R⁶ and R⁷ are hydrogen.

14. The method of claim 10, wherein R¹¹ is hydrogen.

15. The method of claim 10, wherein R¹⁰ is methyl, ethyl, or isopropyl.

16. The method of claim 10, wherein R¹³ is hydrogen.

17. The method of claim 10, wherein the condition is selected from the group consisting of sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, and pancreatic cancer.

18. The method of claim 17, further comprising administering an effective amount of a second therapeutic agent for treating a proliferation disorder to the subject.

* * * * *